US012716060B2

(12) United States Patent
Cheng et al.

(10) Patent No.: US 12,716,060 B2

(45) **Date of Patent: *Aug. 25, 2026**

(54) CRISPR-ASSOCIATED SYSTEMS AND COMPONENTS

(71) Applicant: ARBOR BIOTECHNOLOGIES, INC., Cambridge, MA (US)

(72) Inventors: David R. Cheng, Boston, MA (US); David A. Scott, San Francisco, CA (US); Winston X. Yan, Boston, MA (US)

(73) Assignee: ARBOR BIOTECHNOLOGIES, INC., Cambridge, MA (US)

( * ) Notice: Subject to any disclaimer, the term of this patent is extended or adjusted under 35 U.S.C. 154(b) by 503 days.

This patent is subject to a terminal disclaimer.

(21) Appl. No.: 18/306,009

(22) Filed: Apr. 24, 2023

(65) Prior Publication Data

US 2023/0407281 A1 Dec. 21, 2023

Related U.S. Application Data

(63) Continuation of application No. 16/862,261, filed on Apr. 29, 2020, now Pat. No. 11,667,904, which is a continuation of application No. PCT/US2019/032750, filed on May 16, 2019.

(60) Provisional application No. 62/672,489, filed on May 16, 2018.

(51) Int. Cl.

| | |
|---|---|
| ***C12N 9/22*** | (2006.01) |
| ***A61K 31/7088*** | (2006.01) |
| ***A61K 38/46*** | (2006.01) |
| ***C12N 9/96*** | (2006.01) |
| ***C12N 15/11*** | (2006.01) |
| ***C12N 15/113*** | (2010.01) |
| ***C12N 15/90*** | (2006.01) |
| ***C12Q 1/6832*** | (2018.01) |

(52) U.S. Cl.

CPC ............ *C12N 9/22* (2013.01); *A61K 31/7088* (2013.01); *A61K 38/465* (2013.01); *C12N 9/96* (2013.01); *C12N 15/11* (2013.01); *C12N 15/113* (2013.01); *C12N 15/907* (2013.01); *C12Q 1/6832* (2013.01); *C07K 2319/80* (2013.01); *C12N 2310/20* (2017.05); *C12N 2310/531* (2013.01); *C12N 2800/80* (2013.01)

(58) Field of Classification Search

None

See application file for complete search history.

(56) References Cited

U.S. PATENT DOCUMENTS

| | | | |
|---|---|---|---|
| 5,580,859 | A | 12/1996 | Felgner et al. |
| 5,589,466 | A | 12/1996 | Felgner et al. |
| 5,593,972 | A | 1/1997 | Weiner et al. |
| 8,454,972 | B2 | 6/2013 | Nabel et al. |
| 8,795,965 | B2 | 8/2014 | Zhang |
| 8,871,445 | B2 | 10/2014 | Cong et al. |
| 10,808,245 | B2 | 10/2020 | Chong et al. |
| 11,667,904 | B2 | 6/2023 | Cheng et al. |
| 2017/0211142 | A1 | 7/2017 | Smargon et al. |
| 2018/0371487 | A1 | 12/2018 | Yang et al. |
| 2023/0407281 | A1 | 12/2023 | Cheng et al. |

FOREIGN PATENT DOCUMENTS

| | | | |
|---|---|---|---|
| EP | 3009511 | A2 | 4/2016 |
| WO | 2012164565 | A1 | 12/2012 |
| WO | 2014/093622 | A2 | 6/2014 |
| WO | 2015070083 | A1 | 5/2015 |
| WO | 2016094872 | A1 | 6/2016 |
| WO | 2016094874 | A1 | 6/2016 |
| WO | 2016106236 | A1 | 6/2016 |
| WO | 2016205764 | A1 | 12/2016 |
| WO | 2017070605 | A1 | 4/2017 |
| WO | 2017091630 | A1 | 6/2017 |
| WO | 2017127807 | A1 | 7/2017 |
| WO | 2017219027 | A1 | 12/2017 |
| WO | 2018035250 | A1 | 2/2018 |
| WO | 2018035388 | A1 | 2/2018 |
| WO | 2019178427 | A1 | 9/2019 |
| WO | 2019178428 | A1 | 9/2019 |
| WO | 2020028823 | A1 | 2/2020 |
| WO | 2020181101 | A1 | 9/2020 |

OTHER PUBLICATIONS

Carabias, et al. (Nature Communications 12.1 (2021): 1-12). (Year: 2021).*

Guo et al. (2004, Proc. Natl. Acad. Sci. USA 101: 9205-9210). (Year: 2004).*

Chylinski, et al. "Classification and evolution of type II CRISPR-Cas systems." Nucleic acids research 42.10 (2014): 6091-6105. (Year: 2014).*

(Continued)

*Primary Examiner* — Charles Logsdon

(74) *Attorney, Agent, or Firm* — K&L Gates LLP

(57) ABSTRACT

The disclosure describes novel systems, methods, and compositions for the manipulation of nucleic acids in a targeted fashion. The disclosure describes non-naturally occurring, engineered Type III-E CRISPR-Cas systems, components, and methods for targeted modification of DNA, RNA, and protein substrates. Each system includes one or more protein components and one or more nucleic acid components that together target DNA, RNA, or protein substrates.

17 Claims, 14 Drawing Sheets

Specification includes a Sequence Listing.

(56) References Cited

OTHER PUBLICATIONS

Abudayyeh et al. "C2c2 is a single-component programable RNA-guided RNA-targeting CRISPR effector" Science (2016) vol. 353, No. 6299, pp. aaf5573-1-aaf5573-9.
Allerson et al. "Fully 2'-modified oligonucleotide duplexes with improved in vitro potency and stability compared to unmodified small interfering RNA," J. Med. Chem., 48.4 (2005): 901-904.
Al-Shayeb et al., "Clades of huge phages from across Earth's ecosystems," Nature (2020) vol. 578, pp. 425-431 and Methods pages.
Aravind et al "Classification of the caspase-hemoglobinase fold: detection of new families and implications for the origin of the eukaryotic separins" (2002) Proteins 46(4): 355-67.
Baba et al. "Construction of *Escherichia coli* K-12 in-frame, single-gene knockout mutants: the Keio collection" (2006) Mol. Syst. Biol. 2: 2006.0008.
Bell et al., "A high-throughput screening strategy for detecting CRISPR-Cas9 induced mutations using next-generation sequencing," BMC Genomics (2014) vol. 15, No. 1002, pp. 1-7.
Bramsen et al., "Development of therapeutic-grade small interfering RNAs by chemical engineering," Front. Genet., Aug. 20, 2012; 3:154.
Canver et al., "BCL11A enhancer dissection by Cas9-mediated in situ saturating mutagenesis," Nature, Nov. 12, 2015; 527(7577):192-7.
Chen et al., "CRISPR-Cas12a target binding unleashes indiscriminate single-stranded DNase activity," Science 360 (6387)" 436-9 (Feb. 2018).
Chen et al., "Spatially resolved, highly multiplexed RNA profiling in single cells," Science, Apr. 24, 2015; 348(6233): aaa6090.
Chou-Zheng et al "A type III-A CRISPR-Cas system employs degradosome nucleases to ensure robust immunity" (2019) eLife 8:e45393.
Cooper et al., "RNA and disease," Cell, 136.4 (2009): 777-793.
Databse EMBL Online—Speth D.R. et al. "Candidatus Scalindua brodae CHAT domain protein," retrieved from UNIPARC accession No. UPI0005442945, database Accession No. KHE91663, dated Dec. 14, 2014.
Datlinger et al., "Pooled CRISPR screening with single-cell transcriptome read-out," Nat. Methods., Mar. 2017; 14(3):297-3.
Dong et al., "The crystal structure of Cpf1 in complex with CRISPR RNA," Nature 532(7600): 522-6 (Apr. 2016).
Eckstein et al "Phosphorothioates, essential components of therapeutic oligonucleotides," Nucl. Acid Ther., 24 (2014), pp. 374-387.
Epstein et al "Engineering a Self-Inactivating CRISPR System for AAV Vectors," Mol. Ther., 24 (2016): S50.
Estrella et al., "RNA-activated DNA cleavage by the Type III-B CRISPR-Cas effector complex" (2019) Genes & Dev 30:460-470.
Garrett et al., "CRISPR-based immune systems of the Sulfolobales: complexity and diversity," Biochem Soc Trans (2011) vol. 39, pp. 51-57.
Gaudelli et al., "Programmable base editing of A.T to G.C in genomic DNA without DNA cleavage," Nature 551 (7681): 464-71 (Oct. 2017).
Gerdes et al. "Experimental determination and system level analysis of essential genes in *Escherichia coli* MG1655" (2003) J. Bacteriol. 185(19): 5673-84.
Goldfless et al. "Direct and specific chemical control of eukaryotic translation with a synthetic RNA-protein interaction," Nucl. Acids Res., 40.9 (2012): e64-e64.
Gootenberg et al. "Nucleic acid detection with CRISPR-Cas13a/C2c2," Science, Apr. 28, 2017; 356(6336):438-442.
Hallbrink et al., "Prediction of cell-penetrating peptides," Methods Mol. Biol., 2015; 1324:39-58.
Hammond et al., "A CRISPR-Cas9 gene drive system targeting female reproduction in the malaria mosquito vector *Anopheles gambiae*," Nat. Biotechnol., Jan. 2016; 34(1):78-83.
Hirosawa et al. "Cell-type-specific genome editing with a microRNA-responsive CRISPR-Cas9 switch," Nucl. Acids Res., Jul. 27, 2017; 45(13): e118.
Hlavova et al., "Improving microalgae for biotechnology—from genetics to synthetic biology," Biotechnol. Adv., Nov. 1, 2015; 33:1194-203.
International Search Report and Written Opinion for International Application No. PCT/US2019/022376 dated Jun. 17, 2019.
International Search Report for International Application No. PCT/US2019/022375, mailed Jun. 13, 2019 (6 pages).
International Search Report for PCT/US2019/032750, mailed Sep. 25, 2019.
Kelley et al., "Versatility of chemically synthesized guide RNAs for CRISPR-Cas9 genome editing," J. Biotechnol. Sep. 10, 2016; 233:74-83.
Kim et al., "Efficient Transcriptional Gene Repression by Type V-A CRISPR-Cpf1 from Eubacterium eligens," ACS Synthetic Biology 6(7): 1273-82 (Apr. 2017).
Konermann et al. "Optical control of mammalian endogenous transcription and epigenetic states," Nature, 500.7463 (2013): 472.
Koonin et al., "Diversity, classification and evolution of CRISPR-Cas systems," Current Opinion in Microbiology 37: 67-78 (Jun. 2017).
Liu et al., "C2c1-sgRNA Complex Structure Reveals RNA-Guided DNA Cleavage Mechanism," Mol Cell. 65(2):310-22 (Dec. 2016).
Makarova et al., "An updated evolutionary classification of CRISPR-Cas systems," Nat. Rev. Microbiol. 13(11):722-36 (Sep. 2015).
Makarova et al., "Annotation and Classification of CRISPR-Cas Systems," Methods Mol Biol (2015) vol. 1311, pp. 47-75.
Makarova et al., "Classification and Nomenclature of CRISPR-Cas Systems: Where from Here?" CRISPR J. 1(5):325-36 (Oct. 2018).
Makarova et al., "Unification of Cas protein families and a simple scenario for the origin and evolution of CRISPR-Cas systems," Biology Direct (2011) vol. 6, Article 38, 27 pages.
Murugan et al., "The Revolution Continues: Newly Discovered Systems Expand the CRISPR-Cas Toolkit," Molecular Cell 68(1): 15-25 (Oct. 2017).
Nicolaou et al., "Molecular diagnosis of peanut and legume allergy," Curr. Opin. Allergy Clin. Immunol., Jun. 2011; 11(3):222-8.
Nowak et al., "Guide RNA engineering for versatile Cas9 functionality," Nucl. Acid. Res., Nov. 16, 2016; 44(20):9555-9564.
O'Connell et al. "Programmable RNA recognition and cleavage by CRISPR/Cas9" Nature (2014) vol. 516, No. 7530, pp. 263-266.
Osborne et al., "Transcriptional and post-transcriptional impact of toxic RNA in myotonic dystrophy," Hum. Mol. Genet., Apr. 15, 2009; 18(8):1471-81.
Pausch et al., "CRISPR-Cas-Phi from huge phages is a hypercompact genome editor," Science (2020) vol. 369, pp. 333-337.
Ramakrishna et al., "Gene disruption by cell-penetrating peptide-mediated delivery of Cas9 protein and guide RNA," Genome Res., Jun. 2014;24(6):1020-7.
Ran et al., "Double nicking by RNA-guided CRISPR Cas9 for enhanced genome editing specificity," Cell 154(6):1380-9 (Aug. 2013).
Sequence Alignment of SEQ ID No. 5 with BGX25975, Search conducted on Jun. 5, 2020, 4 pages. (Year: 2020).
Sequence Alignment of SEQ ID No. 5 with BGX25978, Search conducted on Jun. 11, 2020, 7 pages. (Year: 2020).
Sequence Alignment of SEQ ID No. 5 with BGX25997, Search conducted on Jun. 11, 2020, 7 pages. (Year: 2020).
Shmakov et al., "Discovery and Functional Characterization of Diverse Class 2 CRISPR-Cas Systems," Molecular Cell 60(3): 385-97 (Oct. 2015).
Smargon et al. "Cas13b Is a Type VI-B CRISPR-Associated RNA-Guided RNase Differentially Regulated by Accessory Proteins Csx27 and Csx28" Molecular Cell (2017) vol. 65, No. 4, pp. 618-630.
Stella et al., "Class 2 CRISPR-Cas RNA-guided endonucleases: Swiss Army knives of genome editing," Nature Structural & Molecular Biology 24(11): 882-92 (Oct. 2017).
Strutt et al. "RNA-dependent RNA targeting by CRISPR-Cas9" eLIFE (2018) vol. 7, e 32724, pp. 1-17.

(56) References Cited

OTHER PUBLICATIONS

Tamulaitis et al., “Type III CRISPR-Cas Immunity: Major Differences Brushed Aside,” Trends Microbiol (2017) vol. 25, No. 1, pp. 49-61.
Verwaal et al., “CRISPR/Cpf1 enables fast and simple genome editing of *Saccharomyces cerevisiae*,” Yeast, Sep. 8, 2017. doi: 10.1002/yea.3278.
Wright et al. “Rational design of a split-Cas9 enzyme complex,” Proc. Nat’l. Acad. Sci., 112.10 (2015): 2984-2989.
Written Opinion of the International Searching Authority for International Application No. PCT/US2019/022375 (7 pages).
Wu et al., “Structural basis of stringent PAM recognition by CRISPR-C2c1 in complex with sgRNA,” Cell Res. 27(5):705-8 (Apr. 2017).
Yamano et al., “Crystal Structure of Cpf1 in Complex with Guide RNA and Target DNA,” Cell 165(4):949-62 (Apr. 2016).
Yan et al., “Cas13d Is a Compact RNA-Targeting Type VI CRISPR Effector Positively Modulated by a WYL-Domain-Containing Accessory Protein,” Mol. Cell 70(2)327-39.e5 (Mar. 2018).
Yan et al., “Functionally diverse type V CRISPR-Cas systems,” Science 363(6422):88-91 (Dec. 2018).
Yang et al., “PAM-Dependent Target DNA Recognition and Cleavage by C2c1 CRISPR-Cas Endonuclease,” Cell 167(7):1814-28 (Dec. 2016).
Zetsche et al, “A split-Cas9 architecture for inducible genome editing and transcription modulation,” Nature Biotech., 33.2 (2015): 139-142.
Zetsche et al., “Cpf1 is a single RNA-guided endonuclease of a class 2 CRISPR-Cas system,” Cell 163(3), 759-71 (Sep. 2015).
[No Author Listed] GenBank: KHE91659.1 MAG: RAMP superfamily protein [Candidatus Scalindua brodae] Protein NCBI, Submitted Oct. 15, 2014, 2 pages.
GenBank OGR07204. “MAG: hypothetical protein A2511_ 12455 [Deltaproteobacteria bacterium RIFOXYD12_FULL_50_9],” Deposited Oct. 20, 2016. 2 pages.
Makarova et al., “Evolutionary classification of CRISPR-Cas systems: a burst of class 2 and derived variants,” Nat Rev Microbiol (2020) vol. 18, No. 2, pp. 67-83.
Speth et al., “Draft Genome Sequence of Anammox Bacterium “Candidatus Scalindua brodae,” Obtained Using Differential Coverage Binning of Sequencing Data from Two Reactor Enrichments,” Genome Announcements (2015) vol. 3, Issue 1, Article e01415-14, 2 pages.

* cited by examiner

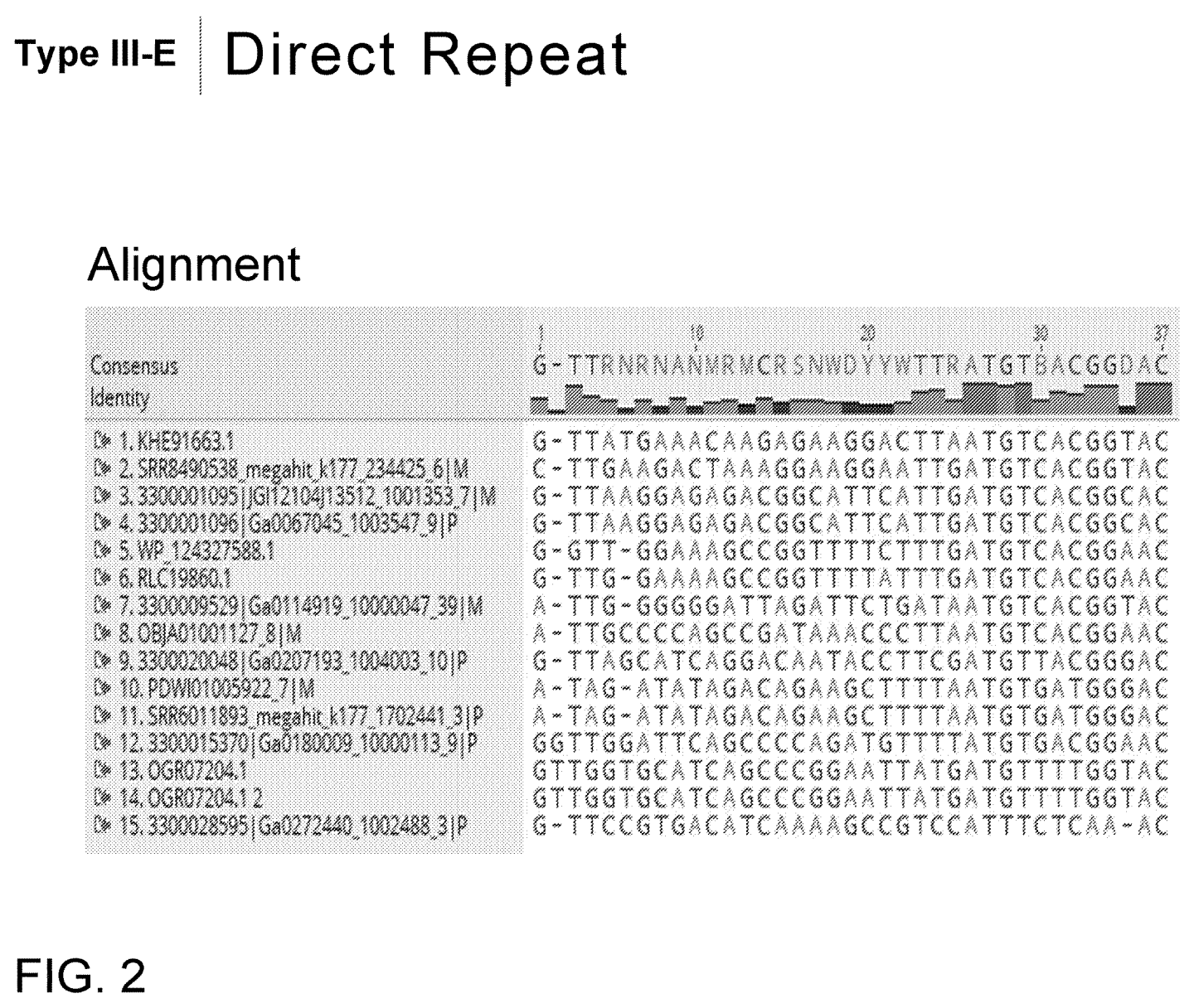

Type III-E | Direct Repeat

Alignment

| | 1 … 10 … 20 … 30 … 37 |
|---|---|
| Consensus | G-TTRNRNANMRMCRSNWDYYWTTRATGTBACGGDAC |
| Identity | |
| 1. KHE91663.1 | G-TTATGAAACAAGAGAAGGACTTAATGTCACGGTAC |
| 2. SRR8490538_megahit_k177_234425_6\|M | C-TTGAAGACTAAAGGAAGGAATTGATGTCACGGTAC |
| 3. 3300001095\|JGI12104J13512_1001353_7\|M | G-TTAAGGAGAGACGGCATTCATTGATGTCACGGCAC |
| 4. 3300001096\|Ga0067045_1003547_9\|P | G-TTAAGGAGAGACGGCATTCATTGATGTCACGGCAC |
| 5. WP_124327588.1 | G-GTT-GGAAAGCCGGTTTTCTTTGATGTCACGGAAC |
| 6. RLC19860.1 | G-TTG-GAAAAGCCGGTTTTATTTGATGTCACGGAAC |
| 7. 3300009529\|Ga0114919_10000047_39\|M | A-TTG-GGGGGATTAGATTCTGATAATGTCACGGTAC |
| 8. OBJA01001127_8\|M | A-TTGCCCCAGCCGATAAACCCTTAATGTCACGGAAC |
| 9. 3300020048\|Ga0207193_1004003_10\|P | G-TTAGCATCAGGACAATACCTTCGATGTTACGGGAC |
| 10. PDWI01005922_7\|M | A-TAG-ATATAGACAGAAGCTTTTAATGTGATGGGAC |
| 11. SRR6011893_megahit_k177_1702441_3\|P | A-TAG-ATATAGACAGAAGCTTTTAATGTGATGGGAC |
| 12. 3300015370\|Ga0180009_10000113_9\|P | GGTTGGATTCAGCCCCAGATGTTTTATGTGACGGAAC |
| 13. OGR07204.1 | GTTGGTGCATCAGCCCGGAATTATGATGTTTTGGTAC |
| 14. OGR07204.1 2 | GTTGGTGCATCAGCCCGGAATTATGATGTTTTGGTAC |
| 15. 3300028595\|Ga0272440_1002488_3\|P | G-TTCCGTGACATCAAAAGCCGTCCATTTCTCAA-AC |

FIG. 2

Type III-E | Effector B

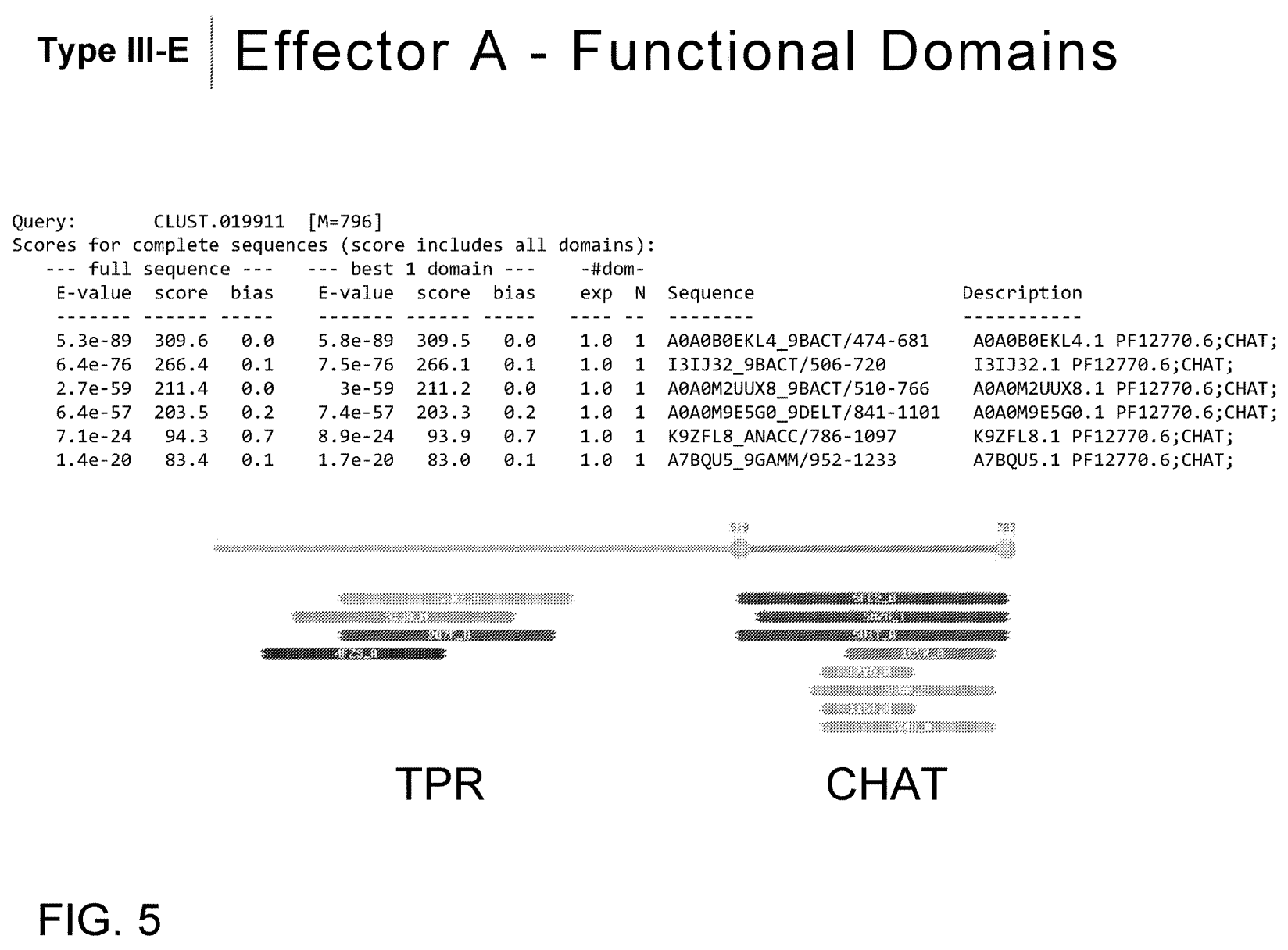

Type III-E | Effector A - Functional Domains

```
Query:       CLUST.019911  [M=796]
Scores for complete sequences (score includes all domains):
   --- full sequence ---   --- best 1 domain ---    -#dom-
    E-value  score  bias    E-value  score  bias    exp  N  Sequence                    Description
    ------- ------ -----    ------- ------ -----   ---- --  --------                    -----------
    5.3e-89  309.6   0.0    5.8e-89  309.5   0.0    1.0  1  A0A0B0EKL4_9BACT/474-681     A0A0B0EKL4.1 PF12770.6;CHAT;
    6.4e-76  266.4   0.1    7.5e-76  266.1   0.1    1.0  1  I3IJ32_9BACT/506-720         I3IJ32.1 PF12770.6;CHAT;
    2.7e-59  211.4   0.0      3e-59  211.2   0.0    1.0  1  A0A0M2UUX8_9BACT/510-766     A0A0M2UUX8.1 PF12770.6;CHAT;
    6.4e-57  203.5   0.2    7.4e-57  203.3   0.2    1.0  1  A0A0M9E5G0_9DELT/841-1101    A0A0M9E5G0.1 PF12770.6;CHAT;
    7.1e-24   94.3   0.7    8.9e-24   93.9   0.7    1.0  1  K9ZFL8_ANACC/786-1097        K9ZFL8.1 PF12770.6;CHAT;
    1.4e-20   83.4   0.1    1.7e-20   83.0   0.1    1.0  1  A7BQU5_9GAMM/952-1233        A7BQU5.1 PF12770.6;CHAT;
```

FIG. 5

SEQUENCE LISTING

```
Sequence total quantity: 328
SEQ ID NO: 1           moltype = AA  length = 716
FEATURE                Location/Qualifiers
source                 1..716
                       mol_type = protein
                       organism = unidentified
                       note = Candidatus Scalindua brodae
SEQUENCE: 1
MNNTEENIDR IQEPTREDID RKEAERLLDE AFNPRTKPVD RKKIINSALK ILIGLYKEKK  60
DDLTSASFIS IARAYYLVSI TILPKGTTIP EKKKEALRKG IEFIDRAINK FNGSILDSQR  120
AFRIKSVLSI EFNRIDREKC DNIKLKNLLN EAVDKGCTDF DTYEWDIQIA IRLCELGVDM  180
EGHFDNLIKS NKANDLQKAK AYYFIKKDDH KAKEHMDKCT ASLKYTPCSH RLWDETVGFI  240
ERLKGDSSTL WRDFAIKTYR SCRVQEKETG TLRLRWYWSR HRVLYDMAFL AVKEQADDEE  300
PDVNVKQAKI KKLAEISDSL KSRFSLRLSD MEKMPKSDDE SNHEFKKFLD KCVTAYQDGY  360
VINRSEDKEG QGENKSTTSK QPEPRPQAKL LELTQVPEGW VVVHFYLNKL EGMGNAIVFD  420
KCANSWQYKE FQYKELFEVF LTWQANYNLY KENAAEHLVT LCKKIGETMP FLFCDNFIPN  480
GKDVLFVPHD FLHRLPLHGS IENKTNGKLF LENHSCCYLP AWSFASEKEA STSDEYVLLK  540
NFDQGHFETL QNNQIWGTQS VKDGASSDDL ENIRNNPRLL TILCHGEANM SNPFRSMLKL  600
ANGGITYLEI LNSVKGLKGS QVILGACETD LVPPLSDVMD EHYSVATALL LIGAAGVVGT  660
MWKVRSNKTK SLIEWKLENI EYKLNEWQKE TGGAAYKDHP PTFYRSIAFR SIGFPL      716

SEQ ID NO: 2           moltype = AA  length = 849
FEATURE                Location/Qualifiers
source                 1..849
                       mol_type = protein
                       organism = unidentified
                       note = Deltaproteobacteria bacterium
SEQUENCE: 2
MNQNIDRAVG AILAIETATP LTESSTLAQR ERHQKLLHDE TKKIEQAFIA LAQPPQCRAV  60
EIAALSRFLQ MTPLAVGPLR KRVICRAEPL KDDAHEQEIA SHFNGLLLRL AKGLLASALN  120
PAGIPWRRRV LWLEKAAHIA HRFDKEPLAD DKERTEAAGV LARCCLHLAL AHLPKGKDKS  180
AMAERQEDLL QSLMWAQKAI VLAGQDKLSG EEYKLLKALV LIELDNLSPG RFQQQLNYVL  240
```

-continued

```
YDLAVIWLER DTATKPFHPQ ELFVLWRYLA TDFEPDLNML LFKGSNTSER TAAVQQASPE  300
AERFRPLLPL IHAWSAWKLD PPNNKIAEVI LQAVNNLDEH QVYEQVWKWT VDFLQELRNT  360
GAVDWQLPAI AAWELCNKKE KELPFGFQIR QYWSRLDSLY RLAFDGALEL KDCMTAARIV  420
DSLKSRTPLT WRDMDTLFAK LPKEKADQLR EAFYSMEVQA RMGFYAEAKE DANKLKKLLA  480
AQVRKIRDIE SVPAGWTVVH FHLREDQDLG YALACRLTAD GMSYWTNHIF PVAGIRRAYD  540
CWLEAYHGME PGAREKSGYQ LVELSEIMGK DLDFLFELAG EDGARGLLFV PHGFSHLLPL  600
HAAKKDGSYL FEKIPSLTLP AWEFAPDVDQ IPVSDGQDFC FISQRANEQD LVGNIERSHT  660
WNGVCNKNAA WTNVLNTNKE WSKAPPRWLV FWCHGQADPH VAFRSKLLLG TLGVSLFEIQ  720
EAALSLTGTK VVLAVCESDL APPEEYEKTD DHLSLAAPFL LKGARQVLAA IWEGAQLDLL  780
KAMKEMLSNQ DKHSWEILRE LQSCWMRQPG AIFNDEYIRL YYAASFRILG FPEVATTNMA  840
TATAQEEIA                                                         849

SEQ ID NO: 3           moltype = AA  length = 751
FEATURE                Location/Qualifiers
source                 1..751
                       mol_type = protein
                       organism = Desulfonema ishimotonii
SEQUENCE: 3
MSNPIRDIQD RLKTAKFDNK DDMMNLASSL YKYEKQLMDS SEATLCQQGL SNRPNSFSQL  60
SQFRDSDIQS KAGGQTGKFW QNEYEACKNF QTHKERRETL EQIIRFLQNG AEEKDADDLL  120
LKTLARAYFH RGLLYRPKGF SVPARKVEAM KKAIAYCEII LDKNEEESEA LRIWLYAAME  180
LRRCGEEYPE NFAEKLFYLA NDGFISELYD IRLFLEYTER EEDNNFLDMI LQENQDRERL  240
FELCLYKARA CFHLNQLNDV RIYGESAIDN APGAFADPFW DELVEFIRML RNKKSELWKE  300
IAIKAWDKCR EKEMKVGNNI YLSWYWARQR ELYDLAFMAQ DGIEKKTRIA DSLKSRTTLR  360
IQELNELRKD AHRKQNRRLE DKLDRIIEQE NEARDGAYLR RNPPCFTGGK REEIPFARLP  420
QNWIAVHFYL NELESHEGGK GGHALIYDPQ KAEKDQWQDK SFDYKELHRK FLEWQENYIL  480
NEEGSADFLV TLCREIEKAM PFLFKSEVIP EDRPVLWIPH GFLHRLPLHA AMKSGNNSNI  540
EIFWERHASR YLPAWHLFDP APYSREESST LLKNFEEYDF QNLENGEIEV YAPSSPKKVK  600
EAIRENPAIL LLLCHGEADM TNPFRSCLKL KNKDMTIFDL LTVEDVRLSG SRILLGACES  660
DMVPPLEFSV DEHLSVSGAF LSHKAGEIVA GLWTVDSEKV DECYSYLVEE KDFLRNLQEW  720
QMAETENFRS ENDSSLFYKI APFRIIGFPA E                                751

SEQ ID NO: 4           moltype = AA  length = 816
FEATURE                Location/Qualifiers
REGION                 1..816
                       note = Description of Unknown: Soil metagenome sequence
source                 1..816
                       mol_type = protein
                       organism = unidentified
SEQUENCE: 4
MEHKTMTEPA GQNPSATDND FEKFIIDTGC VFFATPQEDP KYQNNKVEWH QGLCRFAQND  60
SPPTVIGSAI FFLQKLQEPG LFSGLPVSPE LCSKISKDKN EIVAYHQQCI LRLCEELLVK  120
GREAKEHRER RQAFDQAIKF LLVLKKGTSS DTPSPNGHIH FQDQVSILLA EAYYLRGKII  180
RPKGFSVPAK KIETLEVAEK ILVDLVARDT TGKARRLRAM VHIDLAALRD PADDSGNLQD  240
YRQALEQAVS SIGDTKTCGR DEIVIILARA EDNAGWTGSD GLSARLEELV NNGAAGPLDQ  300
ARAYLLLGQN NLAVTQTEKA ITRMAATDNP TPFSHEDWRL LVRLLRDLKH QNTAGIDKLI  360
LDTWRKVHQI ERQTKNGMHV RWYWSRQRDL YDLAFHAAGN DARLKAQIAD SLKARPALHL  420
GQAADLGLAV EQMEAGLLDR YMPGKMLEQT TDMAAPAAPG SAGWPELPRP WIAVHFYLSN  480
GFGHPEGKQQ GHALIQDSSK GDGKDTWSER TFDYFPIWAA FMTWQENYQR LKKEAAPDLE  540
RLCQVMGRQM PFLFAPEDLP LERPVVFVPH DFLHRLPLHA ALIDNGEESG IPAQSHPITY  600
LPGWWMVTSQ AANPNETASK NTPSPVAPVA LVHWDNSEDI HDIIKQANGT VVVNASRSDW  660
LKLKHNAVGL KVLYCHGQAG YTNPFASSLK LDGGGLYLKD VVKGPPLVGR FILAACESDL  720
VLPASTTLDE YFSFSTGLLQ KGAAEILGTL WEVNETDALS LIETVLRAPA SGNLSFVLRD  780
WLRDNLRSLT TELFYDIAAF RALGGPYPVD TKEEHR                           816

SEQ ID NO: 5           moltype = AA  length = 769
FEATURE                Location/Qualifiers
REGION                 1..769
                       note = Description of Unknown: Dolphin oral metagenome
                        sequence
source                 1..769
                       mol_type = protein
                       organism = unidentified
SEQUENCE: 5
MNTVELLQEE ERLTLDLVFL PPGSKNKEQK KNALVDLLLK IVEHGELTRK YSALLTLSRG  60
ALRGEVHFGE KLLPSPEACA NLAKPEEIKK MIRQHFQYRL DLLEAIVKKA ADNTYSHARR  120
RKALRIAIKE LEQICEEALD ELCFKARLLL AEALFERGRI VRPKGFSEPG KKKELFQKAI  180
NCIEGNCSEE ALRLRARIYL QWYRFFHDEP PCDLDDIFTK ALAVTDDKML KTELLLLCGE  240
RKEPDPYTDD LRALLNDQNV SPLSRARAAV LLEDWERCNV EIYEAIEDLG KTDFFQQDWE  300
LVVTLLKKNY NQFHGWSRAC TRLWEITVEK ESKDAGHGCV LRWYWSRQRD VYNLAFAAFE  360
ECEDKARVVD SLKNRPAHHF SQLEQLAQSS DIIKQWIESE EIINQDSFAH SLRRHEKGAK  420
SHSGGSLRIF PCLPKGWIAV HFFLASWPEP KGYALIHNAD TNTWEQRDFK YEQLWATYIA  480
WQEVSLHNKI RESALLLKSL CETLGKEMRW LFDEFLFPKE RRRVLFVPHD FLHRLPLHMA  540
IDIESQTVFA AKQPVCYLPA YHLQNNITEN KKTSIYALVN LRENKQQKKD EEIFAEKVEK  600
MGAIVRRPAL ESDLLNLNPV PEKLVLYCHG IGHSANPFAS KLCLGDTGVS YRDILALNRS  660
LAGCRVLLFA CETDLVPAQT SSIDEHLSIS NALLQKGAFE VLGSLWALPG KTIYGITKTF  720
IDNDDTSAVL HSSLKRLFEH YEKKNEKTRA QLLYNWASLR VLAPAREFS              769

SEQ ID NO: 6           moltype = AA  length = 778
```

```
FEATURE                Location/Qualifiers
REGION                 1..778
                       note = Description of Unknown: Aquatic-marine-hydrothermal
                        vent microbial mat sequence
source                 1..778
                       mol_type = protein
                       organism = unidentified
SEQUENCE: 6
MRYSSRTNCE AIDNLAEALQ DQENMPEIAR RVLEFEAENA KPENALCQHG LPHTKKAASQ  60
IAGVRDKHSE FYDNALLDLV EEWLKTYEEA KKLTHRERRQ EMEDKIRVLQ PVLQAKGKDA  120
DPRFLSLLAR IYLYRGMLFR PKGFTTPARK IEALKKAVQL SEKAVEKEKD NPNFLRTWAQ  180
AALELEAIPE TSFKVSSGLL KDAAVCINRD GIHSLNDLQV ILEYAESEGK TSFLQHVLVE  240
KRYWKRPFDL FLLKARAAFA LNRMDDVRYF LKSAMDKTPK ALSSPFWDHL VDFLKKLRTK  300
EGSDLWKEMA VAAHRLCREK EVKIANNIYL YRHWARQKSL YNMAFLAQND LKEKAKIADS  360
LKSRPVLRYQ ALREMKEHQN IAKLLEQDDQ ERDGGYHKQQ VEMDERTGKR LSEKMEKAGV  420
SYENLPVPWI SVHFYLNESE NSEDEGSKGY ALIFDALTQS WKERRFDYAK LHRKFMTWQE  480
AYISAKKSSF AKDSLVELCR EIGNTMPFLF DTACIRDGAP VLWIPHGFLH RLPLHAAIRD  540
EATNEIFLEN HASRYLPAWS ILNSASARRG KDSYMIKRFR AEDYEKEPFS ELEDMEWDNE  600
EHEKLATPDD LKHFMAKNPG VFAVLCHGHG DILNPLKSWL ELEGGGVSVL DILRYEKANL  660
SGTRVLLGAC EADMAPPVEY AIDEHVSLSA AFLSHKAQEV IAGLWEINIG EADECYAEIL  720
DCSDLSTELK DWQCDWVEKW RDDVEASGDN STFYHITPFR IMGFPLKLKE NNESEAKQ    778

SEQ ID NO: 7           moltype = AA  length = 860
FEATURE                Location/Qualifiers
REGION                 1..860
                       note = Description of Unknown: Aquatic-marine-deep
                        subsurface sequence
source                 1..860
                       mol_type = protein
                       organism = unidentified
SEQUENCE: 7
MVTPQASKNP AVDEILKQLT PYDMETENAK AIETRKSCIE CLKGICERAQ KQNDWVAFGT  60
ALHFLHELSG TTAPVFYGAV KGQSACGQLH NMQASIKEAV ARITKSRAEH LRDKALKPYG  120
IPYLSRHRFL EKAIRMVWEL LQSDNGWPDS VWLHREASQF IARCFLDRGR LVLPKGSSIP  180
QKKIEALKKA WHWALKGALK AKEDDADSMK LWLEFREYIL QTAKENDADI DSMKLLIEIG  240
LELELYEKSF SPQVNELTRK IASGKLLEDP KSSADWPIID RGRSIGCFDE KQDEALFKLD  300
LNKKEYKELP TLPLLRAKAG HRLKRDLASA FDEASFFRVV CDAVRKLADV PFSSPIWVET  360
IEFLAQLDPG SEIRNAASVA AWQICKLKEE DLDLGLQVRM WWSRHKMLYD LAFHAALSKD  420
DWALAARIAD SPKSRPTIKA LAMESVLDGD TLKGYYELEA RGVARGYDST YHRKKKSLEK  480
AEAKKKRASK DTQGLRPLDF EEDIPAGWAA IHLYLDQDKK GHALMRSAGS TKDGWLYKDF  540
EISDIWQKFQ AWQAADRYNP KFGGAATELH ALCESLGYDD DHLGFLFNKD LPDNLIIIPH  600
DILHLVPIHS VMKNGEILLK QKKCIYLPAW GLPRETDSAS TPEGEGLFDN FEDHDPLRQY  660
LQPVLQAWKH SSVSARNIKV PDATANDVRN YLKNTTNPEW MVFLCHGKAD PVNPYNSGLL  720
LRGSHLTHAA LVELPKKMAG TKVFLGACET DMSPPKQKSV DEHLSVSTAF FQKGASEIAG  780
GLWRVHSAIA KKMVEHISEN RKKPLVDVVW EKQKDWWDNG IQYVVDGITV KVSNCFKKLY  840
YLSSYRVVGF PRAIGENTDE                                              860

SEQ ID NO: 8           moltype = AA  length = 757
FEATURE                Location/Qualifiers
REGION                 1..757
                       note = Description of Unknown:
                        Aquatic-freshwater-groundwater sequence
source                 1..757
                       mol_type = protein
                       organism = unidentified
SEQUENCE: 8
MYSDFPALRL PELSVDQKKL FKISGTNPQL IYILMNEFDG EGDEPFFTGL VPDETDLSEN  60
KQAPLLKELA RHLLKEYEDI GRNRWKHADQ RRVLEKAIRL LDKSHQAEEN VSLELGKAYL  120
YRARIIRPKG FTVPAKKIEA LNNALHFCED ATNHGKAWAD HFAGLVALEL YRCGKTHDNL  180
SELLNKATAD AELSEPDRRV EFYQMRVRLE ELRQDEGNGS PYFIQNVLTK IFEFQEPGME  240
LEKLKVSLQS PSSSKDKISS SLEDLILVLK EYPFSHPLWE DTVRFARRLY FNRLEFWKEL  300
ALRLWEAAED ESRKISSVHL RWYWSRQRDL YDLSFLAALK QGNPNLAAQV TDSAKSRPAL  360
SWQAIERLKH GNEELKDEIE NYAQALSGGY IKGLLKPYRK PEVPNEEKPF FEQHLIDNNL  420
IAIQFYLVHL EEFEKVERSR ERGYALIYDQ ESEKKWSFKT FDFAPIWEKY VAWQSVYFDL  480
PPQQRDASGT QLRYLCEALG KALEFLFKSP EKQFSSNEKS KDILFIPHDF LHRVPLHGAM  540
LDNENVLLKT FNCFYLPAIS YSAKNQGPQQ NKNSVLLYYS GKSEESDDPL FNHLKTKFDT  600
PINFASATDL LDAAQNPPSL LVLYCHGEAD ATNPYLSRLK LKDDLMLLDF ASAAGTFTGS  660
KIFLGACETD LMPPLDAPLD EQISMATIFL IKRSESVIGS MWEAKRMKVL NLLFMKEGLF  720
DHFFEQQREW WKEEYEHTDS NTALYDCLCF RMYRCYF                           757

SEQ ID NO: 9           moltype = AA  length = 822
FEATURE                Location/Qualifiers
REGION                 1..822
                       note = Description of Unknown:
                        Bioremediation-terephthalate-wastewater bioreactor sequence
source                 1..822
                       mol_type = protein
                       organism = unidentified
SEQUENCE: 9
```

```
MFGGVEKNCL ALSLGRHEKR QIYKSILAAG GLLLAQPADE TFLPMITKYY REILAAEVKL  60
AFCLPDEAHN VVYKRDEACR ELVQACRNQA GGLTEQGYQY LGSALLFLSG GLGEAPGLVA  120
LPVLSQELCE ALASREADIH AFHARQGLEV AAAIIERARE PQWQHAQRRQ ALEAVIKDLQ  180
QRSAICPPDL QDRLRLLLAQ AYLERSRIIR PKGFTISPKK KEALDKALEQ LDQVTDTGKT  240
TLDYHRFRGD IFLELGRLEA RTGKEIEACL AEAILFLDPR TPANLTPVDC RLIVAYARLA  300
RDPSYLPLVL GSSKATALDR AWAAYLSNNA SGAAKEINTV LQDLQRRWFS HPDWEGLVDL  360
LVDWARSSQK GWEDLATAAW QVCQKNEQEL RYSGCQLRWY WSRHQDLYDL AFQAAPTLEE  420
KARVADSLKS RPLVRLALAE QLAQAQAKKK RGADVDFAQL IEQDARAYAN QYIAGGLAAG  480
SASAPVAPLS FTELPDEQWL AVHFYLSSGA AAGLKKNMAY ALVYDAKDQK WSCEGPYETT  540
DLWQAYRRWQ DNYAAVSQAS APELESLCRQ IGTTFPFLWA LPSERPVVFI PHGFLHRLPL  600
HMALREDGAT LEVWAATHPS TYLPAWSLRP RADAGGSQNV AAVYLPDELH DAEDFQNILA  660
GQSFAAAASW PVFRKQAGQA RRLALVCHGL AHAVNPFAAR LLLPEEPQLV DFLTDLPALP  720
GSQVFLAACE ADMAPAQEAP LDEHLSLATA FLQKGAREVL GGVFEVNKYL ANELLSSFGA  780
TSAAACYSLL WKWQQARLDN FLDNPDPLNL YWLAPWRVLG LS                    822

SEQ ID NO: 10          moltype = AA  length = 797
FEATURE                Location/Qualifiers
REGION                 1..797
                       note = Description of Unknown:
                        Aquatic-freshwater-freshwater lake sediment sequence
source                 1..797
                       mol_type = protein
                       organism = unidentified
SEQUENCE: 10
MTETNHLSSD YQKAITLETK LAFLRPTQEQ DTIESTRREL AETLSRLVNQ KISPETLSAI  60
TTLHGMDLQG LGVLSGSLPN KDRCAFAGNK KKFSAAWEFH WLQRIDLMRK IIDKASGQDD  120
KLSHASRRQA LGVAINSLEK AIAEIGDTGI LVSKARLDLA RALFHRGRIV RPKGFSVPGK  180
KKELFLKALD QIRIATNNKD DDQTLFLKAE IYLEWLRFFP MELPEDLDVV FKAAQQKADE  240
PLKTNLILMI GERGSAKPIE LEALQNIEVD EKQEPLTRAR AAAISGNWDI CAKYLSEAIK  300
KLEIKSFFHQ DWEEAVELLK KGRTKISNYQ WATICKSLWK LTVQKENRTS NGCHLRWYWS  360
RQREVYDLAF EAAGNDYSKK AKITDSLKGR PALHFAQMET IAEGEDEIKT WIEHQEAGFL  420
NQYISAFESA DQGKKPGNLS WPKLPKGWIA VHFYLGLGTC SGEKKGYALI QNGQDWYQRT  480
FDYEVLWVAY LAWQTMYGKC GHLDDILKQQ EVLSPVVESL CEQIGKEMPW LFDPGLFPEG  540
QAVVFIPHDF LHRLPLHMAL DPKPDPGKAQ LFLSLHLVLS LPAWWQASET NSPPAPDTVK  600
ANEKIFLANF ENPSDAFQSL IDAIPKSVKV ERVAKKSNLL EANSPSLLVV YCNGEAQPGN  660
PFASRLLFSD SGLPVSGILG STINLRRSNI ILGACETDLM LALNKTLDEH ITLSSAFIQK  720
GAELVSGTLW KIHENDEIDF IKLALVENSS LHEQWLKWYD TNIKAYENDP KNNPRVFYKA  780
AAIRIVGKPW TIEDIGK                                                797

SEQ ID NO: 11          moltype = AA  length = 789
FEATURE                Location/Qualifiers
REGION                 1..789
                       note = Description of Unknown:
                        Bioremediation-terephthalate-wastewater bioreactor sequence
source                 1..789
                       mol_type = protein
                       organism = unidentified
SEQUENCE: 11
MAQPADETFL PMITKYYREI LAAEVKLAFC LPDEAHNVVY KRDEACRELV QACRNQAGGL  60
TEQGYQYLGS ALLFLSGGLG EAPGLVALPV LSQELCEALA SREADIHAFH ARQGLEVAAA  120
IIERAREPQW QHAQRRQALE AVIKDLQQRS AICPPDLQDR LRLLLAQAYL ERSRIIRPKG  180
FTISPKKKEA LDKALEQLDQ VTDTGKTTLD YHRFRGDIFL ELGRLEARTG KEIEACLAEA  240
ILFLDPRTPA NLTPVDCRLI VAYARLARDP SYLPLVLGSS KATALDRAWA AYLSNNASGA  300
AKEINTVLQD LQRRWFSHPD WEGLVDLLVD WARSSQKGWE DLATAAWQVC QKNEQELRYS  360
GCQLRWYWSR HQDLYDLAFQ AAPTLEEKAR VADSLKSRPL VRLALAEQLA QAQAKKKRGA  420
DVDFAQLIEQ DARAYANQYI AGGLAAGSAS APVAPLSFTE LPDEQWLAVH FYLSSGAAAG  480
LKKNMAYALV YDAKDQKWSC EGPYETTDLW QAYRRWQDNY AAVSQASAPE LESLCRQIGT  540
TFPFLWALPS ERPVVFIPHG FLHRLPLHMA LREDGATLEV WAATHPSTYL PAWSLRPRAD  600
AGGSQNVAAV YLPDELHDAE DFQNILAGQS FAAAASWPVF RKQAGQARRL ALVCHGLAHA  660
VNPFAARLLL PEEPQLVDFL TDLPALPGSQ VFLAACEADM APAQEAPLDE HLSLATAFLQ  720
KGAREVLGGV FEVNKYLANE LLSSFGATSA AACYSLLWKW QQARLDNFLD NPDPLNLYWL  780
APWRVLGLS                                                         789

SEQ ID NO: 12          moltype = AA  length = 809
FEATURE                Location/Qualifiers
REGION                 1..809
                       note = Description of Unknown: Aquatic-marine-marine
                        sediment sequence
source                 1..809
                       mol_type = protein
                       organism = unidentified
SEQUENCE: 12
MVSMQQSACN EIKNLENSID KDVSELAEAL SHFVQANLQP QTALCQRGIP DKNNAVLKIH  60
KAHNTDIVFS TLFNILEKRL VVYESEVYDE SKSSKKNMNH RQRRQMLEDI IQALIPLKKK  120
VSDSELKLEK LERKESDSVT KLKSDIAQFN YIYAKVYFYR SLLFRPKGRS IPARKIEAIQ  180
EAYSFIKKSL NLSETLSSWR LLGKITLELL SLNEPYLSDD IISSGLHIDE NFCLENNSFI  240
LRNDIQTLLT FSEITKDVSF VEKIPTFENI NIKKKDKDYL LLLIFARIAF LRNKINESDT  300
LLTKAISNAP EAFANPFWDD LVDFITCLKR NNCHVWKKAA IDAHKACYKN ETEIGNIYLR  360
WYWSRQSDLY DLAFISENKL EEKARIADSL KSRPILGFQA LNNMKKNIDI LEQILEQENE  420
```

```
ARDNKYLKKI HSKSRKIFKK EKFIDFKLLD NHWMVIHFYL NELEQCGYAL IFDCETKNTN  480
IQTFRYNELF NTFLSWQETE LHEQKQKENN EEIFNKDLIQ RGKSIHELCC EIGKTMPFIF  540
ELPENKSILW VPHGFIHRLP LHAAISIQTN AFLFEKHESR YLAAWHQLNL KNFGNGEGKH  600
FLRSGGSKFK TITKKCKTDK WEMVKRKANQ KHFFESLNKN LKTLVIICHG ECDITNSFQS  660
CLEISASSVG ESDSNGLINP LEKKSITILD LLKSENNIKG CRIFLGACES DMASPIEFIV  720
DEHLSLSAVL LSLGAKEVIG GLWKLYDIFV EDCYHQLLDS NNLSQSLNEW QLNMAKEWKE  780
DKTDMRYLKL YSFASFRVTG FLPQKKQEP                                   809

SEQ ID NO: 13          moltype = AA  length = 760
FEATURE                Location/Qualifiers
REGION                 1..760
                       note = Description of Unknown: Anammox bioreactor sequence
source                 1..760
                       mol_type = protein
                       organism = unidentified
SEQUENCE: 13
MKNRVQIEAI IRNLQGAARD SKTNKLSENI IAYDEYRKIH KSASLYQFGI IPAKESSSVL  60
AENETNHVAY ENAIFEMAEK NIENFSSEDI HKKRKEMIES ALRLLMGLYK DRHEKLQPRT  120
FVLIAKAYLL RSLITRPKGI TIPEKKKEAL KKGIGFVESA IKKIQSSENI LSHSSDIDLL  180
EKAWRIKSQL YLEYYRVNKD ECDKNTLKEV LENSLISGCD KFDKNIEDVQ IAIRYCELES  240
SREYLEQIIS SHLEGIEFEK ARAYKLLELE NENEDEIRKS MKVVIEEYLS GFSDPLWEDA  300
VEFINKLKSD NKNCWKELSL DMYKVCREQE AETASLHLRW YWSRQRRLYD LAFIAADKEE  360
EKAKIADSLK SRLSLRWSAL EETGKKSKNK REKEEISRIL EAEAVAMLGG YIKGARKILK  420
KRRRPLPDEQ RSIPKDWIVI HFYVNQLENK CYALIYNKDE NTWKCEFVKE YQRLFHVFLT  480
WQTNYNRCKE RAADSLVQLC KEIGNAMPFL FDECIIPQDK NVLFIPHDFL HRLPLHGAIH  540
EKNNGVFLEN HPCCYLPAWS FTAKENNAVV QGSILLKNFP EYSYEELVSN STLWTSPVKD  600
PASPDDLKTI IASPEMLVIL CHGEADAVNP FNARLKLTGN GISHLEILQS TKMILKGSKI  660
ILGACETDLV PPLSDIMDEH LSIATAFLTN GTHEILGTMW QSRPEDIEDI IRLLCDKKTS  720
DTKARGDLWN WQKERIRDYW AGEDAMFYRS VAFRIIGLTI                       760

SEQ ID NO: 14          moltype = AA  length = 1722
FEATURE                Location/Qualifiers
source                 1..1722
                       mol_type = protein
                       organism = unidentified
                       note = Candidatus Scalindua brodae
SEQUENCE: 14
MKSNDMNITV ELTFFEPYRL VEWFDWDARK KSHSAMRGQA FAQWTWKGKG RTAGKSFITG  60
TLVRSAVIKA VEELLSLNNG KWEGVPCCNG SFQTDESKGK KPSFLRKRHT LQWQANNKNI  120
CDKEEACPFC ILLGRFDNAG KVHERNKDYD IHFSNFDLDH KQEKNDLRLV DIASGRILNR  180
VDFDTGKAKD YFRTWEADYE TYGTYTGRIT LRNEHAKKLL LASLGFVDKL CGALCRIEVI  240
KKSESPLPSD TKEQSYTKDD TVEVLSEDHN DELRKQAEVI VEAFKQNDKL EKIRILADAI  300
RTLRLHGEGV IEKDELPDGK EERDKGHHLW DIKVQGTALR TKLKELWQSN KDIGWRKFTE  360
MLGSNLYLIY KKETGGVSTR FRILGDTEYY SKAHDSEGSD LFIPVTPPEG IETKEWIIVG  420
RLKAATPFYF GVQQPSDSIP GKEKKSEDSL VINEHTSFNI LLDKENRYRI PRSALRGALR  480
RDLRTAFGSG CNVSLGGQIL CNCKVCIEMR RITLKDSVSD FSEPPEIRYR IAKNPGTATV  540
EDGSLFDIEV GPEGLTFPFV LRYRGHKFPE QLSSVIRYWE ENDGKNGMAW LGGLDSTGKG  600
RFALKDIKIF EWDLNQKINE YIKERGMRGK EKELLEMGES SLPDGLIPYK FFEERECLFP  660
YKENLKPQWS EVQYTIEVGS PLLTADTISA LTEPGNRDAI AYKKRVYNDG NNAIEPEPRF  720
AVKSETHRGI FRTAVGRRTG DLGKEDHEDC TCDMCIIFGN EHESSKIRFE DLELINGNEF  780
EKLEKHIDHV AIDRFTGGAL DKAKFDTYPL AGSPKKPLKL KGRFWIKKGF SGDHKLLITT  840
ALSDIRDGLY PLGSKGGVGY GWVAGISIDD NVPDDFKEMI NKTEMPLPEE VEESNNGPIN  900
NDYVHPGHQS PKQDHKNKNI YYPHYFLDSG SKVYREKDII THEEFTEELL SGKINCKLET  960
LTPLIIPDTS DENGLKLQGN KPGHKNYKFF NINGELMIPG SELRGMLRTH FEALTKSCFA  1020
IFGEDSTLSW RMNADEKDYK IDSNSIRKME SQRNPKYRIP DELQKELRNS GNGLFNRLYT  1080
SERRFWSDVS NKFENSIDYK REILRCAGRP KNYKGGIIRQ RKDSLMAEEL KVHRLPLYDN  1140
FDIPDSAYKA NDHCRKSATC STSRGCRERF TCGIKVRDKN RVFLNAANNN RQYLNNIKKS  1200
NHDLYLQYLK GEKKIRFNSK VITGSERSPI DVIAELNERG RQTGFIKLSG LNNSNKSQGN  1260
TGTTFNSGWD RFELNILLDD LETRPSKSDY PRPRLLFTKD QYEYNITKRC ERVFEIDKGN  1320
KTGYPVDDQI KKNYEDILDS YDGIKDQEVA ERFDTFTRGS KLKVGDLVYF HIDGDNKIDS  1380
LIPVRISRKC ASKTLGGKLD KALHPCTGLS DGLCPGCHLF GTTDYKGRVK FGFAKYENGP  1440
EWLITRGNNP ERSLTLGVLE SPRPAFSIPD DESEIPGRKF YLHHNGWRII RQKQLEIRET  1500
VQPERNVTTE VMDKGNVFSF DVRFENLREW ELGLLLQSLD PGKNIAHKLG KGKPYGFGSV  1560
KIKIDSLHTF KINSNNDKIK RVPQSDIREY INKGYQKLIE WSGNNSIQKG NVLPQWHVIP  1620
HIDKLYKLLW VPFLNDSKLE PDVRYPVLNE ESKGYIEGSD YTYKKLGDKD NLPYKTRVKG  1680
LTTPWSPWNP FQVIAEHEEQ EVNVTGSRPS VTDKIERDGK MV                    1722

SEQ ID NO: 15          moltype = AA  length = 1403
FEATURE                Location/Qualifiers
VARIANT                1394..1396
                       note = MOD_RES - Any amino acid
source                 1..1403
                       mol_type = protein
                       organism = unidentified
                       note = Deltaproteobacteria bacterium
SEQUENCE: 15
MTKKPGTEDK ATLWGKESAS KSVKTILEES IQGFTVEQKR SFFANLADQL VSRAGEQGAK  60
SVRSQGLIIG RKENYAKPSA QEPTRHHLYR QPSNASAFLA TGWLIAETPF FIGSGTEGQK  120
QTDDQAESLH LRTLRDGHGR FRIPFTTIRG VMDKELRDIL QAGCAKGRSL RAPCPCQVCT  180
```

-continued

```
LMRRIQVRDA IAADILPPDL RMRTRIDPSH GTVAHLFSLE MAPQGLKLPF FLKLKGVETI  240
DPDKELLEIL NDWSAGQCFL GGLWGTGKGR FRLDDLQWHR LELDNADYYT PLLQDRFFAG  300
ETISDLRQGL QSINIQPERI PAQTPSRNMP YCRVDCILEF KSPVLSGDPV AALFESDAPD  360
NVAYKKPVVQ YDETGRLRTT DPGPVEMLTC LKGEGVRGVV AYLAGKAYDQ HDLSHDSCNC  420
TFCQAFGNGQ KAGSLRFDDF MPVQFESDQA GNFSWSPHTP HAMRSDRVAL DVFGGAMPEA  480
KFDDRPLAAS PGKPLNFKST IWYREDMGKE AGKALKRALI DLQNNMAAIG SGGGIGRGWV  540
SRVCFEGDIP DFLEDFPEPI TVTEPEQDSQ LLKNQAVADE TAVSACDTAD APHPLAVTLE  600
PGARYFPRVI IPRAPTVKRD ECVTGQRYHT GRLSGKIFCE LNTLGPLFVP DTDYSAGVPV  660
PISDEQLAEC QLQAVFENTS KFNEFFATYP EETVTKLKDL LCAADDKWIL AVKDITADLR  720
QEIGEDTFQR IIRKAGHKTQ RFHQINDEIG LPGASLRGMV LSNYQILTNS CYRNLKATEE  780
ITRRMPADEA KYRKAGRVTV SGDGAQKKYS IQEMEVLRLP IYDNMNTPDN MPDVAKQATT  840
AKRCNNLMNE AAKTSRVELK ARWREGQSKI KYQIIDALNK VDPIIQVISS SKQINPNNGK  900
TGWGYVKYTG ANVFAKSLVA PIDCLRKKDA GHVCCQVNLN PAWEASNFDI LINEKCPVER  960
QSGPRPTLRC KGQDSAWYTL TKRSERIFTD KKPVPDPINI PPREVKRYNE LRDSYKKNTA  1020
HVPKPLQTFF NQESLANGDL VYFEVNQFGE ASQLTPVSIS RTTDLFPIGG RLPQGHKDLF  1080
PCTAMCLSEC KNCVPASFCE FHSRSHEKLC PACSLAGTTG NRGRIKFSEA WLSGLPKWHS  1140
VSQDNVGRGL GVTMPRLERS RRTWHLPTKD AYLLGQSIYL NHPVPAILPS DQVPSENNQT  1200
VEPLGPKNIF SFQLAFDNLS IEELGLLLYS LELESGMAHR LGRGRALGMG SVQISVKDIQ  1260
IRDNKSFLFS SNISKKSEWI QCGKDEFAQE AWFGESWDNI DHIQRLRQAL TIPVKGDVGC  1320
IRYPKLEAEG GMPDYIKLRK RLTPLCDREE PVRYRINPVQ LARMILPFVP WHGACPALLN  1380
EQVMIEAKRL TELXXXDRAN WPC                                        1403

SEQ ID NO: 16          moltype = AA  length = 1601
FEATURE                Location/Qualifiers
source                 1..1601
                       mol_type = protein
                       organism = Desulfonema ishimotonii
SEQUENCE: 16
MTTTMKISIE FLEPFRMTKW QESTRRNKNN KEFVRGQAFA RWHRNKKDNT KGRPYITGTL  60
LRSAVIRSAE NLLTLSDGKI SEKTCCPGKF DTEDKDRLLQ LRQRSTLRWT DKNPCPDNAE  120
TYCPFCELLG RSGNDGKKAE KKDWRFRIHF GNLSLPGKPD FDGPKAIGSQ RVLNRVDFKS  180
GKAHDFFKAY EVDHTRFPRF EGEITIDNKV SAEARKLLCD SLKFTDRLCG ALCVIRFDEY  240
TPAADSGKQT ENVQAEPNAN LAEKTAEQII SILDDNKKTE YTRLLADAIR SLRRSSKLVA  300
GLPKDHDGKD DHYLWDIGKK KKDENSVTIR QILTTSADTK ELKNAGKWRE FCEKLGEALY  360
LKSKDMSGGL KITRRILGDA EFHGKPDRLE KSRSVSIGSV LKETVVCGEL VAKTPFFFGA  420
IDEDAKQTDL QVLLTPDNKY RLPRSAVRGI LRRDLQTYFD SPCNAELGGR PCMCKTCRIM  480
RGITVMDARS EYNAPPEIRH RTRINPFTGT VAEGALFNME VAPEGIVPFP QLRYRGSEDG  540
LPDALKTVLK WWAEGQAFMS GAASTGKGRF RMENAKYETL DLSDENQRND YLKNWGWRDE  600
KGLEELKKRL NSGLPEPGNY RDPKWHEINV SIEMASPFIN GDPIRAAVDK RGTDVVTFVK  660
YKAEGEEAKP VCAYKAESFR GVIRSAVARI HMEDGVPLTE LTHSDCECLL CQIFGSEYEA  720
GKIRFEDLVF ESDPEPVTFD HVAIDRFTGG AADKKKFDDS PLPGSPARPL MLKGSFWIRR  780
DVLEDEEYCK ALGKALADVN NGLYPLGGKS AIGYGQVKSL GIKGDDKRIS RLMNPAFDET  840
DVAVPEKPKT DAEVRIEAEK VYYPHYFVEP HKKVEREEKP CGHQKFHEGR LTGKIRCKLI  900
TKTPLIVPDT SNDDFFRPAD KEARKEKDEY HKSYAFFRLH KQIMIPGSEL RGMVSSVYET  960
VTNSCFRIFD ETKRLSWRMD ADHQNVLQDF LPGRVTADGK HIQKFSETAR VPFYDKTQKH  1020
FDILDEQEIA GEKPVRMWVK RFIKRLSLVD PAKHPQKKQD NKWKRRKEGI ATFIEQKNGS  1080
YYFNVVTNNG CTSFHLWHKP DNFDQEKLEG IQNGEKLDCW VRDSRYQKAF QEIPENDPDG  1140
WECKEGYLHV VGPSKVEFSD KKGDVINNFQ GTLPSVPNDW KTIRTNDFKN RKRKNEPVFC  1200
CEDDKGNYYT MAKYCETFFF DLKENEEYEI PEKARIKYKE LLRVYNNNPQ AVPESVFQSR  1260
VARENVEKLK SGDLVYFKHN EKYVEDIVPV RISRTVDDRM IGKRMSADLR PCHGDWVEDG  1320
DLSALNAYPE KRLLLRHPKG LCPACRLFGT GSYKGRVRFG FASLENDPEW LIPGKNPGDP  1380
FHGGPVMLSL LERPRPTWSI PGSDNKFKVP GRKFYVHHHA WKTIKDGNHP TTGKAIEQSP  1440
NNRTVEALAG GNSFSFEIAF ENLKEWELGL LIHSLQLEKG LAHKLGMAKS MGFGSVEIDV  1500
ESVRLRKDWK QWRNGNSEIP NWLGKGFAKL KEWFRDELDF IENLKKLLWF PEGDQAPRVC  1560
YPMLRKKDDP NGNSGYEELK DGEFKKEDRQ KKLTTPWTPW A                    1601

SEQ ID NO: 17          moltype = AA  length = 1575
FEATURE                Location/Qualifiers
REGION                 1..1575
                       note = Description of Unknown: Soil metagenome sequence
source                 1..1575
                       mol_type = protein
                       organism = unidentified
SEQUENCE: 17
MRLKINIHFL EPFRLIEWHE QDRRNKGNSR WQRGQSFARW HRRKDNDQGR PYITGTLLRS  60
VVIRAVEEEL ARPDTAWQSC GGLFITPDGQ TKPQHLRHRA TVRARQTAKD KCADRQSACP  120
FCLLLGRFDQ VGKDGDKKGE GLRFDVRFSN LDLPKDFSPR DFDGPQEIGS RRTINRVDDE  180
TGKAHDFFSI WEVDAVREFQ GEIVLAADLP SRDQVESLLH HALGFVDRLC GARCVISIAD  240
QKPAERERT VAAGDEKATI ADYDQVKGLP YTRLRPLADA VRNLRQLDLA ELNKPDGKFL  300
PPGRVNKDGR RVPHYVWDIP LGKGDTLRKR LEFLAASCEG DQAKWRNICE SEGQALYEKS  360
KKLKDSPAAP GRHLGAAEQV RPPQPPVSYS EESINSDLPL AEWIITGTLR AETPFAIGMD  420
APIDDDQTSS RTLVDRDGRY RLPRSTLRGI LRRDLSLASG DQGCQVRLGP ERPCTCPVCL  480
ILRQVVIADT VSETTVPADI RQRIRRNPIT GTAADGGLFD TERGPKGAGF PFSLRYRGHA  540
PMPKALRTVL QWWSAGKCFA GSDGGVGCGR FALDNLEVYR WDLGTFAFRQ AYSENNGLRS  600
PEEEFDLAVI HELAEGLAKE DGQKILKGTE PFTCWQERSW QFSFTGPLLQ GDPLAALNSD  660
TADIISFRRT VVDNGEVLRE PVLRGEGLRG LLRTAVGRVA GDDLLTRSHQ DCKCEICQLF  720
GSEHRAGILR FEDLPPVSPT TVADKRLDHV AIDRFDQSVV EKYDDRPLVG SPKQPLVFKG  780
CFWVQTSGMT HQLTELLAQA WRDIAAGHYP VGGKGGIGYG WINSLVVDGE KITCRPDGDS  840
ISLTTVTGDI PPRPALTPPA GAIYYPHYFL PPNPEHKPKR SDKIIGHHTF ATDPDSFTGR  900
```

-continued

```
ITCKLEVVTP LIVPDTEGEQ PKDQHKNFPF FKINDEIMLP GAPLWAAVSQ VYEALTNSCF  960
RVMKQKRFLS WRMEAEDYKD FYPGRVLDGG KQIKKMGDKA IRMPLYDDST ATGSIKDDQL  1020
ISDCCPKSDE KLQKALATNQ KIALAAKHNQ EYLAQLSPDE REEALQGLKK VSFWTESLAN  1080
NEAPPFLIAK LGEERGKPKR AGYLKITGPN NANIANTNNP DDGGYIPSWK DQFDYSFRLL  1140
GPPRCLPNTK GNREYPRPGF TCVIDGKEYS LTKRCERIFE DISGGENQVV RAVTERVREQ  1200
YREILASYRA NAAGIAEGFR TRMYDTEELR ENDLVYFKTA KQADGKERVV AISPVCISRE  1260
ADDRPLGKRL PAGFQPCSHV CLEDCNTCSA KNCPVPLYRE GWPVNGLCPA CRLFGAQMYK  1320
GRVNFGFARL PDDKQPETKT LTLPLLERPR PTWVLPKSVK GSNTEDATIP GRKFYLRHDG  1380
WRIVMAGTNP ITGESIEKTA NNATVEAIMP GATFTFDIVC ENLDQQELGL LLYSLELEEG  1440
MSHTLGRGKP LGFGNVRIKV EKIEKRLSDG SRREMIPPKG AGLFMTDKVQ DALRGLTEGG  1500
DWHQRPHISG LRRLLTRYPE IKARYPKLSQ GEDKEPGYIE LKSQKDENGV PIYNPNRELR  1560
VSENGPLPWF LLAKK                                                  1575

SEQ ID NO: 18          moltype = AA  length = 1801
FEATURE                Location/Qualifiers
REGION                 1..1801
                       note = Description of Unknown: Dolphin oral metagenome
                        sequence
source                 1..1801
                       mol_type = protein
                       organism = unidentified
SEQUENCE: 18
MIPDLRSLVV HISFLTPYRQ APWFPPEKRR NNNRDWLRMQ SYARWHKVAP EEGHPFITGT  60
LLRSRVIRAV EEELCLANGI WRGVACCPGE FNSQAKKKPK HLRRRTTLQW YPEGAKSCSK  120
QDGRENACPF CLLLDRFGGE KSEEGRKKNN DYDVHFSNLN PFYPGSSPKV WSGPEEIGRL  180
RTLNRIDRLT TKAQDFFRIY EVDQVRDFFG TITLAGDLPR KVDVEFLLRR GLGFVSTLCG  240
AQCEIKVVDL KKKQNNKEDS ILPVSEVPFF LEPEVLAKMC QDVFPSGKLR MLADVILRLR  300
EEGPDNLTLP MGSQGLGGRL PHHLWDVPLV SKDRETQTLR SCLEKIAAQC KSEQTQFRLF  360
CQKLGSSLFR INKGVYLAPN SKISPEPCLD PSKTIRTKGP VPGKQKHRFS LLPPFEWIIT  420
GTLKAQTPFF IPDEQGSHDH TSRKILLTRD FYYRLPRSLL RGIIRRDLHE ATDKGGCRVE  480
LAPDVPCTCQ VCRLLGRMLL ADTTSTTKVA PDMRHRVGVD RSCGIVRDGA LFDTEYGIEG  540
VCFPLEIRYR GNKDLEGPIR QLLSWWQQGL LFLGGDFGIG KGRFRLENMK IHRWDLRDES  600
ARADYVQKCG LRRGVGDDTA INLEKDLSLN LPESGYPWKK HAWKLSFQVP LLTADPIMAQ  660
TRHEEDSVYF QKRIFTSDGR VVLVPALRGE GLRGLLRTAV SRAYGISLIN DEHEDCDCPL  720
CKIFGNEHHA GMLRFDDMVP VGTWNDKKID HVSCSRFDAS VVNKFDDRSL VGSPDSPLHF  780
EGTFWLHRDF QNDVEIKTAL QDFADGLYSI GGKGGIGYGW LFDMEIPRSL RKLNSGFREA  840
SSIQDALLDS AKEIPLSAPL TFTPVKGAVY NPYYYLPFPA EKPERCLVPP SHARLQSDRY  900
TGCLTCELET VSPLLLPDTC REKDGNYKEY PSFRLNNTPM IPGAGLRAAV SQVYEVLTNS  960
CIRIMDQGQT LSWRMSTSEH KDYQPGKITD NGRKIQPMGK QAIRLPLYDE VIHHVSTPGD  1020
TDDLEKLKAI VLELTRPWKE LPEEQKKKRF EKCKNILDGR MLQQKELRAL ENSGFAYWRD  1080
KTSLTFDSFL KDAIEQEYPR YSGDYQRIKA LVVNITLPWK LLKKEERHKR FDKCRRILKG  1140
QQPLTKDERK ALEESGFANW HGRELLFDRF LKDENSCLIK AETTDRVIAS VAKNNRDYLF  1200
EIKQQDFARY KRIIQGLERV PFSLRSLAKS KETSFQIACL GLRRGRFLRK GYLKISGPNN  1260
ANVEISGGSH SNSGYSDIWD DPLDFSFRLS GKSELRPNTQ KTREYPRPSF TCTVDGKQYT  1320
VNKRCERVFE DSAAPAIELP RMVREGYKGI LTDYEQNAKH IPQGFQTRFS SYRELNDGDL  1380
VYYKTDSQGR VTDLAPVCLS RLADDRPLGK RLPEEYRPCA HVCLEECDPC TGKDCPVPIY  1440
REGYPARGFC PACQLFGTQM YKGRVRFSFG VPVNSTRSPQ LKYVTLPSQE RPRPTWVLPE  1500
SCKGKEKDVP GRKFYLRHDG WREMWGDDDK PDSRPSSEEC QDIIEGIGPG EKFHFRVAFE  1560
NLDKNELGRL LYSLELDAGM NHHLGRGKAF GFGQVKIRVT KLERRLEPGQ WRSEKICTDL  1620
PVTSSELVIS SLKKVEERRK LLRLVMTPYK GLTACYPGLE RENGRPGYTD LKMLATYDPY  1680
RELVVQIGSN QPLRPWYEPG KSFKPSPGND CTGRGGSVSK SLISEPKVVP AIAPFCEGVV  1740
KWFNSVKGFG FIETKEQRDI FVHFSAIRGE GYKILEPGEK VRFEIGEGRK GPQAINVIRI  1800
R                                                                 1801

SEQ ID NO: 19          moltype = AA  length = 1652
FEATURE                Location/Qualifiers
REGION                 1..1652
                       note = Description of Unknown: Aquatic-marine-hydrothermal
                        vent microbial mat sequence
source                 1..1652
                       mol_type = protein
                       organism = unidentified
SEQUENCE: 19
MIINITVKFL GPFRMLEWTD PDNRNRKNRE FMRGQAFARW HNSNPQKGSQ PYITGTLVRS  60
AVIRSAENLL MLSEGKVGKE KCCPGEFRTE NRKKRDAMLH LRQRSTLQWK TDKPLCNGKS  120
LCPICELLGR RIGKTDEVKK KGDFRIHFGN LTPLNRYDDP SDIGTQRTLN RVDYATGKAH  180
DFFKVWEIDH SLLSVFQGKI SIADNIGDGA TKLLEDSLRF TDRLCGAICV ISYDCIENSD  240
GKENGKTGEA AHIMGESDAG KTDAENIANA IADMMGTAGE PEKLRILADA VRALRIGKNT  300
VSQLPLDHEG KENHHLWDIG EGKSIRELLL EKAESLPSDQ WRKFCEDVGE ILYLKSKDPT  360
GGLTVSQRIL GDEAFWSKAD RQLNPSAVSI PVTTETLICG KLISETPFFF GTEIEDAKHT  420
NLKVLLDRQN RYRLPRSAIR GVLRRDLRTA FGGKGCNVEL GGRPCLCDVC RIMRGITIMD  480
ARSEYAEPPE IRHRIRLNPY TGTVAEGALF DMELGPQGLS FDFILRYRGK GKSIPKALRN  540
VLKWWTKGQA FLSGAASTGK GIFRLDDLKY ISFDLSDKDK RKDYLDNYGW RNRIEALSLE  600
KMPLDRMNDY AEPLWQKVSV EIEIGSPFLN GDPIRALIEK DGSDIVSFRK YADDSGKEVY  660
AYKAESFRGV VRAALARQHF DKEGKPLDKE GKPLLTLIHQ DCECLICRLF GSEHETGRLR  720
FEDLLFDPQP EPMIFDHVAI DRFTGGAVDK KKFDDCSLPG TPGHPLTLKG CFWIRKELEK  780
PDEDKSEREA LSKALADIHN GLYPLGGKGA IGYGQVMNLK IKGAGDVIKA ALQSESSRMS  840
ASEPEHKKPD SGLKLSFDDK KAVYYPHYFL KPAAEEVNRK PIPTGHETLN SGLLTGKIRC  900
RLTTRTPLIV PDTSNDDFFQ TGVEGHESYA FFSVNGDIML PGSEIRGMLS SVYEALTNSC  960
```

-continued

```
FRVFDEGYRL SWRMEADRNV LMQFKPGRVT DNGLRIEEMK EYRYPFYDRD CSDKKSQEAY  1020
FDEWERSITL TDDSLEKMAE RKGDISPKDL KVLKSLKGKN YKSTEGLLAA FKDKGGDTGG  1080
NILGLIFKYA ERIGDVPRYE HPTDTDRMML SLSEYNRNQK SDGKRAYKII KPASKLGKGA  1140
YFMFAGTSVE NKRICNPACT DKANKSVKGY LKISGPNKLE KYNISEPELD GVPEDRNCQI  1200
IHNRIYLRKI FVANAKKRKE RDRLVGEFAC YDPEKKVTYS MTKRCERIFI KDRGRTLPIT  1260
HEASELFEIL VQEYRENAKR QDTPEVFQTL LPDNGRLNPG DLVYFREEKG KTVEIIPVRI  1320
SRKIDDSPIG KRLREDLRPC HGEWIEGDDL SQLSEYPEKK LFTRNTEGLC PACRLFGTGA  1380
YKGRLRFGFA KLENDPKWLM KNSDGPSHGG PLTLPLLERP RPTWSMPDDT LNRLKKDGKQ  1440
EPKKQKGKKG PQVPGRKFYV HHDGWKEINC GCHPTTKENI VQNQNNRTVE PLDKGNTFSF  1500
EICFENLEPY ELGLLLYTLE LEKGLAHKLG MAKPMGFGSI DIEVENVSLR TDSGQWKDAN  1560
EQISEWTDKG KKDAGKWFKT DWEAAEHIKN LKKLLFLPGE EQNPRVIYPA LKQKDIPNSR  1620
LPGYEELKKN LNMEKRKEML TTPWAPWHPI KK                               1652

SEQ ID NO: 20          moltype = AA  length = 1806
FEATURE                Location/Qualifiers
REGION                 1..1806
                       note = Description of Unknown: Aquatic-marine-deep
                        subsurface sequence
source                 1..1806
                       mol_type = protein
                       organism = unidentified
SEQUENCE: 20
MSDNRIDYDI KLTFFEPFRM SPWVKSHARA KSKTFFRTLS FVRWLETSPE TKEGKEGDSI  60
GVPFIPGTLL RSALLKEVEF LITLKNKYDC CCGEFETPRQ KRDEKKEQGR RFFGRKRPTY  120
EFGNSQPCTD FENACPFCSI LSRSFNNDDW FDDRGNPIVG KVPVHFSNLD VTDSKLKRIR  180
LSAIANQRIV NRVDFRSGKA QDYFKIWEVD NRLCPSFCGK ITIRQDINQV DDLTCLLAAG  240
LAKIKTLAGA LCRVDIIRDK TIDFHQRLIQ KYVGPPGPPH NPTAHPTLPS QPTLSVDVHG  300
LARTIAGTLT GSDKEAYLRR IADAVREMRN RKCSILHEPP FTKTGDKEPV WTIPAVQKAL  360
KETTACVARE SWRLFCEELG EALYKKAKEL KKKDEAIPRL LGDTEYYGQQ AEAPVGTDYR  420
LTASALPKYE WIINGWLEAR TPFFFGVESA SEQTSLAILL TRDHRYRLPR SVLRGALRRD  480
LRTVIGSGCN VELGVDTPCD CDVCRIMSRV IVMDSLSDYQ EPPDIRHRIR INQHSGTVDE  540
GALFDMELGP EGLRFPFRMY FSATCPTADV PLAKVLKMWQ DRPAFLGGDA GTGNGRFRLI  600
KAKTRSEPFD WDGPKSSLNL LMARSYIDLE DHDTLLDSKL ECAKAWKVKD ELTSVWTDYQ  660
YEIDLHSPIL SNDPIAALLD PDWRDAVPVK KRVLQDGGLV PTEKYYIKGS GIRGILRTAV  720
GRNCVNEDGI HLHNLPHDDC PCVLCQLFGS EHHQGMLRFE DAHFENDPMP ETLDHVAIDR  780
FTGRARDKFK FEDAPLIATP DQPIKLKGTF WLKRELHEAS QEVFGKIDDF ECKPKEDSDS  840
LLGAARALWC AFLDLKHGLF PIGSNGGIGY GWVSGLSVSE PDKNKKIPLG QLCRNEGAQE  900
TASTSGEKGE YNPSDAPNSL RQEGHVFNPH YFLRSYRYED KNGKIATHVE RIDLPVTHEA  960
YQDKLTGKIT CKLNTRGPVF VADPSDLVVY FTAKEYEDFV KRWPKSAELL QSLVHEKDGM  1020
KLIPVKQIPK DSPEDGALKE ISEHQGHKGY KFFRLNGSVM IPGSEIRGMV SSVYEALTNS  1080
CFRVFDQRRI LSKRMEADFR TVLTHFKAAR VVPDNNSGSG LSVKEFTNMV RVPVYNCPQT  1140
FFDGLTQGQI SGKEETKLWV KNYEWRISLC NPWTHHSRKS KKEWEKNIPG RILNNQGDKI  1200
VLNISYKQEE RKITLILDDK DRVVLDGITP KQLGGKEEIR LWLRISQYQK AFRKKPDNNG  1260
GWKMQTGYLH IMGPNKVEID SSGTSREGLQ DLPETWKDAQ CNSPDGKIFS GKDGNAVYTM  1320
NKYCEMFFYN EQKKSYRVPQ AVLNQYRQMI EESMSNPQAP PAIFRSKPIR EKDTALKAGD  1380
LVYFRKNENR EGEVDAVIPV RIYRESHRKP LGKRFPDGLH DLRPCTFECL DDCDKCPDRC  1440
NELKEFFNPH PKGLCPACRL FGTTSYKSRV SFGFARLCSE DKKAKWYGVE EDAEQGKPLT  1500
LPLLERPRPT WSMPDKDAKI PGRKFYVHHP HSVDSSIRDM QFDPELSDKE NQGKIRPNKN  1560
NRTVEPLDKG NEFTFDIRFM NLKEWELGLL LYSLQLETGL AHKLGMGKAQ GFGSVEIDVE  1620
KVEIRNGPGD WKSKTSHKIT EWITKGKDKL EKWFKTDDWN NVDHIADLKK FLYFLDPQEI  1680
KPKVRYPSLS RDDDKKDHFP GYVDLKRKPS KEKPNPYYVP EDKRRALLTR PWEPWYVMPK  1740
SSMGTVKWFN EEKNYGFILR DNGEDIFVHR SDINGSLGTL TEGQKVIFEV KQGPKGLQAT  1800
NVKVIS                                                            1806

SEQ ID NO: 21          moltype = AA  length = 1559
FEATURE                Location/Qualifiers
REGION                 1..1559
                       note = Description of Unknown:
                        Aquatic-freshwater-groundwater sequence
source                 1..1559
                       mol_type = protein
                       organism = unidentified
SEQUENCE: 21
MEYTLTLNFI EPFRLIEWHD APDRENLRLR GFSFARWHKD REFGLGRPYI TGTLIRSAVI  60
RAVEEFLWLN NGKTGDVHCC QGEFTKARFY RELTEKRLRR RQTLVWDNNG VCNQDQPCPF  120
CLLLGRYWQP GPGYSENNDV NFGNFSIPQK KKVLLNLEDI AEPRIINRVD QQSGKAEDFF  180
EIREIDHRSC ALFEGKISLS ERAAENKALI SLLNAALPLV NRISGALCYL TMEEVKVMDK  240
SVNGGSDNLS GEAMELKKSD RPGEGSHFAR HPIGAEHASY EKIKTSAGEV VNAFEESNKL  300
VHLRVFSDVI RELRRHDPRK LNLPGGHEDR SGKITDHFLW DMKVESKPLR NWLPDKFNEF  360
NEKHKLPWRI FCESLGQALF LEAKDKAPEQ FTSARPLGAM VSTLESKEPE FLPGRSRQGP  420
RYEWLMRGQL VAEVPFFFGW SVDKNDTDHI SMRLLSARDG RLRLPRSALR GILRRDLNLA  480
FGTNGCRAKL GLRRPCPCPV CNLLKNITIR DSLSDYKRPP QIRHRIRLDH RSGTVAKGAL  540
FDMEVGPTGA IFPFELRLRS TSDKFSKELE QVLLWWKQGL AFLSGAGGTG KGRFRLKELK  600
CIFWDLQNDA GFAHYKETYG GRKKRISDDE LIPWQVTSGD PVSEPPWTAW EINFLVCSPF  660
LTKDPVESLL DPGGTDAVCY RAVYLGENGG IKKRYLLKGE SFRGILRTAV GRRENSLLKE  720
HEECDCVLCR LFGNEHEAGK IRVEDLLIQD EPKEKNLDRV AIDRFTGGAR DKHKFDQKPL  780
TGTPAFPLVL MGKIWIKNDL TDDDKAILKQ ALEDIRCGLY PFGGLGNVGF GWVNYLTCNS  840
DFEQNFDSMN LCFSDKVKVE NEPDKIYWPH YFIPFGPKVV RENKPPGHAY PKTEFHSGRL  900
ICSLKTLTPL IIPDGQPASQ EANGHKSYNF FELSGELCIP GSEIKGMISS VYEALTNSCM  960
```

-continued

```
RIFEEKKRLS WRMKAENLDQ WSPGRITEEA DELFVEEMEE IRLPLYDNPD LLPNIKKEGE  1020
KGFYRTKKIR DSNGRERLKK GQPTGTDSLI NIHSAEIREF LKENKHLSSG QIPTKWFRCF  1080
PHPGKRGFDG LALLKIPKEW HNKNTSGWIA EGYVNLTGTN KVETRRSGKG ISIRETSKDE  1140
QINIIHNEVT LEEKPVNSSK LGQVLRKRAI PKYVTYKNGY EYTMTKRCER IFIPLQKPTK  1200
HIVSRNVENK FLQLCEEYKQ NAEKIPKVFR TRMPKNYKLN DGDLIYFRQE LGEVVEIIPV  1260
RISRAVDDEV LGEKFVNDDF RPCVREILNR ETEKKITSAG FKEVFHHHPK GLCPACAIFG  1320
TTFYKGRVSF GFAYLKNNET KLVENGAYIT LPLLERPRPT WAMPTKDSKV PGRKFYVHHQ  1380
GWKNIVEDSK NESTEKNENN RSVQAIDRNQ VFLFEVRFEN LRPWELGLLI YSLQLEPKLA  1440
HKLGMGKPLG FGSVKIKVEN VTSSRQKDVN DNTLPEAVEK ELKEIWGKET EPDFTRSLEG  1500
LYKALHYESK NGIQVRYPKL EKEKKDDPGE KPGYLELADG PFSTENRKEK LKEIWGNWA   1559

SEQ ID NO: 22          moltype = AA  length = 1549
FEATURE                Location/Qualifiers
REGION                 1..1549
                       note = Description of Unknown:
                        Bioremediation-terephthalate-wastewater bioreactor sequence
source                 1..1549
                       mol_type = protein
                       organism = unidentified
SEQUENCE: 22
MNRYKVSLEF LEPWRINHLG DDRGAAWARW VQTREGYQRP EITGTLVRSA VIRAAEELLA  60
LTGGVWAGQK CCPGEFCTPG GSKPTFRRQR ATRWWGEDSL CTPDSPCPFC QLLGRHDLAG  120
KQARRGGGFH VHFGNLYPVA REGYGSLAEI TRQRTSNRLD WLTGKAQDIL TICEVEELRR  180
FSGLITVAPE LANGEAVSSL LTAAAALVDR LSGAACRLKL QPVEELWSGT AVSLTRAAVP  240
ETAYRQQLEE DIDNYFQELI GDGSQLGPER LRLLADAIRE LRYLPPEQTL PDWLQSLPQG  300
KDGKAHRLWD ALTAQRRPLR NMLQEVAAAY AAPATWRDVV QGLGQALYAH YKKLWPQAMP  360
VRPVGEAEYW QTKFRDRQPS RQRGTWSHEW IITGALQTLT PLYLGTQVEA ARQTSLTVLL  420
TAEGRYRLPR TALRGALRQD LQLASRGQGC LMELNPERPC SCPICQIMRR LTVRDVTSSI  480
ALPPPLVRQR VRRNPWTGIV DEGALFDQEV APEGLRFPFI LRYRGFGGLD AWLQTVLSWW  540
QEGRLFLGGA GGTGKGRLRL TDLRIWRWAL DETGLPTYVA HLGYRGREEE LANSASLPAG  600
VEAVTCSDPA TVPSPWQEVD WEFRFHGPVL ANHPLTALLR GEADAVFTWK VQLEADQQHY  660
REVCTLKGET VRGLVRGLFG KSQGLLTKAH ADCTCLLCRV FGNEHQRGKV RFEDLTLAGE  720
TVPKKRLDHV AIDRISGGAA EQLKFDTQPL YGTPENPLVF AGKFWVHTEL DEEEQKALRA  780
ALTALRDGLA TVGAKGSVGY GWLNGLRLHS GPAWLTDNWQ ETAAAPSDTN TPPEFSWPQL  840
PDLTLDSRKI YYPHYFLPPD LQVPRLSQPH THSLFDPQKY TGWLTCRLTT LTPLIIPDTS  900
SDQTLTTGGP FPAGHQAFQF FRLGDQPLIP GAELRGMISS VFEAITNSCF RVIRPRERLS  960
WRMPAALAPQ FRSGRVEIVN NQYYIRQMDM GRLPLYDDPA TRRLFTPLSL TSGHTLDFVD  1020
DNRTLLQSNP GIREGAIRTD LCFLNRFWLL RPPSAARCPR GNFSLTSGYV KFTGPNKVEV  1080
SRAGAGAGGL PAPPADWTGV RLNQVAGNVP FYQAEQSGVI FTVNKRRERF FISRGNARSY  1140
PVPLATLKRY EQVLKEYRHF AQRGEVPAVF RTVLPDVRHG ASGYNRLNNG DLVYFRVKDD  1200
RWNDQNAPVE HIIPVSISRL VDQKFLGERV PEPLRPCAHV CLEECEACLK QESCPSSFYR  1260
EGTPSRGLCP ACHLFGTTGY QGRVRFGFAR LEREPAWRQN DAGSTAITLP LLEQPRLTWS  1320
MLWERRNAEG TVEERQPVNW VPGRKFYVHH QGWRTIVAQG INPIDGQRLE RNENNRTVEV  1380
LDTGRTFTFQ VFFENLDAWE LGLLLYSLEL EPGLAHKLGM AKAWGFGSVQ IDVASLRRYQ  1440
APGSMTDITC EKDTLLQAGF AWLKEQANSS SWDEIPRLRQ LRQLLRYQED GTLTVRYPIL  1500
KQENAASGQV PGYVELRDQG YRPEEQLRIP WSPWYSPPLE PPPAATAAA             1549

SEQ ID NO: 23          moltype = AA  length = 1668
FEATURE                Location/Qualifiers
REGION                 1..1668
                       note = Description of Unknown:
                        Aquatic-freshwater-freshwater lake sediment sequence
source                 1..1668
                       mol_type = protein
                       organism = unidentified
SEQUENCE: 23
MTTLTIHLHF LEPFRMAPWF SVEKRKKNNP DWQRVQTYAR WHKNTAGDGR GRPFITGYLL  60
RSALIQAVEE ELVFSRGVWS GISCCPGLFF TEPDKDKEKP LNERRRATLG WTENKAICQE  120
EEGREKACPL CLLINRFKEN GEDNVHFGNL SLPGSENERP VWDQPEQIAK LRTLNRVDRA  180
TTKAHDHFKV YEVEDLTDFY GTITFADDLP QREVIESLIR RGLGFISDLC GALCEIRVEK  240
QKPLPTEPKG ITQSKASYVS GLAEMCWEKM AETELRSLAG AVLQLRCSDP KKFTLPKGRI  300
DRNGNRLPHH IWDIELEGNG DKKTLRKHLK ETAEKMAEGG TAFRLFCEDV GNRLFRLSKG  360
IPQETPNRQD AFSDPSQVFN LGRPVYGQEN HRDPMIPSCE WIITGTLTAA SPFFIADELI  420
DDDHISRKLL TTQDFHYRLP RSLLRGILRR DLHEASGGKG CRAELGPESS CICPVCRILN  480
QVKIRDARSD SFVPPDIRQR VKQSHHHRIV QDGALFDTEY GLEGVVFPFE LRFKGEKTID  540
KELRTVMGWW EEGLLFLGGD FGTGKGAFKL GIKQIHRWDL STPGAREEYE QTCGFRAGVP  600
LDANCQGLSP VSNIDFPKVD YPWQKVPWEL AFESPLLTAD PIAAITQDEA DTIYFQKRRL  660
KSDGSVEYIP ALRGEGLRGL IRTATARASG SDHLTVEHED CTCVLCKTFG NEHRSGLLRF  720
DDLEPKNWKD KRIDHVSIDR FDASVVEKFD DRPLIGSPDK PLVFAGAFWI HRDFTENKAL  780
SNGFQDLKSG LYPLGGKVGI GYGRLSKLEL PSDWLPNSAE NESISVSGLL EGSPETSGIP  840
EKPTWKPEPD AIYNPYYYLS RPGDGPKRTL TPVSHATLSK ERYTGRIACF LKVKSPLLLP  900
DSEHDPVAPD KNGTMKAFRL NGTLMIPGSA LRSAVSQVYE ALTDSCFRVM DQKRVLSWRM  960
ETGDHGNYKP GRISESGDQI FPMGEKALRL PLYDMAPGTH SAKYIKELEE LHKKALEGNI  1020
HRLTIAPWEE MPEKTREKKF EKCNKILGRN LTEEEKKNLT DQGMAKLKIS EMELKTLIGR  1080
FKKDEESCIE KAQKTDSNIA EIAKHNRDIL NVLEKETRQR VLAGKEKVPF LTERLAPNND  1140
INFQIVKLLK NSEKNKKNKE IRWGYLKITG PNNANDAVVE TKEEDDKYKL EWEDPLDFSF  1200
CLTGPPKNQP NTQKSRDFPR PGFECIKDDK RYTISKRCER LFEADEKSKP IPIPKRVREG  1260
YKGILEDYQK NAKKIPKAFQ TRLNSDLVYY KSDYVENQIN VTALAPVCIS RLADDRPLGK  1320
RLPVGYQPCS HICLEDCERC TGKACPIPLY REGYPVNGLC PACQLFGAQM YKGRVNFSFA  1380
```

-continued

```
TLTPGKNLEL RNVTLPAQER PRPTWILPKN VQGKDTEIPG AKFYLRHGMW KKIWTDRKDP  1440
RTDKPIEEKN PNNVTIEGIN TGAEFRFDVS FENLDENELG WLLYCLELEE DMSHMLGRGK  1500
PFGFGQVEIK INELARRLAP NAWYTESPKE GSLIHSKLIV KALAGLKSLD SLRLLLTQYN  1560
NLTAYYPELE GKGGKPGYDT LKNSSGYNPH CFLTLQTKGN TPFVYPWFPI PISKPQATKS  1620
DIKPKVENHG ITGNGFKKLV EGDKVTFEIE ERPKGPCAVN VRKVKDIP              1668

SEQ ID NO: 24          moltype = AA  length = 1821
FEATURE                Location/Qualifiers
REGION                 1..1821
                       note = Description of Unknown: Terrestrial-soil sequence
source                 1..1821
                       mol_type = protein
                       organism = unidentified
SEQUENCE: 24
MTTGNTSASH PQFVTLTVCL RFCSPFQIRP WIKETVRNKV KMPSTVNAHA ETAHLPDDQD  60
TDDTQDLLEE ERFERYATAA DWHKGSINGN AKYSPYVRGD LVRSVVDREL QEHFHCYNEK  120
LANENKGCPG KRDRHINAGG KASGFMAHLP AIKDPAGKEI CKGSDNICPV CHFLGAFAEG  180
IKPVKFRNFF SGYYVAKTED LAKQRGRNCY SGQSRKSLDN FTVWEADHTA CPVFFGRIEV  240
NKTLLPKEQI LALLAGGLAR LDNLAGSACR FDIIDKYEGV FEDHEWTANI LPNLLIAARE  300
ALGLPDDEHQ ALLNDFSRFF INPEKSPAVY TSSPVIVPVQ GAVDKVVLLE KAQDIAGRIA  360
ACVSDNPRHL HRLAAAIRTL GWPGRSLASV MTKKPGTEDK ATLWGKESAS KSVKTILEES  420
IQGFTVEQKR SFFANLADQL VSRAGEQGAK SVRSQGLIIG RKENYAKPSA QEPTRHHLYR  480
QPSNASAFLA TGWLIAETPF FIGSGTEGQK QTDDQAESLH LRTLRDGHGR FRIPFTTIRG  540
VMDKELRDIL QAGCAKGRSL RAPCPCQVCT LMRRIQVRDA IAADILPPDL RMRTRIDPSH  600
GTVAHLFSLE MAPQGLKLPF FLKLKGVETI DPDKELLEIL NDWSAGQCFL GGLWGTGKGR  660
FRLDDLQWHR LELDNADYYT PLLQDRFFAG ETISDLRQGL QSINIQPERI PAQTPSRNMP  720
YCRVDCILEF KSPVLSGDPV AALFESDAPD NVAYKKPVVQ YDETGRLRTT DPGPVEMLTC  780
LKGEGVRGVV AYLAGKAYDQ HDLSHDSCNC TFCQAFGNGQ KAGSLRFDDF MPVQFESDQA  840
GNFSWSPHTP HAMRSDRVAL DVFGGAMPEA KFDDRPLAAS PGKPLNFKST IWYREDMGKE  900
AGKALKRALI DLQNNMAAIG SGGGIGRGWV SRVCFEGDIP DFLEDFPEPI TVTEPEQDSQ  960
LLKNQAVADE TAVSACDTAD APHPLAVTLE PGARYFPRVI IPRAPTVKRD ECVTGQRYHT  1020
GRLSGKIFCE LNTLGPLFVP DTDYSAGVPV PISDEQLAEC QLQAVFENTS KFNEFFATYP  1080
EETVTKLKDL LCAADDKWIL AVKDITADLR QEIGEDTFQR IIRKAGHKTQ RFHQINDEIG  1140
LPGASLRGMV LSNYQILTNS CYRNLKATEE ITRRMPADEA KYRKAGRVTV SGDGAQKKYS  1200
IQEMEVLRLP IYDNMNTPDN MPDVAKQATT AKRCNNLMNE AAKTSRVELK ARWREGQSKI  1260
KYQIIDALNK VDPIIQVISS SKQINPNNGK TGWGYVKYTG ANVFAKSLVA PIDCLRKKDA  1320
GHVCCQVNLN PAWEASNFDI LINEKCPVER QSGPRPTLRC KGQDSAWYTL TKRSERIFTD  1380
KKPVPDPINI PPREVKRYNE LRDSYKKNTA HVPKPLQTFF NQESLANGDL VYFEVNQFGE  1440
ASQLTPVSIS RTTDLFPIGG RLPQGHKDLF PCTAMCLSEC KNCVPASFCE FHSRSHEKLC  1500
PACSLAGTTG NRGRIKFSEA WLSGLPKWHS VSQDNVGRGL GVTMPRLERS RRTWHLPTKD  1560
AYLLGQSIYL NHPVPAILPS DQVPSENNQT VEPLGPKNIF SFQLAFDNLS IEELGLLLYS  1620
LELESGMAHR LGRGRALGMG SVQISVKDIQ IRDNKSFLFS SNISKKSEWI QCGKDEFAQE  1680
AWFGESWDNI DHIQRLRQAL TIPVKGDVGC IRYPKLEAEG GMPDYIKLRK RLTPLCDREE  1740
PVRYRINPVQ LARMILPFVP WHGACPALLN EQVMIEAKRL TELLAQENLD MICRTKNCAN  1800
CKQETKKDCL AFRYDRANWP C                                            1821

SEQ ID NO: 25          moltype = AA  length = 1940
FEATURE                Location/Qualifiers
REGION                 1..1940
                       note = Description of Unknown: Aquatic-marine-marine
                        sediment sequence
source                 1..1940
                       mol_type = protein
                       organism = unidentified
SEQUENCE: 25
MKVRIKFFEP IRVMPWVNPS DRKISNEQFM RGQSFARWHR YNKNSNSGKP FITGTLVRSA  60
VIRAAEVLLS LSNGIIENKA CCPGMFETEG AARKKKMHFR QRSTPKWTEN STCNKDNQCP  120
FCELLGRFGN DEIGAVIEKE NNTKRLKYNF HFSNFQPSGN NSYPDHIIIK RTVNRVDYTT  180
GKAHDFFTIS EIDNSFFPAF EGHISISDRV SHEAKKLLSD SLKFIDKLCG SICVFEFDDS  240
TWDDHLHIEK SMEKNDGKEK SEEITKQIIK ILESNSKLDY LRILSDAIRE LARDKEMVHK  300
LPLDYKGKKK HYIWDLAYNK ISIREILCNQ ANKNAKNDYV ELCKTIGKEL YHESQKKTEL  360
LTKPHRILGS KSFYGKPQRD IQPTDAKIVP TEETIFTGKL VSETPFFFGL ENEDKQQTDF  420
TVLLDSQNRF RIPRSALRGV LRRDIRMMSG GNGCDVKLGG RQCLCPVCRM MRNITIMDVR  480
SNKDIIPDIR QRIRINPYTG SVAEGALFSM ELGPQGMEFD FVLRFRGNDS IPKSLKKVLL  540
CWAKGQAFLS GASSTGKGRF KLKNLKFKSF DLSTKEIRND YLNQRGWRNR ENELPLEPLF  600
LTDKYKEINT TLWNKVSVEI KLSSPFLNGD PVRSLVQGQG ADIVSFKKTS LIDDEDIYAY  660
KAESLKGIFR TALARRFHYK DKISQKVLPL TAISHKDCDC PLCRLFGSEF ETGKIRFEDL  720
EFSTNPIPKK FDHVAIDRFT GGAVDKKKFD DCALSATKQK PLLLKGNFWL RPDMTKDDFK  780
YFEKAFLDIK SGFYPLGAKS GIGYGQIEDI SISISDSDDY PRAIKENIKT INNKSYTQEA  840
KNNINDKDTD ESKQSDFQID LKDDAIYYPH YFLKPNKKVD RKTIPINHLT LHDECHTGKI  900
VCTLTTKTPL IIPDTENDDA FGLKKAKLAE DGEKYHKSYS FFSVNDEIMI SGSEIRGMIS  960
SIYEAITNSC FRIFEEKHRL SWRMEAVPEV LEKFIPGRII KINGELKMVE MEEVRYPFYD  1020
KNCPDTKTQK DHFSSKGKGK LYYEQPTFSD KMILSLSEYN RKHQNPGKKE KYKIIKPDSK  1080
SNANFMFTAT PANNTEGYDM DCVHKHSVKG YLKVSGPNKI EKERTDQPAS NKIPMENEIV  1140
IHQKTNRREI TVQNAKKNKK RYRLIPEYIC SEKDTNYIMN KRCERVFIEP EKCNHDGIPI  1200
SKNAIELFKH LVDEYKKNAD QQETPKVFRT KLPEKGELKE GSLVYFRKDS NEVVEIIPVK  1260
ISRKIDDRFI GKRLTKNLRP CHGEWIEKDD LSILDQYPEK KLFTRHPKGL CPACQLFGTG  1320
AYKGRLRFGF ATLTNKPEWL NKEDKDHKLT LPLLERPRPT WAIPDATQAS KVPGRKFFIH  1380
HHAWTDIEKG IDPVTGKAIQ IDVNNRTVQP LDSNNTFTFE INFENLEPHE LGLLLYSLQL  1440
```

-continued

```
ENSLSHKLGM GKAFGFGSID IKVENLLLFD STIDKYKNKT DQVKRFVDEG KNNLLEIFEN  1500
EFDDIEHIKD LKSLLYFPND KNIRVQYPLL RKEDYPDKDL PGYKELKDNF SNGIQIRHNL  1560
LTIPWSPWAY QSKKKLENEK TIYPPLKKIE INNYYDIKKV NIKIPDNAQW VFLTGNNSIG  1620
KSLFLKAIAT GLYGKITEDD ENDIDTNCGI RVFITNEWVN DVKKDYFNQK LSYKNYATYG  1680
PSRLNKLAEG KKTKFPYFSL FNTEGVFYHD IEKEFIKWCD RDSSKFNLLK NIFIKLLPTI  1740
DDIKGIQTKT DFYIGYKEME TGKYEKQSKL ATGNISILRM FGDMFIRFSK EQPDTLPEDF  1800
SGIVIIDELD LHLHPIWLKK IPGLVSKLFP KIRFIASTHS AIPFLGAPKN SVYLNVIRDE  1860
DNNIHVQEID IDLTNLLPNT ILTSPLFNME DITQINLPDI TDVRTEDTYK EIIEIDKIKA  1920
RLKKFAKKDT LFPDKLFKEL                                              1940

SEQ ID NO: 26          moltype = AA  length = 1812
FEATURE                Location/Qualifiers
REGION                 1..1812
                       note = Description of Unknown: Anammox bioreactor sequence
source                 1..1812
                       mol_type = protein
                       organism = unidentified
SEQUENCE: 26
MSKKHFIHLT FLEPYRLAEW HAKADRKKNK RYLRGMSFAQ WHKDKDGIGK PYITGTLLRS  60
AVLNAAEELI SLNQGMWAKE PCCNGKFETE KDKPAVLRKR PTIQWKTGRP AICDPEKQEK  120
KDACPLCMLL GRFDKAGKRH RDNKYDKHDY DIHFDNLNLI TDKKFSHPDD IASERILNRV  180
DYTTGKAHDY FKVWEVDDDQ WWQFTGTITM HDDCSKAKGL LLASLCFVDK LCGALCRIEV  240
TGNNSQDENK EYAHPDTGII TSLNLKYQNN STIHQDAVPL SGSAHDNDEP PVHDNDSSLD  300
NDTITLLSMK AKEIVGAFHE SGKIEKARTL ADVIRAMRLQ KPDIWEKLPK GINDKHHLWD  360
REVNGKKLRN ILEELWRLMS KRNAWRTFCE VLGNELYRCY KEKTGGIVLR FRTLGETEYY  420
PEPEKTEPCL ISDNSIPITP LGGVKEWIII GRLKAETPFY FGAQSSFDST QDDLDLVPDI  480
VNTDEKLEAN EQTSFRILMD KKGRYRIPRS LIRGVLRRDL RTAFGGSGCI VELGRMIPCD  540
CKVCAIMRKI TVMDSRSENI ELPDIRYRIR LNPYTATVDE GALFDMEIGP EGITFPFVFR  600
YRGEDALPRE LWSVIRYWMD GMAWLGGSGS TGKGRFALID IKVFEWDLCN EEGLKAYICS  660
RGLRGIEKEV LLENKTITEI TNLFKTEEVK FFESYSKHIK QLCHEGIINQ MSFSGGLRSY  720
HEYLSPLWTE VKYEIKIASP LLSSDTISAL LNKDNIDCIA YEKRKWENGG IKFVPTIKGE  780
TIRGIVRMAV GKRSGDLGMD DHEDCSCTLC TIFGNEHEAG KLRFEDLEVV EEKLPSEQNS  840
DSNKIPFGPV QDGDGNREKE CVAEVKIYKK KLIDHVAIDR FHGGAEDKMK FNTLPLVGSP  900
ERPIILKGRF WIKKDMVKDY RKKIEDAMVD IRDGLYPIGG KTGIGYGWVT DLTILNPQSG  960
FQIPVKKDIS PEPGTYLTYP SYSAPSLNRG HIYYPHYFLA PANTVHREQE MIGHEQFHKE  1020
QKGELLVSGK IVCTLKTVTP LIIPDTENED AFGLQNTYSG HKNYQFFHIN DEIMVPGSEI  1080
RGMISSVYEA ITNSCFRVYD ETKYITRRLS SEKKDESNDK NKSQDDASQK IRKGLVKKTD  1140
EGFSIIEVER YSMKTKGRTK LVDKVYRLPL YDSEAVIASI KFEQYGEKNE KRNAKILAAI  1200
KRNNVIAEVA RKNLIFLRSL TPEELKKVLQ GEILVKFSLK SGENPNDYLA ELHENGTERG  1260
LIKFTGLNMV NIKNVNEEDK DFNDTWDWEK LNIFHNAHEK RNSLKQGYPR PVLKFIKDRV  1320
EYTIPKRCER IFCIPVKNTI EYKVSSKVCK QYKDVLSDYE KNFGHINKIF TTKIQKRELT  1380
DGDLVYFIPN EGADKTVQAI MPVPLSRITD SRTLGERLPH KNLLPCVHEV NEGLLSGILD  1440
SLDKKLLSIH PEGLCPTCRL FGTTYYKGRV RFGFANLINK PKWLTERENG CGGYVTLPLL  1500
ERPRLTWSVP SDKCDVPGRK FYVHHNGWQE VLRNNDITPK TENNRTVEPL AADNRFTFDV  1560
YFENLREWEL GLLCYCLELE PGMGHKLGMG KPLGFGSVKI AIERLQTFTV HQDDINWKPS  1620
ENEIGVYVQR GREKLVEWFT PSDSHKNMEW NEVKHIKDLR SLLSIPDDKP TVKYPALNKG  1680
AEGAISDYTY ERLSDTKLLP HDKRVEYLRT PWGPWNAFVK EAEYSTSENS DEKGRETIRT  1740
KPKSLPSVKS IGKVKWFDEG KGFGILIMDD GKEVSISKNS IRGNNLLKKD QKVTFHIVQG  1800
LIPKAEDIEI AK                                                      1812

SEQ ID NO: 27          moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 27
gttatgaaac aagagaagga cttaatgtca cggtac                            36

SEQ ID NO: 28          moltype = DNA  length = 37
FEATURE                Location/Qualifiers
misc_feature           1..37
                       note = Description of Artificial Sequence: Synthetic
                        oligonucleotide
source                 1..37
                       mol_type = other DNA
                       organism = synthetic construct
SEQUENCE: 28
gttggtgcat cagcccggaa ttatgatgtt ttggtac                           37

SEQ ID NO: 29          moltype = DNA  length = 35
FEATURE                Location/Qualifiers
misc_feature           1..35
                       note = Description of Artificial Sequence: Synthetic
                        oligonucleotide
source                 1..35
                       mol_type = other DNA
```

```
                       organism = synthetic construct
SEQUENCE: 29
ggttggaaag ccggttttct ttgatgtcac ggaac                           35

SEQ ID NO: 30          moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 30
attgccccag ccgataaacc cttaatgtca cggaac                          36

SEQ ID NO: 31          moltype = DNA  length = 35
FEATURE                Location/Qualifiers
misc_feature           1..35
                       note = Description of Artificial Sequence: Synthetic
                        oligonucleotide
source                 1..35
                       mol_type = other DNA
                       organism = synthetic construct
SEQUENCE: 31
atagatatag acagaagctt ttaatgtgat gggac                           35

SEQ ID NO: 32          moltype = DNA  length = 35
FEATURE                Location/Qualifiers
misc_feature           1..35
                       note = Description of Artificial Sequence: Synthetic
                        oligonucleotide
source                 1..35
                       mol_type = other DNA
                       organism = synthetic construct
SEQUENCE: 32
gttggaaaag ccggttttat ttgatgtcac ggaac                           35

SEQ ID NO: 33          moltype = DNA  length = 35
FEATURE                Location/Qualifiers
misc_feature           1..35
                       note = Description of Artificial Sequence: Synthetic
                        oligonucleotide
source                 1..35
                       mol_type = other DNA
                       organism = synthetic construct
SEQUENCE: 33
attgggggga ttagattctg ataatgtcac ggtac                           35

SEQ ID NO: 34          moltype = DNA  length = 37
FEATURE                Location/Qualifiers
misc_feature           1..37
                       note = Description of Artificial Sequence: Synthetic
                        oligonucleotide
source                 1..37
                       mol_type = other DNA
                       organism = synthetic construct
SEQUENCE: 34
ggttggattc agccccagat gttttatgtg acggaac                         37

SEQ ID NO: 35          moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 35
gttaaggaga gacggcattc attgatgtca cggcac                          36

SEQ ID NO: 36          moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 36
```

-continued

```
gttagcatca ggacaatacc ttcgatgtta cgggac                        36

SEQ ID NO: 37          moltype = DNA  length = 35
FEATURE                Location/Qualifiers
misc_feature           1..35
                       note = Description of Artificial Sequence: Synthetic
                        oligonucleotide
source                 1..35
                       mol_type = other DNA
                       organism = synthetic construct
SEQUENCE: 37
gttccgtgac atcaaaagcc gtccatttct caaac                         35

SEQ ID NO: 38          moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 38
cttgaagact aaaggaagga attgatgtca cggtac                        36

SEQ ID NO: 39          moltype =   length =
SEQUENCE: 39
000

SEQ ID NO: 40          moltype =   length =
SEQUENCE: 40
000

SEQ ID NO: 41          moltype =   length =
SEQUENCE: 41
000

SEQ ID NO: 42          moltype =   length =
SEQUENCE: 42
000

SEQ ID NO: 43          moltype =   length =
SEQUENCE: 43
000

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype =   length =
SEQUENCE: 47
000

SEQ ID NO: 48          moltype =   length =
SEQUENCE: 48
000

SEQ ID NO: 49          moltype =   length =
SEQUENCE: 49
000

SEQ ID NO: 50          moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
SEQUENCE: 50
AYLVGLYTLT PTHPGSGTEL GVVDQPIQRE RHTGFPVIWG QSLKGVLRSY LKLVEKVDEE  60
KINKIFGPPT EKAHEQAGLI SVGDAKILFF PVRSLKGVYA YVTSPLVLNR FKRDLELAGV  120
```

```
SEQ ID NO: 51          moltype = AA  length = 68
FEATURE                Location/Qualifiers
REGION                 1..68
                       note = Description of Artificial Sequence: Synthetic
                        polypeptide
source                 1..68
                       mol_type = protein
                       organism = synthetic construct
SEQUENCE: 51
HHHHDMLNSL HAITGKFKTQ SRLVVGLGDE SVYETSIRLL RNYGVPYIPG SAIKGVTRHL  60
TYYVLAEF                                                           68

SEQ ID NO: 52          moltype =   length =
SEQUENCE: 52
000

SEQ ID NO: 53          moltype =   length =
SEQUENCE: 53
000

SEQ ID NO: 54          moltype =   length =
SEQUENCE: 54
000

SEQ ID NO: 55          moltype =   length =
SEQUENCE: 55
000

SEQ ID NO: 56          moltype =   length =
SEQUENCE: 56
000

SEQ ID NO: 57          moltype =   length =
SEQUENCE: 57
000

SEQ ID NO: 58          moltype =   length =
SEQUENCE: 58
000

SEQ ID NO: 59          moltype =   length =
SEQUENCE: 59
000

SEQ ID NO: 60          moltype =   length =
SEQUENCE: 60
000

SEQ ID NO: 61          moltype =   length =
SEQUENCE: 61
000

SEQ ID NO: 62          moltype =   length =
SEQUENCE: 62
000

SEQ ID NO: 63          moltype =   length =
SEQUENCE: 63
000

SEQ ID NO: 64          moltype =   length =
SEQUENCE: 64
000

SEQ ID NO: 65          moltype =   length =
SEQUENCE: 65
000

SEQ ID NO: 66          moltype =   length =
SEQUENCE: 66
000

SEQ ID NO: 67          moltype =   length =
SEQUENCE: 67
000

SEQ ID NO: 68          moltype =   length =
SEQUENCE: 68
```

-continued

```
000

SEQ ID NO: 69          moltype =   length =
SEQUENCE: 69
000

SEQ ID NO: 70          moltype =   length =
SEQUENCE: 70
000

SEQ ID NO: 71          moltype =   length =
SEQUENCE: 71
000

SEQ ID NO: 72          moltype =   length =
SEQUENCE: 72
000

SEQ ID NO: 73          moltype =   length =
SEQUENCE: 73
000

SEQ ID NO: 74          moltype =   length =
SEQUENCE: 74
000

SEQ ID NO: 75          moltype =   length =
SEQUENCE: 75
000

SEQ ID NO: 76          moltype =   length =
SEQUENCE: 76
000

SEQ ID NO: 77          moltype =   length =
SEQUENCE: 77
000

SEQ ID NO: 78          moltype =   length =
SEQUENCE: 78
000

SEQ ID NO: 79          moltype =   length =
SEQUENCE: 79
000

SEQ ID NO: 80          moltype =   length =
SEQUENCE: 80
000

SEQ ID NO: 81          moltype =   length =
SEQUENCE: 81
000

SEQ ID NO: 82          moltype =   length =
SEQUENCE: 82
000

SEQ ID NO: 83          moltype =   length =
SEQUENCE: 83
000

SEQ ID NO: 84          moltype =   length =
SEQUENCE: 84
000

SEQ ID NO: 85          moltype =   length =
SEQUENCE: 85
000

SEQ ID NO: 86          moltype =   length =
SEQUENCE: 86
000

SEQ ID NO: 87          moltype =   length =
SEQUENCE: 87
000

SEQ ID NO: 88          moltype =   length =
```

-continued

```
SEQUENCE: 88
000

SEQ ID NO: 89           moltype =   length =
SEQUENCE: 89
000

SEQ ID NO: 90           moltype =   length =
SEQUENCE: 90
000

SEQ ID NO: 91           moltype =   length =
SEQUENCE: 91
000

SEQ ID NO: 92           moltype =   length =
SEQUENCE: 92
000

SEQ ID NO: 93           moltype =   length =
SEQUENCE: 93
000

SEQ ID NO: 94           moltype =   length =
SEQUENCE: 94
000

SEQ ID NO: 95           moltype =   length =
SEQUENCE: 95
000

SEQ ID NO: 96           moltype =   length =
SEQUENCE: 96
000

SEQ ID NO: 97           moltype =   length =
SEQUENCE: 97
000

SEQ ID NO: 98           moltype =   length =
SEQUENCE: 98
000

SEQ ID NO: 99           moltype =   length =
SEQUENCE: 99
000

SEQ ID NO: 100          moltype = DNA  length = 36
FEATURE                 Location/Qualifiers
misc_feature            1..36
                        note = Description of Artificial Sequence: Synthetic
                         oligonucleotide
misc_difference         5
                        note = modified_base - a, c, t or g
misc_difference         7
                        note = modified_base - a, c, t or g
misc_difference         9
                        note = modified_base - a, c, t or g
misc_difference         16
                        note = modified_base - a, c, t or g
source                  1..36
                        mol_type = other DNA
                        organism = synthetic construct
SEQUENCE: 100
gttrnrnanm rmcrsnwdyy wttratgtba cggdac                            36

SEQ ID NO: 101          moltype = DNA  length = 13
FEATURE                 Location/Qualifiers
misc_feature            1..13
                        note = Description of Artificial Sequence: Synthetic
                         oligonucleotide
source                  1..13
                        mol_type = other DNA
                        organism = synthetic construct
SEQUENCE: 101
accggctttt cca                                                     13

SEQ ID NO: 102          moltype = DNA  length = 338
FEATURE                 Location/Qualifiers
```

```
misc_feature           1..338
                       note = Description of Artificial Sequence: Synthetic
                        polynucleotide
source                 1..338
                       mol_type = other DNA
                       organism = synthetic construct
SEQUENCE: 102
ttttccgaat cggatgtggg attgctccgg ccctgcctta ttttcatata agaccggctt  60
atccgactat ctccctaata tgacagggaa aatatcttcc cggacttttc accgggatgg  120
tataagaaca gggaaccaga atcatctgtt ccctgaccac tggaaagttt ttcatatcag  180
tatgttgaat cctgtcaccc ctggggcacg gagggatttc caaatatccg atctgatgtt  240
cgtaatcacc ggcttttcca gccaatggct tgagatgatt taagaaactt gtgactggct  300
ttttctggta aaatggattt ttgtataata tcctgttg                          338

SEQ ID NO: 103         moltype = DNA  length = 791
FEATURE                Location/Qualifiers
misc_feature           1..791
                       note = Description of Artificial Sequence: Synthetic
                        polynucleotide
source                 1..791
                       mol_type = other DNA
                       organism = synthetic construct
SEQUENCE: 103
agagtcagga caacactctg taccatagtt gtgggataca gaaagccttt gattaccatc  60
ggaaatccca caaacatccc aatgtgtata taatgatttg atctcagcta tgcgttcctg  120
gtataagttt cttttcggtt ttgcctgcat tgtattaacc tcttttcttc ataaataata  180
aaattataaa atactaaacg ttgaaatatt atgcatctcc ttctcgaaaa atcagatcat  240
ataaaatcaa tttcacccct caccataata agacgtacac tgtgggtgaa aagtgacact  300
ctttttaaat atttttaaat tcaaataact gtttatattg agcaaatgga aatgcatcct  360
ttcctcgtgt tatcatcagt gctgtcattt gaattaatcg tatttaatgg agaaaaggtg  420
acaatttttt ataaaaagac ttgtacaaaa aaattaaatt gtactgaact tttttttgtc  480
actttggttt ggtgattaac gactgaatat attagagtat ttttttctct ttttattctt  540
gaaaaaattg ttcttgaata acagtgttta cttaactaaa gtacctctaa taaatatttg  600
ttcacaccaa aaacagtaag gttataaaga agaaatctgt catgaacaat acagaagaaa  660
acattgaccg tatccaggaa ccgaccagag aagacattga tagaaaagaa gcagaacggc  720
ttcttgatga ggcttttaat ccaaggacca aacccgtcga taggaagaag ataattaatt  780
ctgccctgaa g                                                       791

SEQ ID NO: 104         moltype = DNA  length = 304
FEATURE                Location/Qualifiers
misc_feature           1..304
                       note = Description of Artificial Sequence: Synthetic
                        polynucleotide
source                 1..304
                       mol_type = other DNA
                       organism = synthetic construct
SEQUENCE: 104
aagttgaaga gtgtatccat tactgaaaag ggtcaacgca catatcctgt agatgcatcc  60
ggtagcagga tagcggaaga ggtcagggat tatacgcaga aaccactaaa cgttgttgtg  120
ctgattatta aatatacata tgaagagtaa cgatatgaac atcactgtag aactcacctt  180
ctttgaaccc taccgtctgg ttgagtggtt tgactgggac gcaagaaaaa agagtcatag  240
cgcaatgaga ggtcaggctt tcgcgcagtg gacgtggaaa ggaaaaggtc gcacagcagg  300
caag                                                               304

SEQ ID NO: 105         moltype = DNA  length = 680
FEATURE                Location/Qualifiers
misc_feature           1..680
                       note = Description of Artificial Sequence: Synthetic
                        polynucleotide
source                 1..680
                       mol_type = other DNA
                       organism = synthetic construct
SEQUENCE: 105
agcaccgtta agaagtttgg attcatcagt aaaggtgatg gagaagatat ttttgaaaga  60
atcaaggaaa aatatattaa agcattggaa aacaatatac aattatttga gatctatttg  120
tcggatgaaa aggatactcg gaataaataa cagacaaacg gtttgcgaag aaatacgcga  180
cagggtgatt ggaccgtaac ctcatgatta tatgattgat acacgattta accctgactt  240
gccggttttt gaaaaagttc gcaaaccctg ttttgcttca tgaagtgagt tgggtttgcg  300
aaaaaaggtt attacagcct gatatctaag tagaagagta ccggtattga agaccaaagt  360
tgctgcgtat ggcggtccgg ttgtccttgc tttcgcaagg attccaatac tggaatcctc  420
ccgaaaggga ggtcgcaaaa ggccgttttt cgaaaaccat agtttcatac aaaccggcga  480
tgaggtttgc gaacttttg attgtagtaa gtattattaa aataatggct taatattttt  540
ggtatataca attctcaact ttttcacctt gccggaaatg aggtttgcga aattttagag  600
agccgcatat ctatattatt tacaatcagt tacaaaatgg ccccttctcg ccatatacgt  660
aacctcagag ttgttggagg                                              680

SEQ ID NO: 106         moltype = DNA  length = 386
FEATURE                Location/Qualifiers
misc_feature           1..386
```

```
                         note = Description of Artificial Sequence: Synthetic
                          polynucleotide
source                   1..386
                         mol_type = other DNA
                         organism = synthetic construct
SEQUENCE: 106
ggtttgattg aatattgatg gttgaaaatc gtctgcccta tgggggaggc aatgtcattg  60
aattaagggc aaaatatgga gtgcatcatc cctgcccgag aatgacacta cagtgtcaac  120
atccctttag gtaggcgtcc acgtcagcct ggcgggaatc cagcaacctc tgctttgaga  180
gtcaattcca ttttagttgt cacctttctg atagaatcct cgactaaatc agtaagatga  240
caactgatac tctacttgaa caatttttaa gcaagtccaa tttcatttct gcctatgagc  300
gtattgcctc aaagaaggct gcaggcggat tggataatgt cacggttgaa tcattcggca  360
accgactgga ccagcatatc agcaaa                                        386

SEQ ID NO: 107           moltype = DNA  length = 392
FEATURE                  Location/Qualifiers
misc_feature             1..392
                         note = Description of Artificial Sequence: Synthetic
                          polynucleotide
source                   1..392
                         mol_type = other DNA
                         organism = synthetic construct
SEQUENCE: 107
gttatccttg gccatttaga ggcttcggtc aaaaaggcgc tcgatgcggt cgaaaacatt  60
gcgtctggcc agccaagtaa tgaggactcg ccagtattac ccacgagccc ggcggaggtg  120
gcggttattc actggagcat aaaccagtga ccacaaattt ccggaaatga tgtccacttc  180
gatagtgtag atggtgcgga cgtatcaccc cttccccaag gcagctcaag gagagcaatg  240
atatgaatca aaatatcgat cgtgcggttg gtgcaattct agcgattgaa acagcgacac  300
cccttaccga atcttcaaca ctcgcgcaac gtgaaaggca tcagaagctg ctgcatgatg  360
aaaccaaaaa gattgagcaa gccttcatag cc                                 392

SEQ ID NO: 108           moltype = DNA  length = 1348
FEATURE                  Location/Qualifiers
misc_feature             1..1348
                         note = Description of Artificial Sequence: Synthetic
                          polynucleotide
source                   1..1348
                         mol_type = other DNA
                         organism = synthetic construct
SEQUENCE: 108
ctgcaaagct gttggatgcg ccaacccggt gccattttta atgatgagta catccgcctt  60
tattatgccg cctctttccg gatactgggt ttcccggaag ttgcgactac aaatatggcg  120
actgcaaccg cccaggagga aatagcatga ctaccggcaa cacttccgct tctcacccgc  180
aatttgtcac gttgacagtc tgtttgcgct tttgcagccc cttccagatc cgaccctgga  240
tcaaggaaac ggtgcgcaac aaggttaaaa tgccatccac tgtcaacgct catgctgaaa  300
ctgctcacct gccggatgac caggataccg acgacacaca agatctattg gaagaagaac  360
gttttgagcg gtatgccact gccgctgatt ggcacaaggg aagtatcaac ggaaacgcga  420
agtattcacc ctatgtgagg ggcgatctgg tccgcagcgt ggtggacagg gaattgcagg  480
agcatttcca ctgttataat gaaaagcttg ccaatgagaa taaggggtgc cctggaaaac  540
gggaccgcca tattaacgcc ggcggcaagg cgtccggttt tatggcacac ctgcccgcga  600
tcaaggaccc ggccggcaag gagatctgca agggcagcga taacatctgc ccggtctgcc  660
atttcctcgg ggcgtttgcg gaaggaataa agccggttaa gttcaggaat cggaagatct  720
ggccaagcag cgcggccgga actgttacag cgggcaaagc cggaaatccc ttgataattt  780
tactgtctgg gaagcggatc ataccgcctg ccctgttttc ttcggcagaa tcgaggtgaa  840
caaaactctt ttgccgaaag aacaaatcct cgccctgctg gctggcggcc ttgctcggct  900
tgacaatttg gcgggtgcgg cgagggaggc acttgggcta ccagacgacg agcaccaggc  960
actcctcaac gatttttcaa gatttttcat taatcccgag aaatcgcctg ctgtttatac  1020
ttcctccccg gttattgtcc ctgtccaggg agctgttgat aaggttgtgc tcttggaaaa  1080
agcccaagat atcgccggca gaattgccgc gtgtgtctcc gacaatcccc gccacctcca  1140
tcggctggct gcggctatcc ggaccctggg ctggccgggc cggtctcttg cttcggttat  1200
gactaaaaaa ccgggtaccg aagacaaggc caccctctgg ggaaaagaat cagcgagtaa  1260
atcggtcaag acgattctgg aagaatcaat ccaaggcttc actgtagaac aaaagcgaag  1320
ctttttgcc aaccttgccg accagctc                                       1348

SEQ ID NO: 109           moltype = DNA  length = 340
FEATURE                  Location/Qualifiers
misc_feature             1..340
                         note = Description of Artificial Sequence: Synthetic
                          polynucleotide
source                   1..340
                         mol_type = other DNA
                         organism = synthetic construct
SEQUENCE: 109
cgtatcaatc cggtacaact cgcccgaatg attttaccat ttgtaccttg gcatggtgca  60
tgtcctgctt tgctgaacga acaggtaatg atagaggcca aacgattgac tgagttagac  120
cgcgccaatt ggccatgttg aatgccagca caaccagcta atatatcgaa atcgctggca  180
aagttagctt ttattgtaaa attagatgat taggaacgat ccggcaggtt atttaaatga  240
agtaaagtct ggggtcgtag cataatcgca aaaaaaatta tttaacagaa acaaacaaat  300
agacagcata aagttgaatt gagtattata gaaagcaggg                         340
```

```
SEQ ID NO: 110          moltype = DNA  length = 100
FEATURE                 Location/Qualifiers
misc_feature            1..100
                        note = Description of Artificial Sequence: Synthetic
                         polynucleotide
source                  1..100
                        mol_type = other DNA
                        organism = synthetic construct
SEQUENCE: 110
tttttctgta actattcagc acaccatatt ttagcataac aactgagtag tcattggggc  60
atcataaatt gaggccattt cccttcaaat aataagcgca                        100

SEQ ID NO: 111          moltype = DNA  length = 841
FEATURE                 Location/Qualifiers
misc_feature            1..841
                        note = Description of Artificial Sequence: Synthetic
                         polynucleotide
source                  1..841
                        mol_type = other DNA
                        organism = synthetic construct
SEQUENCE: 111
gagacaaaag agcaacggga tatttttgtt cattttagcg ctattcgggg tgagggttat  60
aaaatcctgg aaccgggcga aaaagtacgt tttgaaatag gtgaggggag aaaaggtccc  120
caggccatca atgttattcg tataagatga caaaattact ccagtctcta ttctttttgt  180
aattacttgt tcgctgtttt gtgaagatta tattaagcta tggagctttc aggtaaaaaa  240
gcgtaaagta cgcgaatatt ctgcgtaaaa ctattccggc tatgaaagat gatgttcata  300
gccggaatag ttttttatcg agtttggtgg ggtattcatt ttgggagatg gttgatgaaa  360
gtttcaaggc agggtttcat ttattggcga tggtttaaat atctctttat tctttcttca  420
acaatctgat attattgttt ttttatctaa agatactctg tttttattta tcgtaaaata  480
ttcgacatac atatgaaacc tttgaaaagg caggagtttg gcgaagatgt agtgattgtg  540
gctaaaatta cggaaaaatt ttttttgtaa aattaaggtg atatgaatat agtttttctg  600
gtgcggtcgc caatttcctt ttttgaaatt aggaaactgg tttggcgaat tttttgacag  660
tatcttttta taataaatac gaatagttgt gattagacag gtgttaattt agtagtattt  720
cccctttaac tgaagaatga ttggcgtaat atttaataac atgagagaac tccttggtat  780
aatagagatt attaagtata gtgtcagaat gcagcttttg tttgttcttt gattctaaag  840
g                                                                  841

SEQ ID NO: 112          moltype = DNA  length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 112
tctcaaaata atgttaaaga aattttcatt ttattttgat ggtttaggcc acactgactt  60
tgtggttctc tttataccga tagaaaaatt ttattttttc gaaaaaaaac actcttccat  120
tcgtaaggtt aaataaaggc aattacttaa ccatctagca atggaggatt gatcatgaaa  180
agcacacatt ctctttttta ccgttttgct catgttgata cctttcgctc cgcatatgaa  240
agaatttctc taaaaaattc cagcccggga cttgatagag tttccgtaga agagttcggc  300
aagaaacttg aaaaaaatat ccaa                                         324

SEQ ID NO: 113          moltype = DNA  length = 303
FEATURE                 Location/Qualifiers
misc_feature            1..303
                        note = Description of Artificial Sequence: Synthetic
                         polynucleotide
source                  1..303
                        mol_type = other DNA
                        organism = synthetic construct
SEQUENCE: 113
attcaggcaa tcctcaatag attggggcag gaggtaaaag gtcgaggtaa ggctttaaca  60
ttgcaggaaa tgatccatcg gcaggcgcag ttgttgaaaa gctatttgat ggataaatct  120
gtttacaaac catatctggc aaggtggtaa cctatgaata cagtcgaatt acttcaggag  180
gaagaacgct tgaccctgga tttggtcttt ttgccaccag gtagtaagaa taaagagcaa  240
aaaaagaatg ctttggtaga ccttttgttg aaaatagtgg agcatgggga attaacccgt  300
aaa                                                                303

SEQ ID NO: 114          moltype = DNA  length = 403
FEATURE                 Location/Qualifiers
misc_feature            1..403
                        note = Description of Artificial Sequence: Synthetic
                         polynucleotide
source                  1..403
                        mol_type = other DNA
                        organism = synthetic construct
SEQUENCE: 114
```

```
atcgacaatg atgatacctc cgctgtgctc catagttcat taaaaagatt atttgagcat  60
tacgagaaga aaaatgaaaa aactcgtgca cagcttctct ataattgggc gtctttacgt  120
gttctcgctc ctgccaggga atttagttga aaaaaaatca taaaatttcc gaaaaaatag  180
atgatgtcga acgtaatagg ttttagagca acgaataacc gttgctctaa aacctatact  240
ctgggagaac atcatgaaaa aagagcacgg taaagaaaac tattctatcg aaacagttgt  300
tttcgtcgtt ttgcaggaca tcatgagtat tgttctaata ccgtttgcgg taatcgcctc  360
aatttatctt tcttattttt ttgagttatc tgtatacaaa tct                    403

SEQ ID NO: 115         moltype = DNA  length = 584
FEATURE                Location/Qualifiers
misc_feature           1..584
                       note = Description of Artificial Sequence: Synthetic
                        polynucleotide
source                 1..584
                       mol_type = other DNA
                       organism = synthetic construct
SEQUENCE: 115
ccccgcgtta tttatccggc cctgaagcag aaggatattc ctaacagcag gcttcccggg  60
tatgaggagt tgaagaagaa cctcaatatg gagaaacgga aagagatgct gacgacccct  120
tgggcccccct ggcatcccat caaaaaataa gatgcctgcg aattcccgga aatatgacag  180
cggatttaaa ggattgaacg gatatcattt tcccaaaaaa tgacagcgga tttaaaggat  240
tgagcggata tccgtttcat cctttgatcc gttgtcatat ttcctacaaa tatgtcgccc  300
ctacggggct ttaatccttt cctcttcttt gtgtcctttg tggctttgtg tgagaaaaac  360
aaaaaatttt tgtcacattt tcagcacaga acacgactaa gtatgcagag aagggaaacg  420
ccctcctttt ctttgtgtcc tttgtggctt tgtgtgagaa aaacaaaaaa tttttgtcac  480
attttcagca cgacatacga ctaagtttgc agaaagggaa aaaacatatc tttttactca  540
taaaggaggt tgccatgaaa aaaacattta tcgtctttgt tctg                    584

SEQ ID NO: 116         moltype = DNA  length = 602
FEATURE                Location/Qualifiers
misc_feature           1..602
                       note = Description of Artificial Sequence: Synthetic
                        polynucleotide
source                 1..602
                       mol_type = other DNA
                       organism = synthetic construct
SEQUENCE: 116
aagcgctggg caactgatga tctgctccgt atggtcgggg atcagatcac tgtgatgagg  60
gggttgctgg aaaagggaga ggattatcgg ccggtggttt acaacagccg gtattccagc  120
gggaagagcg gcctgaaaaa aaagacttga aaaggtcttg acatgggccg ggaaaggggc  180
tatgttcttc tgattataat atcagatcag agggaatatg gcccttatcc cgggaatatc  240
ctgtatttca ggggatcggg cctgttttcc gaatcggatg tgggattgct ccggccctgc  300
cttattttca tataagaccg gcttatccga ctatctccct aatatgacag ggaaaatatc  360
ttcccggact tttcaccggg atggtataag aacagggaac cagaatcatc tgttccctga  420
ccactggaaa gtttttcata tcagtatgtt gaatcctgtc acccctgggg cacggaggga  480
tttccaaata tccgatctga tgttcgtaat caccggcttt tccagccaat ggcttgagat  540
gatttaagaa acttgtgact ggctttttct ggtaaaatgg atttttgtat aatatcctgt  600
tg                                                                  602

SEQ ID NO: 117         moltype = DNA  length = 843
FEATURE                Location/Qualifiers
misc_feature           1..843
                       note = Description of Artificial Sequence: Synthetic
                        polynucleotide
source                 1..843
                       mol_type = other DNA
                       organism = synthetic construct
SEQUENCE: 117
cagctgggtc tcggcctggg cgccaaaatc cgccacgctc tgaccatccc aaccgccggc  60
cgcttttttg gcggctaccc gctgccaggc ggcggacaga ttttccatgg cggtgatggc  120
ggccagttga cgataggtgg tggtagacat cgggacggtg cctcctgcaa ggttctatcc  180
tgttggtcgt cgacgcaagg cctcaggtga ccccctctcc gttattctgc caattttttc  240
ctagggaccg gcctgggcac cgtctgcggc ggggggctgc cgttcaaccc cggccagggc  300
catggaccag attttctttg atttatcatc aggttggctc ctctttcgca aatgctccgg  360
cgccgcgagc ggccaaacca tttgcgaact tggccgatag gcgattattt tatggcaaat  420
caataagata agtgcttttg aggccctttg gcccctcggc ggcgaggggc caaaaagttc  480
gcaaatgccc ctttgggggc cgggcgcccc accatttgcg aaaaaacccg cccggcagcg  540
gccgaggctt ctgccggctg attatatctt atcgatataa ttgaatatta tttttcccca  600
agaccgggtc gaaggcctat tttcgcaaat gcccgccgcg ggccggggga gccaacgtgt  660
tgcgaaaatc cggttctaag caaatcaagg agttaggcca aaaaaagtga tttttggcaa  720
tccggccaag cgccctttgg gggcatttgc gaaaaaatcc ggccggcaaa aacttcttga  780
cattaccggg cattttccat tagagtattg cgtagcagta catatctagc tgatttctcc  840
gtt                                                                 843

SEQ ID NO: 118         moltype = DNA  length = 462
FEATURE                Location/Qualifiers
misc_feature           1..462
                       note = Description of Artificial Sequence: Synthetic
                        polynucleotide
```

```
source                  1..462
                        mol_type = other DNA
                        organism = synthetic construct
SEQUENCE: 118
tatgcgacgg ccttgggcca gcaggatgct ggccctacgg ggttgagcag aggcggcagg  60
ccttgaggac acgtttttga gggcgtttaa cggcaggcgc aggagacggg acgcgaagtg  120
gggttaggga aattaccgcc aggctggaga atagctggcg gtttttgttt ggggggccgg  180
aaaaattttc tgctcctgtc acctcgacgg ttccaagaga gactaatttg ttagaccagg  240
ctccagactg gaagtatttt tgggcgcggc cgcggtgacg gctgtccagc aagcggttgg  300
gacggtttaa acatgactgc aggacattac cagacgattt tggaggccca gattgagctg  360
gccttctgcc tgccggaaga ggcgcataat gtgctgtatg cgcgggatga ggcgtgccgt  420
gagctggtcc aagcctgccg caatcaccgg ggtagcctgc gt                    462

SEQ ID NO: 119          moltype = DNA  length = 315
FEATURE                 Location/Qualifiers
misc_feature            1..315
                        note = Description of Artificial Sequence: Synthetic
                         polynucleotide
source                  1..315
                        mol_type = other DNA
                        organism = synthetic construct
SEQUENCE: 119
gcagagaacg gaggcgcctg gttctatgaa cttttatggc aatggcacag ggatgaaata  60
ggacatctta gcaacataag gaatacgttt gaaagaatga aaagatttga taaatttgcc  120
ccctggaggt ccgtgggatt gggttggtga aaaaaagagg agtggatgtc tgcgcctgaa  180
tatgagatcg atctggataa cgatgaccac cctaccataa ttttaacaga catggatgaa  240
tgttatcata tatgccttaa agcggcagga aacgatccta gctgtgctcg atgcaagata  300
tttatggcag atttc                                                  315

SEQ ID NO: 120          moltype = DNA  length = 850
FEATURE                 Location/Qualifiers
misc_feature            1..850
                        note = Description of Artificial Sequence: Synthetic
                         polynucleotide
source                  1..850
                        mol_type = other DNA
                        organism = synthetic construct
SEQUENCE: 120
ttttaattga cccgcatttt ttgttatatc gaataaccat gaagaaaggc gtccttccca  60
ctccatctca aatctatcag gatttgtttc atagatatgt ttgagacgct ttcggcgctt  120
tgctttatct cttttggcgg cctttcccat tagtcctcct tcttagttca ataatggttt  180
tatccattga tttttcgacc tgatcagagg atctaaactc tgttgggccg gtacctaatt  240
tgatttaatc gaaagaacgt tgtacttttt atctcctcta attcttttgt ttcggatcgt  300
ctggatagtc gtgataaatc tcttacatgt tacagggaat cgtaattttt ctatctgaaa  360
tctcacaagc gctatttcga tagtcggggc taagtaaaaa aatgtgacat gaattgctgg  420
gccaccagaa gaaatttttc actaaccact atagtcttct ggaatgtgaa aaagtgacag  480
aaaaaatatg aggctaaaat gtcacatttt aaataaagcc ccgactataa ttatacggat  540
atatctatag acaacccctt ttgatgaaac cttacaccaa taatcggatg ttaaagttat  600
tgacattaca agatttaatg tgttatttat ttaggctcaa cttttctcaa accatccaga  660
ctatttcaaa atatctgtaa agataataag ggggaatgtt atgtattccg actttcctgc  720
acttaggtta cctgaattat ctgttgatca aaaaaaatta tttaagatct ccgggaccaa  780
cccacagctc atatacatct taatgaacga atttgatgga gagggggatg agcccttctt  840
taccggactt                                                        850

SEQ ID NO: 121          moltype = DNA  length = 308
FEATURE                 Location/Qualifiers
misc_feature            1..308
                        note = Description of Artificial Sequence: Synthetic
                         polynucleotide
source                  1..308
                        mol_type = other DNA
                        organism = synthetic construct
SEQUENCE: 121
gttttaaatc ttttattcat gaaagaaggt ctttttgatc attttttga gcaacaaaga  60
gaatggtgga aagaagagta tgaacatacc gattcgaaca cagctctcta tgattgcttg  120
tgttttcgaa tgtatcggtg ttatttttag gaaaatatat gccctcatac ccttgcttga  180
aatggaatgg cgattgtagc agatgtcctg attcggcaac atgcagaatc gcacagaaag  240
gtttgggaaa ggtatttacg gtttttttca agaaatatct ggcgcgttac tattcttcga  300
aatccgaa                                                          308

SEQ ID NO: 122          moltype = DNA  length = 367
FEATURE                 Location/Qualifiers
misc_feature            1..367
                        note = Description of Artificial Sequence: Synthetic
                         polynucleotide
source                  1..367
                        mol_type = other DNA
                        organism = synthetic construct
SEQUENCE: 122
```

```
atgatgaggc ggtttttctt tgataccagt gcgcttatca aactctatca tgaagaaact  60
ggtacagaaa aactggattc tctgatcgag gccgaaaatc cagttatcat taatgatatg  120
aaattgcctg gcgttatgag ctaatcctta tattaaatgc ttcaggcatc tgaaccttgc  180
aacatatcag gatggtatat aaaccacagg aggaatgatg gaatataccc ttaccctaaa  240
tttcattgaa ccgtttcgct tgattgaatg gcacgatgcg ccagatcggg aaaaccttcg  300
attgaggggg ttttcttttg ccagatggca taaggacagg gaattcggac tgggaaggcc  360
atatatt                                                            367

SEQ ID NO: 123          moltype = DNA  length = 363
FEATURE                 Location/Qualifiers
misc_feature            1..363
                        note = Description of Artificial Sequence: Synthetic
                         polynucleotide
source                  1..363
                        mol_type = other DNA
                        organism = synthetic construct
SEQUENCE: 123
aatggaatcc aggtccgtta tccaaaattg gaaaaagaaa aaaaagatga cccaggtgaa  60
aagccgggct atcttgagct ggcagatggc cctttcagca cggaaaatcg caaggaaaaa  120
ttaaaggaga tttggggtaa ttgggcctga ttaaccaaat atcgaataat caccaaatac  180
atagcctatt ttcaatgata ttcaatagtt ataataccta tttaataatt caatatttat  240
agaatccaag gattatgcat cgccaaaaat acatccataa acgatttaac aatatgaatt  300
tacaaaatga atttatacca ttgggtttta agaatctttt ataataagca aacatagggg  360
ggg                                                                363

SEQ ID NO: 124          moltype = DNA  length = 439
FEATURE                 Location/Qualifiers
misc_feature            1..439
                        note = Description of Artificial Sequence: Synthetic
                         polynucleotide
source                  1..439
                        mol_type = other DNA
                        organism = synthetic construct
SEQUENCE: 124
gatgttccgc caggcacggc agcgattctc cttgggcttt gtagagacgt ggacagattg  60
agggccgcca ttgattcaat tgtttcgggc aagaagacgc gggatgatac gatattctgg  120
atactatacc acaccgtgcc ggagaaatag ggcctgtcgc caaatccact cgggccttcc  180
actacaaaaa ggcttaactc gatagtatat gggtttcctt tttttgagtc cgccggaggc  240
ggacgttgta taaaatcgcg aagtgatttt atgtactgga gaggatatca tggtcacgcc  300
acaagcttct aagaaccccg cagtagatga aatcctgaaa cagctcacac cctatgacat  360
ggagactgag aacgcaaagg ctatcgagac aaggaagtct tgtattgagt gcctgaaagg  420
catttgcgaa agggctcaa                                               439

SEQ ID NO: 125          moltype = DNA  length = 365
FEATURE                 Location/Qualifiers
misc_feature            1..365
                        note = Description of Artificial Sequence: Synthetic
                         polynucleotide
source                  1..365
                        mol_type = other DNA
                        organism = synthetic construct
SEQUENCE: 125
atattgcgcg ataacgggga agatatattt gtccatcgga gcgatattaa tggtagcctt  60
ggcaccctga cagaaggca aaaagtaatc tttgaggtga agcagggtcc aaagggactc  120
caggccacaa atgtgaaggt aatttcataa tcacttggcc gtattgcacc ttaccacaat  180
atctttttga gaatttcata agagctcatt tcaaagtgaa tattcaatcc acggctgttg  240
aaaaaaagcg aaacgccctt gctctttttg tgcgccttct cctttcatcg cctctcaagg  300
actacgtcgc caagataatc ctgtttggaa gtgtgagaaa aggaaaagct aattcagaga  360
gtgat                                                              365

SEQ ID NO: 126          moltype = DNA  length = 344
FEATURE                 Location/Qualifiers
misc_feature            1..344
                        note = Description of Artificial Sequence: Synthetic
                         polynucleotide
source                  1..344
                        mol_type = other DNA
                        organism = synthetic construct
SEQUENCE: 126
tgcttgaaat ggcgtgggca tttgcttttg gccccggctg atatctactc ggcaaagcca  60
caccatacaa taatggaggc tgattcaatg tgacataaaa ttttggggta gcgtctacat  120
gcaaaaatct cggtggtgat tcgtttatac ttatagagtg gatcattttc tgagccgaca  180
cccgagattg agctatgact gccacaatat ttgacaaatt tgcaagcttt gaaaacttct  240
gggccgcctt ccaaaaagtt gctgcaaaga attcagcggg cggcatagac ggcacaaccg  300
ttgagaccta ccaaaagcga gccaagcaac gaatcaatgc cctc                   344

SEQ ID NO: 127          moltype =   length =
SEQUENCE: 127
000
```

-continued

SEQ ID NO: 128 moltype = length =
SEQUENCE: 128
000

SEQ ID NO: 129 moltype = length =
SEQUENCE: 129
000

SEQ ID NO: 130 moltype = length =
SEQUENCE: 130
000

SEQ ID NO: 131 moltype = length =
SEQUENCE: 131
000

SEQ ID NO: 132 moltype = length =
SEQUENCE: 132
000

SEQ ID NO: 133 moltype = length =
SEQUENCE: 133
000

SEQ ID NO: 134 moltype = length =
SEQUENCE: 134
000

SEQ ID NO: 135 moltype = length =
SEQUENCE: 135
000

SEQ ID NO: 136 moltype = length =
SEQUENCE: 136
000

SEQ ID NO: 137 moltype = length =
SEQUENCE: 137
000

SEQ ID NO: 138 moltype = length =
SEQUENCE: 138
000

SEQ ID NO: 139 moltype = length =
SEQUENCE: 139
000

SEQ ID NO: 140 moltype = length =
SEQUENCE: 140
000

SEQ ID NO: 141 moltype = length =
SEQUENCE: 141
000

SEQ ID NO: 142 moltype = length =
SEQUENCE: 142
000

SEQ ID NO: 143 moltype = length =
SEQUENCE: 143
000

SEQ ID NO: 144 moltype = length =
SEQUENCE: 144
000

SEQ ID NO: 145 moltype = length =
SEQUENCE: 145
000

SEQ ID NO: 146 moltype = length =
SEQUENCE: 146
000

SEQ ID NO: 147 moltype = length =
SEQUENCE: 147

000

SEQ ID NO: 148 moltype = length =
SEQUENCE: 148
000

SEQ ID NO: 149 moltype = length =
SEQUENCE: 149
000

SEQ ID NO: 150 moltype = length =
SEQUENCE: 150
000

SEQ ID NO: 151 moltype = length =
SEQUENCE: 151
000

SEQ ID NO: 152 moltype = length =
SEQUENCE: 152
000

SEQ ID NO: 153 moltype = length =
SEQUENCE: 153
000

SEQ ID NO: 154 moltype = length =
SEQUENCE: 154
000

SEQ ID NO: 155 moltype = length =
SEQUENCE: 155
000

SEQ ID NO: 156 moltype = length =
SEQUENCE: 156
000

SEQ ID NO: 157 moltype = length =
SEQUENCE: 157
000

SEQ ID NO: 158 moltype = length =
SEQUENCE: 158
000

SEQ ID NO: 159 moltype = length =
SEQUENCE: 159
000

SEQ ID NO: 160 moltype = length =
SEQUENCE: 160
000

SEQ ID NO: 161 moltype = length =
SEQUENCE: 161
000

SEQ ID NO: 162 moltype = length =
SEQUENCE: 162
000

SEQ ID NO: 163 moltype = length =
SEQUENCE: 163
000

SEQ ID NO: 164 moltype = length =
SEQUENCE: 164
000

SEQ ID NO: 165 moltype = length =
SEQUENCE: 165
000

SEQ ID NO: 166 moltype = length =
SEQUENCE: 166
000

SEQ ID NO: 167 moltype = length =

-continued

SEQUENCE: 167
000

SEQ ID NO: 168 moltype = length =
SEQUENCE: 168
000

SEQ ID NO: 169 moltype = length =
SEQUENCE: 169
000

SEQ ID NO: 170 moltype = length =
SEQUENCE: 170
000

SEQ ID NO: 171 moltype = length =
SEQUENCE: 171
000

SEQ ID NO: 172 moltype = length =
SEQUENCE: 172
000

SEQ ID NO: 173 moltype = length =
SEQUENCE: 173
000

SEQ ID NO: 174 moltype = length =
SEQUENCE: 174
000

SEQ ID NO: 175 moltype = length =
SEQUENCE: 175
000

SEQ ID NO: 176 moltype = length =
SEQUENCE: 176
000

SEQ ID NO: 177 moltype = length =
SEQUENCE: 177
000

SEQ ID NO: 178 moltype = length =
SEQUENCE: 178
000

SEQ ID NO: 179 moltype = length =
SEQUENCE: 179
000

SEQ ID NO: 180 moltype = length =
SEQUENCE: 180
000

SEQ ID NO: 181 moltype = length =
SEQUENCE: 181
000

SEQ ID NO: 182 moltype = length =
SEQUENCE: 182
000

SEQ ID NO: 183 moltype = length =
SEQUENCE: 183
000

SEQ ID NO: 184 moltype = length =
SEQUENCE: 184
000

SEQ ID NO: 185 moltype = length =
SEQUENCE: 185
000

SEQ ID NO: 186 moltype = length =
SEQUENCE: 186
000

-continued

```
SEQ ID NO: 187          moltype =   length =
SEQUENCE: 187
000

SEQ ID NO: 188          moltype =   length =
SEQUENCE: 188
000

SEQ ID NO: 189          moltype =   length =
SEQUENCE: 189
000

SEQ ID NO: 190          moltype =   length =
SEQUENCE: 190
000

SEQ ID NO: 191          moltype =   length =
SEQUENCE: 191
000

SEQ ID NO: 192          moltype =   length =
SEQUENCE: 192
000

SEQ ID NO: 193          moltype =   length =
SEQUENCE: 193
000

SEQ ID NO: 194          moltype =   length =
SEQUENCE: 194
000

SEQ ID NO: 195          moltype =   length =
SEQUENCE: 195
000

SEQ ID NO: 196          moltype =   length =
SEQUENCE: 196
000

SEQ ID NO: 197          moltype =   length =
SEQUENCE: 197
000

SEQ ID NO: 198          moltype =   length =
SEQUENCE: 198
000

SEQ ID NO: 199          moltype =   length =
SEQUENCE: 199
000

SEQ ID NO: 200          moltype =   length =
SEQUENCE: 200
000

SEQ ID NO: 201          moltype =   length =
SEQUENCE: 201
000

SEQ ID NO: 202          moltype =   length =
SEQUENCE: 202
000

SEQ ID NO: 203          moltype =   length =
SEQUENCE: 203
000

SEQ ID NO: 204          moltype =   length =
SEQUENCE: 204
000

SEQ ID NO: 205          moltype =   length =
SEQUENCE: 205
000

SEQ ID NO: 206          moltype =   length =
SEQUENCE: 206
000
```

SEQ ID NO: 207 moltype = length =
SEQUENCE: 207
000

SEQ ID NO: 208 moltype = length =
SEQUENCE: 208
000

SEQ ID NO: 209 moltype = length =
SEQUENCE: 209
000

SEQ ID NO: 210 moltype = length =
SEQUENCE: 210
000

SEQ ID NO: 211 moltype = length =
SEQUENCE: 211
000

SEQ ID NO: 212 moltype = length =
SEQUENCE: 212
000

SEQ ID NO: 213 moltype = length =
SEQUENCE: 213
000

SEQ ID NO: 214 moltype = length =
SEQUENCE: 214
000

SEQ ID NO: 215 moltype = length =
SEQUENCE: 215
000

SEQ ID NO: 216 moltype = length =
SEQUENCE: 216
000

SEQ ID NO: 217 moltype = length =
SEQUENCE: 217
000

SEQ ID NO: 218 moltype = length =
SEQUENCE: 218
000

SEQ ID NO: 219 moltype = length =
SEQUENCE: 219
000

SEQ ID NO: 220 moltype = length =
SEQUENCE: 220
000

SEQ ID NO: 221 moltype = length =
SEQUENCE: 221
000

SEQ ID NO: 222 moltype = length =
SEQUENCE: 222
000

SEQ ID NO: 223 moltype = length =
SEQUENCE: 223
000

SEQ ID NO: 224 moltype = length =
SEQUENCE: 224
000

SEQ ID NO: 225 moltype = length =
SEQUENCE: 225
000

SEQ ID NO: 226 moltype = length =
SEQUENCE: 226

000

SEQ ID NO: 227 moltype = length =
SEQUENCE: 227
000

SEQ ID NO: 228 moltype = length =
SEQUENCE: 228
000

SEQ ID NO: 229 moltype = length =
SEQUENCE: 229
000

SEQ ID NO: 230 moltype = length =
SEQUENCE: 230
000

SEQ ID NO: 231 moltype = length =
SEQUENCE: 231
000

SEQ ID NO: 232 moltype = length =
SEQUENCE: 232
000

SEQ ID NO: 233 moltype = length =
SEQUENCE: 233
000

SEQ ID NO: 234 moltype = length =
SEQUENCE: 234
000

SEQ ID NO: 235 moltype = length =
SEQUENCE: 235
000

SEQ ID NO: 236 moltype = length =
SEQUENCE: 236
000

SEQ ID NO: 237 moltype = length =
SEQUENCE: 237
000

SEQ ID NO: 238 moltype = length =
SEQUENCE: 238
000

SEQ ID NO: 239 moltype = length =
SEQUENCE: 239
000

SEQ ID NO: 240 moltype = length =
SEQUENCE: 240
000

SEQ ID NO: 241 moltype = length =
SEQUENCE: 241
000

SEQ ID NO: 242 moltype = length =
SEQUENCE: 242
000

SEQ ID NO: 243 moltype = length =
SEQUENCE: 243
000

SEQ ID NO: 244 moltype = length =
SEQUENCE: 244
000

SEQ ID NO: 245 moltype = length =
SEQUENCE: 245
000

SEQ ID NO: 246 moltype = length =

SEQUENCE: 246
000

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252
000

SEQ ID NO: 253 moltype = length =
SEQUENCE: 253
000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

-continued

SEQ ID NO: 266 moltype = length =
SEQUENCE: 266
000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =
SEQUENCE: 272
000

SEQ ID NO: 273 moltype = length =
SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

```
SEQ ID NO: 286          moltype =   length =
SEQUENCE: 286
000

SEQ ID NO: 287          moltype =   length =
SEQUENCE: 287
000

SEQ ID NO: 288          moltype =   length =
SEQUENCE: 288
000

SEQ ID NO: 289          moltype =   length =
SEQUENCE: 289
000

SEQ ID NO: 290          moltype =   length =
SEQUENCE: 290
000

SEQ ID NO: 291          moltype =   length =
SEQUENCE: 291
000

SEQ ID NO: 292          moltype =   length =
SEQUENCE: 292
000

SEQ ID NO: 293          moltype =   length =
SEQUENCE: 293
000

SEQ ID NO: 294          moltype =   length =
SEQUENCE: 294
000

SEQ ID NO: 295          moltype =   length =
SEQUENCE: 295
000

SEQ ID NO: 296          moltype =   length =
SEQUENCE: 296
000

SEQ ID NO: 297          moltype =   length =
SEQUENCE: 297
000

SEQ ID NO: 298          moltype =   length =
SEQUENCE: 298
000

SEQ ID NO: 299          moltype =   length =
SEQUENCE: 299
000

SEQ ID NO: 300          moltype = AA  length = 7
FEATURE                 Location/Qualifiers
source                  1..7
                        mol_type = protein
                        organism = Simian virus 40
SEQUENCE: 300
PKKKRKV                                                     7

SEQ ID NO: 301          moltype = AA  length = 16
FEATURE                 Location/Qualifiers
REGION                  1..16
                        note = Description of Unknown: Nucleoplasmin bipartite NLS
                         sequence
source                  1..16
                        mol_type = protein
                        organism = unidentified
SEQUENCE: 301
KRPAATKKAG QAKKKK                                           16

SEQ ID NO: 302          moltype = AA  length = 9
FEATURE                 Location/Qualifiers
REGION                  1..9
```

```
                        note = Description of Unknown: C-myc NLS sequence
source                  1..9
                        mol_type = protein
                        organism = unidentified
SEQUENCE: 302
PAAKRVKLD                                                                9

SEQ ID NO: 303          moltype = AA  length = 11
FEATURE                 Location/Qualifiers
REGION                  1..11
                        note = Description of Unknown: C-myc NLS sequence
source                  1..11
                        mol_type = protein
                        organism = unidentified
SEQUENCE: 303
RQRRNELKRS P                                                             11

SEQ ID NO: 304          moltype = AA  length = 38
FEATURE                 Location/Qualifiers
source                  1..38
                        mol_type = protein
                        organism = Homo sapiens
SEQUENCE: 304
NQSSNFGPMK GGNFGGRSSG PYGGGGQYFA KPRNQGGY                                38

SEQ ID NO: 305          moltype = AA  length = 42
FEATURE                 Location/Qualifiers
REGION                  1..42
                        note = Description of Unknown: IBB domain from
                         importin-alpha sequence
source                  1..42
                        mol_type = protein
                        organism = unidentified
SEQUENCE: 305
RMRIZFKNKG KDTAELRRRR VEVSVELRKA KKDEQILKRR NV                           42

SEQ ID NO: 306          moltype = AA  length = 8
FEATURE                 Location/Qualifiers
REGION                  1..8
                        note = Description of Unknown: Myoma T protein sequence
source                  1..8
                        mol_type = protein
                        organism = unidentified
SEQUENCE: 306
VSRKRPRP                                                                 8

SEQ ID NO: 307          moltype = AA  length = 8
FEATURE                 Location/Qualifiers
REGION                  1..8
                        note = Description of Unknown: Myoma T protein sequence
source                  1..8
                        mol_type = protein
                        organism = unidentified
SEQUENCE: 307
PPKKARED                                                                 8

SEQ ID NO: 308          moltype = AA  length = 8
FEATURE                 Location/Qualifiers
source                  1..8
                        mol_type = protein
                        organism = Homo sapiens
SEQUENCE: 308
PQPKKKPL                                                                 8

SEQ ID NO: 309          moltype = AA  length = 12
FEATURE                 Location/Qualifiers
source                  1..12
                        mol_type = protein
                        organism = Mus musculus
SEQUENCE: 309
SALIKKKKKM AP                                                            12

SEQ ID NO: 310          moltype = AA  length = 5
FEATURE                 Location/Qualifiers
source                  1..5
                        mol_type = protein
                        organism = unidentified
                        note = Influenza virus
SEQUENCE: 310
```

-continued

```
DRLRR                                                       5

SEQ ID NO: 311          moltype = AA  length = 7
FEATURE                 Location/Qualifiers
source                  1..7
                        mol_type = protein
                        organism = unidentified
                        note = Influenza virus
SEQUENCE: 311
PKQKKRK                                                     7

SEQ ID NO: 312          moltype = AA  length = 10
FEATURE                 Location/Qualifiers
source                  1..10
                        mol_type = protein
                        organism = unidentified
                        note = Hepatitis delta virus
SEQUENCE: 312
RKLKKKIKKL                                                  10

SEQ ID NO: 313          moltype = AA  length = 10
FEATURE                 Location/Qualifiers
source                  1..10
                        mol_type = protein
                        organism = Mus musculus
SEQUENCE: 313
REKKKFLKRR                                                  10

SEQ ID NO: 314          moltype = AA  length = 20
FEATURE                 Location/Qualifiers
source                  1..20
                        mol_type = protein
                        organism = Homo sapiens
SEQUENCE: 314
KRKGDEVDGV DEVAKKKSKK                                       20

SEQ ID NO: 315          moltype = AA  length = 17
FEATURE                 Location/Qualifiers
source                  1..17
                        mol_type = protein
                        organism = Homo sapiens
SEQUENCE: 315
RKCLQAGMNL EARKTKK                                          17

SEQ ID NO: 316          moltype = AA  length = 793
FEATURE                 Location/Qualifiers
REGION                  1..793
                        note = Description of Unknown:
                         Aquatic-freshwater-freshwater sediment sequence
source                  1..793
                        mol_type = protein
                        organism = unidentified
SEQUENCE: 316
MSSLPTPLEL LKQKHADLFK GLQFSSKDNK MAGKVLKKDG EEAALAFLSE RGVSRGELPN  60
FRPPAKTLVV AQSRPFEEFP IYRVSEAIQL YVYSLSVKEL ETVPSGSSTK KEHQRFFQDS  120
SVPDFGYTSV QGLNKIFGLA RGIYLGVITR GENQLQKAKS KHEALNKKRR ASGEAETEFD  180
PTPYEYMTPE RKLAKPPGVN HSIMCYVDIS VDEFDFRNPD GIVLPSEYAG YCREINTAIE  240
KGTVDRLGHL KGGPGYIPGH QRKESTTEGP KINFRKGRIR RSYTALYAKR DSRRVRQGKL  300
ALPSYRHHMM RLNSNAESAI LAVIFFGKDW VVFDLRGLLR NVRWRNLFVD GSTPSTLLGM  360
FGDPVIDPKR GVVAFCYKEQ IVPVVSKSIT KMVKAPELLN KLYLKSEDPL VLVAIDLGQT  420
NPVGVGVYRV MNASLDYEVV TRFALESELL REIESYRQRT NAFEAQIRAE TFDAMTSEEQ  480
EEITRVRAFS ASKAKENVCH RFGMPVDAVD WATMGSNTIH IAKWVMRHGD PSLVEVLEYR  540
KDNEIKLDKN GVPKKVKLTD KRIANLTSIR LRFSQETSKH YNDTMWELRR KHPVYQKLSK  600
SKADFSRRVV NSIIRRVNHL VPRARIVFII EDLKNLGKVF HGSGKRELGW DSYFEPKSEN  660
RWFIQVLHKA FSETGKHKGY YIIECWPNWT SCTCPKCSCC DSENRHGEVF RCLACGYTCN  720
TDFGTAPDNL VKIATTGKGL PGPKKRCKGS SKGKNPKIAR SSETGVSVTE SGAPKVKKSS  780
PTQTSQSSSQ SAP                                              793

SEQ ID NO: 317          moltype = AA  length = 761
FEATURE                 Location/Qualifiers
REGION                  1..761
                        note = Description of Unknown: Terrestrial-soil-arctic peat
                         soil sequence
source                  1..761
                        mol_type = protein
                        organism = unidentified
SEQUENCE: 317
MSNKTTPPSP LSLLLRAHFP GLKFESQDYK IAGKKLRDGG PEAVISYLTG KGQAKLKDVK  60
PPAKAFVIAQ SRPFIEWDLV RVSRQIQEKI FGIPATKGRP KQDGLSETAF NEAVASLEVD  120
```

-continued

```
GKSKLNEETR AAFYEVLGLD APSLHAQAQN ALIKSAISIR EGVLKKVENR NEKNLSKTKR  180
RKEAGEEATF VEEKAHDERG YLIHPPGVNQ TIPGYQAVVI KSCPSDFIGL PSGCLAKESA  240
EALTDYLPHD RMTIPKGQPG YVPEWQHPLL NRRKNRRRRD WYSASLNKPK ATCSKRSGTP  300
NRKNSRTDQI QSGRFKGAIP VLMRFQDEWV IIDIRGLLRN ARYRKLLKEK STIPDLLSLF  360
TGDPSIDMRQ GVCTFIYKAG QACSAKMVKT KNAPEILSEL TKSGPVVLVS IDLGQTNPIA  420
AKVSRVTQLS DGQLSHETLL RELLSNDSSD GKEIARYRVA SDRLRDKLAN LAVERLSPEH  480
KSEILRAKND TPALCKARVC AALGLNPEMI AWDKMTPYTE FLATAYLEKG GDRKVATLKP  540
KNRPEMLRRD IKFKGTEGVR IEVSPEAAEA YREAQWDLQR TSPEYLRLST WKQELTKRIL  600
NQLRHKAAKS SQCEVVVMAF EDLNIKMMHG NGKWADGGWD AFFIKKRENR WFMQAFHKSL  660
TELGAHKGVP TIEVTPHRTS ITCTKCGHCD KANRDGERFA CQKCGFVAHA DLEIATDNIE  720
RVALTGKPMP KPESERSGDA KKSVGARKAA FKPEEDAEAA E                      761

SEQ ID NO: 318         moltype = AA  length = 721
FEATURE                Location/Qualifiers
REGION                 1..721
                       note = Description of Unknown: Terrestrial-soil-forest soil
                        sequence
source                 1..721
                       mol_type = protein
                       organism = unidentified
SEQUENCE: 318
MISKMIKPTV SQFLTPGFKL IRNHSRTAGL KLKNEGEEAC KKFVRENEIP KDECPNFQGG  60
PAIANIIAKS REFTEWEIYQ SSLAIQEVIF TLPKDKLPEP ILKEEWRAQW LSEHGLDTVP  120
YKEAAGLNLI IKNAVNTYKG VQVKVDNKNK NNLAKINRKN EIAKLNGEQE ISFEEIKAFD  180
DKGYLLQKPS PNKSIYCYQS VSPKPFITSK YHNVNLPEEY IGYYRKSNEP IVSPYQFDRL  240
RIPIGEPGYV PKWQYTFLSK KENKRRKLSK RIKNVSPILG IICIKKDWCV FDMRGLLRTN  300
HWKKYHKPTD SINDLFDYFT GDPVIDTKAN VVRFRYKMEN GIVNYKPVRE KKGKELLENI  360
CDQNGSCKLA TVDVGQNNPV AIGLFELKKV NGELTKTLIS RHPTPIDFCN KITAYRERYD  420
KLESSIKLDA IKQLTSEQKI EVDNYNNNFT PQNTKQIVCS KLNINPNDLP WDKMISGTHF  480
ISEKAQVSNK SEIYFTSTDK GKTKDVMKSD YKWFQDYKPK LSKEVRDALS DIEWRLRRES  540
LEFNKLSKSR EQDARQLANW ISSMCDVIGI ENLVKKNNFF GGSGKREPGW DNFYKPKKEN  600
RWWINAIHKA LTELSQNKGK RVILLPAMRT SITCPKCKYC DSKNRNGEKF NCLKCGIELN  660
ADIDVATENL ATVAITAQSM PKPTCERSGD AKKPVRARKA KAPEFHDKLA PSYTVVLREA  720
V                                                                  721

SEQ ID NO: 319         moltype =   length =
SEQUENCE: 319
000

SEQ ID NO: 320         moltype = DNA  length = 42
FEATURE                Location/Qualifiers
misc_feature           1..42
                       note = Description of Artificial Sequence: Synthetic
                        oligonucleotide
misc_difference        7
                       note = modified_base - a, c, t, g, unknown or other
misc_difference        11
                       note = modified_base - a, c, t, g, unknown or other
misc_difference        28
                       note = modified_base - a, c, t, g, unknown or other
source                 1..42
                       mol_type = other DNA
                       organism = synthetic construct
SEQUENCE: 320
acgshwncra nvcyhdywsa kkgsyymnwd yrhkgrgacs ag                     42

SEQ ID NO: 321         moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 321
cctgcgaagc cttttgattg ctcagtacgc tgagac                            36

SEQ ID NO: 322         moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 322
cctgcgaaac cttttgattg ctcagtacgc tgagac                            36

SEQ ID NO: 323         moltype = DNA  length = 36
```

-continued

```
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 323
cctgcgaaac cttttgattg ctcagttcgc tgagac                            36

SEQ ID NO: 324         moltype = DNA  length = 31
FEATURE                Location/Qualifiers
misc_feature           1..31
                       note = Description of Artificial Sequence: Synthetic
                        oligonucleotide
source                 1..31
                       mol_type = other DNA
                       organism = synthetic construct
SEQUENCE: 324
cccttttgat tgcccaattc gttgggacca g                                 31

SEQ ID NO: 325         moltype = DNA  length = 37
FEATURE                Location/Qualifiers
misc_feature           1..37
                       note = Description of Artificial Sequence: Synthetic
                        oligonucleotide
source                 1..37
                       mol_type = other DNA
                       organism = synthetic construct
SEQUENCE: 325
ggatccaatc ctttttgatt gcccaattcg ttgggac                           37

SEQ ID NO: 326         moltype = DNA  length = 41
FEATURE                Location/Qualifiers
misc_feature           1..41
                       note = Description of Artificial Sequence: Synthetic
                        oligonucleotide
source                 1..41
                       mol_type = other DNA
                       organism = synthetic construct
SEQUENCE: 326
acggatccaa tcctttttga ttgcccaatt cgttgggacg a                      41

SEQ ID NO: 327         moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 327
ctttcaagac taatagattg ctccttacga ggagac                            36

SEQ ID NO: 328         moltype = DNA  length = 36
FEATURE                Location/Qualifiers
misc_feature           1..36
                       note = Description of Artificial Sequence: Synthetic
                        oligonucleotide
source                 1..36
                       mol_type = other DNA
                       organism = synthetic construct
SEQUENCE: 328
ccaacaacac ccgctcaggg gttccagtac tgagac                            36
```

CRISPR-ASSOCIATED SYSTEMS AND COMPONENTS

CROSS REFERENCE TO RELATED APPLICATIONS

This application is a continuation of U.S. patent application Ser. No. 16/862,261, filed on Apr. 29, 2020, now U.S. Pat. No. 11,667,904, which is a continuation of International Application No, PCT/US2019/032750, filed on May 16, 2019, which claims the benefit of priority of U.S. Application No. 62/672,489, filed on May 16, 2018. The contents of the foregoing applications are hereby incorporated by reference in their entirety.

SEQUENCE LISTING

The instant application contains a Sequence Listing which has been submitted electronically in XML format and is hereby incorporated by reference in its entirety. Said XML copy, created on Jul. 25, 2023, is named 0041US2_A2186-703221_SL.xml and is 214,875 bytes in size.

FIELD OF THE INVENTION

The present disclosure relates to novel CRISPR systems and components, and methods and compositions for the use of CRISPR systems in, for example, nucleic acid detection.

BACKGROUND

Recent application of advances in genome sequencing technologies and analysis have yielded significant insights into the genetic underpinning of biological activities in many diverse areas of nature, ranging from prokaryotic biosynthetic pathways to human pathologies. To fully understand and evaluate the vast quantities of information produced by genetic sequencing technologies, equivalent increases in the scale, efficacy, and ease of technologies for genome and epigenome manipulation are needed. These novel genome and epigenome engineering technologies will accelerate the development of novel applications in numerous areas, including biotechnology, agriculture, and human therapeutics.

Clustered Regularly Interspaced Short Palindromic Repeats (CRIS:PR) and the CRISPR-associated (Cas) genes, collectively known as the CRISPR-Cas or CRISPR/Cas systems, are currently understood to provide immunity to bacteria and archaea against phage infection. The CRISPR-Cas systems of prokaryotic adaptive immunity are an extremely diverse group of proteins effectors, non-coding elements, as well as loci architectures, some examples of which have been engineered and adapted to produce important biotechnologies.

The components of the system involved in host defense include one or more effector proteins capable of modifying DNA or RNA and an RNA guide element that is responsible to targeting these protein activities to a specific sequence on the phage DNA or RNA. The RNA guide is composed of a CRISPR RNA (crRNA) and may require an additional trans-activating RNA (tracrRNA) to enable targeted nucleic acid manipulation by the effector protein(s). The crRNA consists of a direct repeat responsible for protein binding to the crRNA and a spacer sequence that is complementary to the desired nucleic acid target sequence. CRISPR systems can be reprogrammed to target alternative DNA or RNA targets by modifying the spacer sequence of the crRNA.

Citation or identification of any document in this application is not an admission that such document is available as prior art to the present invention.

SUMMARY

The present disclosure provides methods for computational identification of new CRISPR-Cas systems from genomic databases, together with the development of the natural loci into engineered systems, and experimental validation and application translation.

In one aspect, the present disclosure relates to non-naturally occurring Clustered Regularly Interspaced Short Palindromic Repeat (CRISPR)—Cas systems of CLUST.019911 (Type III-E) including a Type III-E RNA guide or a nucleic acid encoding the Type III-E RNA guide, where the Type III-E RNA guide includes a direct repeat sequence and a spacer sequence capable of hybridizing to a target nucleic acid; and at least one Type III-E CRISPR-Cas effector protein or a nucleic acid encoding the effector protein, where the effector protein includes an amino acid sequence that is at least 80% (e.g., 85, 90, 91, 92, 93, 94, 95, 96, 97, 98, 99, or 100%) identical to an amino acid sequence provided in Table 2 or Table 3; where the Type III-E CRISPR-Cas effector protein is capable of binding to the Type III-E RNA guide and of targeting the target nucleic acid sequence complementary to the spacer sequence.

In some embodiments, the Type III-E CRISPR-Cas system also includes two or more Type III-E RNA guides. In some embodiments, the Type III-E RNA guide includes a direct repeat sequence, a spacer sequence, and a second direct repeat sequence, arranged in order within Type III-E the RNA guide. In some embodiments, the Type III-E CRISPR-Cas system includes at least one Repeat Associated Mysterious Protein (RAMP) domain. In certain embodiments, the Type III-E CRISPR-Cas effector protein also includes two or more Repeat Associated Mysterious Protein (RAMP) domains. In some of these embodiments, the RAMP-domain includes at least about 1400 amino acids or least about 1550 amino acids.

In some embodiments, the RAMP-domain includes an amino acid sequence that is homologous to CRISPR Cmr4, CRISPR Cmr6, or CRISPR Cas7. In certain embodiments, the RAMP-domain does not include an amino acid sequence that is homologous to CRISPR Cas10 or CRISPR Cas 5.

In some embodiments, the Type III-E CRISPR-Cas effector also includes a protease domain. In some of these embodiments, the protease domain is activated when the system binds to the target nucleic acid, thereby exhibiting protease activity. In certain embodiments, the protease activity is a peptidase activity, e.g., an endopeptidase or exopeptidase activity, e.g., the protease domain can be a caspase domain. In some embodiments, the caspase domain is a Caspase HetF Associated with Tprs (CHAT) domain.

In some embodiments, the target nucleic acid is a transcriptionally active site.

In certain embodiments, the direct repeat sequence includes a nucleotide sequence that is at least 80% (e.g., 85%, 90%, 91%, 92%, 93%, 94%, 95%, 96%, 97%, 98%, 99%, or 100%) identical to a nucleotide sequence provided in Table 4.

In some embodiments, the target nucleic acid is a DNA or a RNA.

In another aspect, the targeting of the target nucleic acid by the Type III-E CRISPR-Cas effector protein and Type III-E RNA guide results in a modification in the target nucleic acid. For example, the modification of the target nucleic acid can be a cleavage event, such as a double-stranded cleavage event or a single-stranded cleavage event. In some embodiments, the modification of the target nucleic acid is a deletion or an insertion event.

In some embodiments, the system inserts a nucleic acid sequence into a DNA via reverse transcription from an RNA template.

In another aspect, the Type III-E CRISPR-Cas effector protein has non-specific protease activity or non-specific nuclease activity. For example, the non-specific activity can be reduced after targeting the target nucleic acid sequence. In some embodiments, the modification results in cell toxicity.

In another aspect, the Type III-E CRISPR-Cas system is present within a cell. For example the cell can be a eukaryotic cell, such as a prokaryotic cell or a eukaryotic cell.

In other aspects, the Type III-E CRISPR-Cas system includes a tracrRNA.

In yet another aspect, the present disclosure relates to methods of targeting and editing a target nucleic acid. The methods include contacting the target nucleic acid with a Type III-E CRISPR-Cas system described herein.

In another aspect, the present disclosure relates to methods of detecting a target nucleic acid in a sample, wherein the methods include contacting the sample with a Type III-E CRISPR-Cas system described herein and a labeled reporter nucleic acid, where hybridization of the Type III-E guide RNA to the target nucleic acid causes cleavage of the labeled reporter nucleic acid; and measuring a detectable signal produced by cleavage of the labeled reporter nucleic acid, thereby detecting the presence of the target nucleic acid in the sample.

In some embodiments, the methods further include comparing a level of the detectable signal with a reference signal level, and determining an amount of target nucleic acid in the sample based on the level of the detectable signal.

In some embodiments, the measuring is performed using gold nanoparticle detection, fluorescence polarization, colloid phase transition/dispersion, electrochemical detection, or semiconductor based-sensing.

In certain embodiments, the labeled reporter nucleic acid includes a fluorescence-emitting dye pair, a fluorescence resonance energy transfer (FRET) pair, or a quencher/fluorophore pair, where cleavage of the labeled reporter nucleic acid by the effector protein results in an increase or a decrease of the amount of signal produced by the labeled reporter nucleic acid.

In another aspect, the present disclosure relates to methods of detecting a target nucleic acid in a sample, wherein the methods include contacting the sample with a Type III-E CRISPR-Cas system described herein and a labeled reporter peptide, where hybridization of the Type III-E guide RNA to the target nucleic acid causes cleavage of the labeled reporter peptide; and measuring a detectable signal produced by cleavage of the labeled reporter peptide, thereby detecting the presence of the target nucleic acid in the sample.

In yet another aspect, the present disclosure relates to methods of specifically editing a double-stranded nucleic acid, wherein the methods include contacting, under sufficient conditions and for a sufficient amount of time, a Type III-E CRISPR-Cas effector protein and one other enzyme with sequence-specific nicking activity, and a crRNA that guides the Type III-E CRISPR-Cas effector protein to nick the opposing strand relative to the activity of the other sequence-specific nickase; and the double-stranded nucleic acid, where the method results in the formation of a double-stranded break.

In another aspect, the present disclosure relates to methods of editing a double-stranded nucleic acid. The methods include contacting, under sufficient conditions and for a sufficient amount of time, a fusion protein including a the Type III-E CRISPR-Cas effector and a protein domain with DNA modifying activity and a Type III-E RNA guide targeting the double-stranded nucleic acid; and the double-stranded nucleic acid, where the Type III-E CRISPR-Cas effector of the fusion protein is modified to nick a non-target strand of the double-stranded nucleic acid.

In yet another aspect, the present disclosure relates to methods of inducing genotype-specific or transcriptional-state-specific cell death or dormancy in a cell, wherein the methods include contacting a cell with a Type III-E CRISPR-Cas system described herein, where the RNA guide hybridizing to the target DNA causes a collateral DNase activity-mediated cell death or dormancy.

In some embodiments of these methods, the cell is a prokaryotic cell such as an infectious cell or a cell infected with an infectious agent, or a eukaryotic cell such as a mammalian cell. For example, the cell can be a cancer cell. In some embodiments, the cell is a cell infected with a virus, a cell infected with a prion, a fungal cell, a protozoan, or a parasite cell.

In another aspect, the present disclosure relates to methods of treating a condition or disease in a subject in need thereof, e.g., in a human or animal subject. The methods include administering to the subject a Type III-E CRISPR-Cas system described herein, where the spacer sequence is complementary to at least 12 nucleotides of a target nucleic acid associated with the condition or disease; where the Type III-E CRISPR-Cas effector protein associates with the Type III-E RNA guide to form a complex; where the complex binds to a target nucleic acid sequence that is complementary to the at least 12 nucleotides of the spacer sequence; and where upon binding of the complex to the target nucleic acid sequence the Type III-E CRISPR-Cas effector protein cleaves the target nucleic acid, thereby treating the condition or disease in the subject.

In some embodiments, the condition or disease is a cancer or an infectious disease. For example, the cancer can be selected from the group consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

In some embodiments, the Type III-E CRISPR-Cas system described herein is for use as a medicament.

In some embodiments, the Type III-E CRISPR-Cas system described herein is for use in the treatment or prevention of a cancer or an infectious disease.

The term "cleavage event," as used herein, refers to a DNA break in a target nucleic acid created by a nuclease of a CRISPR system described herein. In some embodiments, the cleavage event is a double-stranded DNA break. In some embodiments, the cleavage event is a single-stranded DNA break.

The term "CRISPR-Cas system" as used herein refers to nucleic acids and/or proteins involved in the expression of, or directing the activity of, CRISPR-Cas effectors, including sequences encoding CRISPR-Cas effectors, RNA guides, and other sequences and transcripts from a CRISPR locus.

The term "CRISPR array" as used herein refers to the nucleic acid (e.g., DNA) segment that includes CRISPR repeats and spacers, starting with the first nucleotide of the first CRISPR repeat and ending with the last nucleotide of the last (terminal) CRISPR repeat. Typically, each spacer in a CRISPR array is located between two repeats. The term "CRISPR repeat," or "CRISPR direct repeat," or "direct repeat," as used herein, refers to multiple short direct repeating sequences, which show very little or no sequence variation within a CRISPR array.

The term "CRISPR RNA" or "crRNA" as used herein refers to an RNA molecule comprising a guide sequence used by a CRISPR effector to specifically target a nucleic acid sequence. In some embodiments, the crRNA contains a sequence that mediates target recognition and a sequence that forms a duplex with a tracrRNA. The crRNA:tracrRNA duplex binds to a CRISPR effector.

The term "donor template nucleic acid," as used herein refers to a nucleic acid molecule that can be used by one or more cellular proteins to alter the structure of a target nucleic acid after a CRISPR enzyme described herein has altered a target nucleic acid. In some embodiments, the donor template nucleic acid is a double-stranded nucleic acid. In some embodiments, the donor template nucleic acid is a single-stranded nucleic acid. In some embodiments, the donor template nucleic acid is linear. In some embodiments, the donor template nucleic acid is circular (e.g., a plasmid). In some embodiments, the donor template nucleic acid is an exogenous nucleic acid molecule. In some embodiments, the donor template nucleic acid is an endogenous nucleic acid molecule (e.g., a chromosome).

The term "CRISPR-Cas effector," "CRISPR effector," "effector," "CRISPR-associated protein," "CRISPR enzyme," "Type CRISPR-Cas effector protein," "Type CRISPR-Cas effector," or "Type III-E effector" as used herein refers to a protein that carries out an enzymatic activity or that binds to a target site on a nucleic acid specified by an RNA guide.

In some embodiments, a Type III-E CRISPR-Cas effector protein has nuclease activity, peptidase activity, or protease activity.

The term "RNA guide" as used herein refers to any RNA molecule that facilitates the targeting of a protein described herein to a target nucleic acid. Exemplary "RNA guides" include, but are not limited to, crRNAs, as well as crRNAs fused to tracrRNAs. In some embodiments, an RNA guide includes both a crRNA and a tracrRNA, either as separate RNAs (dual guide) or fused into a single RNA.

As used herein, the term "targeting" refers to the ability of a complex including a CRISPR-associated protein and an RNA guide, such as a crRNA, to preferentially or specifically bind to, e.g., hybridize to, a specific target nucleic acid compared to other nucleic acids that do not have the same or similar sequence as the target nucleic acid.

The terms "trans-activating crRNA." or "tracrRNA" as used herein refer to an RNA including an anti-repeat region complementary to all or part of the direct repeat sequence of a CRISPR RNA (crRNA). A CRISPR effector bound to the crRNA and tracrRNA (RNA guide) form a functional complex capable of binding to a target nucleic acid.

A "transcriptionally-active site" as used herein refers to a site in a nucleic acid sequence comprising promoter regions at which transcription is initiated and actively occurring.

The term "collateral nuclease activity," "collateral DNase activity," or "collateral RNase activity" as used herein in reference to a CRISPR enzyme, refers to non-specific nuclease activity of a CRISPR enzyme after the enzyme has specifically targeted a nucleic acid.

The term "collateral peptidase activity" or "collateral protease activity" as used herein in reference to a CRISPR enzyme, refers to non-specific peptidase or protease activity of a CRISPR enzyme after the enzyme has specifically targeted a nucleic acid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF FIGURE DESCRIPTION

The figures are a series of schematics and nucleic acid and amino acid sequences that represent the results of locus analysis of various protein clusters.

FIG. 1 is a schematic that shows conserved Effector A (e_A), Effector B (e_B), and CRISPR array elements by bacterial genome accession and species for representative Type III-E (CLUST.019911) loci, FIG. 2 is a schematic of a consensus sequence (SEQ ID NO:100) and a multiple sequence alignment under the consensus sequence that are examples of Type III-E direct repeat elements described herein (SEQ ID NOs:27-38).

FIG. 5 is a schematic representation of PFAM domain mapping results for Type III-E (CLUST.019911) Effector A proteins; a schematic of HHpred domain predictions of an exemplary CLUST.019911 Effector A is depicted below, with a C-terminal match to the CHAT domain, and an N-terminal match to the TPR domain.

Figure 7A:
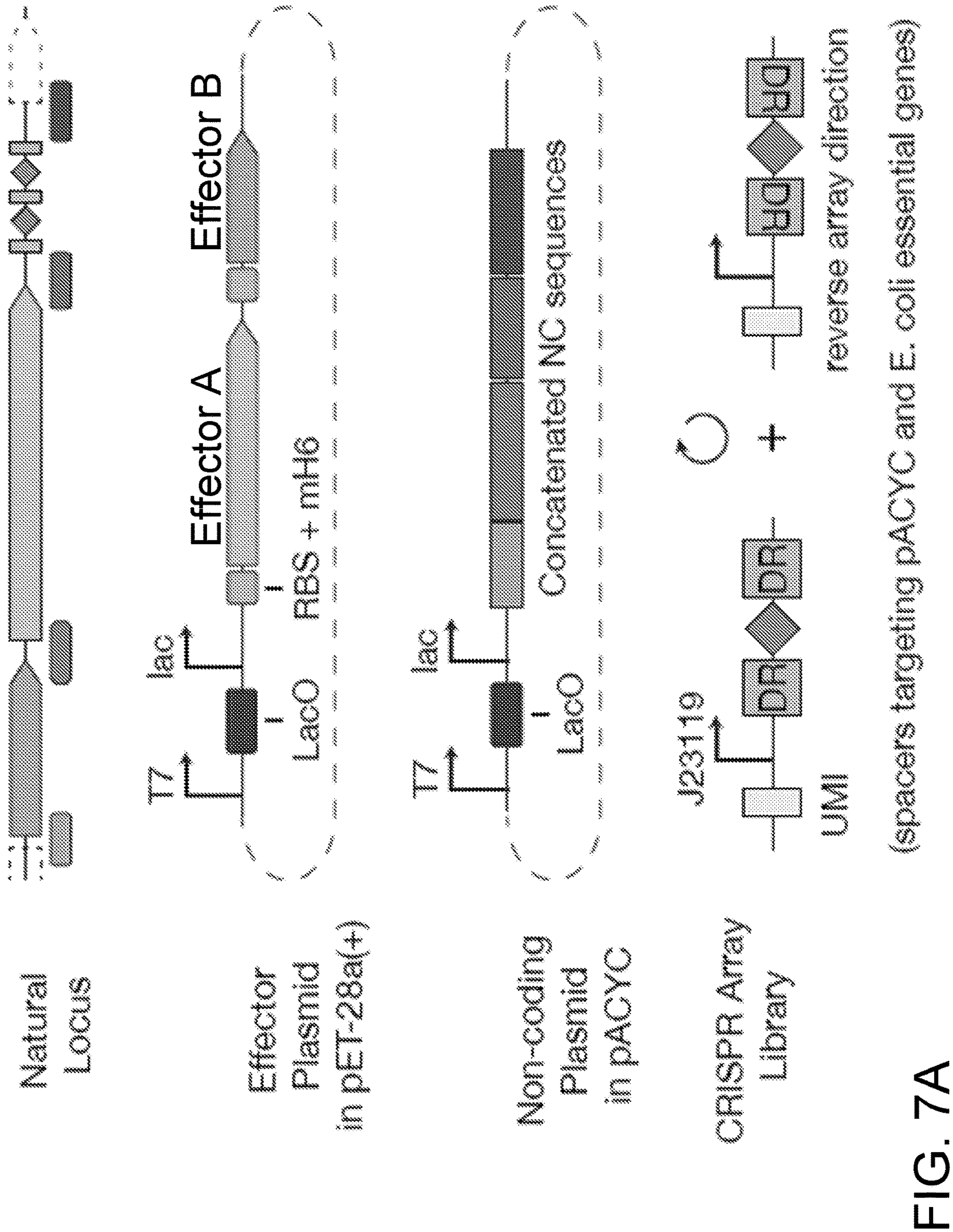
FIG. 7A is a schematic representation of the design of in vivo screen Effector and Non-coding Plasmids. CRISPR array libraries were designed including non-repetitive spacers uniformly sampled from both strands of pACYC184 or *E. coli* essential genes flanked by two DRs and expressed by J23119.
Figure 7B:
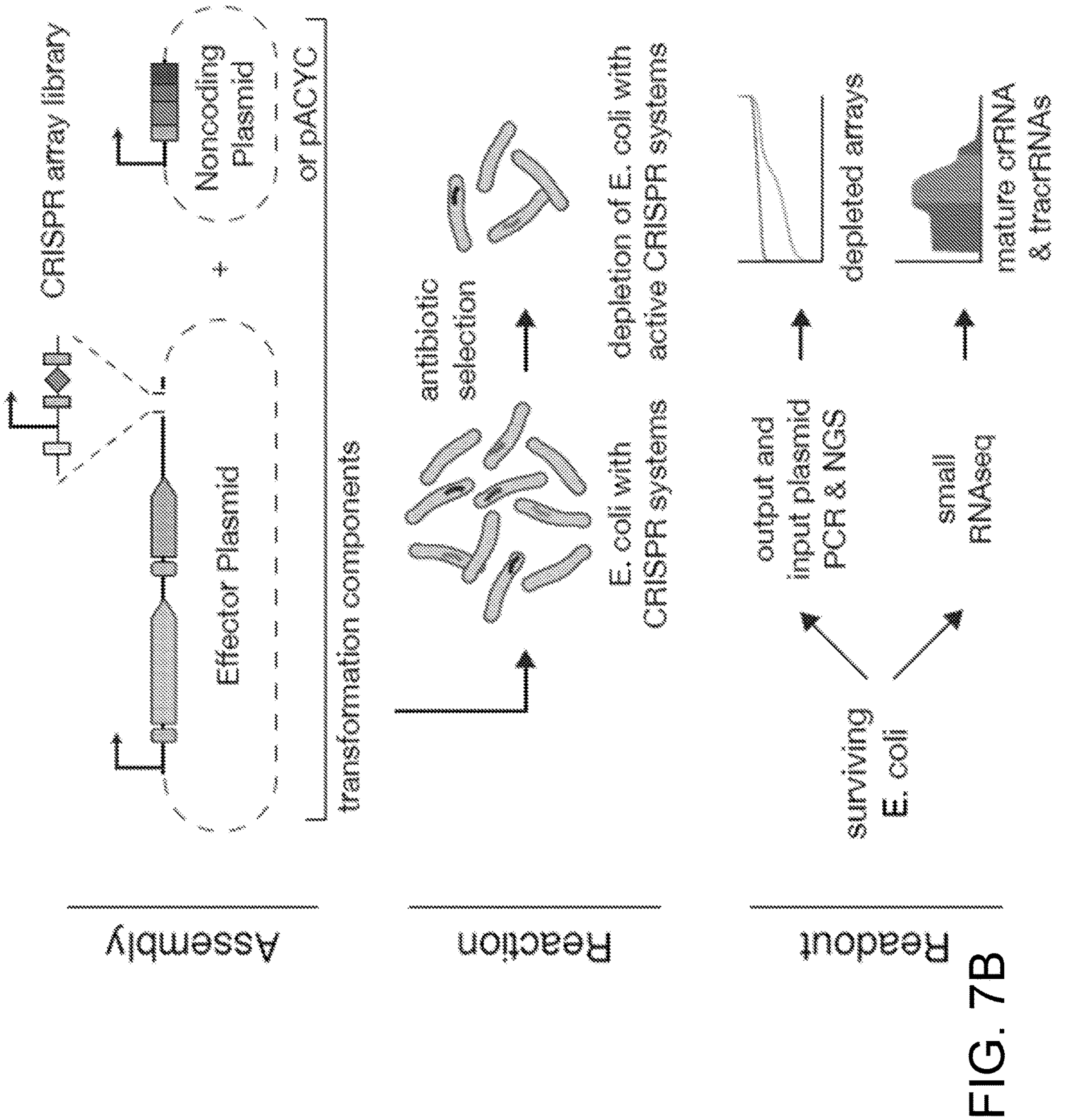

FIG. 7B is a schematic representation of the negative selection screening workflow; 1) CRISPR array libraries were cloned into the Effector Plasmid, 2) the Effector Plasmid and, when present, the Non-coding Plasmid were transformed into *E. coli* followed by outgrowth for negative selection of CRISPR arrays conferring interference against DNA or RNA transcripts from pACYC184 or *E. coli* essential genes, and 3) Targeted sequencing of the Effector Plasmid was used to identify depleted CRISPR arrays and small RNA sequencing was used to identify mature crRNAs and tracrRNAs.

Figure 8:
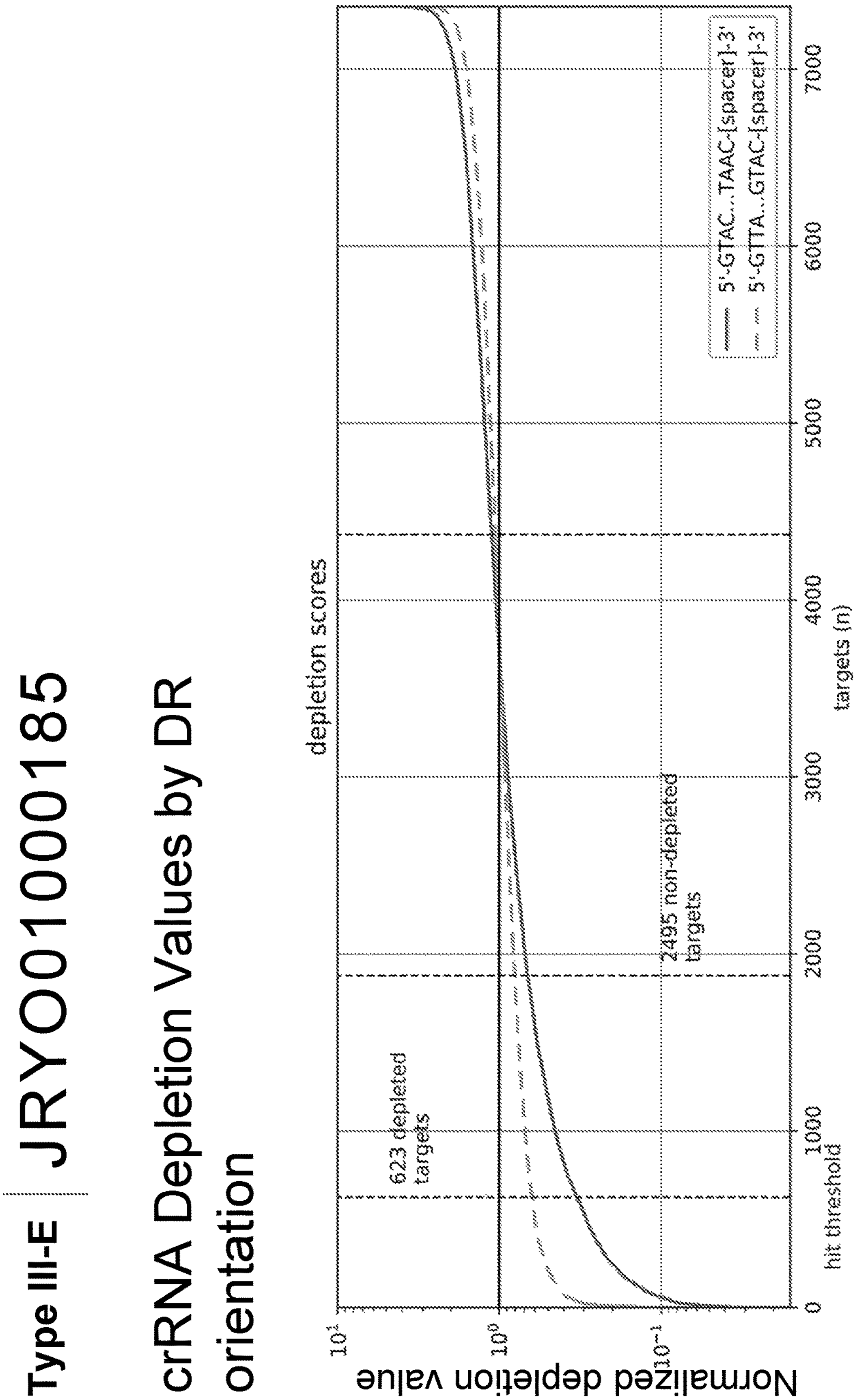

FIG. 8 is a graph that shows depletion values for crRNAs targeting pACYC and *E. coli* essential genes. To quantify depletion, a fold-depletion ratio was calculated as $R_{treated}/R_{input}$ for each direct repeat and spacer. The normalized input read count is computed as:

$R_{input}$=(1+#reads containing crRNA)/total reads without expressing the Type III-E system and RNA guide. The treated read count is computed as:

$R_{treated}$=(1+#reads containing crRNA)/total reads with expression of the Type III-E system and RNA guide. A strongly depleted target has a fold depletion greater than 3, which is marked by the vertical line "hit threshold."

Figure 9:
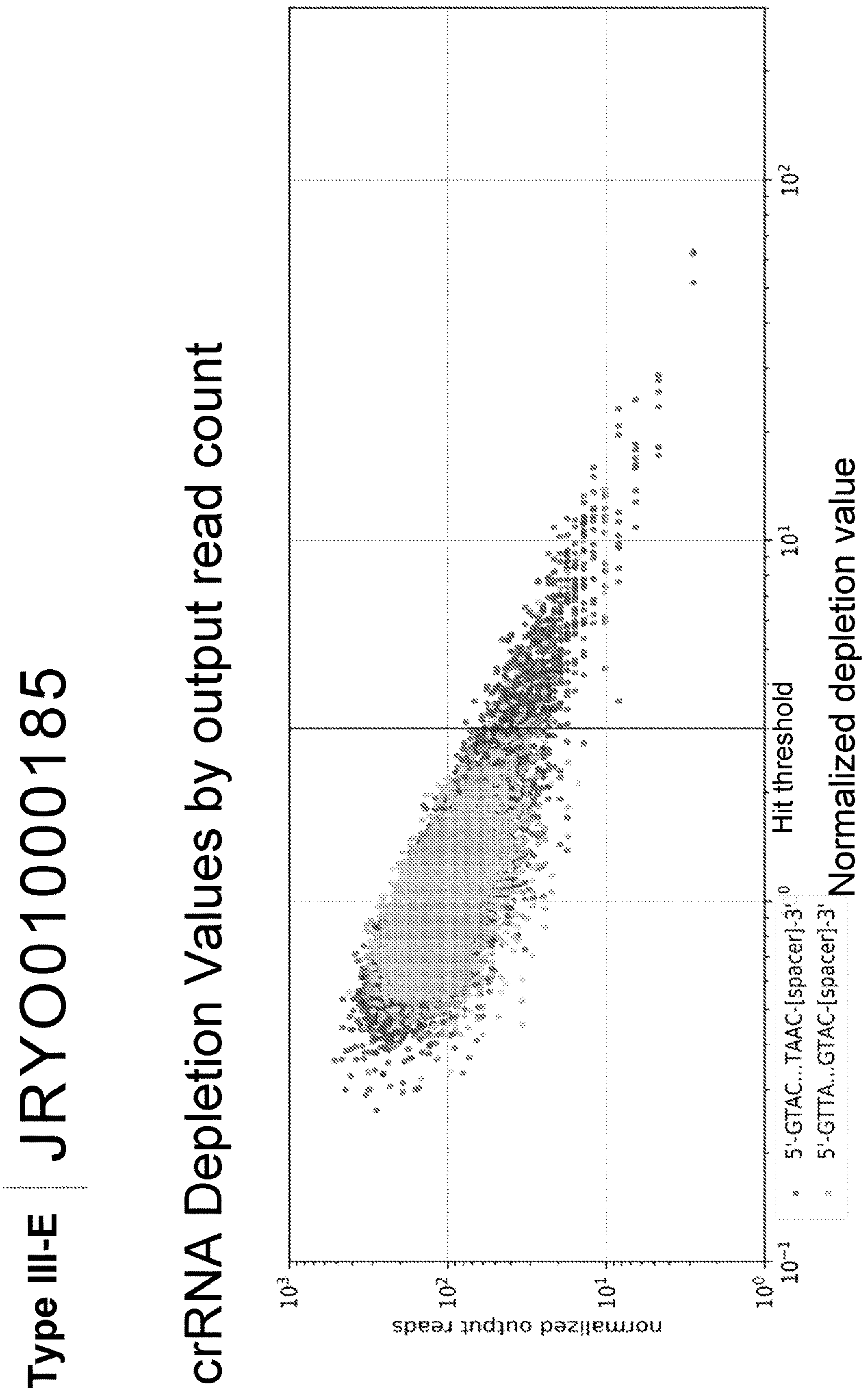

FIG. 9 is a scatter plot where the depletion value and output read count is depicted for each Type III-E system and crRNA tested. Notably, many of the points with high depletion value fall in the range where normalized output read counts are high.

Figure 10:
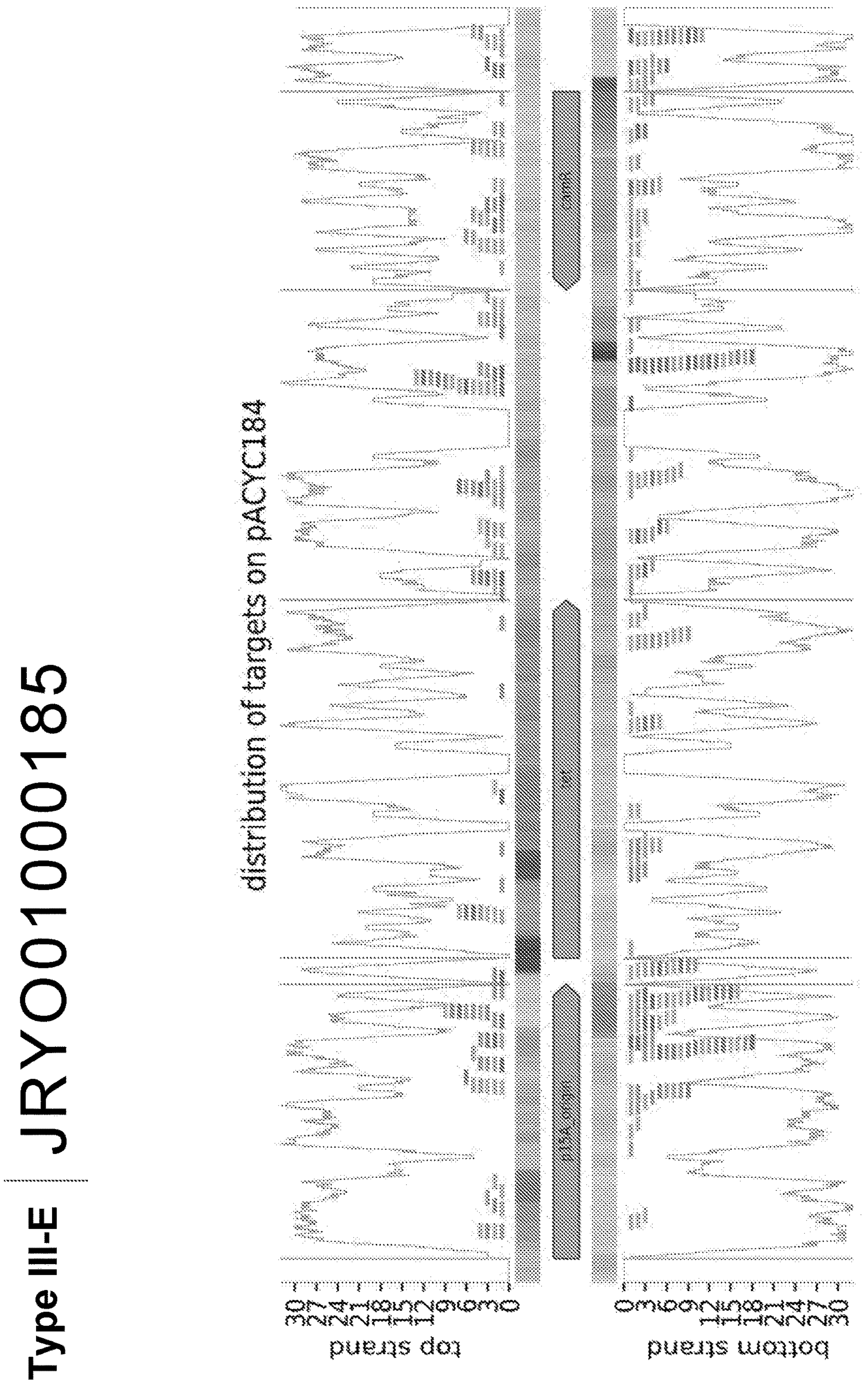

FIG. 10 is a graphic representation of the location of depleted and non-depleted crRNAs for the Type III-E system JRY0010001.85 targeting the pACYC184 plasmid. Targets on the top strand and bottom strand are shown separately, and in relation to the orientation of the annotated genes.

Figure 11:
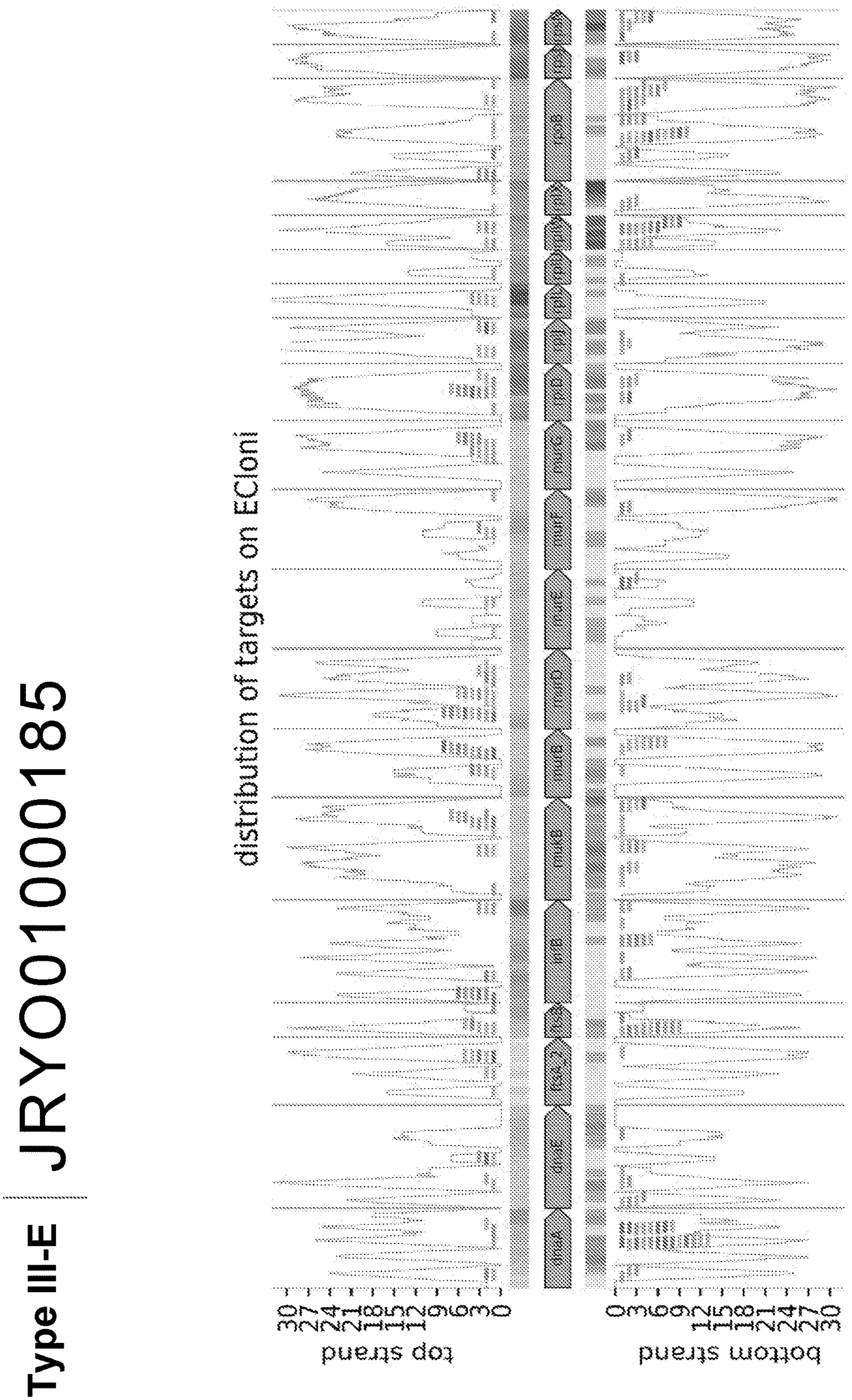

FIG. 11 is a graphic representation of the location of depleted and non-depleted crRNAs for the Type III-E system JRY0010001.85 targeting *E. coli* essential genes (strain *E. Cioni.*). Targets on the top strand and bottom strand are shown separately, and in relation to the orientation of the annotated genes.

Figure 12:
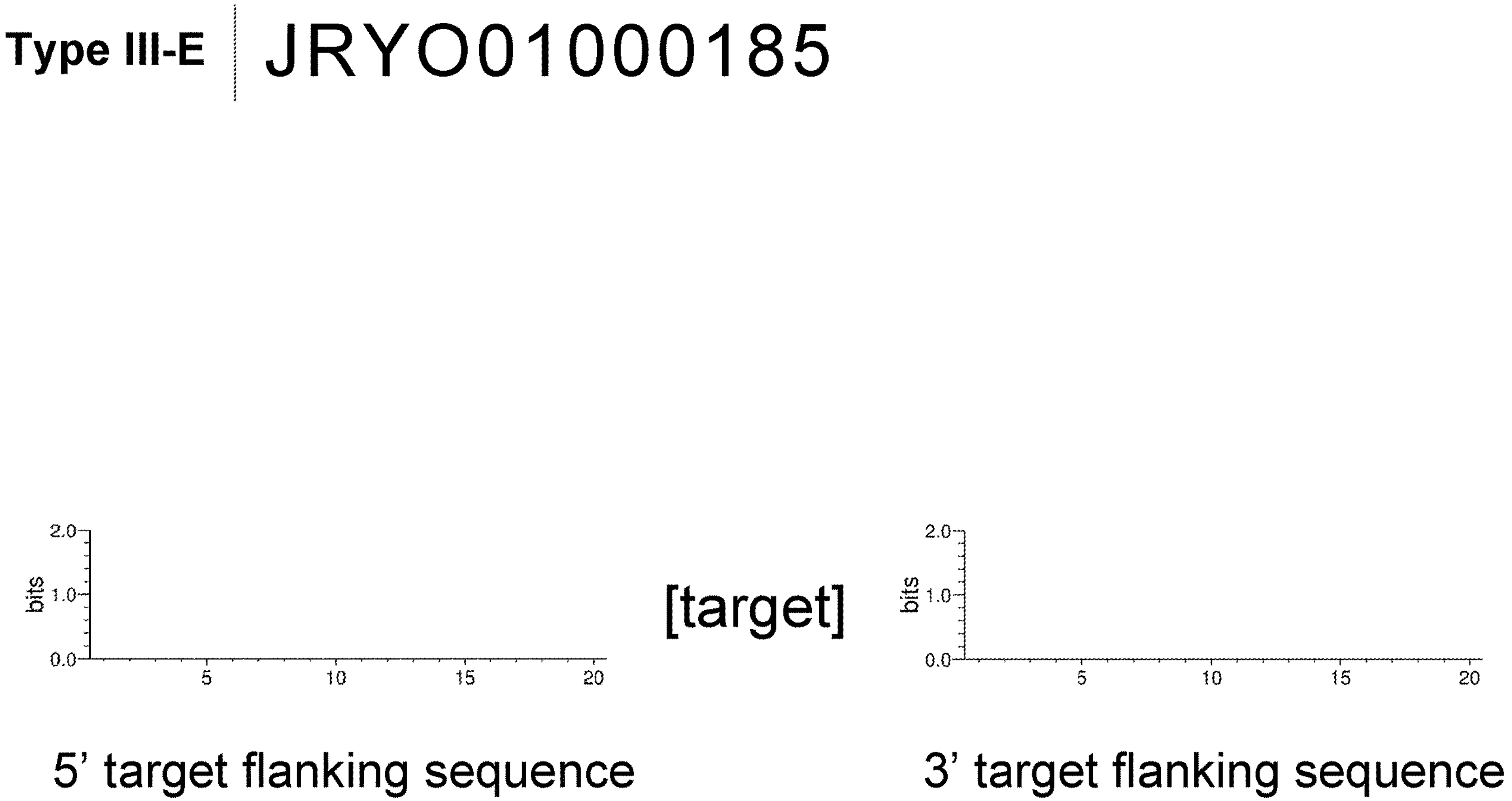

FIG. 12 is a weblogo of the sequences flanking depleted targets for the Type III-E system JRY001000185, indicating there is no prominent motif adjacent to depleted targets (PAM).

DETAILED DESCRIPTION

The broad natural diversity of CRISPR-Cas defense systems contains a wide range of activity mechanisms and functional elements that can be harnessed for programmable biotechnologies. In a natural system, these mechanisms and parameters enable efficient defense against foreign DNA and viruses while providing self vs. non-self discrimination to avoid self-targeting. In an engineered system, the same mechanisms and parameters also provide a diverse toolbox of molecular technologies and define the boundaries of the targeting space. For instance, systems Cas9 and Cas13a have canonical DNA and RNA endonuclease activity and their targeting spaces are defined by the protospacer adjacent motif (PAM) on targeted DNA and protospacer flanking sites (PI'S) on targeted RNA, respectively.

The methods described herein have been used to discover additional mechanisms and parameters within single subunit Class 2 effector systems that can expand the capabilities of RNA-programmable nucleic acid manipulation.

In one aspect, the disclosure relates to the use of computational methods and algorithms to search for and identify novel protein families that exhibit a strong co-occurrence pattern with certain other features within naturally occurring genome sequences. In certain embodiments, these computational methods are directed to identifying protein families that co-occur in close proximity to CRISPR arrays. However, the methods disclosed herein are useful in identifying proteins that naturally occur within close proximity to other features, both non-coding and protein-coding (e.g., fragments of phage sequences in non-coding areas of bacterial loci; or CRISPR Cas1 proteins). It is understood that the methods and calculations described herein may be performed on one or more computing devices.

In some embodiments, a set of genomic sequences is obtained from genomic or metagenomic databases. The databases comprise short reads, or contig level data, or assembled scaffolds, or complete genomic sequences of organisms. Likewise, the database may comprise genomic sequence data from prokaryotic organisms, or eukaryotic organisms, or may include data from metagenomic environmental samples. Examples of database repositories include the National Center for Biotechnology Information (NCBI) RefSeq, NCBI GenBank, NCBI Whole Genome Shotgun (WGS), and the Joint Genome Institute (JGO Integrated Microbial Genomes (BIG).

In some embodiments, a minimum size requirement is imposed to select genome sequence data of a specified minimum length. In certain exemplary embodiments, the minimum contig length may be 100 nucleotides, 500 nt, 1 kb, 1.5 kb, 2 kb. 3 kb. 4 kb, 5 kb, 10 kb, 20 kb, kb, or 50 kb.

In some embodiments, known or predicted proteins are extracted from the complete or a selected set of genome sequence data. In some embodiments, known or predicted proteins are taken from extracting coding sequence (CDS) annotations provided by the source database. In some embodiments, predicted proteins are determined by applying a computational method to identify proteins from nucleotide sequences. In some embodiments, the GeneMark Suite is used to predict proteins from genome sequences. In some embodiments, Prodigal is used to predict proteins from genome sequences. In some embodiments, multiple protein prediction algorithms may be used over the same set of sequence data with the resulting set of proteins de-duplicated.

In some embodiments, CRISPR arrays are identified from the genome sequence data. In some embodiments, PILER-CR is used to identify CRISPR arrays. In some embodiments, CRISPR Recognition Tool (CRT) is used to identify (ABM arrays. In some embodiments, CRISPR arrays are identified by a heuristic that identifies nucleotide motifs repeated a minimum number of times (e.g. 2, 3, or 4 times), where the spacing between consecutive occurrences of a repeated motif does not exceed a specified length (e.g. 50, 100, or 150 nucleotides). In some embodiments, multiple CRISPR array identification tools may be used over the same set of sequence data with the resulting set of CRISPR arrays de-duplicated.

In some embodiments, proteins in close proximity to CRISPR arrays are identified. In some embodiments, proximity is defined as a nucleotide distance, and may be within 20:kb, 15 kb, or 5 kb. In some embodiments, proximity is defined as the number of open reading frames (ORFS) between a protein and a CRISPR array, and certain exemplary distances may be 10, 5, 4, 3, 2, 1, or 0 ORB. The proteins identified as being within close proximity to a CRISPR array are then grouped into clusters of homologous proteins. In some embodiments, blastclust is used to form protein clusters. In certain other embodiments, mmseqs2 is used to form protein clusters.

To establish a pattern of strong co-occurrence between the members of a protein cluster with CR1SPR arrays, a BLAST search of each member of the protein family may be performed over the complete set of known and predicted proteins previously compiled. In some embodiments, LJBLAST or minseqs2 may be used to search for similar proteins. In some embodiments, a search may be performed only for a representative subset of proteins in the family.

In some embodiments, the clusters of proteins within close proximity to CRISPR arrays are ranked or filtered by a metric to determine co-occurrence. One exemplary metric is the ratio of the number of elements in a protein cluster against the number of BLAST matches up to a certain E value threshold. In some embodiments, a constant E value threshold may be used. In other embodiments, the E value threshold may be determined by the most distant members of the protein cluster. In some embodiments, the global set of proteins is clustered and the co-occurrence metric is the ratio of the number of elements of the CRISPR associated cluster against the number of elements of the containing global cluster(s).

In some embodiments, a manual review process is used to evaluate the potential functionality and the minimal set of components of an engineered system based on the naturally occurring locus structure of the proteins in the cluster. In some embodiments, a graphical representation of the protein cluster may assist in the manual review, and may contain information including pairwise sequence similarity, phylogenetic tree, source organisms environments, predicted functional domains, and a graphical depiction of locus structures. In some embodiments, the graphical depiction of locus structures may filter for nearby protein families that have a high representation.

In some embodiments, representation may be calculated by the ratio of the number of related nearby proteins against the size(s) of the containing global cluster(s). In certain exemplary embodiments, the graphical representation of the protein cluster may contain a depiction of the CRISPR array structures of the naturally occurring loci. In some embodiments, the graphical representation of the protein cluster may contain a depiction of the number of conserved direct repeats versus the length of the putative CRISPR array, or the number of unique spacer sequences versus the length of the putative CRISPR array. In some embodiments, the graphical representation of the protein cluster may contain a depiction of various metrics of co-occurrence of the putative effector with CRISPR arrays predict new CRISPR-Cas systems and identify their components.

Pooled-Screening

To efficiently validate the activity of the engineered novel CRISPR-Cas systems and simultaneously evaluate in an unbiased manner different activity mechanisms and functional parameters, we developed a new pooled-screening approach in *E. coli.*

First, from the computational identification of the conserved protein and noncoding, elements of—the novel CRISPR-Cas system, DNA synthesis and molecular cloning was used to assemble the separate components into a single artificial expression vector, which in one embodiment is based on a pET-28a+ backbone. In a second embodiment, the effectors and noncoding elements are transcribed on a single mRNA transcript, and different ribosomal binding sites are used to translate individual effectors.

Second, the natural crRNA and targeting spacers were replaced with a library of unprocessed crRNAs containing non-natural spacers targeting a second plasmid, pACYC184. This crRNA library was cloned into the vector backbone containing the protein effectors and noncoding elements (e.g. pET-28a+), and then subsequently transformed the library into *E. coli* along with the pACYC184 plasmid target. Consequently, each resulting *E. coli* cell contains no more than one targeting spacer. In an alternate embodiment, the library of unprocessed crRNAs containing non-natural spacers additionally target *E. coli* essential genes, drawn from resources such as those described in Baba et at (2006) *Mol. Syst. Biol.* 2: 20060008; and Gerdes et at (2003) *J. Bacteriol.* 185(19): 5673-84, the entire contents of each of which are incorporated herein by reference. In this embodiment, positive, targeted activity of the novel CRISPR-Cas systems that disrupts essential gene function results in cell death or growth arrest. In some embodiments, the essential gene targeting spacers can be combined with the pACYC184 targets to add another dimension to the assay.

Third, the *E. coli* were grown under antibiotic selection. In one embodiment, triple antibiotic selection is used: kanamycin for ensuring successful transformation of the pET-28a+ vector containing the engineered CRISPR-Cas effector system, and chloramphenicol and tetracycline for ensuring successful co-transformation of the pACYC184 target vector. Since pACYC184 normally confers resistance to chloramphenicol and tetracycline, under antibiotic selection, positive activity of the novel CRISPR-Cas system targeting the plasmid will eliminate cells that actively express the effectors, noncoding elements, and specific active elements of the crRNA library.

Examining the population of surviving cells at a later time point compared to an earlier time point results in a depleted signal compared to the inactive crRNAs. In some embodiments, double antibiotic selection is used. For example, withdrawal of either chloramphenicol or tetracycline to remove selective pressure can provide novel information about the targeting substrate, sequence specificity, and potency. In some embodiments, only kanamycin is used to ensure successful transformation of the pET-28a+ vector containing the engineered CRISPR-Cas effector system. This embodiment is suitable for libraries containing spacers targeting *E. coli* essential genes, as no additional selection beyond kanamycin is needed to observe growth alterations. In this embodiment, chloramphenicol and tetracycline dependence is removed, and their targets (if any) in the library provides an additional source of negative or positive information about the targeting substrate, sequence specificity, and potency.

Since the pACYC184 plasmid contains a diverse set of features and sequences that may affect the activity of a CRISPR-Cas system, mapping the active crRNAs from the pooled screen onto pACYC 184 provides patterns of activity that can be suggestive of different activity mechanisms and functional parameters in a broad, hypothesis-agnostic manner. In this way, the features required for reconstituting the novel CRISPR-Cas system in a heterologous prokaryotic species can be more comprehensively tested and studied.

The key advantages of the in vivo pooled-screen described herein include:

(1) Versatility—Plasmid design allows multiple effectors and/or noncoding elements to be expressed; library cloning strategy enables both transcriptional directions of the computationally predicted crRNA to be expressed;

(2) Comprehensive tests of activity mechanisms & functional parameters—Evaluates diverse interference mechanisms, including DNA or RNA cleavage; examines co-occurrence of features such as transcription, plasmid DNA replication; and flanking sequences for crRNA library can be used to reliably determine PAMs with complexity equivalence of 4N's;

(3) Sensitivity—pACYC184 is a low copy plasmid, enabling high sensitivity for CRISPR-Cas activity since even modest interference rates can eliminate the antibiotic resistance encoded by the plasmid; and (4) Efficiency—Optimized molecular biology steps to enable greater speed and throughput RNA-sequencing and protein expression samples can be directly harvested from the surviving cells in the screen.

The novel CRISPR-Cas families described herein were evaluated using this in vivo pooled-screen to evaluate their operational elements, mechanisms and parameters, as well as their ability to be active and reprogrammed in an engineered system outside of their natural cellular environment.

Type III-E CRISPR-Cas System

In one aspect, this disclosure provides the Type III-E CRISPR-Cas system, wherein a Type III-E effector protein may include a Repeat Associated Mysterious Protein (RAMP) domain (see e.g., Makarova and Koonin (2018) *Methods Mol Biol.,* 1311:47-75). In some embodiments, the RAMP-domain containing protein is a single large protein. In some embodiments, the RAMP-domain containing single protein is at least approximately 1400 amino acids. In some embodiments, the RAMP-domain containing single protein is at least approximately 1550 amino acids. In some embodiments, the RAMP-domain containing single protein contains multiple RAMP domains. In some embodiments, the RAMP-domain containing single protein contains domains with homology to CRISPR Cmr4 (e.g., AYLVGLYTLTPTHPGSGTELGVVDQPIQRERHTGFPVIWGQSLKGVLRSYLKLVEKVDEEKINKIFGPPTEKAHEQAGLISVGDAKILFFPVRSLKGVYAYVTSPLVLNRFKRDLELAG V (SEQ ID NO: 50)). In some embodiments, the RAMP-domain containing single protein contains domains with homology to CRISPR Cmr6 (e.g., EIREIRDMLNSLHAITGKFKTQSR LVVGLGDESVYETSIRLLRNYGVPYIPGSAIKGVTRHLTYYVLAEF (SEQ ID NO: 51)). In some embodiments, the RAMP-domain containing single protein contains domains with homology to CRISPR Cas7. In some embodiments, the RAMP-domain containing single protein does not contain a domain with homology to CRISPR Cas10. In some embodiments, the RAMP-domain containing single protein does not contain a domain with homology to CRISPR Cas5.

In one aspect, this disclosure provides the Type III-E CRISPR-Cas system, wherein a Type III-E effector protein includes a protease domain. In some embodiments, a complex formed by a CRISPR-associated protein having a protease domain and an RNA guide is activated upon binding to a target nucleic acid, and exhibits protease activity. In some embodiments, the protease activity of the activated complex may induce programmed cell death (e.g., apoptosis). In some embodiments, the protease domain is a caspase domain. In some embodiments, the caspase domain is a Caspase HetF Associated with Tprs (CHAT) domain (see, e.g., Aravind and Koonin (2002) Proteins 46(4): 355-67). In some embodiments, a first CRISPR-associated protein comprising a CHAT domain interacts with a second effector protein comprising a RAMP domain to form a complex, whereby the second effector protein targets the complex to a target nucleic acid (e.g., as mediated by an RNA guide). In some embodiments, a protease activity of the CRISPR-associated protein comprising a CHAT domain is activated upon binding of the complex to a target nucleic acid (e.g., as mediated by an RNA guide and/or the CRISPR-associated protein comprising a RAMP domain). In some embodiments, a CRISPR-associated protein described herein exhibits a peptidase activity (e.g., endopeptidase or exopeptidase activity).

In some embodiments, the Type III-E CRISPR-Cas system provided herein is specific to a transcriptionally active site (see e.g., Estrella et al., (2019) Genes & Dev 30:460-470). In some embodiments, the Type III-E CRISPR-Cas system provided herein is specific to a site of DNA replication. In some embodiments, the Type III-E CRISPR-Cas system depends on endogenous bacterial host factors (Chou-Zheng and Hatoum-Aslan (2019) eLife 8:e45393).

CRISPR Enzyme Modifications

Deactivated/Inactivated CRISPR Enzymes

Where the CRISPR enzymes described herein have nuclease activity, the CRISPR enzymes can be modified to have diminished nuclease activity, e.g., nuclease inactivation of at least 50%, at least 60%, at least 70%, at least 80%, at least 90%, at least 95%, at least 97%, or 100% as compared with the wild type CRISPR enzymes. The nuclease activity can be diminished by several methods known in the art, e.g., introducing mutations into the nuclease domains of the proteins. In some embodiments, catalytic residues for the nuclease activities are identified, and these amino acid residues can be substituted by different amino acid residues (e.g., glycine or alanine) to diminish the nuclease activity.

The inactivated CRISPR enzymes can comprise or be associated with one or more functional domains (e.g., via fusion protein, linker peptides, "GS" linkers, etc.). These functional domains can have various activities, e.g., methylase activity, demethylase activity, transcription activation activity, transcription repression activity, transcription release factor activity, histone modification activity, RNA cleavage activity, DNA cleavage activity, nucleic acid binding activity, and switch activity (e.g., light inducible). In some embodiments, the functional domains are Krüppel associated box (KRAB), VP64, VP16, Fokl, P65, HSF1, MyoD1, and biotin-APEX.

The positioning of the one or more functional domains on the inactivated CRISPR enzymes allows for correct spatial orientation for the functional domain to affect the target with the attributed functional effect. For example, if the functional domain is a transcription activator (e.g., VP16, VP64, or p65), the transcription activator is placed in a spatial orientation that allows it to affect the transcription of the target. Likewise, a transcription repressor is positioned to affect the transcription of the target, and a nuclease (e.g., Fokl) is positioned to cleave or partially cleave the target. In some embodiments, the functional domain is positioned at the N-terminus of the CRISPR enzyme. In some embodiments, the functional domain is positioned at the C-terminus of the CRISPR enzyme. In some embodiments, the inactivated CRISPR enzyme is modified to comprise a first functional domain at the N-terminus and a second functional domain at the C-terminus.

Split Enzymes

The present disclosure also provides a split version of the CRISPR enzymes described herein. The split version of the CRISPR enzymes may be advantageous for delivery. In some embodiments, the CRISPR enzymes are split to two parts of the enzymes, which together substantially comprises a functioning CRISPR enzyme.

The split can be done in a way that the catalytic domain(s) are unaffected. The CRISPR enzymes may function as a nuclease or may be inactivated enzymes, which are essentially RNA-binding proteins with very little or no catalytic activity (e.g., due to mutation(s) in its catalytic domains).

In some embodiments, the nuclease lobe and α-helical lobe are expressed as separate polypeptides. Although the lobes do not interact on their own, the guide RNA recruits them into a ternary complex that recapitulates the activity of full-length CRISPR enzymes and catalyzes site-specific DNA cleavage. The use of a modified guide RNA abrogates split-enzyme activity by preventing dimerization, allowing for the development of an inducible dimerization system. The split enzyme is described, e.g., in Wright, Addison V., et al. "Rational design of a split-Cas9 enzyme complex," Proc. Nat'l. Acad. Sci., 112.10 (2015): 2984-2989, which is incorporated herein by reference in its entirety.

In some embodiments, the split enzyme can be fused to a dimerization partner, e.g., by employing rapamycin sensitive dimerization domains. This allows the generation of a chemically inducible CRISPR enzyme for temporal control of CRISPR enzyme activity. The CRISPR enzymes can thus be rendered chemically inducible by being split into two fragments and rapamycin-sensitive dimerization domains can be used for controlled reassembly of the CRISPR enzymes.

The split point is typically designed in silico and cloned into the constructs. During this process, mutations can be introduced to the split enzyme and non-functional domains can be removed. In some embodiments, the two parts or fragments of the split CRISPR enzyme (i.e., the N-terminal and C-terminal fragments), can form a full CRISPR enzyme, comprising, e.g., at least 70%, at least 80%, at least 90%, at least 95%, or at least 99% of the sequence of the wild-type CRISPR enzyme.

Self-Activating or Inactivating Enzymes

The CRISPR enzymes described herein can be designed to be self-activating or self-inactivating. In some embodiments, the CRISPR enzymes are self-inactivating. For example, the target sequence can be introduced into the CRISPR enzyme coding constructs. Thus, the CRISPR enzymes can cleave the target sequence, as well as the construct encoding the enzyme thereby self-inactivating their expression. Methods of constructing a self-inactivating CRISPR system is described, e.g., in Epstein, Benjamin E., and David V. Schaffer. "Engineering a Self-Inactivating CRISPR System for AAV Vectors," Mol. Ther., 24 (2016): S50, which is incorporated herein by reference in its entirety.

In some other embodiments, an additional guide RNA, expressed under the control of a weak promoter (e.g., 7SK promoter), can target the nucleic acid sequence encoding the CRISPR enzyme to prevent and/or block its expression (e.g., by preventing the transcription and/or translation of the nucleic acid). The transfection of cells with vectors expressing the CRISPR enzyme, guide RNAs, and guide RNAs that target the nucleic acid encoding the CRISPR enzyme can lead to efficient disruption of the nucleic acid encoding the CRISPR enzyme and decrease the levels of CRISPR enzyme, thereby limiting the genome editing activity.

In some embodiments, the genome editing activity of the CRISPR enzymes can be modulated through endogenous RNA signatures (e.g., miRNA) in mammalian cells. The CRISPR enzyme switch can be made by using a miRNA-complementary sequence in the 5'-UTR of mRNA encoding the CRISPR enzyme. The switches selectively and efficiently respond to miRNA in the target cells. Thus, the switches can differentially control the genome editing by sensing endogenous miRNA activities within a heterogeneous cell population. Therefore, the switch systems can provide a framework for cell-type selective genome editing and cell engineering based on intracellular miRNA information (Hirosawa, Moe et al. "Cell-type-specific genome editing with a microRNA-responsive CRISPR—Cas9 switch," Nucl. Acids Res., 2017 Jul. 27; 45(13): e118).

Inducible CRISPR Enzymes

The CRISPR enzymes can be inducible, e.g., light inducible or chemically inducible. This mechanism allows for activation of the functional domain in the CRISPR enzymes. Light inducibility can be achieved by various methods known in the art, e.g., by designing a fusion complex wherein CRY2 PHR/CIBN pairing is used in split CRISPR Enzymes (see, e.g., Konermann et al. "Optical control of mammalian endogenous transcription and epigenetic states," *Nature,* 500.7463 (2013): 472). Chemical inducibility can be achieved, e.g., by designing a fusion complex wherein FKBP/FRB (FK506 binding protein/FKBP rapamycin binding domain) pairing is used in split CRISPR Enzymes. Rapamycin is required for forming the fusion complex, thereby activating the CRISPR enzymes (see, e.g., Zetsche, Volz, and Zhang, "A split-Cas9 architecture for inducible genome editing and transcription modulation," *Nature Biotech.,* 33.2 (2015): 139-142).

Furthermore, expression of the CRISPR enzymes can be modulated by inducible promoters, e.g., tetracycline or doxycycline controlled transcriptional activation (Tet-On and Tet-Off expression system), hormone inducible gene expression system (e.g., an ecdysone inducible gene expression system), and an arabinose-inducible gene expression system. When delivered as RNA, expression of the RNA targeting effector protein can be modulated via a riboswitch, which can sense a small molecule like tetracycline (see, e.g., Goldfless, Stephen J. et al. "Direct and specific chemical control of eukaryotic translation with a synthetic RNA—protein interaction," *Nucl. Acids Res.,* 40.9 (2012): e64-e64).

Various embodiments of inducible CRISPR enzymes and inducible CRISPR systems are described, e.g., in U.S. Pat. No. 8,871,445, US20160208243, and WO2016205764, each of which is incorporated herein by reference in its entirety.

Functional Mutations

Various mutations or modifications can be introduced into CRISPR enzymes as described herein to improve specificity and/or robustness. In some embodiments, the amino acid residues that recognize the Protospacer Adjacent Motif (PAM) are identified. The CRISPR enzymes described herein can be modified further to recognize different PAMs, e.g., by substituting the amino acid residues that recognize PAM with other amino acid residues.

In some embodiments, the CRISPR-associated proteins include at least one (e.g., 1, 2, 3, 4, 5, 6, 7, 8, 9, or 10) Nuclear Localization Signal (NLS) attached to the N-terminal or C-terminal of the protein. Non-limiting examples of NLSs include an NLS sequence derived from: the NLS of the SV40 virus large T-antigen, having the amino acid sequence PKKKRKV (SEQ ID NO: 300); the NLS from nucleoplasmin (e.g., the nucleoplasmin bipartite NLS with the sequence KRPAATKKAGQAKKKK (SEQ ID NO: 301)); the c-myc NLS having the amino acid sequence PAAKRVKLD (SEQ ID NO: 302) or RQRRNELKRSP (SEQ ID NO: 303); the hRNPA1 M9 NLS having the sequence NQSSNFGPMKGGNFGGRSSGPYGGGGQYFAKPRNQGGY (SEQ ID NO: 304); the sequence RMRIZFKNKGKDTAELRRRRVEVSVELRKAKKDEQILKRRNV (SEQ ID NO: 305) of the IBB domain from importin-alpha; the sequences VSRKRPRP (SEQ ID NO: 306) and PPKKARED (SEQ ID NO: 307) of the myoma T protein; the sequence PQPKKKPL (SEQ ID NO: 308) of human p53; the sequence SALIKKKKKMAP (SEQ ID NO: 309) of mouse c-abl IV; the sequences DRLRR (SEQ ID NO: 310) and PKQKKRK(SEQ ID NO:

311) of the influenza virus NS1; the sequence RKLKKKIKKL (SEQ ID NO: 312) of the Hepatitis virus delta antigen; the sequence REKKKFLKRR (SEQ ID NO: 313) of the mouse Mx1 protein; the sequence KRKGDEVDGVDEVAKKKSKK (SEQ ID NO: 314) of the human poly(ADP-ribose) polymerase; and the sequence RKCLQAGMNLEARKTKK (SEQ ID NO: 315) of the human glucocorticoid receptor. In some embodiments, the CRISPR-associated protein includes at least one (e.g., 1, 2, 3, 4, 5, 6, 7, 8, 9, or 10) Nuclear Export Signal (NES) attached the N-terminal or C-terminal of the protein. In a preferred embodiment, a C-terminal and/or N-terminal NLS or NES is attached for optimal expression and nuclear targeting in eukaryotic cells, e.g., human cells.

In some embodiments, the CRISPR enzymes described herein are mutated at one or more amino acid residues to alter one or more functional activities. For example, in some embodiments, the CRISPR enzyme is mutated at one or more amino acid residues to alter its peptidase or protease activity. In some embodiments, the CRISPR enzyme is mutated at one or more amino acid residues to alter its nuclease activity (e.g., endonuclease activity or exonuclease activity). In some embodiments, the CRISPR enzyme is mutated at one or more amino acid residues to alter its ability to functionally associate with a RNA guide. In some embodiments, the CRISPR enzyme is mutated at one or more amino acid residues to alter its ability to functionally associate with a target nucleic acid.

In some embodiments, the CRISPR enzymes described herein are capable of cleaving a target nucleic acid molecule. In some embodiments, the CRISPR enzyme cleaves both strands of the target nucleic acid molecule. However, in some embodiments, the CRISPR enzyme is mutated at one or more amino acid residues to alter its cleaving activity. For example, in some embodiments, the CRISPR enzyme may comprise one or more mutations that render the enzyme incapable of cleaving a target nucleic acid. In other embodiments, the CRISPR enzyme may comprise one or more mutations such that the enzyme is capable of cleaving a single strand of the target nucleic acid (i.e., nickase activity). In some embodiments, the CRISPR enzyme is capable of cleaving the strand of the target nucleic acid that is complementary to the strand to which the RNA guide hybridizes. In some embodiments, the CRISPR enzyme is capable of cleaving the strand of the target nucleic acid to which the RNA guide hybridizes.

In some embodiments, a CRISPR enzyme described herein may be engineered to comprise a deletion in one or more amino acid residues to reduce the size of the enzyme while retaining one or more desired functional activities (e.g., nuclease activity and the ability to interact functionally with a RNA guide). The truncated CRISPR enzyme may be advantageously used in combination with delivery systems having load limitations.

In one aspect, the present disclosure provides nucleic acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the nucleic sequences described herein. In another aspect, the present disclosure also provides amino acid sequences that are at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% identical to the amino acid sequences described herein.

In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are the same as the sequences described herein. In some embodiments, the nucleic acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from the sequences described herein.

In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as the sequences described herein. In some embodiments, the amino acid sequences have at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from the sequences described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In general, the length of a reference sequence aligned for comparison purposes should be at least 80% of the length of the reference sequence, and in some embodiments is at least 90%, 95%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blosum 62 scoring matrix with a gap penalty of 12, a gap extend penalty of 4, and a frameshift gap penalty of 5.

Beyond the biochemical and diagnostic applications described herein, programmable Type III-E CRISPR-Cas systems described herein have important applications in eukaryotic cells such as genotype-gated cell death or therapeutic modification of the genome, with examples of applications including, but not limited to: targeted, sequence-based destruction of specific cell population, such as for treatment of neoplasms by specific targeting of mutated tumor cells, treatment of infections by destroying cells infected with bacteria or virus, preserving a cell lineage surveilling the genome and destroying mutated cells; additionally, in prokaryotic cellular environments, defense against transformants or infections, as well as defense against spontaneous mutations.

In some embodiments, the CRISPR-associated proteins and accessory proteins described herein can be fused to one or more peptide tags, including a His-tag, GST-tag, FLAG-tag, or myc-tag. In some embodiments, the CRISPR-associated proteins or accessory proteins described herein can be fused to a detectable moiety such as a fluorescent protein (e.g., green fluorescent protein or yellow fluorescent protein). In other embodiments, CRISPR-associated proteins or accessory proteins described herein are fused to a peptide or non-peptide moiety that allows these proteins to enter or localize to a tissue, a cell, or a region of a cell. For instance, a CRISPR-associated protein or accessory protein of this disclosure may comprise a nuclear localization sequence (NLS) such as an SV40 (simian virus 40) NLS, c-Myc NLS, or other suitable monopartite NLS. The NLS may be fused to an N-terminal and/or a C-terminal of the CRISPR-associated protein or accessory protein, and may be fused singly (i.e., a single NLS) or concatenated (e.g., a chain of 2, 3, 4, etc. NLS).

In those embodiments where a tag is fused to a CRISPR-associated protein, such tag may facilitate affinity-based or charge-based purification of the CRISPR-associated protein, e.g., by liquid chromatography or bead separation utilizing an immobilized affinity or ion-exchange reagent. As a non-limiting example, a recombinant CRISPR-associated protein of this disclosure comprises a polyhistidine (His) tag, and for purification is loaded onto a chromatography column comprising an immobilized metal ion (e.g. a Zn', Ni', Cu' ion chelated by a chelating ligand immobilized on the resin, which resin may be an individually prepared resin or a commercially available resin or ready to use column such as the HisTrap FF column commercialized by GE Healthcare Life Sciences, Marlborough, Massachusetts). Following the loading step, the column is optionally rinsed, e.g., using one or more suitable buffer solutions, and the His-tagged protein is then eluted using a suitable elution buffer. Alternatively or additionally, if the recombinant CRISPR-associated protein of this disclosure utilizes a FLAG-tag, such protein may be purified using immunoprecipitation methods known in the industry. Other suitable purification methods for tagged CRISPR-associated proteins or accessory proteins of this disclosure will be evident to those of skill in the art.

The proteins described herein (e.g., CRISPR-associated proteins or accessory proteins) can be delivered or used as either nucleic acid molecules or polypeptides. When nucleic acid molecules are used, the nucleic acid molecule encoding the CRISPR-associated proteins can be codon-optimized, as discussed in further detail below. The nucleic acid can be codon optimized for use in any organism of interest, in particular human cells or bacteria. For example, the nucleic acid can be codon-optimized for any non-human eukaryote including mice, rats, rabbits, dogs, livestock, or non-human primates. Codon usage tables are readily available, for example, at the "Codon Usage Database" and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA).

In some instances, nucleic acids of this disclosure which encode CRISPR-associated proteins or accessory proteins for expression in eukaryotic (e.g., human, or other mammalian cells) cells include one or more introns, i.e., one or more non-coding sequences comprising, at a first end (e.g., a 5' end), a splice-donor sequence and, at second end (e.g., the 3' end) a splice acceptor sequence. Any suitable splice donor/splice acceptor can be used in the various embodiments of this disclosure, including without limitation simian virus 40 (SV40) intron, beta-globin intron, and synthetic introns. Alternatively or additionally, nucleic acids of this disclosure encoding CRISPR-associated proteins or accessory proteins may include, at a 3' end of a DNA coding sequence, a transcription stop signal such as a polyadenylation (polyA) signal. In some instances, the polyA signal is located in close proximity to, or adjacent to, an intron such as the SV40 intron.

RNA Guides

In some embodiments, the CRISPR systems described herein include at least one Type III-E RNA guide. The architecture of many RNA guides is known in the art (see, e.g., International Publication Nos. WO 2014/093622 and WO 2015/070083, the entire contents of each of which are incorporated herein by reference). In some embodiments, the CRISPR systems described herein include multiple RNA guides (e.g., two, three, four, five, six, seven, eight, or more RNA guides).

In some embodiments, the CRISPR systems described herein include at least one Type III-E RNA guide or a nucleic acid encoding at least one Type III-E RNA guide. In some embodiments, the RNA guide includes a crRNA. Generally, the crRNAs described herein include a direct repeat sequence and a spacer sequence. In certain embodiments, the crRNA includes, consists essentially of, or consists of a direct repeat sequence linked to a guide sequence or spacer sequence. In some embodiments, the crRNA includes a direct repeat sequence, a spacer sequence, and a direct repeat sequence (DR-spacer-DR), which is typical of precursor crRNA (pre-crRNA) configurations in other CRISPR systems. In some embodiments, the crRNA includes a truncated direct repeat sequence and a spacer sequence, which is typical of processed or mature crRNA. In some embodiments, the CRISPR-Cas effector protein forms a complex with the RNA guide, and the spacer sequence directs the complex to a sequence-specific binding with the target nucleic acid that is complementary to the spacer sequence.

Guide RNA Modifications

Spacer Lengths

The spacer length of guide RNAs can range from about 15 to 50 nucleotides. In some embodiments, the spacer length of a guide RNA is at least 16 nucleotides, at least 17 nucleotides, at least 18 nucleotides, at least 19 nucleotides, at least 20 nucleotides, at least 21 nucleotides, or at least 22 nucleotides. In some embodiments, the spacer length is from 15 to 17 nucleotides, from 17 to 20 nucleotides, from 20 to 24 nucleotides (e.g., 20, 21, 22, 23, or 24 nucleotides), from 23 to 25 nucleotides (e.g., 23, 24, or 25 nucleotides), from 24 to 27 nucleotides, from 27 to 30 nucleotides, from 30 to 45 nucleotides (e.g., 30, 31, 32, 33, 34, 35, 40, or 45 nucleotides), from 30 or 35 to 40 nucleotides, from 41 to 45 nucleotides, from 45 to 50 nucleotides, or longer. In some embodiments, the direct repeat length of the guide RNA is at least 16 nucleotides, or is from 16 to 20 nucleotides (e.g., 16, 17, 18, 19, or 20 nucleotides). In some embodiments, the direct repeat length of the guide RNA is 19 nucleotides.

The guide RNA sequences can be modified in a manner that allows for formation of the CRISPR complex and successful binding to the target, while at the same time not allowing for successful nuclease activity (i.e., without nuclease activity/without causing indels). These modified guide sequences are referred to as "dead guides" or "dead guide sequences." These dead guides or dead guide sequences may be catalytically inactive or conformationally inactive with regard to nuclease activity. Dead guide sequences are typically shorter than respective guide sequences that result in active RNA cleavage. In some embodiments, dead guides are 5%, 10%, 20%, 30%, 40%, or 50%, shorter than respective guide RNAs that have nuclease activity. Dead guide sequences of guide RNAs can be from 13 to 15 nucleotides in length (e.g., 13, 14, or 15 nucleotides in length), from 15 to 19 nucleotides in length, or from 17 to 18 nucleotides in length (e.g., 17 nucleotides in length).

Thus, in one aspect, the disclosure provides non-naturally occurring or engineered CRISPR systems including a functional CRISPR enzyme as described herein, and a guide RNA (gRNA) wherein the gRNA comprises a dead guide sequence whereby the gRNA is capable of hybridizing to a target sequence such that the CRISPR system is directed to a genomic locus of interest in a cell without detectable cleavage activity.

A detailed description of dead guides is described, e.g., in WO 2016094872, which is incorporated herein by reference in its entirety.

Inducible Guides

Guide RNAs can be generated as components of inducible systems. The inducible nature of the systems allows for spatiotemporal control of gene editing or gene expression. In some embodiments, the stimuli for the inducible systems include, e.g., electromagnetic radiation, sound energy, chemical energy, and/or thermal energy.

In some embodiments, the transcription of guide RNA can be modulated by inducible promoters, e.g., tetracycline or doxycycline controlled transcriptional activation (Tet-On and Tet-Off expression systems), hormone inducible gene expression systems (e.g., ecdysone inducible gene expression systems), and arabinose-inducible gene expression systems. Other examples of inducible systems include, e.g., small molecule two-hybrid transcription activations systems (FKBP, ABA, etc.), light inducible systems (Phytochrome, LOV domains, or cryptochrome), or Light Inducible Transcriptional Effector (LITE). These inducible systems are described, e.g., in WO 2016205764 and U.S. Pat. No. 8,795,965, both of which are incorporated herein by reference in the entirety.

Chemical Modifications

Chemical modifications can be applied to the guide RNA's phosphate backbone, sugar, and/or base. Backbone modifications such as phosphorothioates modify the charge on the phosphate backbone and aid in the delivery and nuclease resistance of the oligonucleotide (see, e.g., Eckstein, "Phosphorothioates, essential components of therapeutic oligonucleotides," *Nucl. Acid Ther.*, 24 (2014), pp. 374-387); modifications of sugars, such as 2'-O-methyl (2'-OMe), 2'-F, and locked nucleic acid (LNA), enhance both base pairing and nuclease resistance (see, e.g., Allerson et al. "Fully 2'-modified oligonucleotide duplexes with improved in vitro potency and stability compared to unmodified small interfering RNA," *J. Med. Chem.*, 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," *Front. Genet.*, 2012 Aug. 20; 3:154). Additionally, RNA is amenable to both 5' and 3' end conjugations with a variety of functional moieties including fluorescent dyes, polyethylene glycol, or proteins.

A wide variety of modifications can be applied to chemically synthesized guide RNA molecules. For example, modifying an oligonucleotide with a 2'-OMe to improve nuclease resistance can change the binding energy of Watson-Crick base pairing. Furthermore, a 2'-OMe modification can affect how the oligonucleotide interacts with transfection reagents, proteins or any other molecules in the cell. The effects of these modifications can be determined by empirical testing.

In some embodiments, the guide RNA includes one or more phosphorothioate modifications. In some embodiments, the guide RNA includes one or more locked nucleic acids for the purpose of enhancing base pairing and/or increasing nuclease resistance.

A summary of these chemical modifications can be found, e.g., in Kelley et al., "Versatility of chemically synthesized guide RNAs for CRISPR-Cas9 genome editing," *J. Biotechnol.* 2016 Sep. 10; 233:74-83; WO 2016205764; and U.S. Pat. No. 8,795,965 B2; each which is incorporated by reference in its entirety.

Sequence Modifications

The sequences and the lengths of the guide RNAs, tracrRNAs, and crRNAs described herein can be optimized. In some embodiments, the optimized length of guide RNA can be determined by identifying the processed form of tracrRNA and/or crRNA, or by empirical length studies for guide RNAs, tracrRNAs, crRNAs, and the tracrRNA tetraloops.

The guide RNAs can also include one or more aptamer sequences. Aptamers are oligonucleotide or peptide molecules that can bind to a specific target molecule. The aptamers can be specific to gene effectors, gene activators, or gene repressors. In some embodiments, the aptamers can be specific to a protein, which in turn is specific to and recruits/binds to specific gene effectors, gene activators, or gene repressors. The effectors, activators, or repressors can be present in the form of fusion proteins. In some embodiments, the guide RNA has two or more aptamer sequences that are specific to the same adaptor proteins. In some embodiments, the two or more aptamer sequences are specific to different adaptor proteins. The adaptor proteins can include, e.g., MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, and PRR1. Accordingly, in some embodiments, the aptamer is selected from binding proteins specifically binding any one of the adaptor proteins as described herein. In some embodiments, the aptamer sequence is a MS2 loop. A detailed description of aptamers can be found, e.g., in Nowak et al., "Guide RNA engineering for versatile Cas9 functionality," *Nucl. Acid. Res.*, 2016 Nov. 16; 44(20):9555-9564; and WO 2016205764, which are incorporated herein by reference in their entirety.

Guide: Target Sequence Matching Requirements

In classic CRISPR systems, the degree of complementarity between a guide sequence and its corresponding target sequence can be about 50%, 60%, 75%, 80%, 85%, 90%, 95%, 97.5%, 99%, or 100%. In some embodiments, the degree of complementarity is 100%. The guide RNAs can be about 5, 10, 11, 12, 13, 14, 15, 16, 17, 18, 19, 20, 21, 22, 23, 24, 25, 26, 27, 28, 29, 30, 40, 45, 50, 75, or more nucleotides in length.

To reduce off-target interactions, e.g., to reduce the guide interacting with a target sequence having low complementarity, mutations can be introduced to the CRISPR systems so that the CRISPR systems can distinguish between target and off-target sequences that have greater than 80%, 85%, 90%, or 95% complementarity. In some embodiments, the degree of complementarity is from 80% to 95%, e.g., about 83%, 84%, 85%, 86%, 87%, 88%, 89%, 90%, 91%, 92%, 93%, 94%, or 95% (for example, distinguishing between a target having 18 nucleotides from an off-target of 18 nucleotides having 1, 2, or 3 mismatches). Accordingly, in some embodiments, the degree of complementarity between a guide sequence and its corresponding target sequence is greater than 94.5%, 95%, 95.5%, 96%, 96.5%, 97%, 97.5%, 98%, 98.5%, 99%, 99.5%, or 99.9%. In some embodiments, the degree of complementarity is 100%.

It is known in the field that complete complementarity is not required, provided there is sufficient complementarity to be functional. Modulations of cleavage efficiency can be exploited by introduction of mismatches, e.g., one or more mismatches, such as 1 or 2 mismatches between spacer sequence and target sequence, including the position of the mismatch along the spacer/target. The more central (i.e., not at the 3' or 5' ends) a mismatch, e.g., a double mismatch, is located; the more cleavage efficiency is affected. Accordingly, by choosing mismatch positions along the spacer sequence, cleavage efficiency can be modulated. For example, if less than 100% cleavage of targets is desired (e.g., in a cell population), 1 or 2 mismatches between spacer and target sequence can be introduced in the spacer sequences.

Methods of Using CRISPR Systems

The CRISPR systems described herein have a wide variety of utilities including modifying (e.g., deleting, inserting, translocating, inactivating, or activating) a target polynucleotide in a multiplicity of cell types. The CRISPR systems have a broad spectrum of applications in, e.g., DNA/RNA detection (e.g., specific high sensitivity enzymatic reporter unlocking (SHERLOCK)), tracking and labeling of nucleic acids, enrichment assays (extracting desired sequence from background), detecting circulating tumor DNA, preparing next generation library, drug screening, disease diagnosis and prognosis, and treating various genetic disorders.

DNA/RNA Detection

In one aspect, the CRISPR systems described herein can be used in DNA/RNA detection. While many CRISPR enzymes target DNA, single effector RNA-guided RNases can be reprogrammed with CRISPR RNAs (crRNAs) to provide a platform for specific RNA sensing. Upon recognition of its RNA target, activated single effector RNA-guided RNases engage in "collateral" cleavage of nearby non-targeted RNAs. This crRNA-programmed collateral cleavage activity allows the CRISPR systems to detect the presence of a specific RNA by triggering programmed cell death or by nonspecific degradation of labeled RNA.

The SHERLOCK method (Specific High Sensitivity Enzymatic Reporter UnLOCKing) provides an in vitro nucleic acid detection platform with attomolar sensitivity based on nucleic acid amplification and collateral cleavage of a reporter RNA, allowing for real-time detection of the target. To achieve signal detection, the detection can be combined with different isothermal amplification steps. For example, recombinase polymerase amplification (RPA) can be coupled with T7 transcription to convert amplified DNA to RNA for subsequent detection. The combination of amplification by RPA, T7 RNA polymerase transcription of amplified DNA to RNA, and detection of target RNA by collateral RNA cleavage-mediated release of reporter signal is referred as SHERLOCK. Methods of using CRISPR in SHERLOCK are described in detail, e.g., in Gootenberg, et al. "Nucleic acid detection with CRISPR-Cas13a/C2c2," *Science,* 2017 Apr. 28; 356(6336):438-442, which is incorporated herein by reference in its entirety.

The RNA targeting effector proteins can further be used in Northern blot assays, which use electrophoresis to separate RNA samples by size. The RNA targeting effector proteins can be used to specifically bind and detect the target RNA sequence. The RNA targeting effector proteins can also be fused to a fluorescent protein (e.g., GFP) and used to track RNA localization in living cells. More particularly, the RNA targeting effector proteins can be inactivated in that they no longer cleave RNAs. Thus, RNA targeting effector proteins can be used to determine the localization of the RNA or specific splice variants, the level of mRNA transcripts, up- or down-regulation of transcripts and disease-specific diagnosis. The RNA targeting effector proteins can be used for visualization of RNA in (living) cells using, for example, fluorescent microscopy or flow cytometry, such as fluorescence-activated cell sorting (FACS), which allows for high-throughput screening of cells and recovery of living cells following cell sorting. A detailed description regarding how to detect DNA and RNA can be found, e.g., in WO 2017070605, which is incorporated herein by reference in its entirety.

In some embodiments, the CRISPR systems described herein can be used in multiplexed error-robust fluorescence in situ hybridization (MERFISH). These methods are described in, e.g., Chen et al., "Spatially resolved, highly multiplexed RNA profiling in single cells," *Science,* 2015 Apr. 24; 348(6233):aaa6090, which is incorporated herein by reference herein in its entirety.

Tracking and Labeling of Nucleic Acids

Cellular processes depend on a network of molecular interactions among proteins, RNAs, and DNAs. Accurate detection of protein-DNA and protein-RNA interactions is key to understanding such processes. In vitro proximity labeling techniques employ an affinity tag combined with, a reporter group, e.g., a photoactivatable group, to label polypeptides and RNAs in the vicinity of a protein or RNA of interest in vitro. After UV irradiation, the photoactivatable groups react with proteins and other molecules that are in close proximity to the tagged molecules, thereby labelling them. Labelled interacting molecules can subsequently be recovered and identified. The RNA targeting effector proteins can for instance be used to target probes to selected RNA sequences. These applications can also be applied in animal models for in vivo imaging of diseases or difficult-to culture cell types. The methods of tracking and labeling of nucleic acids are described, e.g., in U.S. Pat. No. 8,795,965, WO 2016205764, and WO 2017070605; each of which is incorporated herein by reference herein in its entirety.

RNA Isolation, Purification, Enrichment, and/or Depletion

The CRISPR systems (e.g., RNA targeting effector proteins) described herein can be used to isolate and/or purify the RNA. The RNA targeting effector proteins can be fused to an affinity tag that can be used to isolate and/or purify the RNA-RNA targeting effector protein complex. These applications are useful, e.g., for the analysis of gene expression profiles in cells.

In some embodiments, the RNA targeting effector proteins can be used to target a specific noncoding RNA (ncRNA) thereby blocking its activity. In some embodiments, the effector protein as described herein can be used to specifically enrich a particular RNA (including but not limited to increasing stability, etc.), or alternatively, to specifically deplete a particular RNA (e.g., particular splice variants, isoforms, etc.).

These methods are described, e.g., in U.S. Pat. No. 8,795,965, WO 2016205764, and WO 2017070605; each of which is incorporated herein by reference herein in its entirety.

High-Throughput Screening

The CRISPR systems described herein can be used for preparing next generation sequencing (NGS) libraries. For example, to create a cost-effective NGS library, the CRISPR systems can be used to disrupt the coding sequence of a target gene, and the CRISPR enzyme transfected clones can be screened simultaneously by next-generation sequencing (e.g., on the Ion Torrent PGM system). A detailed description regarding how to prepare NGS libraries can be found, e.g., in Bell et al., "A high-throughput screening strategy for detecting CRISPR-Cas9 induced mutations using next-generation sequencing," *BMC Genomics,* 15.1 (2014): 1002, which is incorporated herein by reference in its entirety.

Engineered Microorganisms

Microorganisms (e.g., *E. coli*, yeast, and microalgae) are widely used for synthetic biology. The development of synthetic biology has a wide utility, including various clinical applications. For example, the programmable CRISPR systems can be used to split proteins of toxic domains for targeted cell death, e.g., using cancer-linked RNA as target transcript. Further, pathways involving protein-protein interactions can be influenced in synthetic biological systems with e.g. fusion complexes with the appropriate effectors such as kinases or enzymes.

In some embodiments, guide RNA sequences that target phage sequences can be introduced into the microorganism. Thus, the disclosure also provides methods of vaccinating a microorganism (e.g., a production strain) against phage infection.

In some embodiments, the CRISPR systems provided herein can be used to engineer microorganisms, e.g., to improve yield or improve fermentation efficiency. For example, the CRISPR systems described herein can be used to engineer microorganisms, such as yeast, to generate biofuel or biopolymers from fermentable sugars, or to degrade plant-derived lignocellulose derived from agricultural waste as a source of fermentable sugars. More particularly, the methods described herein can be used to modify the expression of endogenous genes required for biofuel production and/or to modify endogenous genes, which may interfere with the biofuel synthesis. These methods of engineering microorganisms are described e.g., in Verwaal et al., "CRISPR/Cpfl enables fast and simple genome editing of *Saccharomyces cerevisiae," Yeast,* 2017 Sep. 8. doi: 10.1002/yea.3278; and Hlavova et al., "Improving microalgae for biotechnology—from genetics to synthetic biology," *Biotechnol. Adv.,* 2015 Nov. 1; 33:1194-203, both of which are incorporated herein by reference in the entirety.

Application in Plants

The CRISPR systems described herein have a wide variety of utility in plants. In some embodiments, the CRISPR systems can be used to engineer genomes of plants (e.g., improving production, making products with desired post-translational modifications, or introducing genes for producing industrial products). In some embodiments, the CRISPR systems can be used to introduce a desired trait to a plant (e.g., with or without heritable modifications to the genome), or regulate expression of endogenous genes in plant cells or whole plants.

In some embodiments, the CRISPR systems can be used to identify, edit, and/or silence genes encoding specific proteins, e.g., allergenic proteins (e.g., allergenic proteins in peanuts, soybeans, lentils, peas, green beans, and mung beans). A detailed description regarding how to identify, edit, and/or silence genes encoding proteins is described, e.g., in Nicolaou et al., "Molecular diagnosis of peanut and legume allergy," *Curr. Opin. Allergy Clin. Immunol.,* 2011 June; 11(3):222-8, and WO 2016205764 A1; both of which are incorporated herein by reference in the entirety.

Gene Drives

Gene drive is the phenomenon in which the inheritance of a particular gene or set of genes is favorably biased. The CRISPR systems described herein can be used to build gene drives. For example, the CRISPR systems can be designed to target and disrupt a particular allele of a gene, causing the cell to copy the second allele to fix the sequence. Because of the copying, the first allele will be converted to the second allele, increasing the chance of the second allele being transmitted to the offspring. A detailed method regarding how to use the CRISPR systems described herein to build gene drives is described, e.g., in Hammond et al., "A CRISPR-Cas9 gene drive system targeting female reproduction in the malaria mosquito vector *Anopheles gambiae," Nat. Biotechnol.,* 2016 January; 34(1):78-83, which is incorporated herein by reference in its entirety.

Pooled-Screening

As described herein, pooled CRISPR screening is a powerful tool for identifying genes involved in biological mechanisms such as cell proliferation, drug resistance, and viral infection. Cells are transduced in bulk with a library of guide RNA (gRNA)-encoding vectors described herein, and the distribution of gRNAs is measured before and after applying a selective challenge. Pooled CRISPR screens work well for mechanisms that affect cell survival and proliferation, and they can be extended to measure the activity of individual genes (e.g., by using engineered reporter cell lines). Arrayed CRISPR screens, in which only one gene is targeted at a time, make it possible to use RNA-seq as the readout. In some embodiments, the CRISPR systems as described herein can be used in single-cell CRISPR screens. A detailed description regarding pooled CRISPR screenings can be found, e.g., in Datlinger et al., "Pooled CRISPR screening with single-cell transcriptome read-out," *Nat. Methods.,* 2017 March; 14(3):297-301, which is incorporated herein by reference in its entirety.

Saturation Mutagenesis ("Bashing")

The CRISPR systems described herein can be used for in situ saturating mutagenesis. In some embodiments, a pooled guide RNA library can be used to perform in situ saturating mutagenesis for particular genes or regulatory elements. Such methods can reveal critical minimal features and discrete vulnerabilities of these genes or regulatory elements (e.g., enhancers). These methods are described, e.g., in Canver et al., "BCL11A enhancer dissection by Cas9-mediated in situ saturating mutagenesis," *Nature,* 2015 Nov. 12; 527(7577):192-7, which is incorporated herein by reference in its entirety.

RNA-Related Applications

The CRISPR systems described herein can have various RNA-related applications, e.g., modulating gene expression, inhibiting RNA expression, screening RNA or RNA products, determining functions of lincRNA or non-coding RNA, inducing cell dormancy, inducing cell cycle arrest, reducing cell growth and/or cell proliferation, inducing cell anergy, inducing cell apoptosis, inducing cell necrosis, inducing cell death, and/or inducing programmed cell death. A detailed description of these applications can be found, e.g., in WO 2016205764 A1, which is incorporated herein by reference in its entirety.

Modulating Gene Expression

The CRISPR systems described herein can be used to modulate gene expression. The CRISPR systems can be used, together with suitable guide RNAs, to target gene expression, via control of RNA processing. The control of RNA processing can include, e.g., RNA processing reactions such as RNA splicing (e.g., alternative splicing), viral replication, and tRNA biosynthesis. The RNA targeting proteins in combination with suitable guide RNAs can also be used to control RNA activation (RNAa). RNA activation is a small RNA-guided and Argonaute (Ago)-dependent gene regulation phenomenon in which promoter-targeted short double-stranded RNAs (dsRNAs) induce target gene expression at the transcriptional/epigenetic level. RNAa leads to the promotion of gene expression, so control of gene expression may be achieved that way through disruption or reduction of RNAa. In some embodiments, the methods include the use of the RNA targeting CRISPR as substitutes for e.g., interfering ribonucleic acids (such as siRNAs, shRNAs, or dsRNAs). The methods of modulating gene expression are described, e.g., in WO 2016205764, which is incorporated herein by reference in its entirety.

Controlling RNA Interference

Control over interfering RNAs or microRNAs (miRNA) can help reduce off-target effects by reducing the longevity of the interfering RNAs or miRNAs in vivo or in vitro. In some embodiments, the target RNAs can include interfering RNAs, i.e., RNAs involved in the RNA interference pathway, such as small hairpin RNAs (shRNAs), small interfering (siRNAs), etc. In some embodiments, the target RNAs include, e.g., miRNAs or double stranded RNAs (dsRNA).

In some embodiments, if the RNA targeting protein and suitable guide RNAs are selectively expressed (for example spatially or temporally under the control of a regulated promoter, for example a tissue- or cell cycle-specific promoter and/or enhancer), this can be used to protect the cells or systems (in vivo or in vitro) from RNA interference (RNAi) in those cells. This may be useful in neighboring tissues or cells where RNAi is not required or for the purposes of comparison of the cells or tissues where the effector proteins and suitable guide RNAs are and are not expressed (i.e., where the RNAi is not controlled and where it is, respectively). The RNA targeting proteins can be used to control or bind to molecules comprising or consisting of RNAs, such as ribozymes, ribosomes, or riboswitches. In some embodiments, the guide RNAs can recruit the RNA targeting proteins to these molecules so that the RNA targeting proteins are able to bind to them. These methods are described, e.g., in WO 2016205764 and WO 2017070605, both of which are incorporated herein by reference in the entirety.

Modifying Riboswitches and Controlling Metabolic Regulations

Riboswitches are regulatory segments of messenger RNAs that bind small molecules and in turn regulate gene expression. This mechanism allows the cell to sense the intracellular concentration of these small molecules. A specific riboswitch typically regulates its adjacent gene by altering the transcription, the translation or the splicing of this gene. Thus, in some embodiments, the riboswitch activity can be controlled by the use of the RNA targeting proteins in combination with suitable guide RNAs to target the riboswitches. This may be achieved through cleavage of, or binding to, the riboswitch. Methods of using CRISPR systems to control riboswitches are described, e.g., in WO 2016205764 and WO 2017070605, both of which are incorporated herein by reference in their entireties.

Therapeutic Applications

The CRISPR systems described herein can have various therapeutic applications. In some embodiments, the new CRISPR systems can be used to treat various diseases and disorders, e.g., genetic disorders (e.g., monogenetic diseases), diseases that can be treated by nuclease activity (e.g., Pcsk9 targeting, Duchenne Muscular Dystrophy (DMD), BCL11a targeting), and various cancers, etc.

In some embodiments, the CRISPR systems described herein can be used to edit a target nucleic acid to modify the target nucleic acid (e.g., by inserting, deleting, or mutating one or more amino acid residues). For example, in some embodiments the CRISPR systems described herein comprise an exogenous donor template nucleic acid (e.g., a DNA molecule or an RNA molecule), which comprises a desirable nucleic acid sequence. Upon resolution of a cleavage event induced with the CRISPR system described herein, the molecular machinery of the cell will utilize the exogenous donor template nucleic acid in repairing and/or resolving the cleavage event. Alternatively, the molecular machinery of the cell can utilize an endogenous template in repairing and/or resolving the cleavage event. In some embodiments, the CRISPR systems described herein may be used to alter a target nucleic acid resulting in an insertion, a deletion, and/or a point mutation). In some embodiments, the insertion is a scarless insertion (i.e., the insertion of an intended nucleic acid sequence into a target nucleic acid resulting in no additional unintended nucleic acid sequence upon resolution of the cleavage event). Donor template nucleic acids may be double stranded or single stranded nucleic acid molecules (e.g., DNA or RNA). Methods of designing exogenous donor template nucleic acids are described, for example, in PCT Publication No. WO 2016094874 A1, the entire contents of which are expressly incorporated herein by reference.

In one aspect, the CRISPR systems described herein can be used for treating a disease caused by overexpression of RNAs, toxic RNAs and/or mutated RNAs (e.g., splicing defects or truncations). For example, expression of the toxic RNAs may be associated with the formation of nuclear inclusions and late-onset degenerative changes in brain, heart, or skeletal muscle. In some embodiments, the disorder is myotonic dystrophy. In myotonic dystrophy, the main pathogenic effect of the toxic RNAs is to sequester binding proteins and compromise the regulation of alternative splicing (see, e.g., Osborne et al., "RNA-dominant diseases," *Hum. Mol. Genet.,* 2009 Apr. 15; 18(8):1471-81). Myotonic dystrophy (dystrophia myotonica (DM)) is of particular interest to geneticists because it produces an extremely wide range of clinical features. The classical form of DM, which is now called DM type 1 (DM1), is caused by an expansion of CTG repeats in the 3'-untranslated region (UTR) of DMPK, a gene encoding a cytosolic protein kinase. The CRISPR systems as described herein can target overexpressed RNA or toxic RNA, e.g., the DMPK gene or any of the mis-regulated alternative splicing in DM1 skeletal muscle, heart, or brain.

The CRISPR systems described herein can also target trans-acting mutations affecting RNA-dependent functions that cause various diseases such as, e.g., Prader Willi syndrome, Spinal muscular atrophy (SMA), and Dyskeratosis congenita. A list of diseases that can be treated using the CRISPR systems described herein is summarized in Cooper et al., "RNA and disease," *Cell,* 136.4 (2009): 777-793, and WO 2016205764 A1, both of which are incorporated herein by reference in the entirety. Those of skill in this field will understand how to use the new CRISPR systems to treat these diseases.

The CRISPR systems described herein can also be used in the treatment of various tauopathies, including, e.g., primary and secondary tauopathies, such as primary age-related tauopathy (PART)/Neurofibrillary tangle (NFT)-predominant senile dementia (with NFTs similar to those seen in Alzheimer Disease (AD), but without plaques), dementia pugilistica (chronic traumatic encephalopathy), and progressive supranuclear palsy. A useful list of tauopathies and methods of treating these diseases are described, e.g., in WO 2016205764, which is incorporated herein by reference in its entirety.

The CRISPR systems described herein can also be used to target mutations disrupting the cis-acting splicing codes that can cause splicing defects and diseases. These diseases include, e.g., motor neuron degenerative disease that results from deletion of the SMN1 gene (e.g., spinal muscular atrophy), Duchenne Muscular Dystrophy (DMD), frontotemporal dementia, and Parkinsonism linked to chromosome 17 (FTDP-17), and cystic fibrosis.

The CRISPR systems described herein can also be used in methods of treating a condition or disease in a subject in need thereof. The methods include administering to the subject a CRISPR system as described herein, wherein the spacer sequence is complementary to at least 12 (e.g., 12, 13, 14, 15, 16, 17, 18, 19, 20, 21, or more) nucleotides of a target nucleic acid associated with the condition or disease; wherein the Type III-E CRISPR-Cas effector protein associates with the Type III-E RNA guide to form a complex; wherein the complex binds to a target nucleic acid sequence that is complementary to the at least 12 (e.g., 12-21 or more) nucleotides of the spacer sequence; and wherein upon binding of the complex to the target nucleic acid sequence the Type III-E CRISPR-Cas effector protein cleaves the target nucleic acid, thereby treating the condition or disease in the subject.

For example, the condition or disease can be a cancer or an infectious disease. For example, the condition or disease can be a cancer selected from the group including or consisting of Wilms' tumor, Ewing sarcoma, a neuroendocrine tumor, a glioblastoma, a neuroblastoma, a melanoma, skin cancer, breast cancer, colon cancer, rectal cancer, prostate cancer, liver cancer, renal cancer, pancreatic cancer, lung cancer, biliary cancer, cervical cancer, endometrial cancer, esophageal cancer, gastric cancer, head and neck cancer, medullary thyroid carcinoma, ovarian cancer, glioma, lymphoma, leukemia, myeloma, acute lymphoblastic leukemia, acute myelogenous leukemia, chronic lymphocytic leukemia, chronic myelogenous leukemia, Hodgkin's lymphoma, non-Hodgkin's lymphoma, and urinary bladder cancer.

The CRISPR systems described herein can further be used for antiviral activity, in particular against RNA viruses. The effector proteins can target the viral RNAs using suitable guide RNAs selected to target viral RNA sequences.

Furthermore, in vitro RNA sensing assays can be used to detect specific RNA substrates. The RNA targeting effector proteins can be used for RNA-based sensing in living cells. Examples of applications are diagnostics by sensing of, for examples, disease-specific RNAs.

A detailed description of therapeutic applications of the CRISPR systems described herein can be found, e.g., in U.S. Pat. No. 8,795,965, EP 3009511, WO 2016205764, and WO 2017070605; each of which is incorporated herein by reference in its entirety.

Delivery of CRISPR Systems

Through this disclosure and the knowledge in the art, the CRISPR systems described herein, or components thereof, nucleic acid molecules thereof, or nucleic acid molecules encoding or providing components thereof, can be delivered by various delivery systems such as vectors, e.g., plasmids, viral delivery vectors. The new CRISPR enzymes and/or any of the RNAs (e.g., guide RNAs) can be delivered using suitable vectors, e.g., plasmids or viral vectors, such as adeno-associated viruses (AAV), lentiviruses, adenoviruses, and other viral vectors, or combinations thereof. The proteins and one or more guide RNAs can be packaged into one or more vectors, e.g., plasmids or viral vectors.

In some embodiments, the vectors, e.g., plasmids or viral vectors, are delivered to the tissue of interest by, e.g., intramuscular injection, intravenous administration, transdermal administration, intranasal administration, oral administration, or mucosal administration. Such delivery may be either via a single dose, or multiple doses. One skilled in the art understands that the actual dosage to be delivered herein may vary greatly depending upon a variety of factors, such as the vector choices, the target cells, organisms, tissues, the general conditions of the subject to be treated, the degrees of transformation/modification sought, the administration routes, the administration modes, the types of transformation/modification sought, etc.

In certain embodiments, the delivery is via adenoviruses, which can be at a single dose containing at least $1\times10^5$ particles (also referred to as particle units, pu) of adenoviruses. In some embodiments, the dose preferably is at least about $1\times10^6$ particles, at least about $1\times10^7$ particles, at least about $1\times10^8$ particles, and at least about $1\times10^9$ particles of the adenoviruses. The delivery methods and the doses are described, e.g., in WO 2016205764 A1 and U.S. Pat. No. 8,454,972 B2, both of which are incorporated herein by reference in the entirety.

In some embodiments, the delivery is via plasmids. The dosage can be a sufficient number of plasmids to elicit a response. In some cases, suitable quantities of plasmid DNA in plasmid compositions can be from about 0.1 to about 2 mg. Plasmids will generally include (i) a promoter; (ii) a sequence encoding a nucleic acid-targeting CRISPR enzymes, operably linked to the promoter; (iii) a selectable marker; (iv) an origin of replication; and (v) a transcription terminator downstream of and operably linked to (ii). The plasmids can also encode the RNA components of a CRISPR complex, but one or more of these may instead be encoded on different vectors. The frequency of administration is within the ambit of the medical or veterinary practitioner (e.g., physician, veterinarian), or a person skilled in the art.

In another embodiment, the delivery is via liposomes or lipofectin formulations and the like, and can be prepared by methods known to those skilled in the art. Such methods are described, for example, in WO 2016205764 and U.S. Pat. Nos. 5,593,972; 5,589,466; and 5,580,859; each of which is incorporated herein by reference in its entirety.

In some embodiments, the delivery is via nanoparticles or exosomes. For example, exosomes have been shown to be particularly useful in delivery RNA.

Further means of introducing one or more components of the new CRISPR systems to the cell is by using cell penetrating peptides (CPP). In some embodiments, a cell penetrating peptide is linked to the CRISPR enzymes. In some embodiments, the CRISPR enzymes and/or guide RNAs are coupled to one or more CPPs to effectively transport them inside cells (e.g., plant protoplasts). In some embodiments, the CRISPR enzymes and/or guide RNA(s) are encoded by one or more circular or non-circular DNA molecules that are coupled to one or more CPPs for cell delivery.

CPPs are short peptides of fewer than 35 amino acids either derived from proteins or from chimeric sequences capable of transporting biomolecules across cell membrane in a receptor independent manner. CPPs can be cationic peptides, peptides having hydrophobic sequences, amphipathic peptides, peptides having proline-rich and anti-microbial sequences, and chimeric or bipartite peptides. Examples of CPPs include, e.g., Tat (which is a nuclear transcriptional activator protein required for viral replication by HIV type 1), penetratin, Kaposi fibroblast growth factor (FGF) signal peptide sequence, integrin (33 signal peptide sequence, polyarginine peptide Args sequence, Guanine rich-molecular transporters, and sweet arrow peptide. CPPs and methods of using them are described, e.g., in Hallbrink et al., "Prediction of cell-penetrating peptides," *Methods Mol. Biol.*, 2015; 1324:39-58; Ramakrishna et al., "Gene disruption by cell-penetrating peptide-mediated delivery of Cas9 protein and guide RNA," *Genome Res.*, 2014 June; 24(6):1020-7; and WO 2016205764 A1; each of which is incorporated herein by reference in its entirety.

Various delivery methods for the CRISPR systems described herein are also described, e.g., in U.S. Pat. No. 8,795,965, EP 3009511, WO 2016205764, and WO 2017070605; each of which is incorporated herein by reference in its entirety.

EXAMPLES

The invention is further described in the following examples, which do not limit the scope of the invention described in the claims.

Example 1— Identification of Minimal Components for Type III-E (CLUST.019911) CRISPR-Cas System (FIGS. 1-6)

Figure 1:
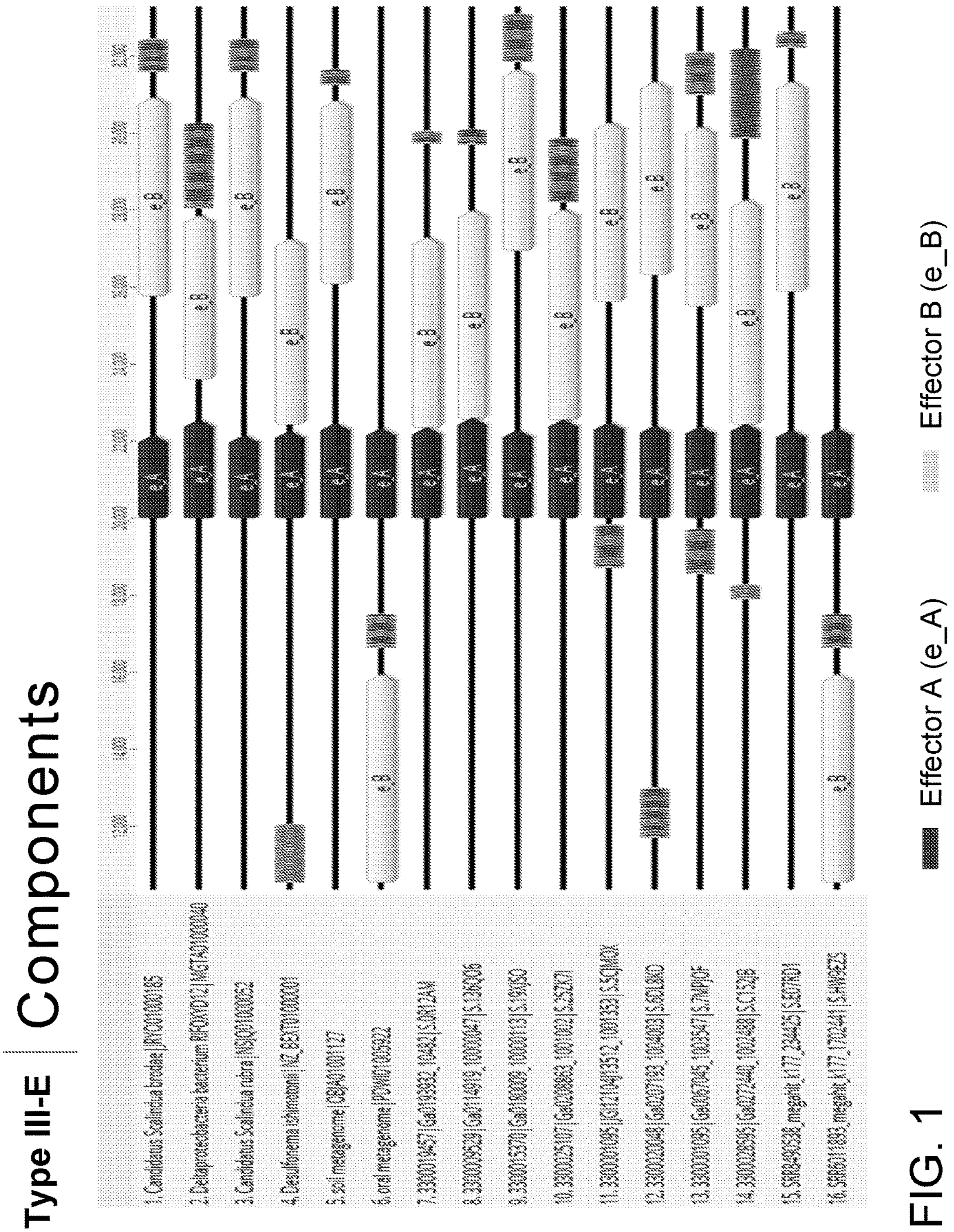
Figure 3A:
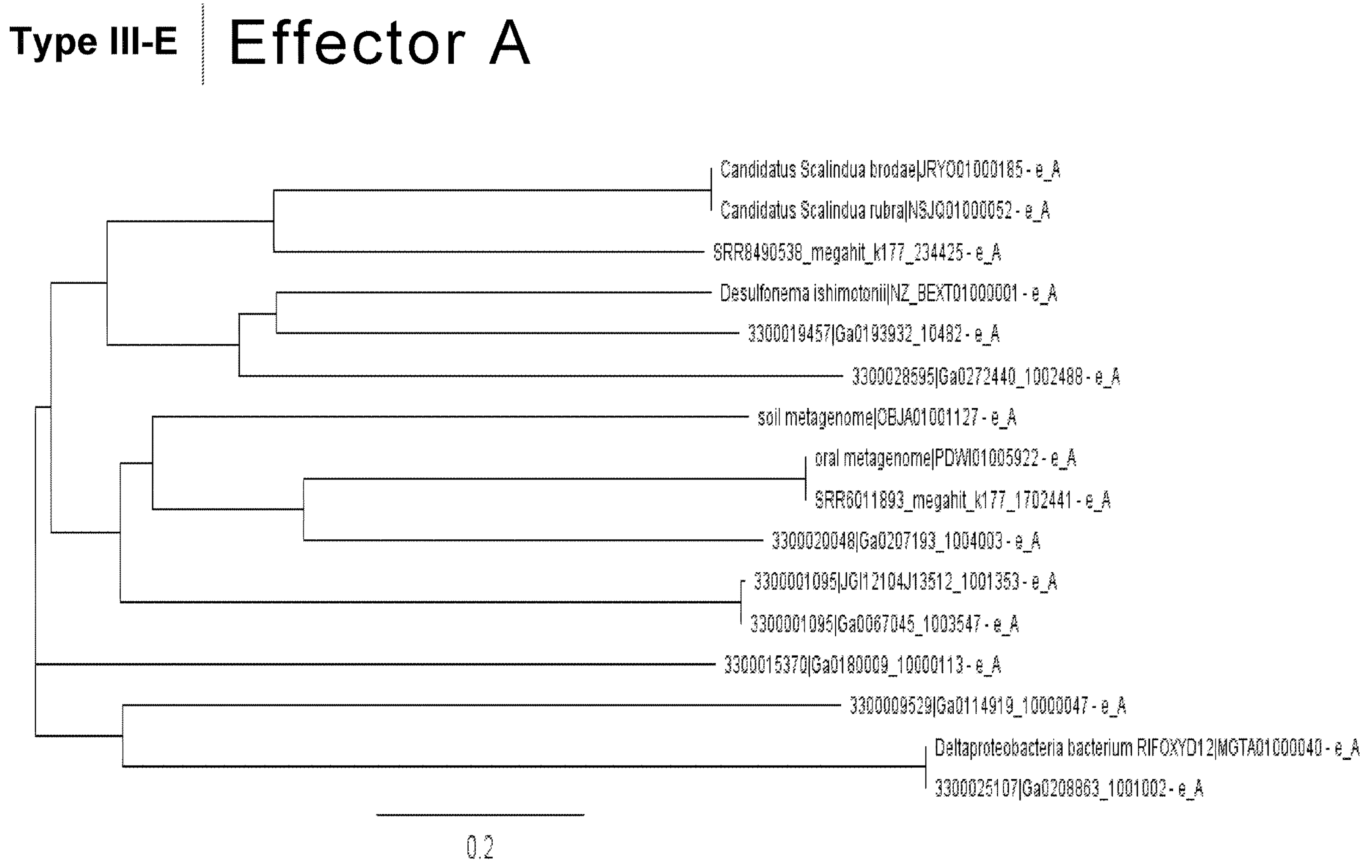
FIG. 3A is a phylogenetic tree of Type III-E (CLUST.019911) Effector A proteins.
Figure 3B:
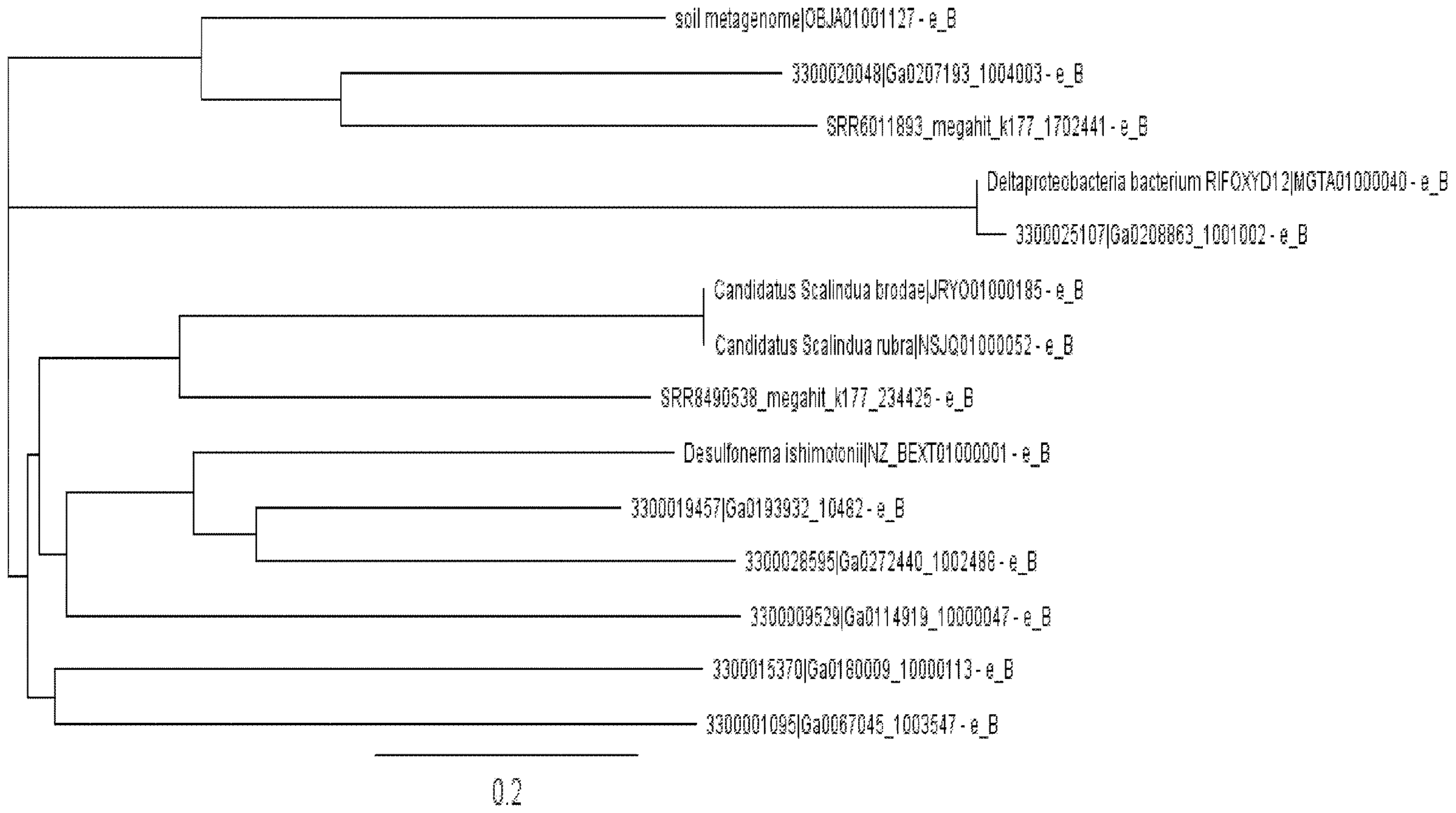
FIG. 3B is a phylogenetic tree of Type III-E (CLUST.019911) Effector B proteins.

This protein family describes a CRISPR system found in organisms including, but not limited to, Deltaproteobacteria, Candidatus Scalindua, and uncultured metagenomic sequences collected from aquatic freshwater and marine environments (FIGS. 3A-3B). Exemplary naturally occurring loci containing this effector complex are depicted in FIG. 1, indicating that the effector protein Effector A (~800 amino acids) has a high co-occurrence with the effector protein Effector B (~1700 aa). Type III-E CRISPR-Cas systems include the exemplary effectors detailed in TABLES 1—3 and crRNAs containing exemplary sequences detailed in TABLE 4.

Type III-E CRISPR-Cas direct repeat sequences (consensus sequence being GTTRNRNANMRMCRSNWDYYWTTRATGTBACGGDAC (SEQ ID NO: 100)) show a conserved TGTNWYGGNAC (SEQ ID NO: 99) at the 3' end (see FIG. 2), wherein the various letters used in these consensus sequences (other than A, G, C, and T) have the following standard meanings:

| | | |
|---|---|---|
| R | A or G | puRine |
| Y | C, T or U | pYrimidines |
| K | G, T or U | bases which are Ketones |
| M | A or C | bases with aMino groups |
| S | C or G | Strong interaction |
| W | A, T or U | Weak interaction |
| B | not A (i.e. C, G, T or U) | B comes after A |
| D | not C (i.e. A, G, T or U) | D comes after C |
| H | not G (i.e., A, C, T or U) | H comes after G |
| V | neither T nor U (i.e. A, C or G) | V comes after U |
| N | A C G T U | Nucleic acid |
| — | gap of indeterminate length | |

FIGS. 3A and 3B show phylogenetic trees of Type III-E effector A and effector B proteins, respectively, showing that the both effectors exhibit diversity.

Figure 4:
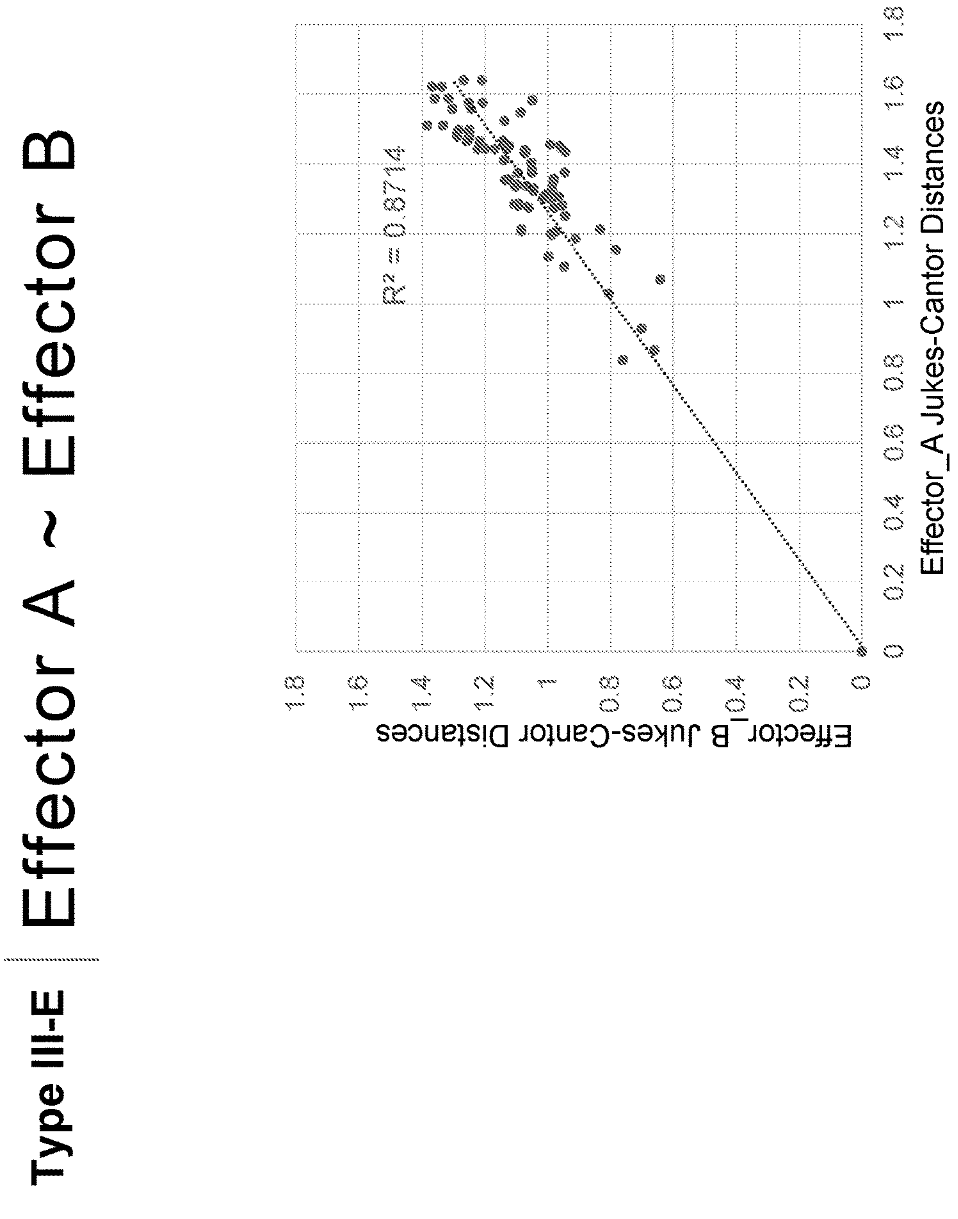
FIG. 4 is a scatter plot that depicts one point for each pair of genomic loci, where the x-value is the pairwise Jukes-Cantor distance of the Type III-E Effector_A proteins from the two loci, and the y-value is the pairwise Jukes Cantor distance of the Type III-E Effector_B proteins from the two loci.

FIG. 4 shows the pairwise Jukes-Cantor distances for effector A and effector B proteins, indicating that two loci containing similar effector A proteins also contain correspondingly similar effector B proteins, indicative of co-evolution and potential functional association.

Figure 6:
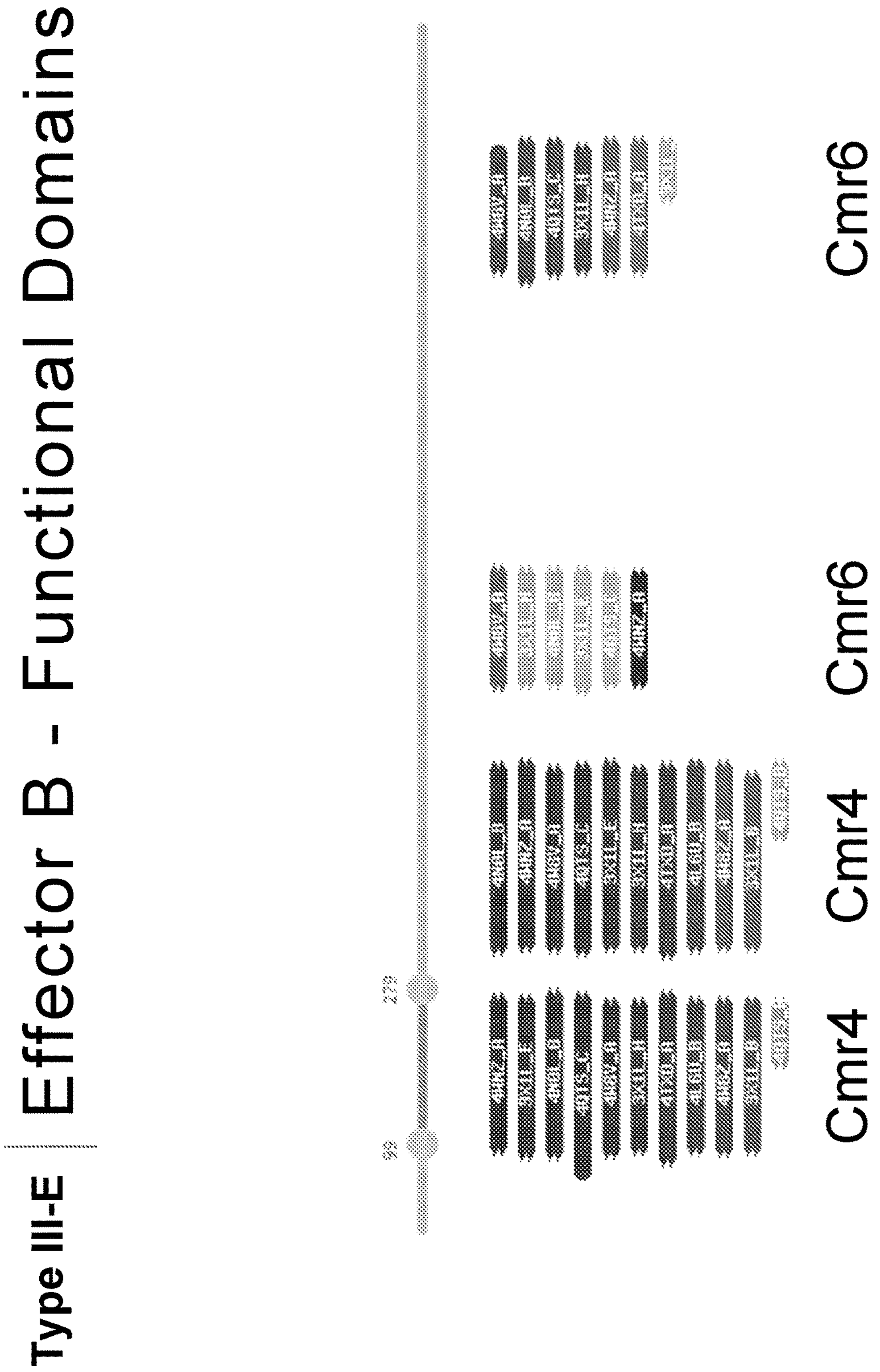
FIG. 6 is a schematic representation of HHpred domain predictions of an example of a Type III-E (CLUST.019911) Effector B, depicting multiple partial matches in different regions of the protein to CRISPR Cmr4 and CRISPR Cmr6.

An HMM profile search of the multiple sequence alignment of Type III-E effector A proteins against the PFAM database indicated the presence of the CHAT domain. HHpred domain predictions of an exemplary Type III-E Effector A are also depicted in FIG. 4, indicating a C-terminal match to the CHAT domain, and an N-terminal match to the TPR domain. HHpred domain predictions of an exemplary Type III-E Effector B are depicted in FIG. 6, which indicates multiple partial matches in different regions of the protein to Cmr4 and Cmr6.

Optionally, the CLUST.019911 CRISPR system includes a transactivating RNA (tracrRNA) with a DR homology as detailed in TABLE 5 and a complete tracrRNA contained in the DR homology loci detailed in TABLE 6. Optionally, the system includes a tracrRNA that is a subset of a non-coding sequence listed in TABLE 7.

Optionally, the system includes a RNA modulator that is a subset of a non-coding sequence listed in TABLE 7.

TABLE 1

Representative Type III-E (CLUST.019911) Effector Proteins

| Source | Effector_A accession | Effector_B accession | # spacers | cas1 | cas2 | Effector_A size | Effector_B size |
|---|---|---|---|---|---|---|---|
| Candidatus Scalindua brodae (JRYO01000185) | KHE91663.1 | JRYO01000185_8\|M | 11 | N | N | 716 | 1722 |
| Deltaproteobacteria bacterium RIFOXYD12_FULL_50_9 (MGTA01000040) | OGR07204.1 | OGR07205.1 | 31 | N | N | 849 | 1403 |
| Desulfonema ishimotonii (NZ_BEXT01000001) | WP_124327588.1 | WP_124327589.1 | 22 | Y | Y | 751 | 1601 |
| soil metagenome (OBJA01001127) | OBJA01001127_8\|M | OBJA01001127_4\|M | 5 | Y | Y | 816 | 1575 |
| oral metagenome (PDWI01005922) | PDWI01005922_7\|M | PDWI01005922_5\|M | 12 | Y | Y | 769 | 1801 |
| aquatic-marine-hydrothermal vent microbial mat (3300019457\|Ga0193932_10482) | RLC19860.1 | 3300019457\|Ga0193932_10482_5\|M | 4 | Y | N | 778 | 1652 |
| aquatic-marine-deep subsurface (3300009529\|Ga0114919_10000047) | 3300009529\|Ga0114919_10000047_39\|M | 3300009529\|Ga0114919_10000047_40\|M | 5 | Y | Y | 860 | 1806 |

TABLE 1-continued

| Representative Type III-E (CLUST.019911) Effector Proteins | | | | | | | |
|---|---|---|---|---|---|---|---|
| Source | Effector_A accession | Effector_B accession | # spacers | cas1 | cas2 | Effector_A size | Effector_B size |
| aquatic-freshwater-groundwater (3300015370\|Ga0180009_10000113) | 3300015370\|Ga0180009_10000113_9\|P | 3300015370\|Ga0180009_10000113_2\|P | 17 | N | N | 757 | 1559 |
| bioremediation-terephthalate-wastewater bioreactor (3300001095\|JGI12104J13512_1001353) | 3300001095\|JGI12104J13512_1001353_7\|M | 3300001095\|JGI12104J13512_1001353_10\|M | 15 | Y | Y | 822 | 1549 |
| aquatic-freshwater-freshwater lake sediment (3300020048\|Ga0207193_1004003) | 3300020048\|Ga0207193_1004003_10\|P | 3300020048\|Ga0207193_1004003_13\|M | 17 | Y | Y | 797 | 1668 |
| bioremediation-terephthalate-wastewater bioreactor (3300001096\|Ga0067045_1003547) | 3300001096\|Ga0067045_1003547_9\|P | 3300001096\|Ga0067045_1003547_12\|M | 31 | Y | Y | 789 | 1549 |
| terrestrial-soil (3300025107\|Ga0208863_1001002) | OGR07204.1 | 3300025107\|Ga0208863_1001002_11\|M | 23 | N | N | 849 | 1821 |
| aquatic-marine-marine sediment (3300028595\|Ga0272440_1002488) | 3300028595\|Ga0272440_1002488_3\|P | 3300028595\|Ga0272440_1002488_4\|M | 39 | N | N | 809 | 1940 |
| anammox bioreactor (SRR8490538) | SRR8490538_megahit_k177_234425_6\|M | SRR8490538_megahit_k177_234425_10\|M | 5 | N | N | 760 | 1812 |
| dolphin oral metagenome (SRR6011893) | SRR6011893_megahit_k177_1702441_3\|P | SRR6011893_megahit_k177_1702441_5\|M | 12 | Y | Y | 769 | 1801 |

TABLE 2

Amino Acid Sequences of Representative Type III-E (CLUST.019911) Effector_A Proteins >KHE91663.1
[*Candidatus Scalindua brodae*]
MNNTEENIDRIQEPTREDIDRKEAERLLDEAFNPRTKPVDRKKIINSALKILIGLYKEKKDDLTSASFISIARAYYLVSITILP
KGTTIPEKKKEALRKGIEFIDRAINKFNGSILDSQRAFRIKSVLSIEFNRIDREKCDNIKLKNLLNEAVDKGCTDFDTYEWDIQ
IAIRLCELGVDMEGHFDNLIKSNKANDLQKAKAYYFIKKDDHKAKEHMDKCTASLKYTPCSHRLWDETVGFIERLKGDSSTLWR
DFAIKTYRSCRVQEKETGTLRLRWYWSRHRVLYDMAFLAVKEQADDEEPDVNVKQAKIKKLAEISDSLKSRFSLRLSDMEKMPK
SDDESNHEFKKFLDKCVTAYQDGYVINRSEDKEGQGENKSTTSKQPEPRPQAKLLELTQVPEGWVVVHFYLNKLEGMGNAIVFD
KCANSWQYKEFQYKELFEVFLTWQANYNLYKENAAEHLVTLCKKIGETMPFLFCDNFIPNGKDVLFVPHDFLHRLPLHGSIENK
TNGKLFLENHSCCYLPAWSFASEKEASTSDEYVLLKNFDQGHFETLQNNQIWGTQSVKDGASSDDLENIRNNPRLLTILCHGEA
NMSNPFRSMLKLANGGITYLEILNSVKGLKGSQVILGACETDLVPPLSDVMDEHYSVATALLLIGAAGVVGTMWKVRSNKTKSL
IEWKLENIEYKLNEWQKETGGAAYKDHPPTFYRSIAFRSIGFPL (SEQ ID NO: 1)

>OGR07204.1
[*Deltaproteobacteria bacterium* RIFOXYD12 FULL 50 9]
MNQNIDRAVGAILAIETATPLTESSTLAQRERHQKLLHDETKKIEQAFIALAQPPQCRAVEIAALSRFLOMTPLAVGPLRKRVI
CRAEPLKDDAHEQEIASHFNGLLLRLAKGLLASALNPAGIPWRRRVLWLEKAAHIAHRFDKEPLADDKERTEAAGVLARCCLHL
ALAHLPKGKDKSAMAERQEDLLQSLMWAQKAIVLAGQDKLSGEEYKLLKALVLIELDNLSPGRFQQQLNYVLYDLAVIWLERDT
ATKPFHPQELFVLWRYLATDFEPDLNMLLFKGSNTSERTAAVQQASPEAERFRPLLPLIHAWSAWKLDPPNNKIAEVILQAVNN
LDEHQVYEQVWKWTVDFLQELRNTGAVDWQLPAIAAWELCNKKEKELPFGFQIRQYWSRLDSLYRLAFDGALELKDCMTAARIV
DSLKSRTPLTWRDMDTLFAKLPKEKADQLREAFYSMEVQARMGFYAEAKEDANKLKKLLAAQVRKIRDIESVPAGWTVVHFHLR
EDQDLGYALACRLTADGMSYWTNHIFPVAGIRRAYDCWLEAYHGMEPGAREKSGYQLVELSEIMGKDLDFLFELAGEDGARGLL
FVPHGFSHLLPLHAAKKDGSYLFEKIPSLTLPAWEFAPDVDQIPVSDGQDFCFISQRANEQDLVGNIERSHTWNGVCNKNAAWT
NVLNTNKEWSKAPPRWLVFWCHGQADPHVAFRSKLLLGTLGVSLFEIQEAALSLTGTKVVLAVCESDLAPPEEYEKTDDHLSLA
APFLLKGARQVLAAIWEGAQLDLLKAMKEMLSNQDKHSWEILRELQSCWMRQPGAIFNDEYIRLYYAASFRILGFPEVATTNMA
TATAQEEIA (SEQ ID NO: 2)

>WP_124327588.1
[*Desulfonema ishimotonii*]
MSNPIRDIQDRLKTAKFDNKDDMMNLASSLYKYEKQLMDSSEATLCQQGLSNRPNSFSQLSQFRDSDIQSKAGGQTGKFWQNEY
EACKNFQTHKERRETLEQIIRFLONGAEEKDADDLLLKTLARAYFHRGLLYRPKGFSVPARKVEAMKKAIAYCEIILDKNEEES
EALRIWLYAAMELRRCGEEYPENFAEKLFYLANDGFISELYDIRLFLEYTEREEDNNFLDMILQENQDRERLFELCLYKARACF
HLNQLNDVRIYGESAIDNAPGAFADPFWDELVEFIRMLRNKKSELWKEIAIKAWDKCREKEMKVGNNIYLSWYWARQRELYDLA
FMAQDGIEKKTRIADSLKSRTTLRIQELNELRKDAHRKQNRRLEDKLDRIIEQENEARDGAYLRRNPPCFTGGKREEIPFARLP
QNWIAVHFYLNELESHEGGKGGHALIYDPQKAEKDQWQDKSFDYKELHRKFLEWQENYILNEEGSADFLVTLCREIEKAMPFLF
KSEVIPEDRPVLWIPHGFLHRLPLHAAMKSGNNSNIEIFWERHASRYLPAWHLFDPAPYSREESSTLLKNFEEYDFQNLENGEI TABLE 2-continued

| Amino Acid Sequences of Representative Type III-E (CLUST.019911) Effector_A Proteins |
|---|
| EVYAPSSPKKVKEAIRENPAILLLLCHGEADMTNPFRSCLKLKNKDMTIFDLLTVEDVRLSGSRILLGACESDMVPPLEFSVDE<br>HLSVSGAFLSHKAGEIVAGLWTVDSEKVDECYSYLVEEKDFLRNLQEWQMAETENFRSENDSSLFYKIAPFRIIGFPAE (SEQ<br>ID NO: 3) |
| >OBJA01001127_8\|M<br>[soil metagenome]<br>MEHKTMTEPAGQNPSATDNDFEKFIIDTGCVFFATPQEDPKYQNNKVEWHQGLCRFAQNDSPPTVIGSAIFFLQKLQEPGLFSG<br>LPVSPELCSKISKDKNEIVAYHQQCILRLCEELLVKGREAKEHRERRQAFDQAIKFLLVLKKGTSSDTPSPNGHIHFQDQVSIL<br>LAEAYYLRGKIIRPKGFSVPAKKIETLEVAEKILVDLVARDTTGKARRLRAMVHIDLAALRDPADDSGNLQDYRQALEQAVSSI<br>GDTKTCGRDEIVIILARAEDNAGWTGSDGLSARLEELVNNGAAGPLDQARAYLLLGQNNLAVTQTEKAITRMAATDNPTPFSHE<br>DWRLLVRLLRDLKHQNTAGIDKLILDTWRKVHQIERQTKNGMHVRWYWSRORDLYDLAFHAAGNDARLKAQIADSLKARPALHL<br>GQAADLGLAVEQMEAGLLDRYMPGKMLEQTTDMAAPAAPGSAGWPELPRPWIAVHFYLSNGFGHPEGKQQGHALIQDSSKGDGK<br>DTWSERTFDYFPIWAAFMTWQENYQRLKKEAAPDLERLCQVMGROMPFLFAPEDLPLERPVVFVPHDFLHRLPLHAALIDNGEE<br>SGIPAQSHPITYLPGWWMVTSQAANPNETASKNTPSPVAPVALVHWDNSEDIHDIIKQANGTVVVNASRSDWLKLKHNAVGLKV<br>LYCHGQAGYTNPFASSLKLDGGGLYLKDVVKGPPLVGRFILAACESDLVLPASTTLDEYFSFSTGLLQKGAAEILGTLWEVNET<br>DALSLIETVLRAPASGNLSFVLRDWLRDNLRSLTTELFYDIAAFRALGGPYPVDTKEEHR (SEQ ID NO: 4) |
| >PDWI01005922_7\|M<br>[oral metagenome]<br>MNTVELLQEEERLTLDLVFLPPGSKNKEQKKNALVDLLLKIVEHGELTRKYSALLTLSRGALRGEVHFGEKLLPSPEACANLAK<br>PEEIKKMIRQHFQYRLDLLEAIVKKAADNTYSHARRRKALRIAIKELEQICEEALDELCFKARLLLAEALFERGRIVRPKGFSE<br>PGKKKELFQKAINCIEGNCSEEALRLRARIYLQWYRFFHDEPPCDLDDIFTKALAVTDDKMLKTELLLLCGERKEPDPYTDDLR<br>ALLNDQNVSPLSRARAAVLLEDWERCNVEIYEAIEDLGKTDFFQQDWELVVTLLKKNYNQFHGWSRACTRLWEITVEKESKDAG<br>HGCVLRWYWSRQRDVYNLAFAAFEECEDKARVVDSLKNRPAHHFSQLEQLAQSSDIIKQWIESEEIINQDSFAHSLRRHEKGAK<br>SHSGGSLRIFPCLPKGWIAVHFFLASWPEPKGYALIHNADTNTWEQRDFKYEQLWATYIAWQEVSLHNKIRESALLLKSLCETL<br>GKEMRWLFDEFLFPKERRRVLFVPHDFLHRLPLHMAIDIESQTVFAAKQPVCYLPAYHLQNNITENKKTSIYALVNLRENKQQK<br>KDEEIFAEKVEKMGAIVRRPALESDLLNLNPVPEKLVLYCHGIGHSANPFASKLCLGDTGVSYRDILALNRSLAGCRVLLFACE<br>TDLVPAQTSSIDEHLSISNALLQKGAFEVLGSLWALPGKTIYGITKTFIDNDDTSAVLHSSLKRLFEHYEKKNEKTRAQLLYNW<br>ASLRVLAPAREFS (SEQ ID NO: 5) |
| >RLC19860.1<br>[aquatic-marine-hydrothermal vent microbial mat]<br>MRYSSRTNCEAIDNLAEALQDQENMPEIARRVLEFEAENAKPENALCQHGLPHTKKAASQIAGVRDKHSEFYDNALLDLVEEWL<br>KTYEEAKKLTHRERRQEMEDKIRVLQPVLQAKGKDADPRFLSLLARIYLYRGMLFRPKGFTTPARKIEALKKAVOLSEKAVEKE<br>KDNPNFLRTWAQAALELEAIPETSFKVSSGLLKDAAVCINRDGIHSLNDLQVILEYAESEGKTSFLQHVLVEKRYWKRPFDLFL<br>LKARAAFALNRMDDVRYFLKSAMDKTPKALSSPFWDHLVDFLKKLRTKEGSDLWKEMAVAAHRLCREKEVKIANNIYLYRHWAR<br>QKSLYNMAFLAQNDLKEKAKIADSLKSRPVLRYQALREMKEHQNIAKLLEQDDQERDGGYHKQQVEMDERTGKRLSEKMEKAGV<br>SYENLPVPWISVHFYLNESENSEDEGSKGYALIFDALTQSWKERRFDYAKLHRKFMTWQEAYISAKKSSFAKDSLVELCREIGN<br>TMPFLFDTACIRDGAPVLWIPHGFLHRLPLHAAIRDEATNEIFLENHASRYLPAWSILNSASARRGKDSYMIKRFRAEDYEKEP<br>FSELEDMEWDNEEHEKLATPDDLKHFMAKNPGVFAVLCHGHGDILNPLKSWLELEGGGVSVLDILRYEKANLSGTRVLLGACEA<br>DMAPPVEYAIDEHVSLSAAFLSHKAQEVIAGLWEINIGEADECYAEILDCSDLSTELKDWQCDWVEKWRDDVEASGDNSTFYHI<br>TPFRIMGFPLKLKENNESEAKQ (SEQ ID NO: 6) |
| >3300009529\|Ga0114919_10000047_39\|M<br>[aquatic-marine-deep subsurface]<br>MVTPQASKNPAVDEILKQLTPYDMETENAKAIETRKSCIECLKGICERAQKQNDWVAFGTALHFLHELSGTTAPVFYGAVKGQS<br>ACGQLHNMQASIKEAVARITKSRAEHLRDKALKPYGIPYLSRHRFLEKAIRMVWELLQSDNGWPDSVWLHREASQFIARCFLDR<br>GRLVLPKGSSIPQKKIEALKKAWHWALKGALKAKEDDADSMKLWLEFREYILQTAKENDADIDSMKLLIEIGLELELYEKSFSP<br>QVNELTRKIASGKLLEDPKSSADWPIIDRGRSIGCFDEKQDEALFKLDLNKKEYKELPTLPLLRAKAGHRLKRDLASAFDEASF<br>FRVVCDAVRKLADVPFSSPIWVETIEFLAQLDPGSEIRNAASVAAWQICKLKEEDLDLGLQVRMWWSRHKMLYDLAFHAALSKD<br>DWALAARIADSPKSRPTIKALAMESVLDGDTLKGYYELEARGVARGYDSTYHRKKKSLEKAEAKKKRASKDTQGLRPLDFEEDI<br>PAGWAAIHLYLDQDKKGHALMRSAGSTKDGWLYKDFEISDIWQKFQAWQAADRYNPKFGGAATELHALCESLGYDDDHLGFLFN<br>KDLPDNLIIIPHDILHLVPIHSVMKNGEILLKQKKCIYLPAWGLPRETDSASTPEGEGLFDNFEDHDPLRQYLQPVLQAWKHSS<br>VSARNIKVPDATANDVRNYLKNTTNPEWMVFLCHGKADPVNPYNSGLLLRGSHLTHAALVELPKKMAGTKVFLGACETDMSPPK<br>QKSVDEHLSVSTAFFQKGASEIAGGLWRVHSAIAKKMVEHISENRKKPLVDVVWEKQKDWWDNGIQYVVDGITVKVSNCFKKLY<br>YLSSYRVVGFPRAIGENTDE (SEQ ID NO: 7) |
| >3300015370\|Ga0180009_10000113_9\|P<br>[aquatic-freshwater-groundwater]<br>MYSDFPALRLPELSVDQKKLFKISGTNPQLIYILMNEFDGEGDEPFFTGLVPDETDLSENKQAPLLKELARHLLKEYEDIGRNR<br>WKHADQRRVLEKAIRLLDKSHQAEENVSLELGKAYLYRARIIRPKGFTVPAKKIEALNNALHFCEDATNHGKAWADHFAGLVAL<br>ELYRCGKTHDNLSELLNKATADAELSEPDRRVEFYQMRVRLEELRQDEGNGSPYFIQNVLTKIFEFQEPGMELEKLKVSLQSPS<br>SSKDKISSSLEDLILVLKEYPFSHPLWEDTVRFARRLYFNRLEFWKELALRLWEAAEDESRKISSVHLRWYWSRORDLYDLSFL<br>AALKQGNPNLAAQVTDSAKSRPALSWQAIERLKHGNEELKDEIENYAQALSGGYIKGLLKPYRKPEVPNEEKPFFEQHLIDNNL<br>IAIQFYLVHLEEFEKVERSRERGYALIYDQESEKKWSFKTFDFAPIWEKYVAWQSVYFDLPPQQRDASGTQLRYLCEALGKALE<br>FLFKSPEKQFSSNEKSKDILFIPHDFLHRVPLHGAMLDNENVLLKTFNCFYLPAISYSAKNOGPQQNKNSVLLYYSGKSEESDD<br>PLFNHLKTKFDTPINFASATDLLDAAQNPPSLLVLYCHGEADATNPYLSRLKLKDDLMLLDFASAAGTFTGSKIFLGACETDLM<br>PPLDAPLDEQISMATIFLIKRSESVIGSMWEAKRMKVLNLLFMKEGLFDHFFEQQREWWKEEYEHTDSNTALYDCLCFRMYRCY<br>F (SEQ ID NO: 8) |
| >3300001095\|JGI12104J13512_1001353_7\|M<br>[bioremediation-terephthalate-wastewater bioreactor]<br>MFGGVEKNCLALSLGRHEKRQIYKSILAAGGLLLAQPADETFLPMITKYYREILAAEVKLAFCLPDEAHNVVYKRDEACRELVQ<br>ACRNQAGGLTEQGYQYLGSALLFLSGGLGEAPGLVALPVLSQELCEALASREADIHAFHARQGLEVAAAIIERAREPQWQHAQR<br>RQALEAVIKDLQQRSAICPPDLQDRLRLLLAQAYLERSRIIRPKGFTISPKKKEALDKALEQLDQVTDTGKTTLDYHRFRGDIF<br>LELGRLEARTGKEIEACLAEAILFLDPRTPANLTPVDCRLIVAYARLARDPSYLPLVLGSSKATALDRAWAAYLSNNASGAAKE<br>INTVLQDLQRRWFSHPDWEGLVDLLVDWARSSQKGWEDLATAAWQVCQKNEQELRYSGCQLRWYWSRHQDLYDLAFQAAPTLEE |

TABLE 2-continued

| Amino Acid Sequences of Representative Type III-E (CLUST.019911) Effector_A Proteins |
|---|
| KARVADSLKSRPLVRLALAEQLAQAQAKKKRGADVDFAQLIEQDARAYANQYIAGGLAAGSASAPVAPLSFTELPDEQWLAVHF<br>YLSSGAAAGLKKNMAYALVYDAKDQKWSCEGPYETTDLWQAYRRWODNYAAVSQASAPELESLCRQIGTTFPFLWALPSERPVV<br>FIPHGFLHRLPLHMALREDGATLEVWAATHPSTYLPAWSLRPRADAGGSQNVAAVYLPDELHDAEDFQNILAGOSFAAAASWPV<br>FRKQAGQARRLALVCHGLAHAVNPFAARLLLPEEPQLVDFLTDLPALPGSQVFLAACEADMAPAQEAPLDEHLSLATAFLQKGA<br>REVLGGVFEVNKYLANELLSSFGATSAAACYSLLWKWQQARLDNFLDNPDPLNLYWLAPWRVLGLS (SEQ ID NO: 9) |
| >3300020048\|Ga0207193_1004003_10\|P<br>[aquatic-freshwater-freshwater lake sediment]<br>MTETNHLSSDYQKAITLETKLAFLRPTQEQDTIESTRRELAETLSRLVNQKISPETLSAITTLHGMDLQGLGVLSGSLPNKDRC<br>AFAGNKKKFSAAWEFHWLQRIDLMRKIIDKASGQDDKLSHASRRQALGVAINSLEKAIAEIGDTGILVSKARLDLARALFHRGR<br>IVRPKGFSVPGKKKELFLKALDQIRIATNNKDDDQTLFLKAEIYLEWLRFFPMELPEDLDVVFKAAQQKADEPLKTNLILMIGE<br>RGSAKPIELEALONIEVDEKQEPLTRARAAAISGNWDICAKYLSEAIKKLEIKSFFHQDWEEAVELLKKGRTKISNYQWATICK<br>SLWKLTVQKENRTSNGCHLRWYWSRQREVYDLAFEAAGNDYSKKAKITDSLKGRPALHFAQMETIAEGEDEIKTWIEHQEAGFL<br>NQYISAFESADQGKKPGNLSWPKLPKGWIAVHFYLGLGTCSGEKKGYALIQNGQDWYQRTFDYEVLWVAYLAWQTMYGKCGHLD<br>DILKQQEVLSPVVESLCEQIGKEMPWLFDPGLFPEGQAVVFIPHDFLHRLPLHMALDPKPDPGKAQLFLSLHLVLSLPAWWQAS<br>ETNSPPAPDTVKANEKIFLANFENPSDAFQSLIDAIPKSVKVERVAKKSNLLEANSPSLLVVYCNGEAQPGNPFASRLLFSDSG<br>LPVSGILGSTINLRRSNIILGACETDLMLALNKTLDEHITLSSAFIQKGAELVSGTLWKIHENDEIDFIKLALVENSSLHEQWL<br>KWYDTNIKAYENDPKNNPRVFYKAAAIRIVGKPWTIEDIGK (SEQ ID NO: 10) |
| >3300001096\|Ga0067045_1003547_9\|P<br>[bioremediation-terephthalate-wastewater bioreactor]<br>MAQPADETFLPMITKYYREILAAEVKLAFCLPDEAHNVVYKRDEACRELVQACRNQAGGLTEQGYQYLGSALLFLSGGLGEAPG<br>LVALPVLSQELCEALASREADIHAFHARQGLEVAAAIIERAREPQWQHAQRRQALEAVIKDLQQRSAICPPDLQDRLRLLLAQA<br>YLERSRIIRPKGFTISPKKKEALDKALEQLDQVTDTGKTTLDYHRFRGDIFLELGRLEARTGKEIEACLAEAILFLDPRTPANL<br>TPVDCRLIVAYARLARDPSYLPLVLGSSKATALDRAWAAYLSNNASGAAKEINTVLQDLQRRWFSHPDWEGLVDLLVDWARSSQ<br>KGWEDLATAAWQVCQKNEQELRYSGCQLRWYWSRHQDLYDLAFQAAPTLEEKARVADSLKSRPLVRLALAEQLAQAQAKKKRGA<br>DVDFAQLIEQDARAYANQYIAGGLAAGSASAPVAPLSFTELPDEQWLAVHFYLSSGAAAGLKKNMAYALVYDAKDQKWSCEGPY<br>ETTDLWQAYRRWODNYAAVSQASAPELESLCRQIGTTFPFLWALPSERPVVFIPHGFLHRLPLHMALREDGATLEVWAATHPST<br>YLPAWSLRPRADAGGSQNVAAVYLPDELHDAEDFQNILAGQSFAAAASWPVFRKQAGOARRLALVCHGLAHAVNPFAARLLLPE<br>EPQLVDFLTDLPALPGSQVFLAACEADMAPAQEAPLDEHLSLATAFLQKGAREVLGGVFEVNKYLANELLSSFGATSAAACYSL<br>LWKWQQARLDNFLDNPDPLNLYWLAPWRVLGLS (SEQ ID NO: 11) |
| >OGR07204.1<br>[terrestrial-soil]<br>MNQNIDRAVGAILAIETATPLTESSTLAQRERHQKLLHDETKKIEQAFIALAQPPQCRAVEIAALSRFLOMTPLAVGPLRKRVI<br>CRAEPLKDDAHEQEIASHFNGLLLRLAKGLLASALNPAGIPWRRRVLWLEKAAHIAHRFDKEPLADDKERTEAAGVLARCCLHL<br>ALAHLPKGKDKSAMAERQEDLLQSLMWAQKAIVLAGQDKLSGEEYKLLKALVLIELDNLSPGRFQQQLNYVLYDLAVIWLERDT<br>ATKPFHPQELFVLWRYLATDFEPDLNMLLFKGSNTSERTAAVQQASPEAERFRPLLPLIHAWSAWKLDPPNNKIAEVILQAVNN<br>LDEHQVYEQVWKWTVDFLQELRNTGAVDWQLPAIAAWELCNKKEKELPFGFQIRQYWSRLDSLYRLAFDGALELKDCMTAARIV<br>DSLKSRTPLTWRDMDTLFAKLPKEKADQLREAFYSMEVQARMGFYAEAKEDANKLKKLLAAQVRKIRDIESVPAGWTVVHFHLR<br>EDQDLGYALACRLTADGMSYWTNHIFPVAGIRRAYDCWLEAYHGMEPGAREKSGYQLVELSEIMGKDLDFLFELAGEDGARGLL<br>FVPHGFSHLLPLHAAKKDGSYLFEKIPSLTLPAWEFAPDVDQIPVSDGQDFCFISQRANEQDLVGNIERSHTWNGVCNKNAAWT<br>NVLNTNKEWSKAPPRWLVFWCHGQADPHVAFRSKLLLGTLGVSLFEIQEAALSLTGTKVVLAVCESDLAPPEEYEKTDDHLSLA<br>APFLLKGARQVLAAIWEGAQLDLLKAMKEMLSNQDKHSWEILRELQSCWMRQPGAIFNDEYIRLYYAASFRILGFPEVATTNMA<br>TATAQEEIA (SEQ ID NO: 2) |
| >3300028595\|Ga0272440_1002488_3\|P<br>[aquatic-marine-marine sediment]<br>MVSMQQSACNEIKNLENSIDKDVSELAEALSHFVQANLQPQTALCORGIPDKNNAVLKIHKAHNTDIVFSTLFNILEKRLVVYE<br>SEVYDESKSSKKNMNHRQRROMLEDIIQALIPLKKKVSDSELKLEKLERKESDSVTKLKSDIAQFNYIYAKVYFYRSLLFRPKG<br>RSIPARKIEAIQEAYSFIKKSLNLSETLSSWRLLGKITLELLSLNEPYLSDDIISSGLHIDENFCLENNSFILRNDIQTLLTFS<br>EITKDVSFVEKIPTFENINIKKKDKDYLLLLIFARIAFLRNKINESDTLLTKAISNAPEAFANPFWDDLVDFITCLKRNNCHVW<br>KKAAIDAHKACYKNETEIGNIYLRWYWSRQSDLYDLAFISENKLEEKARIADSLKSRPILGFQALNNMKKNIDILEQILEQENE<br>ARDNKYLKKIHSKSRKIFKKEKFIDFKLLDNHWMVIHFYLNELEQCGYALIFDCETKNTNIQTFRYNELFNTFLSWQETELHEQ<br>KQKENNEEIFNKDLIQRGKSIHELCCEIGKTMPFIFELPENKSILWVPHGFIHRLPLHAAISIQTNAFLFEKHESRYLAAWHQL<br>NLKNFGNGEGKHFLRSGGSKFKTITKKCKTDKWEMVKRKANQKHFFESLNKNLKTLVIICHGECDITNSFQSCLEISASSVGES<br>DSNGLINPLEKKSITILDLLKSENNIKGCRIFLGACESDMASPIEFIVDEHLSLSAVLLSLGAKEVIGGLWKLYDIFVEDCYHQ<br>LLDSNNLSQSLNEWQLNMAKEWKEDKTDMRYLKLYSFASFRVTGFLPQKKQEP (SEQ ID NO: 12) |
| >SRR8490538_megahit_k177_234425_6\|M<br>[anammox bioreactor]<br>MKNRVQIEAIIRNLQGAARDSKTNKLSENIIAYDEYRKIHKSASLYQFGIIPAKESSSVLAENETNHVAYENAIFEMAEKNIEN<br>FSSEDIHKKRKEMIESALRLLMGLYKDRHEKLQPRTFVLIAKAYLLRSLITRPKGITIPEKKKEALKKGIGFVESAIKKIQSSE<br>NILSHSSDIDLLEKAWRIKSQLYLEYYRVNKDECDKNTLKEVLENSLISGCDKFDKNIEDVQIAIRYCELESSREYLEQIISSH<br>LEGIEFEKARAYKLLELENENEDEIRKSMKVVIEEYLSGFSDPLWEDAVEFINKLKSDNKNCWKELSLDMYKVCREQEAETASL<br>HLRWYWSRQRRLYDLAFIAADKEEEKAKIADSLKSRLSLRWSALEETGKKSKNKREKEEISRILEAEAVAMLGGYIKGARKILK<br>KRRRPLPDEQRSIPKDWIVIHFYVNQLENKCYALIYNKDENTWKCEFVKEYQRLFHVFLTWQTNYNRCKERAADSLVQLCKEIG<br>NAMPFLFDECIIPQDKNVLFIPHDFLHRLPLHGAIHEKNNGVFLENHPCCYLPAWSFTAKENNAVVQGSILLKNFPEYSYEELV<br>SNSTLWTSPVKDPASPDDLKTIIASPEMLVILCHGEADAVNPFNARLKLTGNGISHLEILQSTKMILKGSKIILGACETDLVPP<br>LSDIMDEHLSIATAFLINGTHEILGTMWQSRPEDIEDIIRLLCDKKTSDTKARGDLWNWQKERIRDYWAGEDAMFYRSVAFRII<br>GLTI (SEQ ID NO: 13) |
| >SRR6011893_megahit_k177_1702441_3\|P<br>[dolphin oral metagenome]<br>MNTVELLQEEERLTLDLVFLPPGSKNKEQKKNALVDLLLKIVEHGELTRKYSALLTLSRGALRGEVHFGEKLLPSPEACANLAK<br>PEEIKKMIRQHFQYRLDLLEAIVKKAADNTYSHARRRKALRIAIKELEQICEEALDELCFKARLLLAEALFERGRIVRPKGFSE<br>PGKKKELFQKAINCIEGNCSEEALRLRARIYLQWYRFFHDEPPCDLDDIFTKALAVTDDKMLKTELLLLCGERKEPDPYTDDLR |

TABLE 2-continued

| Amino Acid Sequences of Representative Type III-E (CLUST.019911) Effector_A Proteins |
|---|
| ALLNDQNVSPLSRARAAVLLEDWERCNVEIYEAIEDLGKTDFFQQDWELVVTLLKKNYNQFHGWSRACTRLWEITVEKESKDAG<br>HGCVLRWYWSRQRDVYNLAFAAFEECEDKARVVDSLKNRPAHHFSQLEQLAQSSDIIKQWIESEEIINQDSFAHSLRRHEKGAK<br>SHSGGSLRIFPCLPKGWIAVHFFLASWPEPKGYALIHNADTNTWEQRDFKYEQLWATYIAWQEVSLHNKIRESALLLKSLCETL<br>GKEMRWLFDEFLFPKERRRVLFVPHDFLHRLPLHMAIDIESQTVFAAKQPVCYLPAYHLQNNITENKKTSIYALVNLRENKQQK<br>KDEEIFAEKVEKMGAIVRRPALESDLLNLNPVPEKLVLYCHGIGHSANPFASKLCLGDTGVSYRDILALNRSLAGCRVLLFACE<br>TDLVPAQTSSIDEHLSISNALLQKGAFEVLGSLWALPGKTIYGITKTFIDNDDTSAVLHSSLKRLFEHYEKKNEKTRAQLLYNW<br>ASLRVLAPAREFS (SEQ ID NO: 5) |

TABLE 3

| Amino Acid Sequences of Representative Type III-E (CLUST.019911) Effector_B Proteins |
|---|
| >JRYO01000185_8\|M<br>[*Candidatus Scalindua brodae*]<br>MKSNDMNITVELTFFEPYRLVEWFDWDARKKSHSAMRGQAFAQWTWKGKGRTAGKSFITGTLVRSAVIKAVEELLSLNNGKWEG<br>VPCCNGSFQTDESKGKKPSFLRKRHTLQWQANNKNICDKEEACPFCILLGRFDNAGKVHERNKDYDIHFSNFDLDHKQEKNDLR<br>LVDIASGRILNRVDFDTGKAKDYFRTWEADYETYGTYTGRITLRNEHAKKLLLASLGFVDKLCGALCRIEVIKKSESPLPSDTK<br>EQSYTKDDTVEVLSEDHNDELRKQAEVIVEAFKQNDKLEKIRILADAIRTLRLHGEGVIEKDELPDGKEERDKGHHLWDIKVQG<br>TALRTKLKELWQSNKDIGWRKFTEMLGSNLYLIYKKETGGVSTRFRILGDTEYYSKAHDSEGSDLFIPVTPPEGIETKEWIIVG<br>RLKAATPFYFGVQQPSDSIPGKEKKSEDSLVINEHTSFNILLDKENRYRIPRSALRGALRRDLRTAFGSGCNVSLGGQILCNCK<br>VCIEMRRITLKDSVSDFSEPPEIRYRIAKNPGTATVEDGSLFDIEVGPEGLTFPFVLRYRGHKFPEQLSSVIRYWEENDGKNGM<br>AWLGGLDSTGKGRFALKDIKIFEWDLNQKINEYIKERGMRGKEKELLEMGESSLPDGLIPYKFFEERECLFPYKENLKPQWSEV<br>QYTIEVGSPLLTADTISALTEPGNRDAIAYKKRVYNDGNNAIEPEPRFAVKSETHRGIFRTAVGRRTGDLGKEDHEDCTCDMCI<br>IFGNEHESSKIRFEDLELINGNEFEKLEKHIDHVAIDRFTGGALDKAKFDTYPLAGSPKKPLKLKGRFWIKKGFSGDHKLLITT<br>ALSDIRDGLYPLGSKGGVGYGWVAGISIDDNVPDDFKEMINKTEMPLPEEVEESNNGPINNDYVHPGHQSPKQDHKNKNIYYPH<br>YFLDSGSKVYREKDIITHEEFTEELLSGKINCKLETLTPLIIPDTSDENGLKLQGNKPGHKNYKFFNINGELMIPGSELRGMLR<br>THFEALTKSCFAIFGEDSTLSWRMNADEKDYKIDSNSIRKMESQRNPKYRIPDELQKELRNSGNGLFNRLYTSERRFWSDVSNK<br>FENSIDYKREILRCAGRPKNYKGGIIRQRKDSLMAEELKVHRLPLYDNFDIPDSAYKANDHCRKSATCSTSRGCRERFTCGIKV<br>RDKNRVFLNAANNNRQYLNNIKKSNHDLYLQYLKGEKKIRFNSKVITGSERSPIDVIAELNERGRQTGFIKLSGLNNSNKSQGN<br>TGTTFNSGWDRFELNILLDDLETRPSKSDYPRPRLLFTKDQYEYNITKRCERVFEIDKGNKTGYPVDDQIKKNYEDILDSYDGI<br>KDQEVAERFDTFTRGSKLKVGDLVYFHIDGDNKIDSLIPVRISRKCASKTLGGKLDKALHPCTGLSDGLCPGCHLFGTTDYKGR<br>VKFGFAKYENGPEWLITRGNNPERSLTLGVLESPRPAFSIPDDESEIPGRKFYLHHNGWRIIRQKQLEIRETVQPERNVTTEVM<br>DKGNVFSFDVRFENLREWELGLLLQSLDPGKNIAHKLGKGKPYGFGSVKIKIDSLHTFKINSNNDKIKRVPQSDIREYINKGYQ<br>KLIEWSGNNSIQKGNVLPQWHVIPHIDKLYKLLWVPFLNDSKLEPDVRYPVLNEESKGYIEGSDYTYKKLGDKDNLPYKTRVKG<br>LTTPWSPWNPFQVIAEHEEQEVNVTGSRPSVTDKIERDGKMV (SEQ ID NO: 14) |
| >OGR07205.1<br>[*Deltaproteobacteria bacterium* RIFOXYD12_FULL_50_9]<br>MTKKPGTEDKATLWGKESASKSVKTILEESIQGFTVEQKRSFFANLADQLVSRAGEQGAKSVRSQGLIIGRKENYAKPSAQEPT<br>RHHLYRQPSNASAFLATGWLIAETPFFIGSGTEGQKQTDDQAESLHLRTLRDGHGRFRIPFTTIRGVMDKELRDILQAGCAKGR<br>SLRAPCPCQVCTLMRRIQVRDAIAADILPPDLRMRTRIDPSHGTVAHLFSLEMAPQGLKLPFFLKLKGVETIDPDKELLEILND<br>WSAGQCFLGGLWGTGKGRFRLDDLQWHRLELDNADYYTPLLQDRFFAGETISDLRQGLQSINIQPERIPAQTPSRNMPYCRVDC<br>ILEFKSPVLSGDPVAALFESDAPDNVAYKKPVVQYDETGRLRTTDPGPVEMLTCLKGEGVRGVVAYLAGKAYDQHDLSHDSCNC<br>TFCQAFGNGQKAGSLRFDDFMPVQFESDQAGNFSWSPHTPHAMRSDRVALDVFGGAMPEAKFDDRPLAASPGKPLNFKSTIWYR<br>EDMGKEAGKALKRALIDLQNNMAAIGSGGGIGRGWVSRVCFEGDIPDFLEDFPEPITVTEPEQDSQLLKNQAVADETAVSACDT<br>ADAPHPLAVTLEPGARYFPRVIIPRAPTVKRDECVTGQRYHTGRLSGKIFCELNTLGPLFVPDTDYSAGVPVPISDEQLAECQL<br>QAVFENTSKFNEFFATYPEETVTKLKDLLCAADDKWILAVKDITADLRQEIGEDTFQRIIRKAGHKTQRFHQINDEIGLPGASL<br>RGMVLSNYQILTNSCYRNLKATEEITRRMPADEAKYRKAGRVTVSGDGAQKKYSIQEMEVLRLPIYDNMNTPDNMPDVAKQATT<br>AKRCNNLMNEAAKTSRVELKARWREGQSKIKYQIIDALNKVDPIIQVISSSKQINPNNGKTGWGYVKYTGANVFAKSLVAPIDC<br>LRKKDAGHVCCQVNLNPAWEASNFDILINEKCPVERQSGPRPTLRCKGQDSAWYTLTKRSERIFTDKKPVPDPINIPPREVKRY<br>NELRDSYKKNTAHVPKPLQTFFNQESLANGDLVYFEVNQFGEASQLTPVSISRTTDLFPIGGRLPQGHKDLFPCTAMCLSECKN<br>CVPASFCEFHSRSHEKLCPACSLAGTTGNRGRIKFSEAWLSGLPKWHSVSQDNVGRGLGVTMPRLERSRRTWHLPTKDAYLLGQ<br>SIYLNHPVPAILPSDQVPSENNQTVEPLGPKNIFSFQLAFDNLSIEELGLLLYSLELESGMAHRLGRGRALGMGSVQISVKDIQ<br>IRDNKSFLFSSNISKKSEWIQCGKDEFAQEAWFGESWDNIDHIQRLRQALTIPVKGDVGCIRYPKLEAEGGMPDYIKLRKRLTP<br>LCDREEPVRYRINPVQLARMILPFVPWHGACPALLNEQVMIEAKRLTELXXXDRANWPC (SEQ ID NO: 15) |
| >WP 124327589.1<br>[*Desulfonema ishimotonii*]<br>MTTTMKISIEFLEPFRMTKWQESTRRNKNNKEFVRGQAFARWHRNKKDNTKGRPYITGTLLRSAVIRSAENLLTLSDGKISEKT<br>CCPGKFDTEDKDRLLQLRQRSTLRWTDKNPCPDNAETYCPFCELLGRSGNDGKKAEKKDWRFRIHFGNLSLPGKPDFDGPKAIG<br>SQRVLNRVDFKSGKAHDFFKAYEVDHTRFPRFEGEITIDNKVSAEARKLLCDSLKFTDRLCGALCVIRFDEYTPAADSGKQTEN<br>VQAEPNANLAEKTAEQIISILDDNKKTEYTRLLADAIRSLRRSSKLVAGLPKDHDGKDDHYLWDIGKKKKDENSVTIRQILTTS<br>ADTKELKNAGKWREFCEKLGEALYLKSKDMSGGLKITRRILGDAEFHGKPDRLEKSRSVSIGSVLKETVVCGELVAKTPFFFGA<br>IDEDAKQTDLQVLLTPDNKYRLPRSAVRGILRRDLQTYFDSPCNAELGGRPCMCKTCRIMRGITVMDARSEYNAPPEIRHRTRI<br>NPFTGTVAEGALFNMEVAPEGIVFPFQLRYRGSEDGLPDALKTVLKWWAEGQAFMSGAASTGKGRFRMENAKYETLDLSDENQR<br>NDYLKNWGWRDEKGLEELKKRLNSGLPEPGNYRDPKWHEINVSIEMASPFINGDPIRAAVDKRGTDVVTFVKYKAEGEEAKPVC<br>AYKAESFRGVIRSAVARIHMEDGVPLTELTHSDCECLLCQIFGSEYEAGKIRFEDLVFESDPEPVTFDHVAIDRFTGGAADKKK<br>FDDSPLPGSPARPLMLKGSFWIRRDVLEDEEYCKALGKALADVNNGLYPLGGKSAIGYGQVKSLGIKGDDKRISRLMNPAFDET<br>DVAVPEKPKTDAEVRIEAEKVYYPHYFVEPHKKVEREEKPCGHQKFHEGRLTGKIRCKLITKTPLIVPDTSNDDFFRPADKEAR<br>KEKDEYHKSYAFFRLHKQIMIPGSELRGMVSSVYETVTNSCFRIFDETKRLSWRMDADHQNVLQDFLPGRVTADGKHIQKFSET<br>ARVPFYDKTQKHFDILDEQEIAGEKPVRMWVKRFIKRLSLVDPAKHPQKKQDNKWKRRKEGIATFIEQKNGSYYFNVVTNNGCT<br>SFHLWHKPDNFDQEKLEGIQNGEKLDCWVRDSRYQKAFQEIPENDPDGWECKEGYLHVVGPSKVEFSDKKGDVINNFQGTLPSV<br>PNDWKTIRTNDFKNRKRKNEPVFCCEDDKGNYYTMAKYCETFFFDLKENEEYEIPEKARIKYKELLRVYNNNPQAVPESVFQSR |

TABLE 3-continued

Amino Acid Sequences of Representative Type III-E (CLUST.019911) Effector_B Proteins VARENVEKLKSGDLVYFKHNEKYVEDIVPVRISRTVDDRMIGKRMSADLRPCHGDWVEDGDLSALNAYPEKRLLLRHPKGLCPA
CRLFGTGSYKGRVRFGFASLENDPEWLIPGKNPGDPFHGGPVMLSLLERPRPTWSIPGSDNKFKVPGRKFYVHHHAWKTIKDGN
HPTTGKAIEQSPNNRTVEALAGGNSFSFEIAFENLKEWELGLLIHSLQLEKGLAHKLGMAKSMGFGSVEIDVESVRLRKDWKQW
RNGNSEIPNWLGKGFAKLKEWFRDELDFIENLKKLLWFPEGDQAPRVCYPMLRKKDDPNGNSGYEELKDGEFKKEDRQKKLTTP
WTPWA (SEQ ID NO: 16)

>OBJA01001127_4|M
[soil metagenome]
MRLKINIHFLEPFRLIEWHEQDRRNKGNSRWQRGQSFARWHRRKDNDQGRPYITGTLLRSVVIRAVEEELARPDTAWQSCGGLF
ITPDGQTKPQHLRHRATVRARQTAKDKCADRQSACPFCLLLGRFDQVGKDGDKKGEGLRFDVRFSNLDLPKDFSPRDFDGPQEI
GSRRTINRVDDETGKAHDFFSIWEVDAVREFQGEIVLAADLPSRDQVESLLHHALGFVDRLCGARCVISIADQKPAEREERTVA
AGDEKATIADYDQVKGLPYTRLRPLADAVRNLRQLDLAELNKPDGKFLPPGRVNKDGRRVPHYVWDIPLGKGDTLRKRLEFLAA
SCEGDQAKWRNICESEGQALYEKSKKLKDSPAAPGRHLGAAEQVRPPQPPVSYSEESINSDLPLAEWIITGTLRAETPFAIGMD
APIDDDQTSSRTLVDRDGRYRLPRSTLRGILRRDLSLASGDQGCQVRLGPERPCTCPVCLILRQVVIADTVSETTVPADIRQRI
RRNPITGTAADGGLFDTERGPKGAGFPFSLRYRGHAPMPKALRTVLQWWSAGKCFAGSDGGVGCGRFALDNLEVYRWDLGTFAF
RQAYSENNGLRSPEEEFDLAVIHELAEGLAKEDGQKILKGTEPFTCWQERSWQFSFTGPLLQGDPLAALNSDTADIISFRRTVV
DNGEVLREPVLRGEGLRGLLRTAVGRVAGDDLLTRSHQDCKCEICQLFGSEHRAGILRFEDLPPVSPTTVADKRLDHVAIDRFD
QSVVEKYDDRPLVGSPKQPLVFKGCFWVQTSGMTHQLTELLAQAWRDIAAGHYPVGGKGGIGYGWINSLVVDGEKITCRPDGDS
ISLTTVTGDIPPRPALTPPAGAIYYPHYFLPPNPEHKPKRSDKIIGHHTFATDPDSFTGRITCKLEVVTPLIVPDTEGEQPKDQ
HKNFPFFKINDEIMLPGAPLWAAVSQVYEALTNSCFRVMKQKRFLSWRMEAEDYKDFYPGRVLDGGKQIKKMGDKAIRMPLYDD
STATGSIKDDQLISDCCPKSDEKLQKALATNQKIALAAKHNQEYLAQLSPDEREEALQGLKKVSFWTESLANNEAPPFLIAKLG
EERGKPKRAGYLKITGPNNANIANTNNPDDGGYIPSWKDQFDYSFRLLGPPRCLPNTKGNREYPRPGFTCVIDGKEYSLTKRCE
RIFEDISGGENQVVRAVTERVREQYREILASYRANAAGIAEGFRTRMYDTEELRENDLVYFKTAKQADGKERVVAISPVCISRE
ADDRPLGKRLPAGFQPCSHVCLEDCNTCSAKNCPVPLYREGWPVNGLCPACRLFGAQMYKGRVNFGFARLPDDKQPETKTLTLP
LLERPRPTWVLPKSVKGSNTEDATIPGRKFYLRHDGWRIVMAGTNPITGESIEKTANNATVEAIMPGATFTFDIVCENLDQQEL
GLLLYSLELEEGMSHTLGRGKPLGFGNVRIKVEKIEKRLSDGSRREMIPPKGAGLFMTDKVQDALRGLTEGGDWHQRPHISGLR
RLLTRYPEIKARYPKLSQGEDKEPGYIELKSQKDENGVPIYNPNRELRVSENGPLPWFLLAKK (SEQ ID NO: 17)

>PDWI01005922_5|M
[oral metagenome]
MIPDLRSLVVHISFLTPYRQAPWFPPEKRRNNNRDWLRMQSYARWHKVAPEEGHPFITGTLLRSRVIRAVEEELCLANGIWRGV
ACCPGEFNSQAKKKPKHLRRRTTLQWYPEGAKSCSKQDGRENACPFCLLLDRFGGEKSEEGRKKNNDYDVHFSNLNPFYPGSSP
KVWSGPEEIGRLRTLNRIDRLTTKAQDFFRIYEVDQVRDFFGTITLAGDLPRKVDVEFLLRRGLGFVSTLCGAQCEIKVVDLKK
KQNNKEDSILPVSEVPFFLEPEVLAKMCQDVFPSGKLRMLADVILRLREEGPDNLTLPMGSQGLGGRLPHHLWDVPLVSKDRET
QTLRSCLEKIAAQCKSEQTQFRLFCQKLGSSLFRINKGVYLAPNSKISPEPCLDPSKTIRTKGPVPGKQKHRFSLLPPFEWIIT
GTLKAQTPFFIPDEQGSHDHTSRKILLTRDFYYRLPRSLLRGIIRRDLHEATDKGGCRVELAPDVPCTCQVCRLLGRMLLADTT
STTKVAPDMRHRVGVDRSCGIVRDGALFDTEYGIEGVCFPLEIRYRGNKDLEGPIRQLLSWWQQGLLFLGGDFGIGKGRFRLEN
MKIHRWDLRDESARADYVQKCGLRRGVGDDTAINLEKDLSLNLPESGYPWKKHAWKLSFQVPLLTADPIMAQTRHEEDSVYFQK
RIFTSDGRVVLVPALRGEGLRGLLRTAVSRAYGISLINDEHEDCDCPLCKIFGNEHHAGMLRFDDMVPVGTWNDKKIDHVSCSR
FDASVVNKFDDRSLVGSPDSPLHFEGTFWLHRDFQNDVEIKTALQDFADGLYSIGGKGGIGYGWLFDMEIPRSLRKLNSGFREA
SSIQDALLDSAKEIPLSAPLTFTPVKGAVYNPYYYLPFPAEKPERCLVPPSHARLQSDRYTGCLTCELETVSPLLLPDTCREKD
GNYKEYPSFRLNNTPMIPGAGLRAAVSQVYEVLTNSCIRIMDQGQTLSWRMSTSEHKDYQPGKITDNGRKIQPMGKQAIRLPLY
DEVIHHVSTPGDTDDLEKLKAIVLELTRPWKELPEEQKKKRFEKCKNILDGRMLQQKELRALENSGFAYWRDKTSLTFDSFLKD
AIEQEYPRYSGDYQRIKALVVNITLPWKLLKKEERHKRFDKCRRILKGQQPLTKDERKALEESGFANWHGRELLFDRFLKDENS
CLIKAETTDRVIASVAKNNRDYLFEIKQQDFARYKRIIQGLERVPFSLRSLAKSKETSFQIACLGLRRGRFLRKGYLKISGPNN
ANVEISGGSHSNSGYSDIWDDPLDFSFRLSGKSELRPNTQKTREYPRPSFTCTVDGKQYTVNKRCERVFEDSAAPAIELPRMVR
EGYKGILTDYEQNAKHIPQGFQTRFSSYRELNDGDLVYYKTDSQGRVTDLAPVCLSRLADDRPLGKRLPEEYRPCAHVCLEECD
PCTGKDCPVPIYREGYPARGFCPACQLFGTQMYKGRVRFSFGVPVNSTRSPQLKYVTLPSQERPRPTWVLPESCKGKEKDVPGR
KFYLRHDGWREMWGDDDKPDSRPSSEECQDIIEGIGPGEKFHFRVAFENLDKNELGRLLYSLELDAGMNHHLGRGKAFGFGQVK
IRVTKLERRLEPGQWRSEKICTDLPVTSSELVISSLKKVEERRKLLRLVMTPYKGLTACYPGLERENGRPGYTDLKMLATYDPY
RELVVQIGSNQPLRPWYEPGKSFKPSPGNDCTGRGGSVSKSLISEPKVVPAIAPFCEGVVKWFNSVKGFGFIETKEQRDIFVHF
SAIRGEGYKILEPGEKVRFEIGEGRKGPQAINVIRIR (SEQ ID NO: 18)

>3300019457|Ga0193932_10482_5|M
[aquatic-marine-hydrothermal vent microbial mat]
MIINITVKFLGPFRMLEWTDPDNRNRKNREFMRGQAFARWHNSNPQKGSQPYITGTLVRSAVIRSAENLLMLSEGKVGKEKCCP
GEFRTENRKKRDAMLHLRQRSTLQWKTDKPLCNGKSLCPICELLGRRIGKTDEVKKKGDFRIHFGNLTPLNRYDDPSDIGTQRT
LNRVDYATGKAHDFFKVWEIDHSLLSVFQGKISIADNIGDGATKLLEDSLRFTDRLCGAICVISYDCIENSDGKENGKTGEAAH
IMGESDAGKTDAENIANAIADMMGTAGEPEKLRILADAVRALRIGKNTVSQLPLDHEGKENHHLWDIGEGKSIRELLLEKAESL
PSDQWRKFCEDVGEILYLKSKDPTGGLTVSQRILGDEAFWSKADRQLNPSAVSIPVTTETLICGKLISETPFFFGTEIEDAKHT
NLKVLLDRQNRYRLPRSAIRGVLRRDLRTAFGGKGCNVELGGRPCLCDVCRIMRGITIMDARSEYAEPPEIRHRIRLNPYTGTV
AEGALFDMELGPQGLSFDFILRYRGKGKSIPKALRNVLKWWTKGQAFLSGAASTGKGIFRLDDLKYISFDLSDKDKRKDYLDNY
GWRNRIEALSLEKMPLDRMNDYAEPLWQKVSVEIEIGSPFLNGDPIRALIEKDGSDIVSFRKYADDSGKEVYAYKAESFRGVVR
AALARQHFDKEGKPLDKEGKPLLTLIHQDCECLICRLFGSEHETGRLRFEDLLFDPQPEPMIFDHVAIDRFTGGAVDKKKFDDC
SLPGTPGHPLTLKGCFWIRKELEKPDEDKSEREALSKALADIHNGLYPLGGKGAIGYGQVMNLKIKGAGDVIKAALQSESSRMS
ASEPEHKKPDSGLKLSFDDKKAVYYPHYFLKPAAEEVNRKPIPTGHETLNSGLLTGKIRCRLTTRTPLIVPDTSNDDFFQTGVE
GHESYAFFSVNGDIMLPGSEIRGMLSSVYEALTNSCFRVFDEGYRLSWRMEADRNVLMQFKPGRVTDNGLRIEEMKEYRYPFYD
RDCSDKKSQEAYFDEWERSITLTDDSLEKMAERKGDISPKDLKVLKSLKGKNYKSTEGLLAAFKDKGGDTGGNILGLIFKYAER
IGDVPRYEHPTDTDRMMLSLSEYNRNQKSDGKRAYKIIKPASKLGKGAYFMFAGTSVENKRICNPACTDKANKSVKGYLKISGP
NKLEKYNISEPELDGVPEDRNCQIIHNRIYLRKIFVANAKKRKERDRLVGEFACYDPEKKVTYSMTKRCERIFIKDRGRTLPIT
HEASELFEILVQEYRENAKRQDTPEVFQTLLPDNGRLNPGDLVYFREEKGKTVEIIPVRISRKIDDSPIGKRLREDLRPCHGEW
IEGDDLSQLSEYPEKKLFTRNTEGLCPACRLFGTGAYKGRLRFGFAKLENDPKWLMKNSDGPSHGGPLTLPLLERPRPTWSMPD
DTLNRLKKDGKQEPKKQKGKKGPQVPGRKFYVHHDGWKEINCGCHPTTKENIVQNQNNRTVEPLDKGNTFSFEICFENLEPYEL
GLLLYTLELEKGLAHKLGMAKPMGFGSIDIEVENVSLRTDSGQWKDANEQISEWTDKGKKDAGKWFKTDWEAAEHIKNLKKLLF
LPGEEQNPRVIYPALKQKDIPNSRLPGYEELKKNLNMEKRKEMLTTPWAPWHPIKK (SEQ ID NO: 19)

TABLE 3-continued

| Amino Acid Sequences of Representative Type III-E (CLUST.019911) Effector_B Proteins |
|---|
| >3300009529\|Ga0114919_10000047_40\|M<br>[aquatic-marine-deep subsurface]<br>MSDNRIDYDIKLTFFEPFRMSPWVKSHARAKSKTFFRTLSFVRWLETSPETKEGKEGDSIGVPFIPGTLLRSALLKEVEFLITL<br>KNKYDCCCGEFETPRQKRDEKKEQGRRFFGRKRPTYEFGNSQPCTDFENACPFCSILSRSFNNDDWFDDRGNPIVGKVPVHFSN<br>LDVTDSKLKRIRLSAIANQRIVNRVDFRSGKAQDYFKIWEVDNRLCPSFCGKITIRQDINQVDDLTCLLAAGLAKIKTLAGALC<br>RVDIIRDKTIDFHQRLIQKYVGPPGPPHNPTAHPTLPSQPTLSVDVHGLARTIAGTLTGSDKEAYLRRIADAVREMRNRKCSIL<br>HEPPFTKTGDKEPVWTIPAVQKALKETTACVARESWRLFCEELGEALYKKAKELKKKDEAIPRLLGDTEYYGQQAEAPVGTDYR<br>LTASALPKYEWIINGWLEARTPFFFGVESASEQTSLAILLTRDHRYRLPRSVLRGALRRDLRTVIGSGCNVELGVDTPCDCDVC<br>RIMSRVIVMDSLSDYQEPPDIRHRIRINQHSGTVDEGALFDMELGPEGLRFPFRMYFSATCPTADVPLAKVLKMWQDRPAFLGG<br>DAGTGNGRFRLIKAKTRSEPFDWDGPKSSLNLLMARSYIDLEDHDTLLDSKLECAKAWKVKDELTSVWTDYQYEIDLHSPILSN<br>DPIAALLDPDWRDAVPVKKRVLQDGGLVPTEKYYIKGSGIRGILRTAVGRNCVNEDGIHLHNLPHDDCPCVLCQLFGSEHHQGM<br>LRFEDAHFENDPMPETLDHVAIDRFTGRARDKFKFEDAPLIATPDQPIKLKGTFWLKRELHEASQEVFGKIDDFECKPKEDSDS<br>LLGAARALWCAFLDLKHGLFPIGSNGGIGYGWVSGLSVSEPDKNKKIPLGQLCRNEGAQETASTSGEKGEYNPSDAPNSLRQEG<br>HVFNPHYFLRSYRYEDKNGKIATHVERIDLPVTHEAYQDKLTGKITCKLNTRGPVFVADPSDLVVYFTAKEYEDFVKRWPKSAE<br>LLQSLVHEKDGMKLIPVKQIPKDSPEDGALKEISEHQGHKGYKFFRLNGSVMIPGSEIRGMVSSVYEALTNSCFRVFDQRRILS<br>KRMEADFRTVLTHFKAARVVPDNNSGSGLSVKEFTNMVRVPVYNCPQTFFDGLTQGQISGKEETKLWVKNYEWRISLCNPWTHH<br>SRKSKKEWEKNIPGRILNNQGDKIVLNISYKQEERKITLILDDKDRVVLDGITPKQLGGKEEIRLWLRISQYQKAFRKKPDNNG<br>GWKMQTGYLHIMGPNKVEIDSSGTSREGLQDLPETWKDAQCNSPDGKIFSGKDGNAVYTMNKYCEMFFYNEQKKSYRVPQAVLN<br>QYRQMIEESMSNPQAPPAIFRSKPIREKDTALKAGDLVYFRKNENREGEVDAVIPVRIYRESHRKPLGKRFPDGLHDLRPCTFE<br>CLDDCDKCPDRCNELKEFFNPHPKGLCPACRLFGTTSYKSRVSFGFARLCSEDKKAKWYGVEEDAEQGKPLTLPLLERPRPTWS<br>MPDKDAKIPGRKFYVHHPHSVDSSIRDMQFDPELSDKENQGKIRPNKNNRTVEPLDKGNEFTFDIRFMNLKEWELGLLLYSLQL<br>ETGLAHKLGMGKAQGFGSVEIDVEKVEIRNGPGDWKSKTSHKITEWITKGKDKLEKWFKTDDWNNVDHIADLKKFLYFLDPQEI<br>KPKVRYPSLSRDDDKKDHFPGYVDLKRKPSKEKPNPYYVPEDKRRALLTRPWEPWYVMPKSSMGTVKWFNEEKNYGFILRDNGE<br>DIFVHRSDINGSLGTLTEGQKVIFEVKQGPKGLQATNVKVIS (SEQ ID NO: 20) |
| >3300015370\|Ga0180009_10000113_2\|P<br>[aquatic-freshwater-groundwater]<br>MEYTLTLNFIEPFRLIEWHDAPDRENLRLRGFSFARWHKDREFGLGRPYITGTLIRSAVIRAVEEFLWLNNGKTGDVHCCQGEF<br>TKARFYRELTEKRLRRRQTLVWDNNGVCNQDQPCPFCLLLGRYWQPGPGYSENNDVNFGNFSIPQKKKVLLNLEDIAEPRIINR<br>VDQQSGKAEDFFEIREIDHRSCALFEGKISLSERAAENKALISLLNAALPLVNRISGALCYLTMEEVKVMDKSVNGGSDNLSGE<br>AMELKKSDRPGEGSHFARHPIGAEHASYEKIKTSAGEVVNAFEESNKLVHLRVFSDVIRELRRHDPRKLNLPGGHEDRSGKITD<br>HFLWDMKVESKPLRNWLPDKFNEFNEKHKLPWRIFCESLGQALFLEAKDKAPEQFTSARPLGAMVSTLESKEPEFLPGRSRQGP<br>RYEWLMRGQLVAEVPFFFGWSVDKNDTDHISMRLLSARDGRLRLPRSALRGILRRDLNLAFGTNGCRAKLGLRRPCPCPVCNLL<br>KNITIRDSLSDYKRPPQIRHRIRLDHRSGTVAKGALFDMEVGPTGAIFPFELRLRSTSDKFSKELEQVLLWWKQGLAFLSGAGG<br>TGKGRFRLKELKCIFWDLQNDAGFAHYKETYGGRKKRISDDELIPWQVTSGDPVSEPPWTAWEINFLVCSPFLTKDPVESLLDP<br>GGTDAVCYRAVYLGENGGIKKRYLLKGESFRGILRTAVGRRENSLLKEHEECDCVLCRLFGNEHEAGKIRVEDLLIQDEPKEKN<br>LDRVAIDRFTGGARDKHKFDQKPLTGTPAFPLVLMGKIWIKNDLTDDDKAILKQALEDIRCGLYPFGGLGNVGFGWVNYLTCNS<br>DFEQNFDSMNLCFSDKVKVENEPDKIYWPHYFIPFGPKVVRENKPPGHAYPKTEFHSGRLICSLKTLTPLIIPDGQPASQEANG<br>HKSYNFFELSGELCIPGSEIKGMISSVYEALTNSCMRIFEEKKRLSWRMKAENLDQWSPGRITEEADELFVEEMEEIRLPLYDN<br>PDLLPNIKKEGEKGFYRTKKIRDSNGRERLKKGQPTGTDSLINIHSAEIREFLKENKHLSSGQIPTKWFRCFPHPGKRGFDGLA<br>LLKIPKEWHNKNTSGWIAEGYVNLTGTNKVETRRSGKGISIRETSKDEQINIIHNEVTLEEKPVNSSKLGQVLRKRAIPKYVTY<br>KNGYEYTMTKRCERIFIPLQKPTKHIVSRNVENKFLQLCEEYKQNAEKIPKVFRTRMPKNYKLNDGDLIYFRQELGEVVEIIPV<br>RISRAVDDEVLGEKFVNDDFRPCVREILNRETEKKITSAGFKEVFHHHPKGLCPACAIFGTTFYKGRVSFGFAYLKNNETKLVE<br>NGAYITLPLLERPRPTWAMPTKDSKVPGRKFYVHHQGWKNIVEDSKNESTEKNENNRSVQAIDRNQVFLFEVRFENLRPWELGL<br>LIYSLQLEPKLAHKLGMGKPLGFGSVKIKVENVTSSRQKDVNDNTLPEAVEKELKEIWGKETEPDFTRSLEGLYKALHYESKNG<br>IQVRYPKLEKEKKDDPGEKPGYLELADGPFSTENRKEKLKEIWGNWA (SEQ ID NO: 21) |
| >3300001095\|JGI12104J13512_1001353_10\|M<br>[bioremediation-terephthalate-wastewater bioreactor]<br>MNRYKVSLEFLEPWRINHLGDDRGAAWARWVQTREGYQRPEITGTLVRSAVIRAAEELLALTGGVWAGQKCCPGEFCTPGGSKP<br>TFRRQRATRWWGEDSLCTPDSPCPFCQLLGRHDLAGKQARRGGGFHVHFGNLYPVAREGYGSLAEITRQRTSNRLDWLTGKAQD<br>ILTICEVEELRRFSGLITVAPELANGEAVSSLLTAAAALVDRLSGAACRLKLQPVEELWSGTAVSLTRAAVPETAYRQQLEEDI<br>DNYFQELIGDGSQLGPERLRLLADAIRELRYLPPEQTLPDWLQSLPQGKDGKAHRLWDALTAQRRPLRNMLQEVAAAYAAPATW<br>RDVVQGLGQALYAHYKKLWPQAMPVRPVGEAEYWQTKFRDRQPSRQRGTWSHEWIITGALQTLTPLYLGTQVEAARQTSLTVLL<br>TAEGRYRLPRTALRGALRQDLQLASRGQGCLMELNPERPCSCPICQIMRRLTVRDVTSSIALPPPLVRQRVRRNPWTGIVDEGA<br>LFDQEVAPEGLRFPFILRYRGFGGLDAWLQTVLSWWQEGRLFLGGAGGTGKGRLRLTDLRIWRWALDETGLPTYVAHLGYRGRE<br>EELANSASLPAGVEAVTCSDPATVPSPWQEVDWEFRFHGPVLANHPLTALLRGEADAVFTWKVQLEADQQHYREVCTLKGETVR<br>GLVRGLFGKSQGLLTKAHADCTCLLCRVFGNEHQRGKVRFEDLTLAGETVPKKRLDHVAIDRISGGAAEQLKFDTQPLYGTPEN<br>PLVFAGKFWVHTELDEEEQKALRAALTALRDGLATVGAKGSVGYGWLNGLRLHSGPAWLTDNWQETAAAPSDTNTPPEFSWPQL<br>PDLTLDSRKIYYPHYFLPPDLQVPRLSQPHTHSLFDPQKYTGWLTCRLTTLTPLIIPDTSSDQTLTTGGPFPAGHQAFQFFRLG<br>DQPLIPGAELRGMISSVFEAITNSCFRVIRPRERLSWRMPAALAPQFRSGRVEIVNNQYYIRQMDMGRLPLYDDPATRRLFTPL<br>SLTSGHTLDFVDDNRTLLQSNPGIREGAIRTDLCFLNRFWLLRPPSAARCPRGNFSLTSGYVKFTGPNKVEVSRAGAGAGGLPA<br>PPADWTGVRLNQVAGNVPFYQAEQSGVIFTVNKRRERFFISRGNARSYPVPLATLKRYEQVLKEYRHFAQRGEVPAVFRTVLPD<br>VRHGASGYNRLNNGDLVYFRVKDDRWNDQNAPVEHIIPVSISRLVDQKFLGERVPEPLRPCAHVCLEECEACLKQESCPSSFYR<br>EGTPSRGLCPACHLFGTTGYQGRVRFGFARLEREPAWRQNDAGSTAITLPLLEQPRLTWSMLWERRNAEGTVEERQPVNWVPGR<br>KFYVHHQGWRTIVAQGINPIDGQRLERNENNRTVEVLDTGRTFTFQVFFENLDAWELGLLLYSLELEPGLAHKLGMAKAWGFGS<br>VQIDVASLRRYQAPGSMTDITCEKDTLLQAGFAWLKEQANSSSWDEIPRLRQLRQLLRYQEDGTLTVRYPILKQENAASGQVPG<br>YVELRDQGYRPEEQLRIPWSPWYSPPLEPPPAATAAA (SEQ ID NO: 22) |
| >3300020048\|Ga0207193_1004003_13\|M<br>[aquatic-freshwater-freshwater lake sediment]<br>MTTLTIHLHFLEPFRMAPWFSVEKRKKNNPDWQRVQTYARWHKNTAGDGRGRPFITGYLLRSALIQAVEEELVFSRGVWSGISC<br>CPGLFFTEPDKDKEKPLNERRRATLGWTENKAICQEEEGREKACPLCLLINRFKENGEDNVHFGNLSLPGSENERPVWDQPEQI<br>AKLRTLNRVDRATTKAHDHFKVYEVEDLTDFYGTITFADDLPQREVIESLIRRGLGFISDLCGALCEIRVEKQKPLPTEPKGIT<br>QSKASYVSGLAEMCWEKMAETELRSLAGAVLQLRCSDPKKFTLPKGRIDRNGNRLPHHIWDIELEGNGDKKTLRKHLKETAEKM<br>AEGGTAFRLFCEDVGNRLFRLSKGIPQETPNRQDAFSDPSQVFNLGRPVYGQENHRDPMIPSCEWIITGTLTAASPFFIADELI |

TABLE 3-continued

Amino Acid Sequences of Representative Type III-E (CLUST.019911) Effector_B Proteins DDDHISRKLLTTQDFHYRLPRSLLRGILRRDLHEASGGKGCRAELGPESSCICPVCRILNQVKIRDARSDSFVPPDIRQRVKQS
HHHRIVQDGALFDTEYGLEGVVFPFELRFKGEKTIDKELRTVMGWWEEGLLFLGGDFGTGKGAFKLGIKQIHRWDLSTPGAREE
YEQTCGFRAGVPLDANCQGLSPVSNIDFPKVDYPWQKVPWELAFESPLLTADPIAAITQDEADTIYFQKRRLKSDGSVEYIPAL
RGEGLRGLIRTATARASGSDHLTVEHEDCTCVLCKTFGNEHRSGLLRFDDLEPKNWKDKRIDHVSIDRFDASVVEKFDDRPLIG
SPDKPLVFAGAFWIHRDFTENKALSNGFQDLKSGLYPLGGKVGIGYGRLSKLELPSDWLPNSAENESISVSGLLEGSPETSGIP
EKPTWKPEPDAIYNPYYYLSRPGDGPKRTLTPVSHATLSKERYTGRIACFLKVKSPLLLPDSEHDPVAPDKNGTMKAFRLNGTL
MIPGSALRSAVSQVYEALTDSCFRVMDQKRVLSWRMETGDHGNYKPGRISESGDQIFPMGEKALRLPLYDMAPGTHSAKYIKEL
EELHKKALEGNIHRLTIAPWEEMPEKTREKKFEKCNKILGRNLTEEEKKNLTDQGMAKLKISEMELKTLIGRFKKDEESCIEKA
QKTDSNIAEIAKHNRDILNVLEKETRQRVLAGKEKVPFLTERLAPNNDINFQIVKLLKNSEKNKKNKEIRWGYLKITGPNNAND
AVVETKEEDDKYKLEWEDPLDFSFCLTGPPKNQPNTQKSRDFPRPGFECIKDDKRYTISKRCERLFEADEKSKPIPIPKRVREG
YKGILEDYQKNAKKIPKAFQTRLNSDLVYYKSDYVENQINVTALAPVCISRLADDRPLGKRLPVGYQPCSHICLEDCERCTGKA
CPIPLYREGYPVNGLCPACQLFGAQMYKGRVNFSFATLTPGKNLELRNVTLPAQERPRPTWILPKNVQGKDTEIPGAKFYLRHG
MWKKIWTDRKDPRTDKPIEEKNPNNVTIEGINTGAEFRFDVSFENLDENELGWLLYCLELEEDMSHMLGRGKPFGFGQVEIKIN
ELARRLAPNAWYTESPKEGSLIHSKLIVKALAGLKSLDSLRLLLTQYNNLTAYYPELEGKGGKPGYDTLKNSSGYNPHCFLTLQ
TKGNTPFVYPWFPIPISKPQATKSDIKPKVENHGITGNGFKKLVEGDKVTFEIEERPKGPCAVNVRKVKDIP (SEQ ID NO: 23)

>3300001096|Ga0067045_1003547_12|M
[bioremediation-terephthalate-wastewater bioreactor]
MNRYKVSLEFLEPWRINHLGDDRGAAWARWVQTREGYQRPEITGTLVRSAVIRAAEELLALTGGVWAGQKCCPGEFCTPGGSKP
TFRRQRATRWWGEDSLCTPDSPCPFCQLLGRHDLAGKQARRGGGFHVHFGNLYPVAREGYGSLAEITRQRTSNRLDWLTGKAQD
ILTICEVEELRRFSGLITVAPELANGEAVSSLLTAAAALVDRLSGAACRLKLQPVEELWSGTAVSLTRAAVPETAYRQQLEEDI
DNYFQELIGDGSQLGPERLRLLADAIRELRYLPPEQTLPDWLQSLPQGKDGKAHRLWDALTAQRRPLRNMLQEVAAAYAAPATW
RDVVQGLGQALYAHYKKLWPQAMPVRPVGEAEYWQTKFRDRQPSRQRGTWSHEWIITGALQTLTPLYLGTQVEAARQTSLTVLL
TAEGRYRLPRTALRGALRQDLQLASRGQGCLMELNPERPCSCPICQIMRRLTVRDVTSSIALPPPLVRQRVRRNPWTGIVDEGA
LFDQEVAPEGLRFPFILRYRGFGGLDAWLQTVLSWWQEGRLFLGGAGGTGKGRLRLTDLRIWRWALDETGLPTYVAHLGYRGRE
EELANSASLPAGVEAVTCSDPATVPSPWQEVDWEFRFHGPVLANHPLTALLRGEADAVFTWKVQLEADQQHYREVCTLKGETVR
GLVRGLFGKSQGLLTKAHADCTCLLCRVFGNEHQRGKVRFEDLTLAGETVPKKRLDHVAIDRISGGAAEQLKFDTQPLYGTPEN
PLVFAGKFWVHTELDEEEQKALRAALTALRDGLATVGAKGSVGYGWLNGLRLHSGPAWLTDNWQETAAAPSDTNTPPEFSWPQL
PDLTLDSRKIYYPHYFLPPDLQVPRLSQPHTHSLFDPQKYTGWLTCRLTTLTPLIIPDTSSDQTLTTGGPFPAGHQAFQFFRLG
DQPLIPGAELRGMISSVFEAITNSCFRVIRPRERLSWRMPAALAPQFRSGRVEIVNNQYYIRQMDMGRLPLYDDPATRRLFTPL
SLTSGHTLDFVDDNRTLLQSNPGIREGAIRTDLCFLNRFWLLRPPSAARCPRGNFSLTSGYVKFTGPNKVEVSRAGAGAGGLPA
PPADWTGVRLNQVAGNVPFYQAEQSGVIFTVNKRRERFFISRGNARSYPVPLATLKRYEQVLKEYRHFAQRGEVPAVFRTVLPD
VRHGASGYNRLNNGDLVYFRVKDDRWNDQNAPVEHIIPVSISRLVDQKFLGERVPEPLRPCAHVCLEECEACLKQESCPSSFYR
EGTPSRGLCPACHLFGTTGYQGRVRFGFARLEREPAWRQNDAGSTAITLPLLEQPRLTWSMLWERRNAEGTVEERQPVNWVPGR
KFYVHHQGWRTIVAQGINPIDGQRLERNENNRTVEVLDTGRTFTFQVFFENLDAWELGLLLYSLELEPGLAHKLGMAKAWGFGS
VQIDVASLRRYQAPGSMTDITCEKDTLLQAGFAWLKEQANSSSWDEIPRLRQLRQLLRYQEDGTLTVRYPILKQENAASGQVPG
YVELRDQGYRPEEQLRIPWSPWYSPPLEPPPAATAAA (SEQ ID NO: 22)

>3300025107|Ga0208863_1001002_11|M
[terrestrial-soil]
MTTGNTSASHPQFVTLTVCLRFCSPFQIRPWIKETVRNKVKMPSTVNAHAETAHLPDDQDTDDTQDLLEEERFERYATAADWHK
GSINGNAKYSPYVRGDLVRSVVDRELQEHFHCYNEKLANENKGCPGKRDRHINAGGKASGFMAHLPAIKDPAGKEICKGSDNIC
PVCHFLGAFAEGIKPVKFRNFFSGYYVAKTEDLAKQRGRNCYSGQSRKSLDNFTVWEADHTACPVFFGRIEVNKTLLPKEQILA
LLAGGLARLDNLAGSACRFDIIDKYEGVFEDHEWTANILPNLLIAAREALGLPDDEHQALLNDFSRFFINPEKSPAVYTSSPVI
VPVQGAVDKVVLLEKAQDIAGRIAACVSDNPRHLHRLAAAIRTLGWPGRSLASVMTKKPGTEDKATLWGKESASKSVKTILEES
IQGFTVEQKRSFFANLADQLVSRAGEQGAKSVRSQGLIIGRKENYAKPSAQEPTRHHLYRQPSNASAFLATGWLIAETPFFIGS
GTEGQKQTDDQAESLHLRTLRDGHGRFRIPFTTIRGVMDKELRDILQAGCAKGRSLRAPCPCQVCTLMRRIQVRDAIAADILPP
DLRMRTRIDPSHGTVAHLFSLEMAPQGLKLPFFLKLKGVETIDPDKELLEILNDWSAGQCFLGGLWGTGKGRFRLDDLQWHRLE
LDNADYYTPLLQDRFFAGETISDLRQGLQSINIQPERIPAQTPSRNMPYCRVDCILEFKSPVLSGDPVAALFESDAPDNVAYKK
PVVQYDETGRLRTTDPGPVEMLTCLKGEGVRGVVAYLAGKAYDQHDLSHDSCNCTFCQAFGNGQKAGSLRFDDFMPVQFESDQA
GNFSWSPHTPHAMRSDRVALDVFGGAMPEAKFDDRPLAASPGKPLNFKSTIWYREDMGKEAGKALKRALIDLQNNMAAIGSGGG
IGRGWVSRVCFEGDIPDFLEDFPEPITVTEPEQDSQLLKNQAVADETAVSACDTADAPHPLAVTLEPGARYFPRVIIPRAPTVK
RDECVTGQRYHTGRLSGKIFCELNTLGPLFVPDTDYSAGVPVPISDEQLAECQLQAVFENTSKFNEFFATYPEETVTKLKDLLC
AADDKWILAVKDITADLRQEIGEDTFQRIIRKAGHKTQRFHQINDEIGLPGASLRGMVLSNYQILTNSCYRNLKATEEITRRMP
ADEAKYRKAGRVTVSGDGAQKKYSIQEMEVLRLPIYDNMNTPDNMPDVAKQATTAKRCNNLMNEAAKTSRVELKARWREGQSKI
KYQIIDALNKVDPIIQVISSSKQINPNNGKTGWGYVKYTGANVFAKSLVAPIDCLRKKDAGHVCCQVNLNPAWEASNFDILINE
KCPVERQSGPRPTLRCKGQDSAWYTLTKRSERIFTDKKPVPDPINIPPREVKRYNELRDSYKKNTAHVPKPLQTFFNQESLANG
DLVYFEVNQFGEASQLTPVSISRTTDLFPIGGRLPQGHKDLFPCTAMCLSECKNCVPASFCEFHSRSHEKLCPACSLAGTTGNR
GRIKFSEAWLSGLPKWHSVSQDNVGRGLGVTMPRLERSRRTWHLPTKDAYLLGQSIYLNHPVPAILPSDQVPSENNQTVEPLGP
KNIFSFQLAFDNLSIEELGLLLYSLELESGMAHRLGRGRALGMGSVQISVKDIQIRDNKSFLFSSNISKKSEWIQCGKDEFAQE
AWFGESWDNIDHIQRLRQALTIPVKGDVGCIRYPKLEAEGGMPDYIKLRKRLTPLCDREEPVRYRINPVQLARMILPFVPWHGA
CPALLNEQVMIEAKRLTELLAQENLDMICRTKNCANCKQETKKDCLAFRYDRANWPC (SEQ ID NO: 24)

>3300028595|Ga0272440_1002488_4|M
[aquatic-marine-marine sediment]
MKVRIKFFEPIRVMPWVNPSDRKISNEQFMRGQSFARWHRYNKNSNSGKPFITGTLVRSAVIRAAEVLLSLSNGIIENKACCPG
MFETEGAARKKKMHFRQRSTPKWTENSTCNKDNQCPFCELLGRFGNDEIGAVIEKENNTKRLKYNFHFSNFQPSGNNSYPDHII
IKRTVNRVDYTTGKAHDFFTISEIDNSFFPAFEGHISISDRVSHEAKKLLSDSLKFIDKLCGSICVFEFDDSTWDDHLHIEKSM
EKNDGKEKSEEITKQIIKILESNSKLDYLRILSDAIRELARDKEMVHKLPLDYKGKKKHYIWDLAYNKISIREILCNQANKNAK
NDYVELCKTIGKELYHESQKKTELLTKPHRILGSKSFYGKPQRDIQPTDAKIVPTEETIFTGKLVSETPFFFGLENEDKQQTDF
TVLLDSQNRFRIPRSALRGVLRRDIRMMSGGNGCDVKLGGRQCLCPVCRMMRNITIMDVRSNKDIIPDIRQRIRINPYTGSVAE
GALFSMELGPQGMEFDFVLRFRGNDSIPKSLKKVLLCWAKGQAFLSGASSTGKGRFKLKNLKFKSFDLSTKEIRNDYLNQRGWR
NRENELPLEPLFLTDKYKEINTTLWNKVSVEIKLSSPFLNGDPVRSLVQGQGADIVSFKKTSLIDDEDIYAYKAESLKGIFRTA
LARRFHYKDKISQKVLPLTAISHKDCDCPLCRLFGSEFETGKIRFEDLEFSTNPIPKKFDHVAIDRFTGGAVDKKKFDDCALSA
TKQKPLLLKGNFWLRPDMTKDDFKYFEKAFLDIKSGFYPLGAKSGIGYGQIEDISISISDSDDYPRAIKENIKTINNKSYTQEA
KNNINDKDTDESKQSDFQIDLKDDAIYYPHYFLKPNKKVDRKTIPINHLTLHDECHTGKIVCTLTTKTPLIIPDTENDDAFGLK TABLE 3-continued Amino Acid Sequences of Representative Type III-E (CLUST.019911) Effector_B Proteins KAKLAEDGEKYHKSYSFFSVNDEIMISGSEIRGMISSIYEAITNSCFRIFEEKHRLSWRMEAVPEVLEKFIPGRIIKINGELKM
VEMEEVRYPFYDKNCPDTKTQKDHFSSKGKGKLYYEQPTFSDKMILSLSEYNRKHQNPGKKEKYKIIKPDSKSNANFMFTATPA
NNTEGYDMDCVHKHSVKGYLKVSGPNKIEKERTDQPASNKIPMENEIVIHQKTNRREITVQNAKKNKKRYRLIPEYICSEKDTN
YIMNKRCERVFIEPEKCNHDGIPISKNAIELFKHLVDEYKKNADQQETPKVFRTKLPEKGELKEGSLVYFRKDSNEVVEIIPVK
ISRKIDDRFIGKRLTKNLRPCHGEWIEKDDLSILDQYPEKKLFTRHPKGLCPACQLFGTGAYKGRLRFGFATLINKPEWLNKED
KDHKLTLPLLERPRPTWAIPDATQASKVPGRKFFIHHHAWTDIEKGIDPVTGKAIQIDVNNRTVQPLDSNNTFTFEINFENLEP
HELGLLLYSLQLENSLSHKLGMGKAFGFGSIDIKVENLLLFDSTIDKYKNKTDQVKRFVDEGKNNLLEIFENEFDDIEHIKDLK
SLLYFPNDKNIRVQYPLLRKEDYPDKDLPGYKELKDNFSNGIQIRHNLLTIPWSPWAYQSKKKLENEKTIYPPLKKIEINNYYD
IKKVNIKIPDNAQWVFLTGNNSIGKSLFLKAIATGLYGKITEDDENDIDTNCGIRVFITNEWVNDVKKDYFNQKLSYKNYATYG
PSRLNKLAEGKKTKFPYFSLFNTEGVFYHDIEKEFIKWCDRDSSKFNLLKNIFIKLLPTIDDIKGIQTKTDFYIGYKEMETGKY
EKQSKLATGNISILRMFGDMFIRFSKEQPDTLPEDFSGIVIIDELDLHLHPIWLKKIPGLVSKLFPKIRFIASTHSAIPFLGAP
KNSVYLNVIRDEDNNIHVQEIDIDLTNLLPNTILTSPLFNMEDITQINLPDITDVRTEDTYKEIIEIDKIKARLKKFAKKDTLF
PDKLFKEL (SEQ ID NO: 25)

>SRR8490538_megahit_k177_234425_10|M
[anammox bioreactor]
MSKKHFIHLTFLEPYRLAEWHAKADRKKNKRYLRGMSFAQWHKDKDGIGKPYITGTLLRSAVLNAAEELISLNQGMWAKEPCCN
GKFETEKDKPAVLRKRPTIQWKTGRPAICDPEKQEKKDACPLCMLLGRFDKAGKRHRDNKYDKHDYDIHFDNLNLITDKKFSHP
DDIASERILNRVDYTTGKAHDYFKVWEVDDDQWWQFTGTITMHDDCSKAKGLLLASLCFVDKLCGALCRIEVTGNNSQDENKEY
AHPDTGIITSLNLKYQNNSTIHQDAVPLSGSAHDNDEPPVHDNDSSLDNDTITLLSMKAKEIVGAFHESGKIEKARTLADVIRA
MRLQKPDIWEKLPKGINDKHHLWDREVNGKKLRNILEELWRLMSKRNAWRTFCEVLGNELYRCYKEKTGGIVLRFRTLGETEYY
PEPEKTEPCLISDNSIPITPLGGVKEWIIIGRLKAETPFYFGAQSSFDSTQDDLDLVPDIVNTDEKLEANEQTSFRILMDKKGR
YRIPRSLIRGVLRRDLRTAFGGSGCIVELGRMIPCDCKVCAIMRKITVMDSRSENIELPDIRYRIRLNPYTATVDEGALFDMEI
GPEGITFPFVFRYRGEDALPRELWSVIRYWMDGMAWLGGSGSTGKGRFALIDIKVFEWDLCNEEGLKAYICSRGLRGIEKEVLL
ENKTITEITNLFKTEEVKFFESYSKHIKQLCHEGIINQMSFSGGLRSYHEYLSPLWTEVKYEIKIASPLLSSDTISALLNKDNI
DCIAYEKRKWENGGIKFVPTIKGETIRGIVRMAVGKRSGDLGMDDHEDCSCTLCTIFGNEHEAGKLRFEDLEVVEEKLPSEQNS
DSNKIPFGPVQDGDGNREKECVAEVKIYKKKLIDHVAIDRFHGGAEDKMKFNTLPLVGSPERPIILKGRFWIKKDMVKDYRKKI
EDAMVDIRDGLYPIGGKTGIGYGWVTDLTILNPQSGFQIPVKKDISPEPGTYLTYPSYSAPSLNRGHIYYPHYFLAPANTVHRE
QEMIGHEQFHKEQKGELLVSGKIVCTLKTVTPLIIPDTENEDAFGLQNTYSGHKNYQFFHINDEIMVPGSEIRGMISSVYEAIT
NSCFRVYDETKYITRRLSSEKKDESNDKNKSQDDASQKIRKGLVKKTDEGFSIIEVERYSMKTKGRTKLVDKVYRLPLYDSEAV
IASIKFEQYGEKNEKRNAKILAAIKRNNVIAEVARKNLIFLRSLTPEELKKVLQGEILVKFSLKSGENPNDYLAELHENGTERG
LIKFTGLNMVNIKNVNEEDKDFNDTWDWEKLNIFHNAHEKRNSLKQGYPRPVLKFIKDRVEYTIPKRCERIFCIPVKNTIEYKV
SSKVCKQYKDVLSDYEKNFGHINKIFTTKIQKRELTDGDLVYFIPNEGADKTVQAIMPVPLSRITDSRTLGERLPHKNLLPCVH
EVNEGLLSGILDSLDKKLLSIHPEGLCPTCRLFGTTYYKGRVRFGFANLINKPKWLTERENGCGGYVTLPLLERPRLTWSVPSD
KCDVPGRKFYVHHNGWQEVLRNNDITPKTENNRTVEPLAADNRFTFDVYFENLREWELGLLCYCLELEPGMGHKLGMGKPLGFG
SVKIAIERLQTFTVHQDDINWKPSENEIGVYVQRGREKLVEWFTPSDSHKNMEWNEVKHIKDLRSLLSIPDDKPTVKYPALNKG
AEGAISDYTYERLSDTKLLPHDKRVEYLRTPWGPWNAFVKEAEYSTSENSDEKGRETIRTKPKSLPSVKSIGKVKWFDEGKGFG
ILIMDDGKEVSISKNSIRGNNLLKKDQKVTFHIVQGLIPKAEDIEIAK (SEQ ID NO: 26)

>SRR6011893_megahit_k177_1702441_5|M
[dolphin oral metagenome]
MIPDLRSLVVHISFLTPYRQAPWFPPEKRRNNNRDWLRMQSYARWHKVAPEEGHPFITGTLLRSRVIRAVEEELCLANGIWRGV
ACCPGEFNSQAKKKPKHLRRRTTLQWYPEGAKSCSKQDGRENACPFCLLLDRFGGEKSEEGRKKNNDYDVHFSNLNPFYPGSSP
KVWSGPEEIGRLRTLNRIDRLTTKAQDFFRIYEVDQVRDFFGTITLAGDLPRKVDVEFLLRRGLGFVSTLCGAQCEIKVVDLKK
KQNNKEDSILPVSEVPFFLEPEVLAKMCQDVFPSGKLRMLADVILRLREEGPDNLTLPMGSQGLGGRLPHHLWDVPLVSKDRET
QTLRSCLEKIAAQCKSEQTQFRLFCQKLGSSLFRINKGVYLAPNSKISPEPCLDPSKTIRTKGPVPGKQKHRFSLLPPFEWIIT
GTLKAQTPFFIPDEQGSHDHTSRKILLTRDFYYRLPRSLLRGIIRRDLHEATDKGGCRVELAPDVPCTCQVCRLLGRMLLADTT
STTKVAPDMRHRVGVDRSCGIVRDGALFDTEYGIEGVCFPLEIRYRGNKDLEGPIRQLLSWWQQGLLFLGGDFGIGKGRFRLEN
MKIHRWDLRDESARADYVQKCGLRRGVGDDTAINLEKDLSLNLPESGYPWKKHAWKLSFQVPLLTADPIMAQTRHEEDSVYFQK
RIFTSDGRVVLVPALRGEGLRGLLRTAVSRAYGISLINDEHEDCDCPLCKIFGNEHHAGMLRFDDMVPVGTWNDKKIDHVSCSR
FDASVVNKFDDRSLVGSPDSPLHFEGTFWLHRDFQNDVEIKTALQDFADGLYSIGGKGGIGYGWLFDMEIPRSLRKLNSGFREA
SSIQDALLDSAKEIPLSAPLTFTPVKGAVYNPYYYLPFPAEKPERCLVPPSHARLQSDRYTGCLTCELETVSPLLLPDTCREKD
GNYKEYPSFRLNNTPMIPGAGLRAAVSQVYEVLTNSCIRIMDQGQTLSWRMSTSEHKDYQPGKITDNGRKIQPMGKQAIRLPLY
DEVIHHVSTPGDTDDLEKLKAIVLELTRPWKELPEEQKKKRFEKCKNILDGRMLQQKELRALENSGFAYWRDKTSLTFDSFLKD
AIEQEYPRYSGDYQRIKALVVNITLPWKLLKKEERHKRFDKCRRILKGQQPLTKDERKALEESGFANWHGRELLFDRFLKDENS
CLIKAETTDRVIASVAKNNRDYLFEIKQQDFARYKRIIQGLERVPFSLRSLAKSKETSFQIACLGLRRGRFLRKGYLKISGPNN
ANVEISGGSHSNSGYSDIWDDPLDFSFRLSGKSELRPNTQKTREYPRPSFTCTVDGKQYTVNKRCERVFEDSAAPAIELPRMVR
EGYKGILTDYEQNAKHIPQGFQTRFSSYRELNDGDLVYYKTDSQGRVTDLAPVCLSRLADDRPLGKRLPEEYRPCAHVCLEECD
PCTGKDCPVPIYREGYPARGFCPACQLFGTQMYKGRVRFSFGVPVNSTRSPQLKYVTLPSQERPRPTWVLPESCKGKEKDVPGR
KFYLRHDGWREMWGDDDKPDSRPSSEECQDIIEGIGPGEKFHFRVAFENLDKNELGRLLYSLELDAGMNHHLGRGKAFGFGQVK
IRVTKLERRLEPGQWRSEKICTDLPVTSSELVISSLKKVEERRKLLRLVMTPYKGLTACYPGLERENGRPGYTDLKMLATYDPY
RELVVQIGSNQPLRPWYEPGKSFKPSPGNDCTGRGGSVSKSLISEPKVVPAIAPFCEGVVKWFNSVKGFGFIETKEQRDIFVHF
SAIRGEGYKILEPGEKVRFEIGEGRKGPQAINVIRIR (SEQ ID NO: 18)

TABLE 4

| Consensus Type III-E (CLUST.019911) Direct Repeat Sequence and Nucleotide Sequences of Representative Type III-E (CLUST.019911) Direct Repeats | |
|---|---|
| CLUST.019911 Effector_A Protein Accession | Direct Repeat Nucleotide Sequence |
| CONSENSUS DIRECT REPEAT SEQUENCE | GTTRNRNANMRMCRSNWDYYWTTRATGTBACGGDAC (SEQ ID NO: 100) |
| KHE91663.1 (SEQ ID NO: 1) | GTTATGAAACAAGAGAAGGACTTAATGTCACGGTAC (SEQ ID NO: 27) |
| OGR07204.1 (SEQ ID NO: 2) | GTTGGTGCATCAGCCCGGAATTATGATGTTTTGGTAC (SEQ ID NO: 28) |
| WP_124327588.1 (SEQ ID NO: 3) | GGTTGGAAAGCCGGTTTTCTTTGATGTCACGGAAC (SEQ ID NO: 29) |
| OBJA01001127_8\|M (SEQ ID NO: 4) | ATTGCCCCAGCCGATAAACCCTTAATGTCACGGAAC (SEQ ID NO: 30) |
| PDWI01005922_7\|M (SEQ ID NO: 5) | ATAGATATAGACAGAAGCTTTTAATGTGATGGGAC (SEQ ID NO: 31) |
| RLC19860.1 (SEQ ID NO: 6) | GTTGGAAAAGCCGGTTTTATTTGATGTCACGGAAC (SEQ ID NO: 32) |
| 3300009529\|Ga0114919_10000047_39\|M (SEQ ID NO: 7) | ATTGGGGGGATTAGATTCTGATAATGTCACGGTAC (SEQ ID NO: 33) |
| 3300015370\|Ga0180009_10000113_9\|P (SEQ ID NO: 8) | GGTTGGATTCAGCCCCAGATGTTTTATGTGACGGAAC (SEQ ID NO: 34) |
| 3300001095\|JGI12104J13512_1001353_7\|M (SEQ ID NO: 9) | GTTAAGGAGAGACGGCATTCATTGATGTCACGGCAC (SEQ ID NO: 35) |
| 3300020048\|Ga0207193_1004003_10\|P (SEQ ID NO: 10) | GTTAGCATCAGGACAATACCTTCGATGTTACGGGAC (SEQ ID NO: 36) |
| 3300001096\|Ga0067045_1003547_9\|P (SEQ ID NO: 11) | GTTAAGGAGAGACGGCATTCATTGATGTCACGGCAC (SEQ ID NO: 35) |
| OGR07204.1 (SEQ ID NO: 2) | GTTGGTGCATCAGCCCGGAATTATGATGTTTTGGTAC (SEQ ID NO: 28) |
| 3300028595\|Ga0272440_1002488_3\|P (SEQ ID NO: 12) | GTTCCGTGACATCAAAAGCCGTCCATTTCTCAAAC (SEQ ID NO: 37) |
| SRR8490538_megahit_k177_234425_6\|M (SEQ ID NO: 13) | CTTGAAGACTAAAGGAAGGAATTGATGTCACGGTAC (SEQ ID NO: 38) |
| SRR6011893_megahit_k177_1702441_3\|P (SEQ ID NO: 5) | ATAGATATAGACAGAAGCTTTTAATGTGATGGGAC (SEQ ID NO: 31) |

TABLE 5

| Direct Repeat Homology-Containing Regions of Representative Type III-E (CLUST.019911) Systems | | | | | |
|---|---|---|---|---|---|
| family | effector accession | homologous region | start | end | strand |
| CLUST.019911 | S.XXMH0-MGM_5 | ACCGGCTTTTCCA (SEQ ID NO: 101) | 29649 | 29662 | BS |

TABLE 6

Direct Repeat Homology-Containing Loci Sequences of Representative Type III-E (CLUST.019911) Systems >CLUST.019911|S.XXMH0-MGM_5|29649|29662
TTTTCCGAATCGGATGTGGGATTGCTCCGGCCCTGCCTTATTTTCATATAAGACCGGCTTATCCGACTATCTCCCTAATATGA
CAGGGAAAATATCTTCCCGGACTTTTCACCGGGATGGTATAAGAACAGGGAACCAGAATCATCTGTTCCCTGACCACTGGAAA
GTTTTTCATATCAGTATGTTGAATCCTGTCACCCCTGGGGCACGGAGGGATTTCCAAATATCCGATCTGATGTTCGTAATCAC
CGGCTTTTCCAGCCAATGGCTTGAGATGATTTAAGAAACTTGTGACTGGCTTTTTCTGGTAAAATGGATTTTTGTATAATATC
CTGTTG (SEQ ID NO: 102)

TABLE 7

Non-Coding Flank Sequences of Representative Type III-E (CLUST.019911) Systems

>CLUST.019911|JRYO01000185_8|19509|20000
AGAGTCAGGACAACACTCTGTACCATAGTTGTGGGATACAGAAAGCCTTTGATTACCATCGGAAATCCCACAAACATCCCAAT
GTGTATATAATGATTTGATCTCAGCTATGCGTTCCTGGTATAAGTTTCTTTTCGGTTTTGCCTGCATTGTATTAACCTCTTTT
CTTCATAAATAATAAAATTATAAAATACTAAACGTTGAAATATTATGCATCTCCTTCTCGAAAAATCAGATCATATAAAATCA
ATTTCACCCCTCACCATAATAAGACGTACACTGTGGGTGAAAAGTGACACTCTTTTTAAATATTTTTAAATTCAAATAACTGT
TTATATTGAGCAAATGGAAATGCATCCTTTCCTCGTGTTATCATCAGTGCTGTCATTTGAATTAATCGTATTTAATGGAGAAA
AGGTGACAATTTTTTATAAAAAGACTTGTACAAAAAAATTAAATTGTACTGAACTTTTTTTTGTCACTTTGGTTTGGTGATTA
ACGACTGAATATATTAGAGTATTTTTTTCTCTTTTTATTCTTGAAAAAATTGTTCTTGAATAACAGTGTTTACTTAACTAAAG
TACCTCTAATAAATATTTGTTCACACCAAAAACAGTAAGGTTATAAAGAAGAAATCTGTCATGAACAATACAGAAGAAAACAT
TGACCGTATCCAGGAACCGACCAGAGAAGACATTGATAGAAAAGAAGCAGAACGGCTTCTTGATGAGGCTTTTAATCCAAGGA
CCAAACCCGTCGATAGGAAGAAGATAATTAATTCTGCCCTGAAG (SEQ ID NO: 103)

>CLUST.019911|JRYO01000185_8|25772|25776
AAGTTGAAGAGTGTATCCATTACTGAAAAGGGTCAACGCACATATCCTGTAGATGCATCCGGTAGCAGGATAGCGGAAGAGGT
CAGGGATTATACGCAGAAACCACTAAACGTTGTTGTGCTGATTATTAAATATACATATGAAGAGTAACGATATGAACATCACT
GTAGAACTCACCTTCTTTGAACCCTACCGTCTGGTTGAGTGGTTTGACTGGGACGCAAGAAAAAAGAGTCATAGCGCAATGAG
AGGTCAGGCTTTCGCGCAGTGGACGTGGAAAGGAAAAGGTCGCACAGCAGGCAAG (SEQ ID NO: 104)

>CLUST.019911|JRYO01000185_8|31078|31608
AGCACCGTTAAGAAGTTTGGATTCATCAGTAAAGGTGATGGAGAAGATATTTTTGAAAGAATCAAGGAAAAATATATTAAAGC
ATTGGAAAACAATATACAATTATTTGAGATCTATTTGTCGGATGAAAAGGATACTCGGAATAAATAACAGACAAACGGTTTGC
GAAGAAATACGCGACAGGGTGATTGGACCGTAACCTCATGATTATATGATTGATACACGATTTAACCCTGACTTGCCGGTTTT
TGAAAAAGTTCGCAAACCCTGTTTTGCTTCATGAAGTGAGTTGGGTTTGCGAAAAAAGGTTATTACAGCCTGATATCTAAGTA
GAAGAGTACCGGTATTGAAGACCAAAGTTGCTGCGTATGGCGGTCCGGTTGTCCTTGCTTTCGCAAGGATTCCAATACTGGAA
TCCTCCCGAAAGGGAGGTCGCAAAAGGCCGTTTTTCGAAAACCATAGTTTCATACAAACCGGCGATGAGGTTTGCGAACTTTT
TGATTGTAGTAAGTATTATTAAAATAATGGCTTAATATTTTTGGTATATACAATTCTCAACTTTTTCACCTTGCCGGAAATGA
GGTTTGCGAAATTTTAGAGAGCCGCATATCTATATTATTTACAATCAGTTACAAAATGGCCCCTTCTCGCCATATACGTAACC
TCAGAGTTGTTGGAGG (SEQ ID NO: 105)

>CLUST.019911|JRYO01000185_8|32437|32673
GGTTTGATTGAATATTGATGGTTGAAAATCGTCTGCCCTATGGGGGAGGCAATGTCATTGAATTAAGGGCAAAATATGGAGTG
CATCATCCCTGCCCGAGAATGACACTACAGTGTCAACATCCCTTTAGGTAGGCGTCCACGTCAGCCTGGCGGGAATCCAGCAA
CCTCTGCTTTGAGAGTCAATTCCATTTTAGTTGTCACCTTTCTGATAGAATCCTCGACTAAATCAGTAAGATGACAACTGATA
CTCTACTTGAACAATTTTTAAGCAAGTCCAATTTCATTTCTGCCTATGAGCGTATTGCCTCAAAGAAGGCTGCAGGCGGATTG
GATAATGTCACGGTTGAATCATTCGGCAACCGACTGGACCAGCATATCAGCAAA (SEQ ID NO: 106)

>CLUST.019911|MGTA01000040_4|19908|20000
GTTATCCTTGGCCATTTAGAGGCTTCGGTCAAAAAGGCGCTCGATGCGGTCGAAAACATTGCGTCTGGCCAGCCAAGTAATGA
GGACTCGCCAGTATTACCCACGAGCCCGGCGGAGGTGGCGGTTATTCACTGGAGCATAAACCAGTGACCACAAATTTCCGGAA
ATGATGTCCACTTCGATAGTGTAGATGGTGCGGACGTATCACCCCTTCCCCAAGGCAGCTCAAGGAGAGCAATGATATGAATC
AAAATATCGATCGTGCGGTTGGTGCAATTCTAGCGATTGAAACAGCGACACCCCTTACCGAATCTTCAACACTCGCGCAACGT
GAAAGGCATCAGAAGCTGCTGCATGATGAAACCAAAAAGATTGAGCAAGCCTTCATAGCC (SEQ ID NO: 107)

>CLUST.019911|MGTA01000040_4|22550|23634
CTGCAAAGCTGTTGGATGCGCCAACCCGGTGCCATTTTTAATGATGAGTACATCCGCCTTTATTATGCCGCCTCTTTCCGGAT
ACTGGGTTTCCCGGAAGTTGCGACTACAAATATGGCGACTGCAACCGCCCAGGAGGAAATAGCATGACTACCGGCAACACTTC
CGCTTCTCACCCGCAATTTGTCACGTTGACAGTCTGTTTGCGCTTTTGCAGCCCCTTCCAGATCCGACCCTGGATCAAGGAAA
CGGTGCGCAACAAGGTTAAAATGCCATCCACTGTCAACGCTCATGCTGAAACTGCTCACCTGCCGGATGACCAGGATACCGAC
GACACACAAGATCTATTGGAAGAAGAACGTTTTGAGCGGTATGCCACTGCCGCTGATTGGCACAAGGGAAGTATCAACGGAAA
CGCGAAGTATTCACCCTATGTGAGGGGCGATCTGGTCCGCAGCGTGGTGGACAGGGAATTGCAGGAGCATTTCCACTGTTATA
ATGAAAAGCTTGCCAATGAGAATAAGGGGTGCCCTGGAAAACGGGACCGCCATATTAACGCCGGCGGCAAGGCGTCCGGTTTT
ATGGCACACCTGCCCGCGATCAAGGACCCGGCCGGCAAGGAGATCTGCAAGGGCAGCGATAACATCTGCCCGGTCTGCCATTT
CCTCGGGGCGTTTGCGGAAGGAATAAAGCCGGTTAAGTTCAGGAATCGGAAGATCTGGCCAAGCAGCGCGGCCGGAACTGTTA
CAGCGGGCAAAGCCGGAAATCCCTTGATAATTTTACTGTCTGGGAAGCGGATCATACCGCCTGCCCTGTTTTCTTCGGCAGAA
TCGAGGTGAACAAAACTCTTTTGCCGAAAGAACAAATCCTCGCCCTGCTGGCTGGCGGCCTTGCTCGGCTTGACAATTTGGCG
GGTGCGGCGAGGGAGGCACTTGGGCTACCAGACGACGAGCACCAGGCACTCCTCAACGATTTTTCAAGATTTTTCATTAATCC
CGAGAAATCGCCTGCTGTTTATACTTCCTCCCCGGTTATTGTCCCTGTCCAGGGAGCTGTTGATAAGGTTGTGCTCTTGGAAA
AAGCCCAAGATATCGCCGGCAGAATTGCCGCGTGTGTCTCCGACAATCCCCGCCACCTCCATCGGCTGGCTGCGGCTATCCGG
ACCCTGGGCTGGCCGGGCCGGTCTCTTGCTTCGGTTATGACTAAAAAACCGGGTACCGAAGACAAGGCCACCCTCTGGGGAAA
AGAATCAGCGAGTAAATCGGTCAAGACGATTCTGGAAGAATCAATCCAAGGCTTCACTGTAGAACAAAAGCGAAGCTTTTTTG
CCAACCTTGCCGACCAGCTC (SEQ ID NO: 108)

TABLE 7-continued

Non-Coding Flank Sequences of Representative Type III-E (CLUST.019911) Systems

>CLUST.019911|MGTA01000040_4|27846|28045
CGTATCAATCCGGTACAACTCGCCCGAATGATTTTACCATTTGTACCTTGGCATGGTGCATGTCCTGCTTTGCTGAACGAACA
GGTAATGATAGAGGCCAAACGATTGACTGAGTTAGACCGCGCCAATTGGCCATGTTGAATGCCAGCACAACCAGCTAATATAT
CGAAATCGCTGGCAAAGTTAGCTTTTATTGTAAAATTAGATGATTAGGAACGATCCGGCAGGTTATTTAAATGAAGTAAAGTC
TGGGGTCGTAGCATAATCGCAAAAAAAATTATTTAACAGAAACAAACAAATAGACAGCATAAAGTTGAATTGAGTATTATAGA
AAGCAGGG (SEQ ID NO: 109)

>CLUST.019911|MGTA01000040_4|30276|42550
TTTTTCTGTAACTATTCAGCACACCATATTTTAGCATAACAACTGAGTAGTCATTGGGGCATCATAAATTGAGGCCATTTCCC
TTCAAATAATAAGCGCA (SEQ ID NO: 110)

>CLUST.019911|S.12JQSS-MGM_10|15939|16630
GAGACAAAAGAGCAACGGGATATTTTTGTTCATTTTAGCGCTATTCGGGGTGAGGGTTATAAAATCCTGGAACCGGGCGAAAA
AGTACGTTTTGAAATAGGTGAGGGGAGAAAAGGTCCCCAGGCCATCAATGTTATTCGTATAAGATGACAAAATTACTCCAGTC
TCTATTCTTTTTGTAATTACTTGTTCGCTGTTTTGTGAAGATTATATTAAGCTATGGAGCTTTCAGGTAAAAAAGCGTAAAGT
ACGCGAATATTCTGCGTAAAACTATTCCGGCTATGAAAGATGATGTTCATAGCCGGAATAGTTTTTTATCGAGTTTGGTGGGG
TATTCATTTTGGGAGATGGTTGATGAAAGTTTCAAGGCAGGGTTTCATTTATTGGCGATGGTTTAAATATCTCTTTATTCTTT
CTTCAACAATCTGATATTATTGTTTTTTTATCTAAAGATACTCTGTTTTTATTTATCGTAAAATATTCGACATACATATGAAA
CCTTTGAAAAGGCAGGAGTTTGGCGAAGATGTAGTGATTGTGGCTAAAATTACGGAAAAATTTTTTTTGTAAAATTAAGGTGA
TATGAATATAGTTTTTCTGGTGCGGTCGCCAATTTCCTTTTTTGAAATTAGGAAACTGGTTTGGCGAATTTTTTGACAGTATC
TTTTTATAATAAATACGAATAGTTGTGATTAGACAGGTGTTAATTTAGTAGTATTTCCCCTTTAACTGAAGAATGATTGGCGT
AATATTTAATAACATGAGAGAACTCCTTGGTATAATAGAGATTATTAAGTATAGTGTCAGAATGCAGCTTTTGTTTGTTCTTT
GATTCTAAAGG (SEQ ID NO: 111)

>CLUST.019911|S.12JQSS-MGM_10|17528|17702
TCTCAAAATAATGTTAAAGAAATTTTCATTTTATTTTGATGGTTTAGGCCACACTGACTTTGTGGTTCTCTTTATACCGATAG
AAAAATTTTATTTTTTCGAAAAAAAACACTCTTCCATTCGTAAGGTTAAATAAAGGCAATTACTTAACCATCTAGCAATGGAG
GATTGATCATGAAAAGCACACATTCTCTTTTTTACCGTTTTGCTCATGTTGATACCTTTCGCTCCGCATATGAAAGAATTTCT
CTAAAAAATTCCAGCCCGGGACTTGATAGAGTTTCCGTAGAAGAGTTCGGCAAGAAACTTGAAAAAAATATCCAA (SEQ ID
NO: 112)

>CLUST.019911|S.12JQSS-MGM_10|19997|20000
ATTCAGGCAATCCTCAATAGATTGGGGCAGGAGGTAAAAGGTCGAGGTAAGGCTTTAACATTGCAGGAAATGATCCATCGGCA
GGCGCAGTTGTTGAAAAGCTATTTGATGGATAAATCTGTTTACAAACCATATCTGGCAAGGTGGTAACCTATGAATACAGTCG
AATTACTTCAGGAGGAAGAACGCTTGACCCTGGATTTGGTCTTTTTGCCACCAGGTAGTAAGAATAAAGAGCAAAAAAAGAAT
GCTTTGGTAGACCTTTTGTTGAAAATAGTGGAGCATGGGGAATTAACCCGTAAA (SEQ ID NO: 113)

>CLUST.019911|S.12JQSS-MGM_10|22310|22413
ATCGACAATGATGATACCTCCGCTGTGCTCCATAGTTCATTAAAAAGATTATTTGAGCATTACGAGAAGAAAAATGAAAAAAC
TCGTGCACAGCTTCTCTATAATTGGGCGTCTTTACGTGTTCTCGCTCCTGCCAGGGAATTTAGTTGAAAAAAAATCATAAAAT
TTCCGAAAAAATAGATGATGTCGAACGTAATAGGTTTTAGAGCAACGAATAACCGTTGCTCTAAAACCTATACTCTGGGAGAA
CATCATGAAAAAAGAGCACGGTAAAGAAAACTATTCTATCGAAACAGTTGTTTTCGTCGTTTTGCAGGACATCATGAGTATTG
TTCTAATACCGTTTGCGGTAATCGCCTCAATTTATCTTTCTTATTTTTTTGAGTTATCTGTATACAAATCT (SEQ ID NO:
114)

>CLUST.019911|S.XXMH0-MGM_5|27292|27576
CCCCGCGTTATTTATCCGGCCCTGAAGCAGAAGGATATTCCTAACAGCAGGCTTCCCGGGTATGAGGAGTTGAAGAAGAACCT
CAATATGGAGAAACGGAAAGAGATGCTGACGACCCCTTGGGCCCCCTGGCATCCCATCAAAAAATAAGATGCCTGCGAATTCC
CGGAAATATGACAGCGGATTTAAAGGATTGAACGGATATCATTTTCCCAAAAAATGACAGCGGATTTAAAGGATTGAGCGGAT
ATCCGTTTCATCCTTTGATCCGTTGTCATATTTCCTACAAATATGTCGCCCCTACGGGGCTTTAATCCTTTCCTCTTCTTTGT
GTCCTTTGTGGCTTTGTGTGAGAAAAACAAAAAATTTTTGTCACATTTTCAGCACAGAACACGACTAAGTATGCAGAGAAGGG
AAACGCCCTCCTTTTCTTTGTGTCCTTTGTGGCTTTGTGTGAGAAAAACAAAAAATTTTTGTCACATTTTCAGCACGACATAC
GACTAAGTTTGCAGAAAGGGAAAAAACATATCTTTTTACTCATAAAGGAGGTTGCCATGAAAAAAACATTTATCGTCTTTGTT
CTG (SEQ ID NO: 115)

>CLUST.019911|S.XXMH0-MGM_5|29288|29740
AAGCGCTGGGCAACTGATGATCTGCTCCGTATGGTCGGGGATCAGATCACTGTGATGAGGGGGTTGCTGGAAAAGGGAGAGGA
TTATCGGCCGGTGGTTTACAACAGCCGGTATTCCAGCGGGAAGAGCGGCCTGAAAAAAAAGACTTGAAAAGGTCTTGACATGG
GCCGGGAAAGGGGCTATGTTCTTCTGATTATAATATCAGATCAGAGGGAATATGGCCCTTATCCCGGGAATATCCTGTATTTC
AGGGGATCGGGCCTGTTTTCCGAATCGGATGTGGGATTGCTCCGGCCCTGCCTTATTTTCATATAAGACCGGCTTATCCGACT
ATCTCCCTAATATGACAGGGAAAATATCTTCCCGGACTTTTCACCGGGATGGTATAAGAACAGGGAACCAGAATCATCTGTTC
CCTGACCACTGGAAAGTTTTTCATATCAGTATGTTGAATCCTGTCACCCCTGGGGCACGGAGGGATTTCCAAATATCCGATCT
GATGTTCGTAATCACCGGCTTTTCCAGCCAATGGCTTGAGATGATTTAAGAAACTTGTGACTGGCTTTTTCTGGTAAAATGGA
TTTTTGTATAATATCCTGTTG (SEQ ID NO: 116)

>CLUST.019911|S.MJ1HS-PDG_1|18611|19304
CAGCTGGGTCTCGGCCTGGGCGCCAAAATCCGCCACGCTCTGACCATCCCAACCGCCGGCCGCTTTTTTGGCGGCTACCCGCT
GCCAGGCGGCGGACAGATTTTCCATGGCGGTGATGGCGGCCAGTTGACGATAGGTGGTGGTAGACATCGGGACGGTGCCTCCT
GCAAGGTTCTATCCTGTTGGTCGTCGACGCAAGGCCTCAGGTGACCCCCTCTCCGTTATTCTGCCAATTTTTTCCTAGGGACC
GGCCTGGGCACCGTCTGCGGCGGGGGGCTGCCGTTCAACCCCGGCCAGGGCCATGGACCAGATTTTCTTTGATTTATCATCAG
GTTGGCTCCTCTTTCGCAAATGCTCCGGCGCCGCGAGCGGCCAAACCATTTGCGAACTTGGCCGATAGGCGATTATTTTATGG
CAAATCAATAAGATAAGTGCTTTTGAGGCCCTTTGGCCCCTCGGCGGCGAGGGGCCAAAAAGTTCGCAAATGCCCCTTTGGGG
GCCGGGCGCCCCACCATTTGCGAAAAAACCCGCCCGGCAGCGGCCGAGGCTTCTGCCGGCTGATTATATCTTATCGATATAAT
TGAATATTATTTTTCCCCAAGACCGGGTCGAAGGCCTATTTTCGCAAATGCCCGCCGCGGGCCGGGGGAGCCAACGTGTTGCG
AAAATCCGGTTCTAAGCAAATCAAGGAGTTAGGCCAAAAAAAGTGATTTTTGGCAATCCGGCCAAGCGCCCTTTGGGGGCATT
TGCGAAAAAATCCGGCCGGCAAAAACTTCTTGACATTACCGGGCATTTTCCATTAGAGTATTGCGTAGCAGTACATATCTAGC
TGATTTCTCCGTT (SEQ ID NO: 117)

TABLE 7-continued

| Non-Coding Flank Sequences of Representative Type III-E (CLUST.019911) Systems |
|---|
| >CLUST.019911\|S.MJ1HS-PDG_1\|19688\|20000<br>TATGCGACGGCCTTGGGCCAGCAGGATGCTGGCCCTACGGGGTTGAGCAGAGGCGGCAGGCCTTGAGGACACGTTTTTGAGGG<br>CGTTTAACGGCAGGCGCAGGAGACGGGACGCGAAGTGGGGTTAGGGAAATTACCGCCAGGCTGGAGAATAGCTGGCGGTTTTT<br>GTTTGGGGGGCCGGAAAAATTTTCTGCTCCTGTCACCTCGACGGTTCCAAGAGAGACTAATTTGTTAGACCAGGCTCCAGACT<br>GGAAGTATTTTTGGGCGCGGCCGCGGTGACGGCTGTCCAGCAAGCGGTTGGGACGGTTTAAACATGACTGCAGGACATTACCA<br>GACGATTTTGGAGGCCCAGATTGAGCTGGCCTTCTGCCTGCCGGAAGAGGCGCATAATGTGCTGTATGCGCGGGATGAGGCGT<br>GCCGTGAGCTGGTCCAAGCCTGCCGCAATCACCGGGGTAGCCTGCGT (SEQ ID NO: 118) |
| >CLUST.019911\|S.MJ1HS-PDG_1\|22355\|22370<br>GCAGAGAACGGAGGCGCCTGGTTCTATGAACTTTTATGGCAATGGCACAGGGATGAAATAGGACATCTTAGCAACATAAGGAA<br>TACGTTTGAAAGAATGAAAAGATTTGATAAATTTGCCCCCTGGAGGTCCGTGGGATTGGGTTGGTGAAAAAAAGAGGAGTGGA<br>TGTCTGCGCCTGAATATGAGATCGATCTGGATAACGATGACCACCCTACCATAATTTTAACAGACATGGATGAATGTTATCAT<br>ATATGCCTTAAAGCGGCAGGAAACGATCCTAGCTGTGCTCGATGCAAGATATTTATGGCAGATTTC (SEQ ID NO: 119) |
| >CLUST.019911\|S.TJLN2-PDG_0\|19450\|20000<br>TTTTAATTGACCCGCATTTTTTGTTATATCGAATAACCATGAAGAAAGGCGTCCTTCCCACTCCATCTCAAATCTATCAGGAT<br>TTGTTTCATAGATATGTTTGAGACGCTTTCGGCGCTTTGCTTTATCTCTTTTGGCGGCCTTTCCCATTAGTCCTCCTTCTTAG<br>TTCAATAATGGTTTTATCCATTGATTTTTCGACCTGATCAGAGGATCTAAACTCTGTTGGGCCGGTACCTAATTTGATTTAAT<br>CGAAAGAACGTTGTACTTTTTATCTCCTCTAATTCTTTTGTTTCGGATCGTCTGGATAGTCGTGATAAATCTCTTACATGTTA<br>CAGGGAATCGTAATTTTTCTATCTGAAATCTCACAAGCGCTATTTCGATAGTCGGGGCTAAGTAAAAAAATGTGACATGAATT<br>GCTGGGCCACCAGAAGAAATTTTTCACTAACCACTATAGTCTTCTGGAATGTGAAAAAGTGACAGAAAAAATATGAGGCTAAA<br>ATGTCACATTTTAAATAAAGCCCCGACTATAATTATACGGATATATCTATAGACAACCCCTTTTGATGAAACCTTACACCAAT<br>AATCGGATGTTAAAGTTATTGACATTACAAGATTTAATGTGTTATTTATTTAGGCTCAACTTTTCTCAAACCATCCAGACTAT<br>TTCAAAATATCTGTAAAGATAATAAGGGGGAATGTTATGTATTCCGACTTTCCTGCACTTAGGTTACCTGAATTATCTGTTGA<br>TCAAAAAAAATTATTTAAGATCTCCGGGACCAACCCACAGCTCATATACATCTTAATGAACGAATTTGATGGAGAGGGGGATG<br>AGCCCTTCTTTACCGGACTT (SEQ ID NO: 120) |
| >CLUST.019911\|S.TJLN2-PDG_0\|22274\|22282<br>GTTTTAAATCTTTTATTCATGAAAGAAGGTCTTTTTGATCATTTTTTTGAGCAACAAAGAGAATGGTGGAAAGAAGAGTATGA<br>ACATACCGATTCGAACACAGCTCTCTATGATTGCTTGTGTTTTCGAATGTATCGGTGTTATTTTTAGGAAAATATATGCCCTC<br>ATACCCTTGCTTGAAATGGAATGGCGATTGTAGCAGATGTCCTGATTCGGCAACATGCAGAATCGCACAGAAAGGTTTGGGAA<br>AGGTATTTACGGTTTTTTTCAAGAAATATCTGGCGCGTTACTATTCTTCGAAATCCGAA (SEQ ID NO: 121) |
| >CLUST.019911\|S.TJLN2-PDG_0\|26892\|26965<br>ATGATGAGGCGGTTTTTCTTTGATACCAGTGCGCTTATCAAACTCTATCATGAAGAAACTGGTACAGAAAAACTGGATTCTCT<br>GATCGAGGCCGAAAATCCAGTTATCATTAATGATATGAAATTGCCTGGCGTTATGAGCTAATCCTTATATTAAATGCTTCAGG<br>CATCTGAACCTTGCAACATATCAGGATGGTATATAAACCACAGGAGGAATGATGGAATATACCCTTACCCTAAATTTCATTGA<br>ACCGTTTCGCTTGATTGAATGGCACGATGCGCCAGATCGGGAAAACCTTCGATTGAGGGGGTTTTCTTTTGCCAGATGGCATA<br>AGGACAGGGAATTCGGACTGGGAAGGCCATATATT (SEQ ID NO: 122) |
| >CLUST.019911\|S.TJLN2-PDG_0\|31645\|31858<br>AATGGAATCCAGGTCCGTTATCCAAAATTGGAAAAAGAAAAAAAAGATGACCCAGGTGAAAAGCCGGGCTATCTTGAGCTGGC<br>AGATGGCCCTTTCAGCACGGAAAATCGCAAGGAAAAATTAAAGGAGATTTGGGGTAATTGGGCCTGATTAACCAAATATCGAA<br>TAATCACCAAATACATAGCCTATTTTCAATGATATTCAATAGTTATAATACCTATTTAATAATTCAATATTTATAGAATCCAA<br>GGATTATGCATCGCCAAAAATACATCCATAAACGATTTAACAATATGAATTTACAAAATGAATTTATACCATTGGGTTTTAAG<br>AATCTTTTATAATAAGCAAACATAGGGGGGG (SEQ ID NO: 123) |
| >CLUST.019911\|S.J3DH2-PDG_7\|19861\|20000<br>GATGTTCCGCCAGGCACGGCAGCGATTCTCCTTGGGCTTTGTAGAGACGTGGACAGATTGAGGGCCGCCATTGATTCAATTGT<br>TTCGGGCAAGAAGACGCGGGATGATACGATATTCTGGATACTATACCACACCGTGCCGGAGAAATAGGGCCTGTCGCCAAATC<br>CACTCGGGCCTTCCACTACAAAAAGGCTTAACTCGATAGTATATGGGTTTCCTTTTTTTGAGTCCGCCGGAGGCGGACGTTGT<br>ATAAAATCGCGAAGTGATTTTATGTACTGGAGAGGATATCATGGTCACGCCACAAGCTTCTAAGAACCCCGCAGTAGATGAAA<br>TCCTGAAACAGCTCACACCCTATGACATGGAGACTGAGAACGCAAAGGCTATCGAGACAAGGAAGTCTTGTATTGAGTGCCTG<br>AAAGGCATTTGCGAAAGGGCTCAA (SEQ ID NO: 124) |
| >CLUST.019911\|S.J3DH2-PDG_7\|27996\|28061<br>ATATTGCGCGATAACGGGGAAGATATATTTGTCCATCGGAGCGATATTAATGGTAGCCTTGGCACCCTGACAGAAGGGCAAAA<br>AGTAATCTTTGAGGTGAAGCAGGGTCCAAAGGGACTCCAGGCCACAAATGTGAAGGTAATTTCATAATCACTTGGCCGTATTG<br>CACCTTACCACAATATCTTTTTGAGAATTTCATAAGAGCTCATTTCAAAGTGAATATTCAATCCACGGCTGTTGAAAAAAAGC<br>GAAACGCCCTTGCTCTTTTTGTGCGCCTTCTCCTTTCATCGCCTCTCAAGGACTACGTCGCCAAGATAATCCTGTTTGGAAGT<br>GTGAGAAAAGGAAAAGCTAATTCAGAGAGTGAT (SEQ ID NO: 125) |
| >CLUST.019911\|S.J3DH2-PDG_7\|30118\|30312<br>TGCTTGAAATGGCGTGGGCATTTGCTTTTGGCCCCGGCTGATATCTACTCGGCAAAGCCACACCATACAATAATGGAGGCTGA<br>TTCAATGTGACATAAAATTTTGGGGTAGCGTCTACATGCAAAAATCTCGGTGGTGATTCGTTTATACTTATAGAGTGGATCAT<br>TTTCTGAGCCGACACCCGAGATTGAGCTATGACTGCCACAATATTTGACAAATTTGCAAGCTTTGAAAACTTCTGGGCCGCCT<br>TCCAAAAAGTTGCTGCAAAGAATTCAGCGGGCGGCATAGACGGCACAACCGTTGAGACCTACCAAAAGCGAGCCAAGCAACGA<br>ATCAATGCCCTC (SEQ ID NO: 126) |

Example 2: In Vivo Bacterial Validation of Engineered Type III-E (CLUST.019911) CRISPR-Cas Systems (FIGS. 7A-12)

Having identified the minimal components of Type III-E CRISPR-Cas systems, we selected one system for functional validation, from *Candidatus* Scalindua brodae (JRY001000185, SEQ ID NO: 1, SEQ ID NO: 14).

Methods

Gene Synthesis and Oligo Library Cloning

The *E. coli* codon-optimized protein sequences for CRISPR effectors, accessory proteins were cloned into pET-28a(+) (EMD-Millipore) to create the Effector Plasmid. Noncoding sequences flanking Cas genes (including 150 nt of terminal CDS coding sequence) or the CRISPR array were synthesized (Genscript) into pACYC184 (New England Biolabs) to create the Non-coding Plasmid (FIG. 7A). Effector mutants (e.g., D513A or A513D) plasmids were cloned by site directed mutagenesis using the indicated primers in the sequence table: sequence changes were first introduced into PCR fragments, which were then re-assembled into a plasmid using NEBuilder HiFi DNA Assembly Master Mix or NEB Gibson Assembly Master Mix (New England Biolabs) following the manufacturer's instructions.

For the pooled spacer library, we first computationally designed an oligonucleotide library synthesis (OLS) pool (Agilent) to express a minimal CRISPR array of "repeat-spacer-repeat" sequences. The "repeat" elements were derived from the consensus direct repeat sequence found in the CRISPR array associated with the effector, and "spacer" represents 8,900 sequences targeting the pACYC184 plasmid and *E. coli* essential genes, or negative control non-targeting sequences. The spacer length was determined by the mode of the spacer lengths found in the endogenous CRISPR array. Flanking the minimal CRISPR array were unique PCR priming sites that enabled amplification of a specific library from a larger pool of oligo synthesis.

We next cloned the minimal CRISPR array library into the Effector Plasmid to create an Effector Plasmid library. We appended flanking restriction sites, a unique molecular identifier, and a J23119 promoter for array expression onto the oligo library using PCR (NEBNext High-Fidelity 2×PCR Master Mix), and then used NEB Golden Gate Assembly Master Mix (New England Biolabs) to assemble the full plasmid library of effectors with their targeting arrays. This represented the "input library" for the screen.

In Vivo *E. coli* Screen

We performed the in vivo screen using electrocompetent *E. cioni* EXPRESS BL21(DE3) *E. coli* cells (Lucigen), unless otherwise indicated. Competent cells were co-transformed with the Effector Plasmid and/or Non-coding (FIG. 7B). The cells were electroporated with the "input library" according to the manufacturer's protocols using a Gene Pulser Xcell® (Bio-rad) with a 1.0 mm cuvette. The cells were plated onto bioassay plates containing both Chloramphenicol (Fisher) and Kanamycin (Alfa Aesar), and grown for 11 hours, after which we estimated the approximate colony count to ensure sufficient library representation and harvested the cells.

Plasmid DNA fractions were extracted from the harvested cells to create the 'output library' using a QIAprep® Spin Miniprep Kit (Qiagen), while total RNA=17nt was harvested by lysing the harvested cells in Direct-zol® (Zymo Research), followed by extraction using the Direct-zol RNA miniprep kit (Zymo Research).

The next generation sequencing library for the DNA depletion signal was prepared by performing a PCR on both the input and output libraries, using custom primers flanking the CRISPR array cassette of the Effector Plasmid library and containing barcodes and handles compatible with Illumina sequencing chemistry. This library was then normalized, pooled, and loaded onto a Nextseq 550 (Illumina) to evaluate the activity of the effectors.

Bacterial Screen Sequencing Analysis

Next generation sequencing data for screen input and output libraries were demultiplexed using Illumina bc12fastq. Reads in resulting fastq files for each sample contained the CRISPR array elements for the screening plasmid library. The direct repeat sequence of the CRISPR array was used to determine the array orientation, and the spacer sequence was mapped to the source (pACYC184 or *E. coli* essential genes) or negative control sequence (GFP) to determine the corresponding target. For each sample, the total number of reads for each unique array element ($r_a$) in a given plasmid library was counted and normalized as follows: ($r_a$+1)/total reads for all library array elements. The depletion score was calculated by dividing normalized output reads for a given array element by normalized input reads.

To identify specific parameters resulting in enzymatic activity and bacterial cell death, we used next generation sequencing (NGS) to quantify and compare the representation of individual CRISPR arrays (i.e., repeat-spacer-repeat) in the PCR product of the input and output plasmid libraries. We defined the fold depletion for each CRISPR array as the normalized input read count divided by the normalized output read count (with 1 added to avoid division by zero). An array was considered to be "strongly depleted" if the fold depletion was greater than 3. When calculating the array fold depletion across biological replicates, we took the maximum fold depletion value for a given CRISPR array across all experiments (i.e. a strongly depleted array must be strongly depleted in all biological replicates).

FIG. 8 shows the degree of interference activity (depletion ratio) of the engineered Type III-E compositions by plotting for a given target the normalized ratio of sequencing reads in the screen output versus the screen input. The results are plotted for each crRNA transcriptional orientation. In the functional screen for each composition, an active effector, or effector and accessory complex, complexed with an active crRNA (expressed as a DR::spacer::DR) will interfere with *E. coli* essential gene function or the ability of the pACYC184 to confer *E. coli* resistance to chloramphenicol and tetracycline, resulting in cell death and depletion of the spacer element within the pool. Comparing the results of deep sequencing the initial DNA library (screen input) versus the surviving transformed *E. coli* (screen output) suggest specific target sequences and DR transcriptional orientation that enable an active, programmable CRISPR system. The screen also indicates that the effector complex is only active with one orientation of the DR.

FIG. 9 depicts the measured interference activity (depletion ratio) against the sequencing read coverage of the screen output. Notably, many of the points with depletion values above the hit threshold fall in the range where normalized output read counts are high (e.g. above 10), indicating the depletion ratio measurement is unlikely to be a technical artifact.

FIGS. 10 and 11 depict the location of strongly depleted targets for the Type III-E CRISPR-Cas system targeting pACYC184 and *E. coli* E. Cloni essential genes. Notably, the location of strongly depleted targets appears dispersed throughout the potential target space.

FIG. 12 depicts a weblogo of the sequences flanking depleted targets, indicating the absence of a prominent PAM.

Together, the interference activity displayed in the *E. coli* screen with the Type III-E CRISPR system suggests a programmable system capable of sequence-specific bacterial cell death or dormancy, which may yield new modalities of programmable CRISPR activities based on the Type III-E effectors.

Example 3—Identification of Transactivating RNA Elements

In addition to an effector protein, a crRNA, and an accessory protein, some CRISPR systems as described herein also include an additional small RNA that activates robust enzymatic activity referred to as a transactivating RNA (tracrRNA). Such tracrRNAs typically include a complementary region that hybridizes to the crRNA. The crRNA-tracrRNA hybrid forms a complex with an enzymatic module formed by an effector and an accessory protein resulting in the activation of programmable enzymatic activity.

TracrRNA sequences are identified as described herein by searching genomic sequences flanking CRISPR arrays for short sequence motifs that are homologous to the direct repeat portion of the crRNA. Search methods include exact or degenerate sequence matching for the complete direct repeat (DR) or DR subsequences. For example, a DR of length n nucleotides can be decomposed into a set of overlapping 6-10 nt kmers. These kmers are aligned to sequences flanking a CRISPR locus, and regions of homology with 1 or more kmer alignments are identified as DR homology regions for experimental validation as tracrRNAs. Alternatively, RNA cofold free energy can be calculated for the complete DR or DR subsequences and short kmer sequences from the genomic sequence flanking the elements of a CRISPR system. Flanking sequence elements with low minimum free energy structures are identified as DR homology regions for experimental validation as tracrRNAs. Notably, tracrRNA elements frequently occur within close proximity to CRISPR associated genes or a CRISPR array. As an alternative to searching for DR homology regions to identify tracrRNA elements, non-coding sequences flanking CRISPR associated proteins or the CRISPR array can be isolated by cloning or gene synthesis for direct experimental validation of tracrRNAs.

Experimental validation of tracrRNA elements is performed using small RNA sequencing of the host organism for a CRISPR system or synthetic sequences expressed heterologously in non-native species. Alignment of small RNA sequences from the originating genomic locus is used to identify expressed RNA products containing DR homology regions and stereotyped processing typical of complete tracrRNA elements.

Complete tracrRNA candidates identified by RNA sequencing are validated in vitro or in vivo by expressing the crRNA and effector in combination with or without the tracrRNA candidate, and monitoring the activation of effector enzymatic activity. Constructs are engineered to have the expression of tracrRNAs can be driven by promoters including, but not limited to, U6, U1, and H1 promoters for expression in mammalian cells or J23119 promoter for expression in bacteria. In some instances, a tracrRNA can be fused with a crRNA and expressed as a single guide RNA.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An engineered, non-naturally occurring Clustered Regularly Interspaced Short Palindromic Repeat (CRISPR)-Cas system comprising:

an RNA guide comprising a direct repeat sequence and a spacer sequence capable of hybridizing to a target nucleic acid, or a nucleic acid encoding the RNA guide; and a CRISPR-associated protein, wherein the CRISPR-associated protein comprises an amino acid sequence that is at least 97% identical to the amino acid sequence of SEQ ID NO: 316, SEQ ID NO: 317, or SEQ ID NO: 318, or a nucleic acid encoding the CRISPR-associated protein;

wherein the CRISPR-associated protein is capable of binding to the RNA guide and of targeting the target nucleic acid sequence complementary to the spacer sequence.

2. The system of claim 1, wherein the CRISPR-associated protein comprises an amino acid sequence that is at least 97% identical to the amino acid sequence of SEQ ID NO: 316.

3. The system of claim 1, wherein the CRISPR-associated protein comprises an amino acid sequence that is at least 97% identical to the amino acid sequence of SEQ ID NO: 317.

4. The system of claim 1, wherein the CRISPR-associated protein comprises an amino acid sequence that is at least 97% identical to the amino acid sequence of SEQ ID NO: 318.

5. The system of claim 1, wherein the CRISPR-associated protein comprises a RuvC domain.

6. The system of claim 1, wherein the CRISPR-associated protein comprises an OrfB_Zn_ribbon domain.

7. The system of claim 1, wherein the direct repeat sequence comprises a nucleic acid sequence of TGRGAC.

8. The system of claim 1, wherein the direct repeat sequence comprises a nucleic acid sequence of any of SEQ ID NOs: 321-328, or a sequence having at least 90% identity thereto.

9. The system of claim 1, wherein the direct repeat sequence forms a stem-loop.

10. The system of claim 1, wherein the spacer sequence has a length of 15-50 nucleotides.

11. The system of claim 1, wherein the CRISPR-associated protein is capable of recognizing a protospacer adjacent motif (PAM).

12. The system of claim 1, wherein the target nucleic acid is a DNA.

13. The system of claim 1, wherein the targeting of the target nucleic acid by the CRISPR-associated protein and the RNA guide results in a modification in the target nucleic acid.

14. The system of claim 13, wherein the modification in the target nucleic acid is a double stranded cleavage event.

15. The system of claim 13, wherein the modification in the target nucleic acid is a single stranded cleavage event.

16. The system of claim 1, within a cell.

17. A method of targeting and editing the target nucleic acid, the method comprising contacting the target nucleic acid with the system of claim 1.

* * * * *